(12) United States Patent
Brasca et al.

(10) Patent No.: US 10,479,778 B2
(45) Date of Patent: Nov. 19, 2019

(54) SUBSTITUTED PYRROLES ACTIVE AS KINASES INHIBITORS

(71) Applicant: NERVIANO MEDICAL SCIENCES S.r.l., Nerivano (IT)

(72) Inventors: Maria Gabriella Brasca, Nerviano (IT); Simona Bindi, Milan (IT); Marina Caldarelli, Milan (IT); Marcella Nesi, Saronno (IT); Sten Christian Orrenius, Nerviano (IT); Achille Panzeri, Merate (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

(21) Appl. No.: 15/599,025

(22) Filed: May 18, 2017

(65) Prior Publication Data

US 2017/0253579 A1 Sep. 7, 2017

Related U.S. Application Data

(62) Division of application No. 14/418,555, filed as application No. PCT/EP2013/065598 on Jul. 24, 2013, now Pat. No. 9,688,661.

(30) Foreign Application Priority Data

Aug. 2, 2012 (EP) .................................. 12178946

(51) Int. Cl.

| | |
|---|---|
| *C07D 487/04* | (2006.01) |
| *A61K 31/19* | (2006.01) |
| *A61P 35/00* | (2006.01) |
| *A61P 35/02* | (2006.01) |
| *A61P 25/04* | (2006.01) |
| *C07F 5/04* | (2006.01) |
| *C07F 7/08* | (2006.01) |
| *A61P 29/00* | (2006.01) |
| *A61P 37/06* | (2006.01) |
| *A61P 19/02* | (2006.01) |
| *C07D 403/04* | (2006.01) |
| *C07D 401/04* | (2006.01) |
| *A61K 31/506* | (2006.01) |
| *A61K 31/52* | (2006.01) |
| *A61K 31/53* | (2006.01) |
| *A61P 35/04* | (2006.01) |
| *A61P 37/00* | (2006.01) |
| *C07D 473/00* | (2006.01) |
| *A61K 31/519* | (2006.01) |
| *A61K 45/06* | (2006.01) |
| *C07D 473/04* | (2006.01) |

(52) U.S. Cl.
CPC .......... *C07D 403/04* (2013.01); *A61K 31/506* (2013.01); *A61K 31/519* (2013.01); *A61K 31/52* (2013.01); *A61K 31/53* (2013.01); *A61K 45/06* (2013.01); *A61P 19/02* (2018.01); *A61P 29/00* (2018.01); *A61P 35/00* (2018.01); *A61P 35/02* (2018.01); *A61P 35/04* (2018.01); *A61P 37/00* (2018.01); *A61P 37/06* (2018.01); *C07D 401/04* (2013.01); *C07D 473/00* (2013.01); *C07D 487/04* (2013.01); *C07F 5/04* (2013.01); *C07F 7/083* (2013.01)

(58) Field of Classification Search
CPC ........................... C07D 487/04; A61K 31/519
See application file for complete search history.

(56) References Cited

U.S. PATENT DOCUMENTS

2015/0166512 A1 6/2015 Brasca et al.

FOREIGN PATENT DOCUMENTS

| WO | 2007/070514 A1 | 6/2007 |
| WO | 2007/110344 A1 | 10/2007 |

OTHER PUBLICATIONS

Dymock, et al. (Expert Opin. Ther. Pat., 2013, 23(4), pp. 449-501).*
Alvarez J.V. et al., "Signal Transducer and Activator of Transcription 3 is Required for the Oncogenic Effects of Non-Small-Cell Lung Cancer-Associated Mutations of the Epidermal Growth Factor Receptor", Cancer Research 66(6):3162-3168 (Mar. 15, 2006).
Ara T. et al., "Interleukin-6 in Bone Metastasis and Cancer Progression", Eur J. Cancer 46(7):1223-1231 (May 2010).
Baker SJ et al., "Hematopoietic Cytokine Receptor Signaling", Oncogene 26:6724-6737 (2007).
Ban M. et al., "Replication Analysis Identifies TYK2 as a Multiple Sclerosis Susceptibility Factor", European Journal of Human Genetics 17:1309-1313 (2009).
Baxter E et al., "Acquired Mutation of the Tyrosine Kinase JAK2 in Human Myeloproliferative Disorders", Lancet 365:1054-1061 (Mar. 19, 2005).
Campbell P.J. et al., "The Myeloproliferative Disorders", The New England Journal of Medicine 23:2452-2466 (Dec. 7, 2006).

(Continued)

*Primary Examiner* — Susanna Moore
(74) *Attorney, Agent, or Firm* — Scully, Scott, Murphy & Presser, P.C.

(57) ABSTRACT

The present invention relates to substituted pyrrole compounds which modulate the activity of protein kinases and are therefore useful in treating diseases caused by dysregulated protein kinase activity, in particular Jak family kinases. The present invention also provides methods for preparing these compounds, pharmaceutical compositions comprising these compounds, and methods of treating diseases utilizing such compounds or the pharmaceutical compositions containing them.

16 Claims, No Drawings

Specification includes a Sequence Listing.

(56) References Cited

OTHER PUBLICATIONS

Clevenger C.V., "Roles and Regulation of Stat Family Transcription Factors in Human Breast Cancer", American Journal of Pathology 165(5):1449-1460 (Nov. 2004).
Cohen P., "The Development and Therapeutic Potential of Protein Kinase Inhibitors", Current Opinion in Chemical Biology 3:459-465 (1999).
Cohen P., "Protein Kinases-The Major Drug Targets of the Twenty-First Century", Nature Reviews-Drug Discovery 1:309-315 (Apr. 2002).
Colombo M. et al., "A Fully Automated Method for Accurate Mass Determination Using High-Performance Liquid Chromatography With a Quadrupole/Orthogonal Acceleration Time-of-Flight Mass Spectrometer", Rapid Communications in Mas Spectrometry 18:511-517 (2004).
Constantinescu S.N. et al., "Mining for JAK-STAT Mutations in Cancer", Trends in Biochemical Sciences 33(3):122-131 (2007).
Couturier N. et al., "Tyrosine Kinase 2 Variant Influences T Lymphocyte Polarization and Multiple Sclerosis Susceptibility", Brain 134:693-703 (2011).
Davidsen S.K. et al., "Di-Tert-Butyl N-Acylimidodicarbonates as Isolable Acylating Agents: Mild Conversion of Primary Carboxamides to Substituted Amides", J. Org. Chem. 56(18):5482-5485 (1991).
Ghoreschi K. et al., "Janus Kinases in Immune Cell Signaling", Immunol Rev. 228(1):273-287 (Mar. 2009).
Godeny M.D. et al., "Jak2 Tyrosine Kinase and Cancer: How Good Cells Get HiJAKed", Anti-Cancer Agents in Medicinal Chemistry 7:643-650 (2007).
Hercus T.R. et al., "The Granulocyte-Macrophase Colony-Stimulating Factor Receptor: Linking its Structure to Cell Signaling and its Role in Disease", Blood 114(7):1289-1298 (Aug. 13, 2009).
Ihle J.N., "Cytokine Receptor Signalling", Nature 377:591-594 (Oct. 19, 1995).
Ishizaki M. et al., "Involvement of Tyrosine Kinase-2 in Both the IL-12/Th1 and IL-23/Th17 Axes In Vivo", The Journal of Immunology 187:181-189 (2011).
James C. et al., "A Unique Clonal JAK2 Mutation Leading to Constitutive Signalling Causes Polycythaemia Vera", Nature 434:1144-1148 (Apr. 28, 2005).
Jeong E G et al., "Somatic Mutations of JAK1 and JAK3 in Acute Leukemias and Solid Cancers", Clin Cancer Res 14(12):3716-3721 (Jun. 15, 2008).
Jiang Q et al., "Use of In Situ Isopropoxide Protection in the Metal-Halogen Exchange of Arylboronates", J. Org. Chem. 72(17):6618-6620 (2007).
Jolicoeur B. et al., "Pyrrole Protection", Tetrahedron 62:11531-11563 (2006).
Kiss R. et al., "Recent Developments on JAK2 Inhibitors: A Patent Review", Expert Opinion, Therapeutic Patents 20(4):471-495 (2010).
Kralovics R. et al., "A Gain-of-Function Mutation of JAK2 in Myeloproliferative Disorders", The New England Journal of Medicine 1779-1790 (Apr. 28, 2005).
Lacronique V. et al., "A TEL-JAK2 Fusion Protein With Constitutive Kinase Activity in Human Leukemia", Science 278:1309-1312 (Nov. 14, 1997).

Levine R.L. et al., "Activating Mutation in the Tyrosine Kinase JAK2 in Polycythemia Vera, Essential Thrombocythemia, and Myeloid Metaplasia With Myelofibrosis", Cancer Cell 7:387-397 (Apr. 2005).
Leonard W.J. et al., "JAKS and STATS: Biological Implications", Annu. Rev. Immunol. 16:293-322 (1998).
Menichincheri M. et al., "Cdc7 Kinase Inhibitors: 5-Heteroaryl-3-Carboxamido-2-Aryl Pyrroles as Potential Antitumor Agents", Journal of Medicinal Chemistry 53:7296-7315 (2010).
Minegishi Y. et al., "Human Tyrosine Kinase 2 Deficiency Reveals its Requisite Roles in Multiple Cytokine Signals Involved in Innate and Acquired Immunity", Immunity 25:745-755 (Nov. 2006).
Miyaura N. et al., "Palladium-Catalyzed Cross-Coupling Reactions of Organoboron Compounds", Chem. Rev. 95:2457-2483 (1995).
Mullighan C.G. et al., "JAK Mutations in High-Risk Childhood Acute Lymphoblastic Leukemia", PNAS 106(23):9414-9418 (Jun. 9, 2009).
Murray P.J., "The JAK-STAT Signaling Pathway: Input and Output Integration", The Journal of Immunology 178:2623-2629 (2007).
Norman P., "Selective JAK1 Inhibitor and Selective Tyk2 Inhibitor Patents", Expert Opinion, Therapeutic Patents 22(10):1233-1249 (2012).
Notarangelo L.D. et al., "Mutations in Severe Combined Immune Deficiency (SCID) Due to JAK3 Deficiency", Human Mutation 18:255-263 (2001).
Roodman G.D., "New Potential Targets for Treating Myeloma Bone Disease", Clin Cancer Res 12(20 Suppl): 6270s-6273s (Oct. 15, 2006).
Russell S.M. et al., "Mutation of Jak3 in a Patient with SCID: Essential Role of Jak3 in Lymphoid Development", Science 270:797-800 (Nov. 3, 1995).
Sayyah J. et al., "Jak2 Inhibitors: Rationale and Role as Therapeutic Agents in Hematologic Malignancies", Curr Oncol Rep. 11(2):117-124 (Mar. 2009).
Shide K. et al., "Development of ET, Primary Myelofibrosis and PV in Mice Expressing JAK2 V617F", Leukemia 22:87-95 (2008).
Silver J.S. et al., "gp130 at the Nexus of Inflammation, Autoimmunity, and Cancer", Journal of Leukocyte Biology 88:1145-1156 (Dec. 2010).
Spivak J.L. et al., "Animal Models of the MPD: Lack of the Clones", Blood 108(5):1427-1428 (Sep. 1, 2006).
Sullivan B.A. et al., "Mechanisms for Glycolipid Antigen-Driven Cytokine Polarization by Va14i NKT Cells", The Journal of Immunology 184:141-153 (2010).
Suzuki A., "Cross-Coupling Reactions of Organoboron Compounds with Organic Halides", Metal-Catalyzed Cross-Coupling Reactions, 1st edition, pp. 49-97 (1998).
Velculescu V.E., "Defining the Blueprint of the Cancer Genome", Carcinogenesis 29(6):1087-1091 (2008).
Wallace T.A. et al., "Jak2 Tyrosine Kinase-A Mediator of Both Housekeeping and Ligand-Dependent Gene Expression?", Cell Biochemistry and Biophysics 44:213-222 (2006).
International Search Report dated Jan. 27, 2014 received from related Application No. PCT/EP2013/065598.
U.S. Final Office Action dated Nov. 10, 2016 received in U.S. Appl. No. 14/418,555.
U.S. non-Final Office Action dated May 5, 2016 received in U.S. Appl. No. 14/418,555.

* cited by examiner

SUBSTITUTED PYRROLES ACTIVE AS KINASES INHIBITORS

CROSS-REFERENCE TO RELATED APPLICATIONS

The present application is a divisional of co-pending application having U.S. Ser. No. 14/418,555, filed on Jan. 30, 2015, which is a 371 of International Application having Serial No. PCT/EP2013/065598, filed on Jul. 24, 2013, which claims benefit of European Patent Application No. 12178946.5, filed on Aug. 2, 2012, the contents of all of which are incorporated herein by reference.

INCORPORATION BY REFERENCE OF SEQUENCE LISTING

The Sequence Listing in an ASCII text file, named 31662_Sequence_Listing.txt of 1 KB, created on Jan. 14, 2015, and submitted to the United States Patent and Trademark Office via EFS-Web, is incorporated herein by reference.

The present invention relates to certain substituted pyrrole compounds, which modulate the activity of protein kinases. The compounds of this invention are therefore useful in treating diseases related to dysregulated kinases activity, for example cancer, cell proliferative disorders, viral infections, immune disorders, neurodegenerative disorders, cardiovascular diseases and bone related diseases.

The present invention also provides methods for preparing these compounds, pharmaceutical compositions comprising these compounds, and methods of treating diseases utilizing pharmaceutical compositions comprising these compounds.

Protein kinases mediate intracellular signaling by affecting a phosphoryl transfer from a nucleoside triphosphate to a protein acceptor that is involved in a signaling pathway. These phosphorylation events act as molecular on/off switches that can modulate or regulate the target protein's biological function and are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-3 (IL-3), IL-2) and growth factors (e.g., granulocyte macrophage-colony-stimulating factor (GM-CSF), fibroblast growth factor (FGF) and Erythropoietin (EPO)). An extracellular stimulus may affect one or more cellular responses related to cell growth, migration, differentiation, secretion of hormones, activation of transcription factors, muscle contraction, glucose metabolism, control of protein synthesis and regulation of the cell cycle.

The malfunction of protein kinases (PKs) is the hallmark of numerous diseases. A large share of the oncogenes and proto-oncogenes involved in human cancers encode for PKs. The enhanced activities of PKs are also implicated in many non-malignant diseases that include, but are not limited to, autoimmune diseases, inflammatory diseases, psoriasis, bone diseases, metabolic diseases, neurological and neurodegenerative diseases, cardiovascular diseases, allergies and asthma, Alzheimer's disease, and hormone-related diseases. Accordingly, there has been a substantial effort in medicinal chemistry to find protein kinase inhibitors that are effective as therapeutic agents. For a general reference to PKs malfunctioning or deregulation see Current Opinions in Chemical Biology 1999, 3: 459-465; Nature Rev. Drug Discov. 2002, 1: 309-315 and Carcinogenesis 2008, 29: 1087-191.

The JAKs are a family of non-receptor tyrosine kinases consisting of JAK1, JAK2, JAK3 and TYK2.

Whereas JAK1, JAK2 and TYK2 are expressed ubiquitously in mammals, JAK3 is primarily expressed in hematopoietic cells. The JAKs play a crucial role in hematopoietic cytokine and growth factors signaling (Nature 1995, 377: 591-594, Annu. Rev. Immunol. 1998, 16: 293-322) and are critically involved in cell growth, survival, development and differentiation of myeloid and immune cells. Effective innate and adaptive immune responses require functional JAK signaling to protect the organism from infections or tumors and mutations leading to loss of function make up some of the most common inherited severe immunodeficiencies. As a consequence JAK/STAT signaling has been implicated in the mediation of many abnormal immune responses such as allergies, asthma, autoimmune diseases, transplant rejection, rheumatoid arthritis, amyotrophic lateral sclerosis and multiple sclerosis as well as in solid and hematological malignancies like leukemias and lymphomas (Immunol Rev. 2009, 228: 273-287).

In particular JAK2 kinase is exclusively involved in the signal transduction mediated by Erythropoietin (EPO), Thrombopoietin (TPO), Growth Hormone (GH), Prolactin (PR) and by cytokines that signal through the common beta chain receptor IL-3, granulocyte-macrophage colony-stimulating factor (GM-CSF) and IL-5. In addition, JAK2 together with JAK1 and/or TYK2 are important for the cytokines that signal through gp130 receptors (e.g. IL-6, IL-11), Type II cytokine receptors like IL-10, IL-19, IL-20 and IL-22, p40-containing containing cytokine receptors IL-12 and IL-23 and for the signal of Type I and II IFNs receptors (Immunol Rev. 2009; 228: 273-287). JAK3 kinase is primarily expressed in hematopoietic cells and is selectively associated with the common γ chain (γc), which is a shared component of the receptors for IL-2, IL-4, IL-7, IL-9, IL-15, and IL-21 that are cytokines involved in lymphoid development and function, and homeostasis of the immune system. TYK2 is primarily associated with Interferons, IL-12 and IL-23 involved in regulation of Th1 and Th17 cells that play a key role in autoimmune disease. All these growth factors and cytokines are mainly involved in proliferation and differentiation of Myeloid cells, inflammatory response and cancer (Blood. 2009, 114: 1289-1298, Clin Cancer Res. 2006, 12: 6270s-6273s, J Leukoc Biol. 2010, 88: 1145-1156, Eur J Cancer. 2010, 46: 1223-1231, J. Immunol. 2010, 184: 141-147, J. Immunol. 2011, 187: 181-189, Brain 2011, 134: 693-703).

The binding of the ligand to the specific receptor seems to induce a conformational change in the receptor that allows trans- and/or autophosphorylation of the two bound JAK molecules. Activated JAK then phosphorylates specific tyrosine residues on the cytoplasmic tails of the receptors, creating docking sites for the SH2 domain of Signal Transducers and Activators of Transcription proteins (STAT). Once bound to the receptors, STATs are themselves phosphorylated by JAK on tyrosine residues. Phosphorylated STATs dimerize and translocate into the nucleus, where they regulate gene transcription. Thus, JAKs are responsible for transducing a signal from the cell surface to the nucleus through a tyrosine phosphorylation signalling mechanism (J. Immun. 2007, 178:2623-2629, Oncogene 2007, 26: 6724-6737 and Cell Biochem Biophys. 2006, 44: 213-222).

JAKs are characterized by 7 distinct JAK homology regions (JH1 to JH7), among these the JH1 regions form the kinase domain and is immediately adjacent to the pseudo-kinase domain (JH2) within the C-terminal half of the protein. The function of the pseudo-kinase domain is to negatively regulate the activity of the kinase domain (N. Engl. J. Med 2006, 355: 2452-2466). It should be point out that the majority of JAK activating mutations identified in tumors are in pseudo-kinase domain. For example an activating point mutation of JAK2 (Valine to Phenylalanine substitution, JAK2-V617F) in the pseudo-kinase domain together with other activating mutations, in the JAK2 exon12 and in the TPO Receptor (MPLW515L/K), have been identified in Hematopoietic cells of patients with myeloproliferative disorders or MPD (Nature 2005, 434: 1144-8, N Engl J Med 2005, 352: 1779-90, Lancet 2005, 365: 1054-61, Cancer Cell 2005, 7: 387-97, Blood 2006, 108: 1427-1428 and Leukemia 2008, 22: 87-95). All of this data suggests that JAK2 is a suitable target for the development of a MPD specific therapy (Curr. Onc. Reports 2009, 11: 117-124). In addition, the JAK/STAT pathway has been shown to be activated not only by mutation but also by amplification, translocation, silencing of JAK/STAT pathway inhibitors SOCS proteins and overexpression of cytokines in solid and hematological malignancies like, but not limited to, AML, ALL, Hodgkin's Lymphoma, Diffuse large B cell Lymphoma and Mediastinal large B-Cell Lymphoma, Lung, Prostate, Colon and Breast cancer. General observation about the role of JAK in cancer refer to Science 1997, 278:1309-1312; Oncogene 2007, 26: 6724-6737; Trends in Biochemical Sciences 2007, 33: 122-131, PNAS 2009, 106: 9414-9418, Anti-Cancer Agents Med Chem 2007, 7, 643-650.

Data from experimental mice and clinical observations have unraveled multiple signaling events mediated by JAKs in innate and adaptive immunity. Deficiency of JAK3 or TYK2 results in defined clinical disorders, which are also evident in mouse models. A striking phenotype associated with inactivating JAK3 mutations is severe combined immunodeficiency syndrome (Science 1995, 270: 797-800, Hum Mutat 2001, 18: 255-63), whereas mutation of TYK2 results in another primary immunodeficiency termed autosomal recessive hyperimmunoglobulin E syndrome (Immunity 2006, 25: 745-755). Combined this data supports the use of JAK inhibitors in several different diseases such as abnormal immune responses like allergies, asthma, autoimmune diseases, transplant rejection, rheumatoid arthritis, amyotrophic lateral sclerosis and multiple sclerosis as well as in solid and hematological malignancies like MPD, leukemias and lymphomas. General observations about the pharmaceutical intervention in the JAK/STAT pathway have been reviewed in J. Leukoc Biol. 2010, 88:1145-1156, Eur J. Cancer. 2010, 46: 1223-1231, Immunol Rev. 2009, 228: 273-287, Trends Blood. 2009, 114: 1289-1298, Clin Cancer Res. 2008, 14:3716-3721, Biochem. Sciences, 2007, 33: 122-131, Clin Cancer Res. 2006, 12: 6270s-6273s, Cancer Res 2006, 66: 3162-3168, AJP 2004, 165: 1449-146, Eur J Hum Genet 2009, 17: 1309-13.

Substituted pyridyl- and pyrimidinyl-pyrrole derivatives and their preparation have been disclosed in WO2007/110344, and their use for the treatment of diseases associated with a dysregulated protein activity, in particular an altered Cdc7 kinase activity, was indicated.

Heteroaryl substituted pyrrolo[2,3-B]pyridines and pyrimidines and their preparation have been disclosed in WO2007/070514. In particular, this document discloses several substituted pyrazoles useful in the treatment of diseases related to activity of Janus kinase.

The present inventors have discovered that the substituted pyrroles of formula (I), described below, are potent JAK inhibitors and are thus useful in therapy of cancer, cell proliferative disorders, viral infections, immune disorders, neurodegenerative disorders, cardiovascular diseases and bone related diseases.

Accordingly, a first object of the present invention is to provide a substituted pyrrole compound represented by formula (I)

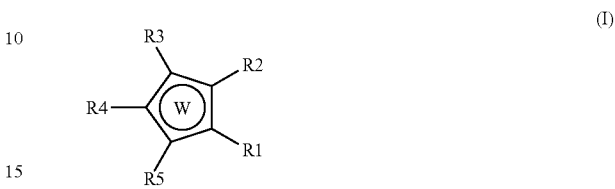

wherein:
Ring W is a pyrrole;
R1 is an optionally substituted aryl or heteroaryl;
R2 is CN or CONR6R7 wherein R6 and R7 are independently hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, aryl-alkyl, heteroaryl, heteroaryl-alkyl, heterocyclyl and heterocyclyl-alkyl, or R6 and R7, taken together with the nitrogen atom to which they are bonded, may form an optionally substituted 5 to 7 membered heterocyclyl group optionally containing one additional heteroatom selected from N, O and S;
R3 is hydrogen, halo or an optionally substituted group selected from straight or branched $C_1$-$C_6$ alkyl, $C_3$-$C_7$ cycloalkyl, cycloalkyl-alkyl, heterocyclyl and heterocyclyl-alkyl;
R4 is an optionally substituted heteroaryl group selected from

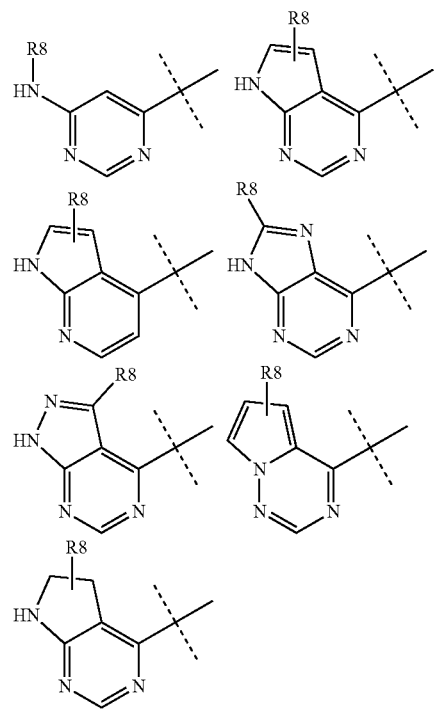

wherein:
R8 is hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, aryl-alkyl, heteroaryl, heteroaryl-alkyl, heterocyclyl and heterocyclyl-alkyl, COR9, CONR10R11 and SO$_2$R12, wherein:
R9 is a group optionally substituted selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, aryl-alkyl, heteroaryl, heteroaryl-alkyl, heterocyclyl and heterocyclyl-alkyl;
R10 and R11 are independently hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, aryl-alkyl, heteroaryl, heteroaryl-alkyl, heterocyclyl and heterocyclyl-alkyl, or R10 and R11, taken together with the nitrogen atom to which they are bonded, may form an optionally substituted 5 to 7 membered heterocyclyl group optionally containing one additional heteroatom selected from N, O and S;
R12 is a group optionally substituted selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, aryl-alkyl, heteroaryl, heteroaryl-alkyl, heterocyclyl and heterocyclyl-alkyl;
R5 is hydrogen, halo or an optionally substituted group selected from straight or branched $C_1$-$C_6$ alkyl, $C_3$-$C_7$ cycloalkyl, cycloalkyl-alkyl, heterocyclyl and heterocyclyl-alkyl;
or a pharmaceutically acceptable salt thereof.

The present invention also provides methods of preparing the pyrrole compounds, represented by formula (I), prepared through a process consisting of standard synthetic transformations.

The present invention also provides a method for treating diseases caused by and/or associated with a dysregulated protein kinase activity, particularly ABL, ACK1, AKT1, ALK, AUR1, AUR2, BRK, BUB1, CDC7/DBF4, CDK2/CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, Lck, Lyn, MAPKAPK2, MELK, MET, MNK2, MPS1, MST4, NEK6, NIM1, P38alpha, PAK4, PDGFR, PDK1, PERK, PIM1, PIM2, PKAalpha, PKCbeta, PLK1, RET, ROS1, SULU1, Syk, TLK2, TRKA, TYK2, VEGFR2, VEGFR3, ZAP70, more particularly JAK family kinases, which comprises administering to a mammal in need thereof, more particularly a human, an effective amount of a substituted pyrrole compound represented by formula (I) as defined above.

A preferred method of the present invention is to treat a disease caused by and/or associated with a dysregulated protein kinase activity selected from the group consisting of cancer, cell proliferative disorders, viral infections, immune-related disorders, neurodegenerative disorders, cardiovascular diseases and bone related diseases.

Another preferred method of the present invention is to treat specific types of cancer including but not limited to: carcinoma such as bladder, breast, brain, colon, kidney, liver, lung, including small cell lung cancer, head and neck, esophagus, gall-bladder, ovary, uterine, pancreas, stomach, cervix, thyroid, prostate, and skin, including squamous cell carcinoma; hematopoietic tumors of lymphoid lineage including leukaemia, T and B acute lymphoblastic leukemia (ALL), including DS-ALL, B-cell lymphoma, T-cell-lymphoma, Hodgkin's lymphoma, non-Hodgkin's lymphoma, Multiple Myeloma, hairy cell lymphoma, Burkett's lymphoma and mantle cell lymphoma; hematopoietic tumors of myeloid lineage, including acute and chronic myelogenous leukemias, acute megakaryoblastic leukemia, myelodysplastic syndrome and promyelocytic leukemia, myeloproliferative disorders like Polycythemia Vera (PV), Essential Thrombocythemia (ET), Primary myelofibrosis and myelofibrosis secondary to PV and ET, chronic myelomonocytic leukemia; tumors of mesenchymal origin, including sarcoma, fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer, Kaposi's sarcoma, mesothelioma.

Another preferred method of the present invention is to treat specific types of cell proliferative disorders including but not limited to: benign prostate hyperplasia, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections comprising the prevention of AIDS development in HIV-infected individuals.

A preferred method of the present invention is to treat immune-related disorders including but not limited to: transplant rejection, skin disorders like psoriasis, allergies, asthma and autoimmune-mediated diseases such as rheumatoid arthritis (RA), Multiple sclerosis, systemic lupus erythematosus (SLE), Crohn's disease and amyotrophic lateral sclerosis.

Another preferred method of the present invention is to treat neurodegenerative disorders including but not limited to: Alzheimer's disease, degenerative nerve diseases, encephalitis, Stroke, Parkinson's Disease, Multiple Sclerosis, Amyotrophic Lateral Sclerosis (ALS or Lou Gehrig's Disease), Huntington's Disease and Pick's Disease.

Another preferred method of the present invention is to treat cardiovascular diseases including but not limited to: atherosclerosis primary or secondary to diabetes, heart attack and stroke.

Another preferred method of the present invention is to treat bone loss diseases including but not limited to osteoporosis and bone metastasis.

In addition, the method of the present invention also provides tumor angiogenesis and metastasis inhibition as well as the treatment of organ transplant rejection and host versus graft disease.

Moreover, the method of the present invention further comprises subjecting the mammal in need thereof to a radiation therapy or chemotherapy regimen in combination with at least one cytostatic or cytotoxic agent.

The present invention also provides a pharmaceutical composition comprising a therapeutically effective amount of a compound of formula (I) or a pharmaceutically acceptable salt thereof, as defined above, and at least one pharmaceutically acceptable excipient, carrier and/or diluent.

In addition the present invention provides a pharmaceutical composition of a compound of the formula (I) further comprising one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents like anti-HER agents, anti-EGFR agents, anti-Abl, anti-angiogenesis agents (e.g. angiogenesis inhibitors), farnesyl transferase inhibitors, histone deacetylases inhibitors, ras-raf signal transduction pathway inhibitors, Akt pathway inhibitors, cell cycle inhibitors, other CDK inhibitors, tubulin binding agents, topoisomerase I inhibitors, topoisomerase II inhibitors, and the like.

The present invention further provides an in vitro method for inhibiting JAK family kinase proteins activity which comprises contacting the said protein with an effective amount of a compound of formula (I) as defined above.

Additionally, the invention provides a product or kit comprising a compound of formula (I) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

Unless otherwise specified, when referring to the compounds of the formula (I) per s as well as to any pharmaceutical composition thereof or to any therapeutic treatment comprising them, the present invention includes all of the hydrates, solvates, complexes, metabolites, pharmaceutically acceptable prodrugs, pharmaceutically acceptable bio-precursors, carriers, N-oxides and pharmaceutically acceptable salts of the compounds of this invention.

A metabolite of a compound of the formula (I) is any compound into which this same compound of the formula (I) is converted in vivo, for instance upon administration to a mammal in need thereof, Typically, without however representing a limiting example, upon administration of a compound of the formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of the formula (I).

"Pharmaceutically acceptable prodrug" and "pharmaceutically acceptable bio-precursors" are any covalently bonded compounds, which release in vivo the active parent drug according to the formula (I).

The terms "pharmaceutically acceptable prodrug" and "pharmaceutically acceptable bio-precursors" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the active parent drug, according to formula (I), in vivo, for example by hydrolysis in blood. A discussion is provided in T. Higuchi and V. Stella, Pro-drugs as Novel Delivery Systems, Vol. 14 of the A.C.S. Symposium Series, and in Edward B. Roche, Bioreversible Carriers in Drug Design, American Pharmaceutical Association and Pergamon Press, 1987.

N-oxides are compounds of the formula (I) wherein nitrogen and oxygen are tethered through a dative bond. Pharmaceutically acceptable salts of the compounds of the formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid.

Pharmaceutically acceptable salts of the compounds of the formula (I) also include the salts with inorganic or organic bases, e.g., alkali or alkaline-earth metals, especially sodium, potassium, calcium, ammonium or magnesium hydroxides, carbonates or bicarbonates, acyclic or cyclic amines.

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

In the present description, unless otherwise specified, the following terms have the following meanings. Ring W is a pyrrole of formula (Ia), (Ib), (Ic), (Id) or (Ie)

(Ia)

(Ib)

(Ic)

-continued

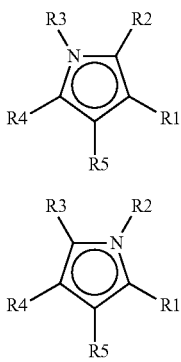

(Id)

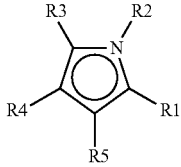

(Ie)

wherein R1, R2, R3, R4 and R5 are as defined above.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. The aryl ring can be optionally further fused or linked to aromatic and non-aromatic carbocyclic and heterocyclic rings. Non limiting examples of such aryl groups are phenyl, α- or β-naphthyl or biphenyl groups.

The term "heteroaryl" refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, indazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl, benzopyranyl, 2,3-dihydrobenzoxazinyl, 2,3-dihydroquinoxalinyl and the like.

With the term "heterocyclyl" (also known as "heterocycloalkyl") we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "straight or branched $C_1$-$C_6$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "$C_3$-$C_7$ cycloalkyl", we intend, unless otherwise provided, 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene, cyclohexadiene, cycloeptane, cycloeptene, cycloeptadiene.

With the term "straight or branched $C_2$-$C_6$ alkenyl" we intend any of the groups such as, for instance, vinyl, allyl, 1-propenyl, isopropenyl, 1-butenyl, 2-butenyl, 3-butenyl, 2-pentenyl, 1-hexenyl, and the like.

With the term "straight or branched $C_2$-$C_6$ alkynyl" we intend any of the groups such as, for instance, ethynyl, 2-propynyl, 4-pentynyl, and the like.

According to the present invention and unless otherwise provided, any of the above R1, R2, R3, R4, R5, R6, R7, R8, R9, R10, R11 and R12 group may be optionally substituted, in any of their free positions, by one or more groups, for instance 1 to 6 groups, independently selected from: halogen atom, nitro, oxo (=O), cyano, $C_1$-$C_6$ alkyl, polyfluorinated alkyl, polyfluorinated alkoxy, alkenyl, alkynyl, hydroxyalkyl, hydroxyalkylamino, hydroxyheterocyclyl, aryl, arylalkyl, heteroaryl, heteroaryl-alkyl, heterocyclyl, heterocyclyl-alkyl, $C_3$-$C_7$ cycloalkyl, cycloalky-alkyl, alkyl-aryl, alkyl-heteroaryl, alkyl-heterocyclyl, alkyl-cycloalkyl, alkyl-aryl-alkyl, alkyl-heteroaryl-alkyl, alkyl-heterocyclyl-alkyl, alkyl-cycloalkyl-alkyl, alkyl-heterocyclyl-heterocyclyl, heterocyclyl-heterocyclyl, heterocyclyl-alkyl-heterocyclyl, heterocyclyl-alkylamino, alkyl-heterocyclyl-alkylamino, hydroxy, alkoxy, aryloxy, heterocyclyloxy, alkyl-heterocyclyoxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, amino-alkylamino, dialkylamino, dialkylamino-heterocyclyl, dialkylamino-alkylamino, arylamino, arylalkylamino, diarylamino, heterocyclylamino, alkyl-heterocyclylamino, alkyl-heterocyclylcarbonyl, formylamino, alkylcarbonylamino, arylcarbonylamino, heterocyclylcarbonylamino, alkyl-heterocyclylcarbonylamino, aminocarbonyl, alkylaminocarbonyl, dialkylaminocarbonyl, arylaminocarbonyl, heterocyclylaminocarbonyl, alkoxycarbonylamino, alkoxycarbonylamino-alkylamino, alkoxycarbonylheterocyclyl-alkylamino, alkoxy-aryl-alkyl, hydroxylamino-carbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, with the term "halogen atom" we intend a fluorine, chlorine, bromine or iodine atom.

With the term "cyano" we intend a —CN residue.

With the term "nitro" we intend a —NO$_2$ group.

With the term "polyfluorinated alkyl or alkoxy" we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term "alkoxy", "cyclyloxy", "aryloxy", "heterocyclyloxy" and derivatives thereof we intend any of the above $C_1$-$C_6$ alkyl, $C_3$-$C_7$ cycloalkyl, aryl or heterocyclyl groups linked to the rest of the molecule through an oxygen atom (—O—).

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

Preferably, a compound of the formula (I) is characterized in that Ring W is a substituted pyrrole of the formula (Ia), (Ib) or (Id):

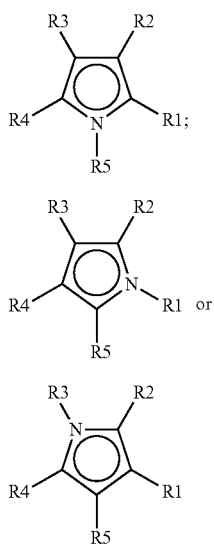

wherein R1, R2, R3, R4 and R5 are as defined above.

More preferably, a compound of the formula (I) is characterized in that R1 is optionally substituted aryl and W, R2, R3, R4 and R5 are as defined above.

Another more preferably compound of the formula (I) is characterized in that R1 is optionally substituted heteroaryl and W, R2, R3, R4 and R5 are as defined above.

Even more preferably, a compound of the formula (I) is characterized in that R2 is CN, and W, R1, R3, R4 and R5 are as defined above.

Another even more preferably compound of the formula (I) is characterized in that R2 is CONR6R7 and W, R1, R3, R4, R5, R6 and R7 are as defined above.

Most preferably, a compound of the formula (I) is characterized in that R3 is hydrogen and W, R1, R2, R4 and R5 are as defined above.

Another most preferably compound of the formula (I) is characterized in that R5 is hydrogen and W, R1, R2, R3 and R4 are as defined above.

Specific, not limiting, preferred compounds (cmpds.) of the invention, whenever appropriate in the form of pharmaceutically acceptable salts, are the following:

5-(6-Aminopyrimidin-4-yl)-2-(5-chloro-2-ethylphenyl)-1H-pyrrole-3-carbonitrile (compd 9);

1-(5-Chloro-2-methylphenyl)-4-(7H-pyrrolo[2,3-d]pyrimidin-4-yl)-1H-pyrrole-2-carbonitrile (compd 63);

1-(5-Chloro-2-ethylphenyl)-4-(7H-pyrrolo[2,3-d]pyrimidin-4-yl)-1H-pyrrole-2-carbonitrile (compd 68);

1-[2-Chloro-5-(trifluoromethyl)phenyl]-4-(7H-pyrrolo[2,3-d]pyrimidin-4-yl)-1H-pyrrole-2-carbonitrile (compd 72);

3-(5-Chloro-2-methylphenyl)-5-(7H-pyrrolo[2,3-d]pyrimidin-4-yl)-1H-pyrrole-2-carboxamide (compd 123);

3-(5-Chloro-2-ethylphenyl)-5-(7H-pyrrolo[2,3-d]pyrimidin-4-yl)-1H-pyrrole-2-carboxamide (compd 124);

3-[2-Ethyl-5-(trifluoromethyl)phenyl]-5-(7H-pyrrolo[2,3-d]pyrimidin-4-yl)-1H-pyrrole-2-carboxamide (compd 125);

3-(5-Chloro-2-methylphenyl)-N-methyl-5-(7H-pyrrolo[2,3-d]pyrimidin-4-yl)-1-pyrrole-2-carboxamide (compd 129);

3-(5-Chloro-2-ethylphenyl)-N-methyl-5-(7H-pyrrolo[2,3-d]pyrimidin-4-yl)-1H-pyrrole-2-carboxamide (compd 130);

3-[2-Ethyl-5-(trifluoromethyl)phenyl]-N-methyl-5-(7H-pyrrolo[2,3-d]pyrimidin-4-yl)-1H-pyrrole-2-carboxamide (compd 131);

5-(6-Aminopyrimidin-4-yl)-2-(5-chloro-2-methylphenyl)-1H-pyrrole-3-carboxamide (compd 189);

2-(5-Chloro-2-methylphenyl)-5-[6-(methylamino)pyrimidin-4-yl]-1H-pyrrole-3-carboxamide (compd 190);

2-(5-Chloro-2-methylphenyl)-5-(7H-pyrrolo[2,3-d]pyrimidin-4-yl)-1H-pyrrole-3-carboxamide (compd 191);

2-(5-Chloro-2-methylphenyl)-5-(1H-pyrrolo[2,3-b]pyridin-4-yl)-1H-pyrrole-3-carboxamide (compd 192);

5-(6-Aminopyrimidin-4-yl)-2-(5-chloro-2-ethylphenyl)-1H-pyrrole-3-carboxamide (compd 197);

2-(5-Chloro-2-ethylphenyl)-5-[6-(methylamino)pyrimidin-4-yl]-1H-pyrrole-3-carboxamide (compd 198);

2-(5-Chloro-2-ethylphenyl)-5-(7H-pyrrolo[2,3-d]pyrimidin-4-yl)-1H-pyrrole-3-carboxamide (compd 199);

5-(6-Aminopyrimidin-4-yl)-2-[2-chloro-5-(trifluoromethyl)phenyl]-1H-pyrrole-3-carboxamide (compd 204);

2-[2-chloro-5-(trifluoromethyl)phenyl]-5-[6-(methylamino)pyrimidin-4-yl]-1H-pyrrole-3-carboxamide (compd 205);

2-[2-Chloro-5-(trifluoromethyl)phenyl]-5-(7H-pyrrolo[2,3-d]pyrimidin-4-yl)-1H-pyrrole-3-carboxamide (compd 206);

5-(6-Aminopyrimidin-4-yl)-2-[2-methyl-5-(trifluoromethyl)phenyl]-1H-pyrrole-3-carboxamide (compd 211);

5-[6-(Methylamino)pyrimidin-4-yl]-2-[2-methyl-5-(trifluoromethyl)phenyl]-1H-pyrrole-3-carboxamide (compd 212):

2-[2-Methyl-5-(trifluoromethyl)phenyl]-5-7H-pyrrolo[2,3-]pyrimidin-4-yl)-1H-pyrrole-3-carboxamide (compd 213);

5-(6-Aminopyrimidin-4-yl)-2-[2-ethyl-5-(trifluoromethyl)phenyl]-1H-pyrrole-3-carboxamide (compd 218);

2-[2-Ethyl-5-(trifluoromethyl)phenyl]-5-[6-(methylamino)pyrimidin-4-yl]-1H-pyrrole-3-carboxamide (compd 219);

2-[2-Ethyl-5-(trifluoromethyl)phenyl]-5-(7H-pyrrolo[2,3-d]pyrimidin-4-yl)-1H-pyrrole-3-carboxamide (compd 220);

1-(5-Chloro-2-methylphenyl)-4-(7H-pyrrolo[2,3-d]pyrimidin-4-yl)-1H-pyrrole-2-carboxamide (compd 229);

1-(5-Chloro-2-methylphenyl)-4-(6,7-dihydro-5H-pyrrolo[2,3-d]pyrimidin-4-yl)-1H-pyrrole-2-carboxamide (compd 234);

4-(6-Aminopyrimidin-4-yl)-1-(5-chloro-2-ethylphenyl)-1H-pyrrole-2-carboxamide (compd 235):

1-(5-Chloro-2-ethylphenyl)-4-[6-(methylamino)pyrimidin-4-yl]-1H-pyrrole-2-carboxamide (compd 236);

1-(5-Chloro-2-ethylphenyl)-4-(7H-pyrrolo[2,3-d]pyrimidin-4-yl)-1H-pyrrole-2-carboxamide (compd 237);

1-(5-Chloro-2-ethylphenyl)-4-(pyrrolo[2,1-f][1,2,4]triazin-4-yl)-1H-pyrrole-2-carboxamide (compd 240);

1-(5-Chloro-2-ethylphenyl)-4-(6,7-dihydro-5H-pyrrolo[2,3-d]pyrimidin-4-yl)-1H-pyrrole-2-carboxamide (compd 241);

1-[2-Chloro-5-(trifluoromethyl)phenyl]-4-(7H-pyrrolo[2,3-d]pyrimidin-4-yl)-1H-pyrrole-2-carboxamide (compd 244);

1-[2-Chloro-5-(trifluoromethyl)phenyl]-4-(9H-purin-6-yl)-1H-pyrrole-2-carboxamide (compd 245);

1-[2-Chloro-5-(trifluoromethyl)phenyl]-4-(1H-pyrazolo[3,4-d]pyrimidin-4-yl)-1H-pyrrole-2-carboxamide (compd 246);

4-(6-Aminopyrimidin-4-yl)-1-[2-ethyl-5-(trifluoromethyl)phenyl]-1H-pyrrole-2-carboxamide (compd 256);

4-(5-Chloro-2-methylphenyl)-1-(7H-pyrrolo[2,3-d]pyrimidin-4-yl)-1H-pyrrole-3-carboxamide (compd 270);

5-(6-Aminopyrimidin-4-yl)-2-(5-chloro-2-ethylphenyl)-N-methyl-1H-pyrrole-3-carboxamide (compd 301);

2-(5-Chloro-2-ethylphenyl)-N-methyl-5-[6-(methylamino)pyrimidin-4-yl]-1H-pyrrole-3-carboxamide (compd 302);

2-(5-Chloro-2-ethylphenyl)-N-methyl-5-(7H-pyrrolo[2,3-d]pyrimidin-4-yl)-1H-pyrrole-3-carboxamide (compd 303);

2-[2-Methyl-5-(trifluoromethyl)phenyl]-N-methyl-5-(7H-pyrrolo[2,3-d]pyrimidin-4-yl)-1H-pyrrole-3-carboxamide (compd 318);

5-(6-Aminopyrimidin-4-yl)-2-[2-ethyl-5-(trifluoromethyl)phenyl]-N-methyl-1H-pyrrole-3-carboxamide (compd 321);

2-[2-Ethyl-5-(trifluoromethyl)phenyl]-N-methyl-5-[6-(methylamino)pyrimidin-4-yl]-1H-pyrrole-3-carboxamide (compd 322);

2-[2-Ethyl-5-(trifluoromethyl)phenyl]-N-methyl-5-(7H-pyrrolo[2,3-d]pyrimidin-4-yl)-1H-pyrrole-3-carboxamide (compd 323);

5-(6-Aminopyrimidin-4-yl)-2-(5-chloro-2-methylphenyl)-1-(2-hydroxyethyl)-1H-pyrrole-3-carboxamide (compd 331) and 5-(6-Aminopyrimidin-4-yl)-3-(5-chloro-2-methylphenyl)-1-(2-hydroxyethyl)-1H-pyrrole-2-carboxamide (compd 335).

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the at will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

The compounds of this invention can be prepared from readily available starting materials using the following general methods and procedures. Unless otherwise indicated, the starting materials are known compounds or may be prepared from known compounds according to well known procedures. It will be appreciated that, where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures. Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

A compound of formula (I) can be prepared according to the general synthetic processes described hereafter in Schemes A, B, C, D, E and F.

The reported Scheme A shows the preparation of a compound of formula (Ia) wherein R1, R3, R4 are as defined above, R2 is CN and R5 is hydrogen.

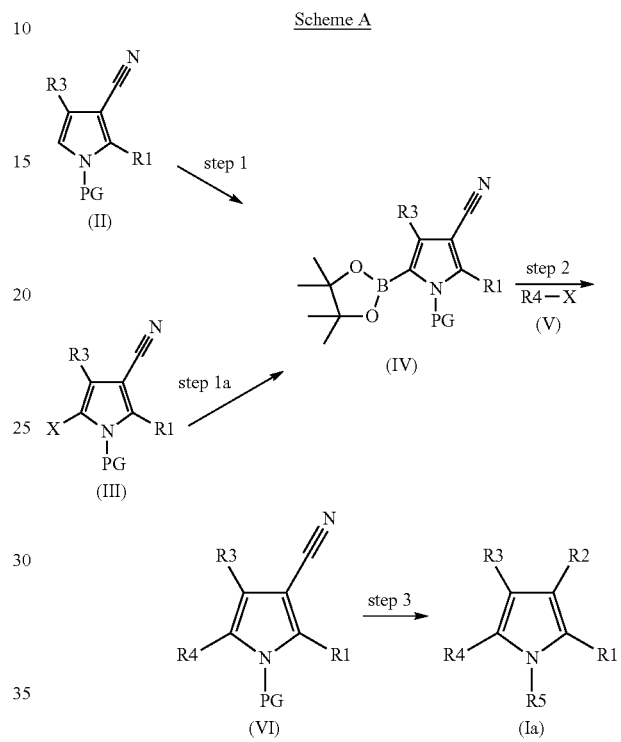

In the above Scheme R1, R3, R4 are as defined above, R2 is CN, R5 is hydrogen, X is halogen, and PG is a protecting group such as SEM, Boc or benzenesulfonyl.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, a process of the present invention comprises the following steps:

Step 1: Reaction of a Derivative of Formula (II)

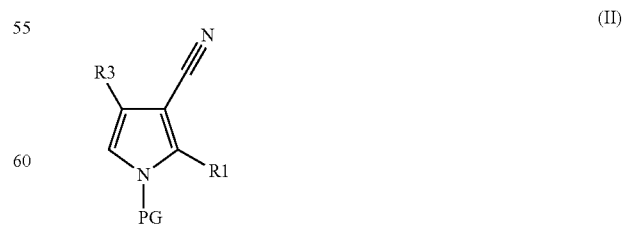

wherein R1 and R3 are as defined above and PG is a protecting group such as benzenesulfonyl with 2-isopropoxy-4,4,5,5-tetramethyl-1,3,2-dioxyborolane;

Alternatively:

Step 1a: Reaction of a Halo Derivative of Formula (III)

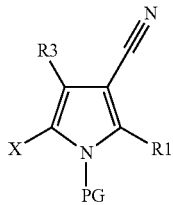

(III)

wherein R1, R3 are as defined above, X is halogen, and PG is a protecting group such as SEM, Boc, with 2-isopropoxy-4,4,5,5-tetramethyl-1,3,2-dioxyborolane;

Step 2: Metal-Catalyzed Coupling Reaction of the Resultant Compound of Formula (IV)

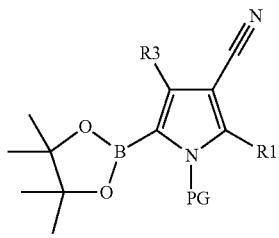

(IV)

wherein R1, R3 are as defined above and PG is a protecting group such as SEM, Boc, benzenesulfonyl with a halo derivative of formula (V)

R4-x  (V)

wherein R4 is as defined above and X is halogen;

Step 3: Deprotection of the Resultant Compound of Formula (VI)

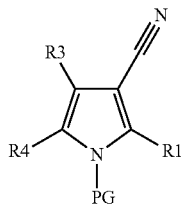

(VI)

wherein R1, R3, R4 are as defined above and PG is a protecting group such as SEM, Boc, benzenesulfonyl to give a compound of formula (Ia)

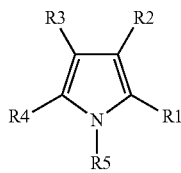

(Ia)

wherein R1, R3, R4 are as defined above, R2 is CN and R5 is hydrogen;

optionally converting a compound of the formula (Ia) into another different compound of the formula (Ia), and, if desired, converting a compound of the formula (Ia) into a pharmaceutically acceptable salt thereof or converting a salt into the free compound (Ia).

According to the Step 1 of Scheme A, the conversion of a compound of general formula (II) into a compound of formula (IV) can be accomplished by reaction with 2-isopropoxy-4,4,5,5-tetramethyl-1,3,2-dioxyborolane in the presence of lithium diisopropylamide in THF at −78° C.

According to the Step 1a of Scheme A, the conversion of a halo derivative of general formula (III) into a compound of formula (IV) can be accomplished by a subsequent halogen-lithium exchange and reaction with 2-isopropoxy-4,4,5,5-tetramethyl-1,3,2-dioxyborolane in THF at −78° C. (Q. Jiang, M. Ryan, P. Zhichkin, *J. Org. Chem.*, 2007, 72, 6618-6620).

According to the Step 2 of Scheme A, metal-catalyzed coupling reaction of a compound of formula (IV) with a halo derivative of general formula (V) to give a compound of formula (VI) can be accomplished in a variety of ways. Preferably, a compound of formula (VI) can be prepared from an intermediate of formula (IV) by Pd-catalyzed Suzuki-Miyaura coupling. Transition metal-catalyzed couplings of (hetero)aryl halides with (hetero)aryl boronic acids or boronic-esters are well known to the person skilled in the art, see references: a) Miyaura, Norio; Suzuki, Akira (1979). "Palladium-Catalyzed Cross-Coupling Reactions of Organoboron Compounds". *Chemical Reviews* 95 (7): 2457-2483; b) Suzuki, A. In Metal-Catalyzed Cross-Coupling Reactions, Diederich, F., and Stang, P. J., Eds.; Wiley-VCH: New York, 1998, pp. 49-97. In the so called Suzuki-Miyaura reaction, coupling reaction of (hetero)aryl boronic acids or boronic-esters with (hetero)aryl halides is typically triggered by palladium complex. Phosphine-palladium complexes such as tetrakis(triphenylphosphine)palladium(0) are used for this reaction but also bis(triphenylphosphine)palladium (II) chloride, [1,1'-bis(diphenylphosphino) ferrocene] dichloro palladium(II) may be employed. A base such as potassium phosphate, sodium carbonate, cesium carbonate, potassium carbonate, potassium t-butoxide, tetraethyl ammonium hydroxide, triethylamine is added and tetrahydrofurane, dioxane, N,N-dimethylformamide, ethanol and toluene may be used as reaction media. Typically temperatures range from room temperature to 150° C. Conventional heating along with microwave irradiation may be employed. Reaction duration ranges from about 30 min to about 96 hours. Various Pd-catalyst/base/solvent combinations have been described in the literature, which allow the fine-tuning of the reaction conditions in order to allow for a broad set of additional functional groups on both coupling partners.

According to the Step 3 of Scheme A, the removal of the protecting group PG on the pyrrole ring of a compound of formula (VI) may be carried out following procedures which are well known in the art (Jolicoeur, B.; Chapman, E. E.; Thommpson, A.; Lubell, W. D. *Tetrahedron* 2006, 62, 11531). Depending on the protecting group of choice, the following conditions may be employed: tert-butoxycarbonyl (Boc) may be removed in the presence of TFA in DCM or by Na$_2$CO$_3$ in DME, DMF at a temperature ranging from room temperature to 130° C.; 2-(trimethylsilyl)ethoxymethyl (SEM) and triisopropylsilyl (TIPS) may be removed with TBAF, HF.Py or TFA in solvents such as THF, DCM at room temperature or below; benzenesulfonyl (Bs) and toluensulfonyl (Ts) groups may be removed with KOH, NaOH, K$_2$CO$_3$, LiOH, Triton B, magnesium also in the presence of ammonium chloride in solvents such as methanol, tetrahydrofurane, dioxane at temperatures ranging from room temperature to reflux; trimethylsilylethylsulfonyl (SES) group may be removed using TBAF in THF at room temperature; 4-methoxy-benzyl (MB) and 2,4-dimethoxybenzyl (DMB) groups may be removed by exposure to acid in the presence of anisole to trap the benzyl carbonium ion (e.g. 5% $H_2SO_4$, TFA, anisole).

The present invention further provides an alternative process for the preparation of a compound of formula (Ia) wherein R2 is CONR6R7, R5 is hydrogen and R1, R3, R4, R6 and R7 are as defined above.

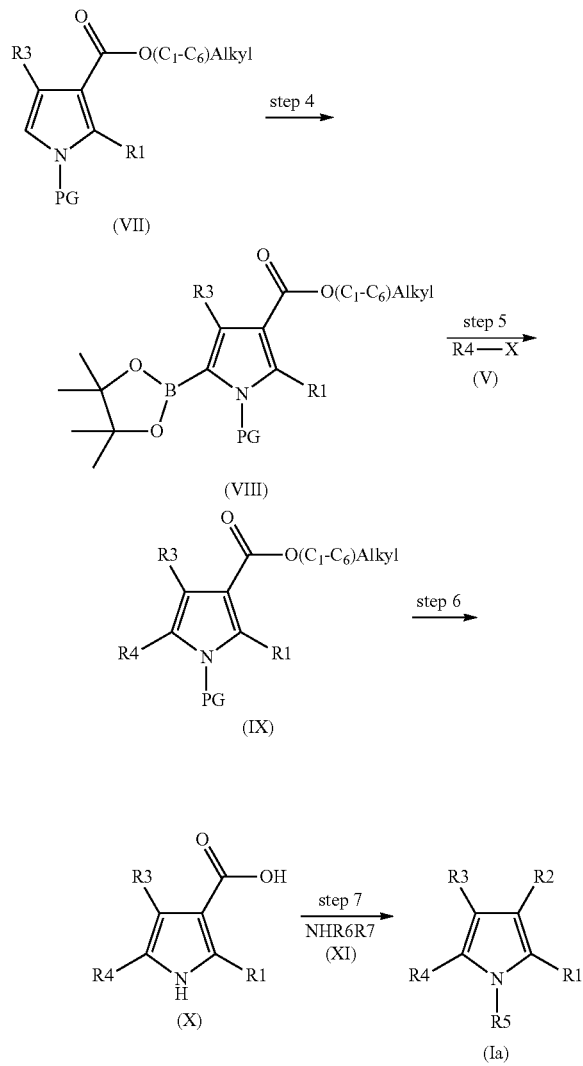

In the above Scheme R2 is CONR6R7, R5 is hydrogen, R1, R3, R4, R6 and R7 are as defined above, X is halogen and PG is a protecting group such as benzenesulfonyl.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, a process of the present invention comprises the following steps:

Step 4: Reaction of a Derivative of Formula (VII)

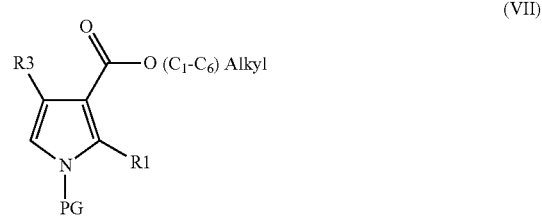

wherein R1 and R3 are as defined above and PG is a protecting group such as benzenesulfonyl with 2-isopropoxy-4,4,5,5-tetramethyl-1,3,2-dioxyborolane;

Step 5: Metal-Catalyzed Coupling Reaction of the Resultant Compound of Formula (VIII)

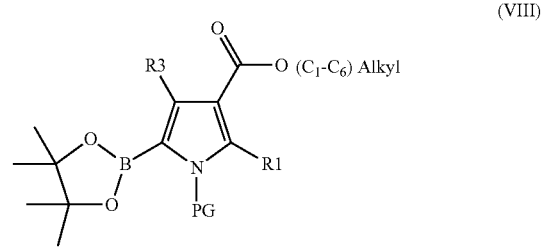

wherein R1 and R3 are as defined above and PG is a protecting group such as benzenesulfonyl with a halo derivative of formula (V), as defined above;

Step 6: Hydrolysis Under Basic Conditions of the Resultant Carboxylic Ester of Formula (IX)

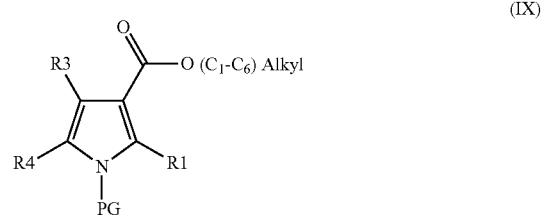

wherein R1, R3, R4 and PG are as defined above;
Step 7: Amidation of the Resultant Carboxylic Acid of Formula (X)

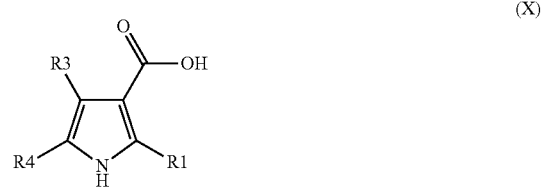

wherein R1, R3 and R4 are as defined above, through reaction with an amine derivative of formula (XI) NHR6R7 (XI)

wherein R6 and R7 are as defined above, to give a compound of formula (Ia)

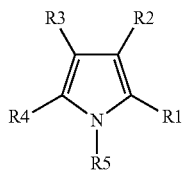
(Ia)

wherein R2 is CONR6R7, R5 is hydrogen, R1, R3, R4, R6 and R7 are as defined above;
optionally converting a compound of the formula (Ia) into another different compound of the formula (Ia), and, if desired, converting a compound of the formula (Ia) into a pharmaceutically acceptable salt thereof or converting a salt into the free compound (Ia).

According to the Step 4 of Scheme B, the conversion of a compound of general formula (VII) into a compound of formula (VIII) can be accomplished by reaction already described in Step 1 of Scheme A.

According to the Step 5 of Scheme B, metal-catalyzed coupling reaction of a compound of formula (VIII) with a halo derivative of general formula (V) to give a compound of formula (IX) can be accomplished in a variety of ways already described in Step 2 of Scheme A.

According to the Step 6 of Scheme B, hydrolysis of the resultant carboxylic ester of formula (IX) into the carboxylic acid of formula (X) can be accomplished in a variety of ways. Typically LiOH.H$_2$O in THF or NaOH or KOH in alcoholic solution is used, at a temperature ranging from room temperature to 150° C., for a time ranging from about 30 min to about 96 hours. Conventional heating along with microwave irradiation may be employed. In the mean time removal of benzenesulfonyl-protecting group occurs.

According to the Step 7 of Scheme B, the conversion of a carboxylic acid of formula (X) into a carboxamide of formula (Ia) can be accomplished in a variety of ways and experimental conditions, which are widely known in the art for the preparation of carboxamides. As an example, a compound of formula (X) can be converted into its corresponding acyl chloride in the presence of thionyl chloride or oxalyl chloride, in a suitable solvent, such as toluene, dichloromethane, chloroform, diethyl ether, tetrahydrofuran, dioxane, at a temperature ranging from about −10° C. to reflux and for a period of time varying from about 1 hour to about 96 hours. The acyl chloride can be isolated by evaporation of the solvent and further reacted with 33% ammonium hydroxide solution or with an amine NHR6R7 (XI) in a suitable solvent, such as toluene, dichloromethane, chloroform, diethyl ether, tetrahydrofuran, dioxane, at a temperature ranging from about −10° C. to reflux and for a period of time varying from about 1 hour to about 96 hours. Alternatively, a compound of formula (X) can be reacted with the ammonium salt of 1-hydroxybenzotriazole or with an amine NHR6R7 (XI) in the presence of a carbodiimide such as dicyclohexyl carbodiimide, diisopropyl carbodiimide, 1-ethyl-3-(3'-dimethylamino)carbodiimide hydrochloric acid salt and hydroxybenzotriazole. Preferably, this reaction is carried out in a suitable solvent such as, for instance, tetrahydrofuran, dichloromethane, toluene, dioxane, N,N-dimethylformamide and in the presence of a proton scavenger such as, for example, triethylamine, N,N-diisopropylethylamine, at a temperature ranging from room temperature to reflux, for a time ranging from about 30 min to about 96 hours.

The reported Scheme C shows the preparation of a compound of formula (Ib) wherein R1, R3, R4 and R5 are as defined above and R2 is CN.

Scheme C

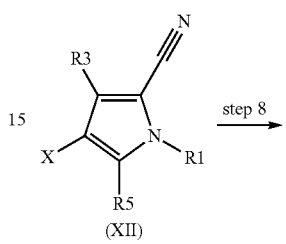

In the above Scheme R1, R3, R4 and R5 are as defined above, X is halogen and R2 is CN.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, a process of the present invention comprises the following steps:

Step 8: Reaction of a Halo Derivative of Formula (XII)

(XII)

wherein R1, R3 and R5 are as defined above and X is halogen with 2-isopropoxy-4,4,5,5-tetramethyl-1,3,2-dioxyborolane;

Step 9: Metal-Catalyzed Coupling Reaction of the Resultant Compound of Formula (XIII)

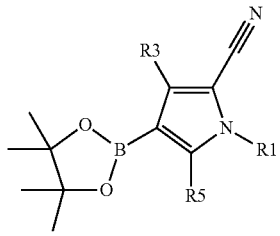

(XIII)

wherein R1, R3 and R5 are as defined above, with a halo derivative of formula (V), as defined above, to give a compound of formula (Ib)

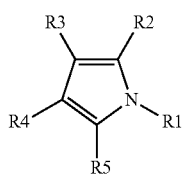

(Ib)

wherein R1, R3, R4 and R5 are as defined above and R2 is CN;

optionally converting a compound of the formula (Ib) into another different compound of the formula (Ib), and, if desired, converting a compound of the formula (Ib) into a pharmaceutically acceptable salt thereof or converting a salt into the free compound (Ib).

According to the Step 8 of Scheme C, the conversion of a halo derivative of general formula (XII) into a compound of formula (XIII) may be carried out under the condition already described in Step 1a of Scheme A.

According to the Step 9 of Scheme C, metal-catalyzed coupling reaction of a compound of formula (XIII) with a halo derivative of general formula (V) to give a compound of formula (Ib) can be accomplished in a variety of ways already described in Step 2 of Scheme A.

The reported Scheme D shows the preparation of a compound of formula (Ic) wherein R1, R3, R4 and R5 are as defined above and R2 is CN.

Scheme D

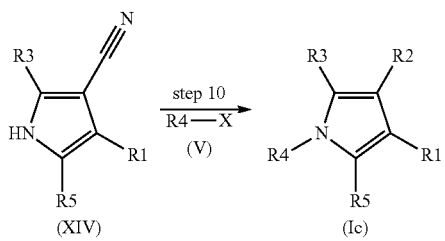

In the above Scheme R1, R3, R4 and R5 are as defined above, X is halogen and R2 is CN.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, a process of the present invention comprises the following step:

Step 10: Reaction of a Derivative of Formula (XIV)

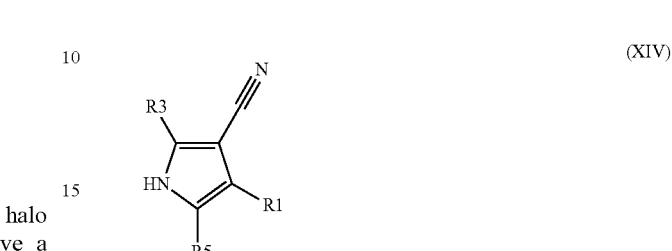

(XIV)

wherein R1, R3 and R5 are as defined above, with a halo derivative of formula (V), as defined above, in the presence of a base or metal-catalyzed to give a compound of formula (Ic)

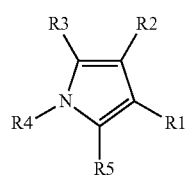

(Ic)

wherein R1, R3, R4 and R5 are as defined above and R2 is CN;

optionally converting a compound of the formula (Ic) into another different compound of the formula (Ic), and, if desired, converting a compound of the formula (Ic) into a pharmaceutically acceptable salt thereof or converting a salt into the free compound (Ic).

According to the Step 10 of Scheme D, the reaction of a compound of formula (XIV) with a halo derivative of general formula (V) to give a compound of formula (Ic) may be carried out in the presence of a base such as sodium hydride and tetrahydrofurane or dioxane may be used as reaction media. Typically temperatures range from 5° C. to reflux. Reaction duration ranges from about 30 min to about 24 hours. Alternately, metal-catalyzed coupling reaction of a compound of formula (XIV) with a halo derivative of general formula (V) to give a compound of formula (Ic) can be accomplished in the presence of tris(dibenzylideneacetone)dipalladium and tri-tert-butylphosphine. A base such as sodium carbonate, cesium carbonate, potassium carbonate is added and tetrahydrofurane, dioxane, N,N-dimethylformamide and toluene may be used as reaction media. Typically temperatures range from room temperature to 150° C. Conventional heating along with microwave irradiation may be employed. Reaction duration ranges from about 30 min to about 24 hours.

The reported Scheme E shows the preparation of a compound of formula (Id) wherein R2 is CONR6R7, R3 is hydrogen and R1, R4, R5, R6 and R7 are as defined above.

Scheme E

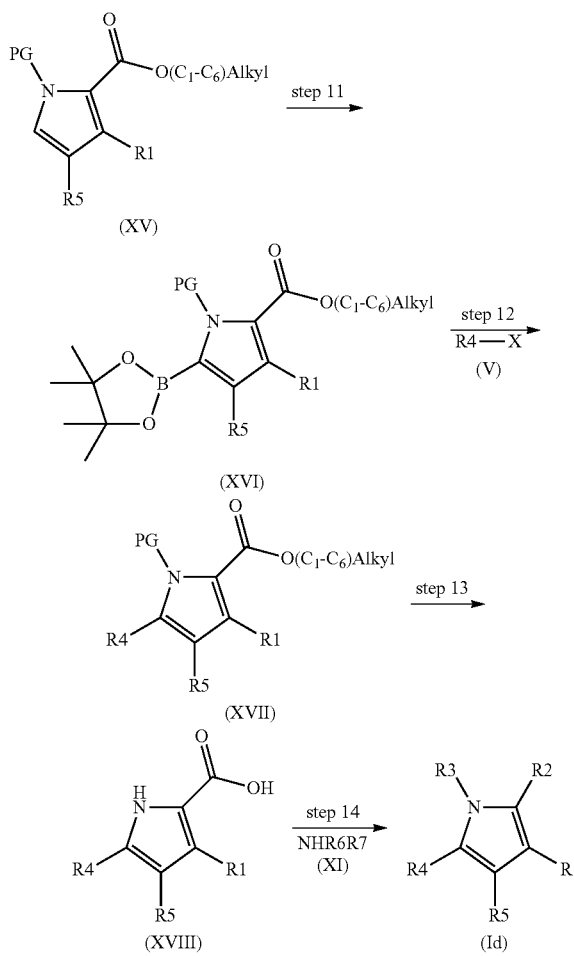

In the above Scheme R2 is CONR6R7, R3 is hydrogen, R1, R4, R5, R6 and R7 are as defined above, X is halogen and PG is a protecting group such as benzenesulfonyl.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, a process of the present invention comprises the following steps:

Step 11: Reaction of a Derivative of Formula (XV)

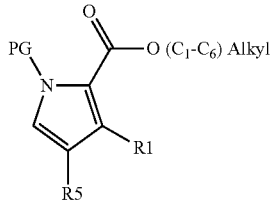
(XV)

wherein R1 and R5 are as defined above and PG is a protecting group such as benzenesulfonyl with 2-isopropoxy-4,4,5,5-tetramethyl-1,3,2-dioxyborolane;

Step 12: Metal-Catalyzed Coupling Reaction of the Resultant Compound of Formula (XVI)

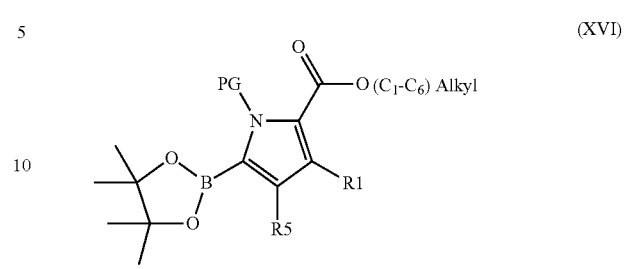

wherein R1 and R5 are as defined above and PG is a protecting group such as benzenesulfonyl with a halo derivative of formula (V), as defined above;

Step 13: Hydrolysis Under Basic Conditions of the Resultant Carboxylic Ester of Formula (XVII)

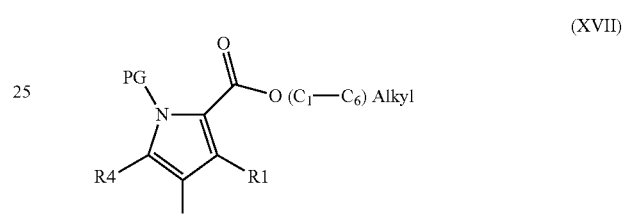

wherein R1, R4 and R5 are as defined above and PG is a protecting group;

Step 14: Amidation of the Resultant Carboxylic Acid of Formula (XVIII)

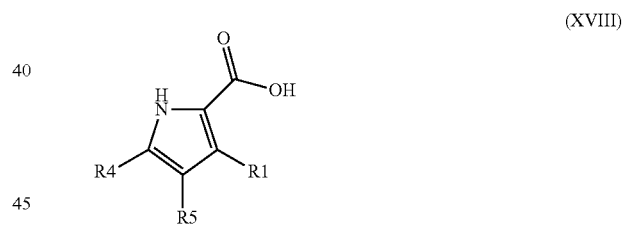

wherein R1, R4 and R5 are as defined above, through reaction with an amine derivative of formula (XI), as defined above, to give a compound of formula (Id)

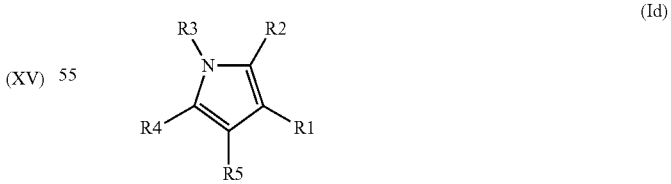

wherein R1, R4, R5, R6 and R7 are as defined above and R3 is hydrogen;

optionally converting a compound of the formula (Id) into another different compound of the formula (Id), and, if desired, converting a compound of the formula (Id) into a pharmaceutically acceptable salt thereof or converting a salt into the free compound (Id).

According to the Step 11 of Scheme E, the conversion of a compound of general formula (XV) into a compound of formula (XVI) can be accomplished by reaction already described in Step 1 of Scheme A.

According to the Step 12 of Scheme E, metal-catalyzed coupling reaction of a compound of formula (XVI) with a halo derivative of general formula (V) to give a compound of formula (XVII) can be accomplished in a variety of ways already described in Step 2 of Scheme A.

According to the Step 13 of Scheme E, hydrolysis of the resultant carboxylic ester of formula (XVII) into the carboxylic acid of formula (XVIII) can be accomplished by reaction already described in Step 6 of Scheme B.

According to the Step 14 of Scheme E, the conversion of a carboxylic acid of formula (XVIII) into a carboxamide of formula (Id) can be accomplished in a variety of ways and experimental conditions, already described in Step 7 of Scheme B.

The reported Scheme F shows the preparation of a compound of formula (Ie) wherein R2 is CONR6R7 and R1, R3, R4, R5, R6 and R7 are as defined above.

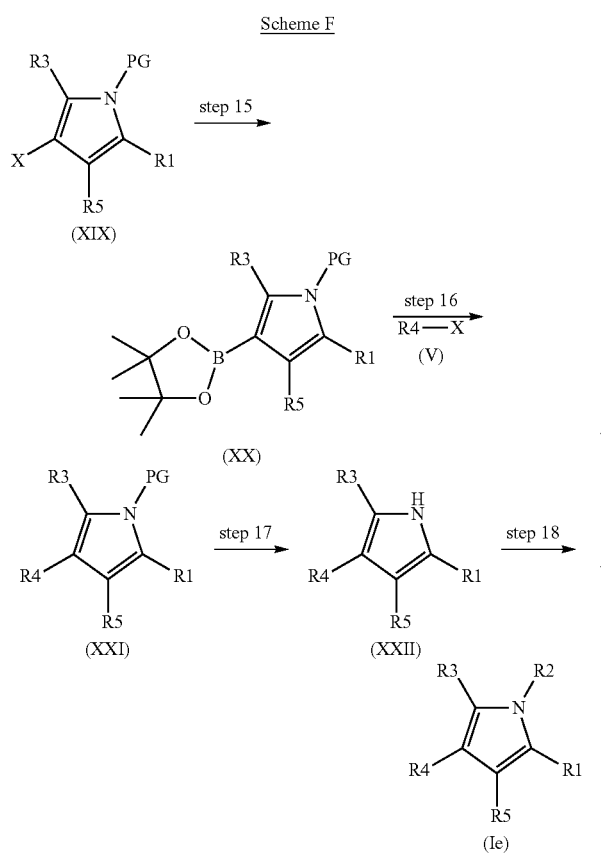

In the above Scheme R1, R3, R4 and R5 are as defined above, R2 is CONR6R7 wherein R6 and R7 are as defined above, X is halogen and PG is a protecting group such as Boc.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, a process of the present invention comprises the following steps:

Step 15: Reaction of a Halo Derivative of Formula (XIX)

wherein R1, R3 and R5 are as defined above, PG is a protecting group such as Boc and X is halogen with 2-isopropoxy-4,4,5,5-tetramethyl-1,3,2-dioxyborolane;

Step 16: Metal-Catalyzed Coupling Reaction of the Resultant Compound of Formula (XX)

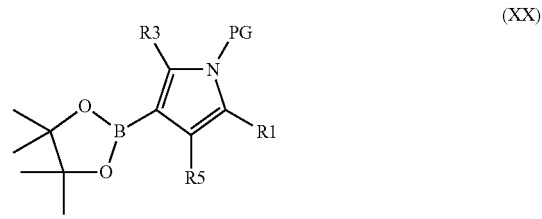

wherein R1, R3 and R5 are as defined above and PG is a protecting group such as Boc, with a halo derivative of formula (V), as defined above;

Step 17: Deprotection of the Resultant Compound of Formula (XXI)

wherein R1, R3, R4 and R5 are as defined above and PG is a protecting group such as Boc;

Step 18: Reaction of the Resultant Compound of Formula (XXII)

wherein R1, R3, R4 and R5 are as defined above, with an amine derivative of formula (XI), as defined above, in the presence of triphosgene, to give a compound of formula (Ie)

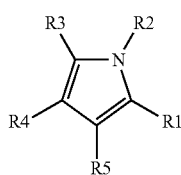

(Ie)

wherein R2 is CONR6R7 and R1, R3, R4, R5, R6 and R7 are as defined above;
optionally converting a compound of the formula (Ie) into another different compound of the formula (Ie), and, if desired, converting a compound of the formula (Ie) into a pharmaceutically acceptable salt thereof or converting a salt into the free compound (Ie).

According to the Step 15 of Scheme F, the conversion of a halo derivative of general formula (XIX) into a compound of formula (XX) may be carried out under the condition already described in Step 1a of Scheme A.

According to the Step 16 of Scheme F, metal-catalyzed coupling reaction of a compound of formula (XX) with a halo derivative of general formula (V) to give a compound of formula (XXI) can be accomplished in a variety of ways already described in Step 2 of Scheme A.

According to the Step 17 of Scheme F, deprotection of the compound of formula (XXI) to give a compound of formula (XXII) may be carried out under the condition already described in Step 3 of Scheme A.

According to Step 18 of the Scheme F, the compound of formula (XXII) is reacted with an amine of formula (XI) in the presence of triphosgene to give a compound of formula (Ie), The reaction is carried out in a suitable halogenated hydrocarbon, preferably dichloromethane, and in the presence of a suitable amine such as diisopropylethylamine or triethylamine at room temperature.

As indicated above, a compound of the formula (I), which is prepared according to the processes object of the invention, can be conveniently converted into another compound of the formula (I) by operating according to well-known synthetic conditions, the following being examples of possible conversions:

conv.1) converting a compound of the formula (I), wherein R2 is CN, into the corresponding compound of formula (I), wherein R2 is CONH$_2$, by hydrolising in acidic conditions,

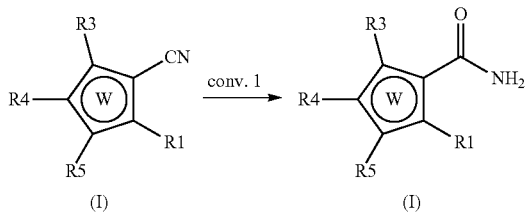

preferably performed in glacial acetic acid or trifluoroacetic acid and concentrated sulfuric acid, more preferably in ratios between 1 to 1 and 5 to 1, optionally in the presence of water, at a temperature between room temperature and 120° C., in particular at a temperature from 60° C. to 90° C.

conv.2) converting a compound of the formula (I), wherein R2 is CONH$_2$, into the corresponding compound of formula (I), wherein R2 is CONR6R7 wherein R6 and R7 are as defined above but not both hydrogen;

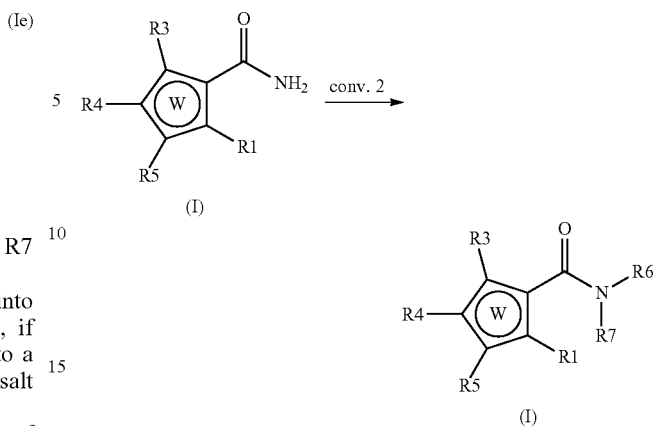

by hexaustive tert-butoxycarbonylation of a compound of the formula (I), treatment with an amine derivative of formula (XXIII)

NHR6R7    (XXIII)

wherein R6 and R7 are as defined above but not both hydrogen and deprotection of tert-butoxycarbonyl protecting groups (Mild conversion of primary carboxamides to substituted amides (S. K. Davidsen et al. *J. Org. Chem.* 1991, 56, 5482-5485).

conv.3) converting a compound of the formula (Ia), wherein R5 is hydrogen or (Id) wherein R3 is hydrogen, into the corresponding compound of formula (Ia) or (Id), wherein R5 or R3 respectively is an optionally substituted group selected from straight or branched C$_1$-C$_6$ alkyl, C$_3$-C$_7$ cycloalkyl, cycloalkyl-alkyl, heterocyclyl and heterocyclyl-alkyl,

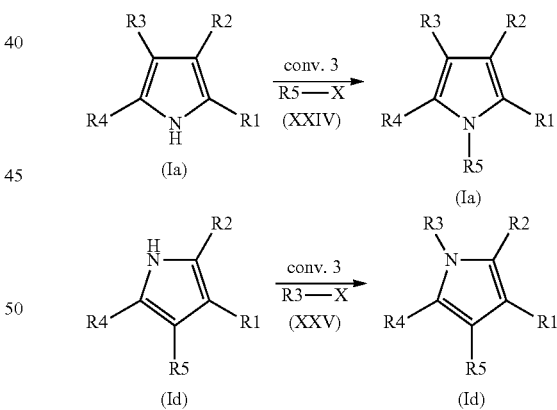

by treatment with optionally substituted alkyl halide of the formula R5-X (XXIV) or R3-X (XXV), wherein R5 or R3 is as defined above and X is halogen, in a solvent such as N,N-dimethylformamide and in the presence of a base at a temperature ranging from room temperature to reflux from about 30 min to about 96 hours.

From all of the above it is clear to the skilled person that any compound of the formula (I) bearing a functional group which can be further derivatized to another functional group, by working according to methods well known in the art thus leading to other compounds of the formula (I), is intended to be comprised within the scope of the present invention.

Needless to say, also any of the intermediates of the above described processes could be converted into a different intermediate, if wanted and necessary, by operating in an analogous way as in any one of the conversion reaction here above described.

From all of the above, it is clear to the skilled person that when preparing the compounds of the formula (I) according to any one of the aforementioned process variants, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of the formula (I) prepared according to the process described above are obtained as mixture of isomers, their separation using conventional techniques into the single isomers of the formula (I), is within the scope of the present invention.

The final compounds may be isolated and purified using conventional procedures, for example chromatography and/or crystallization and salt formation.

The compounds of the formula (I) as defined above can be converted into pharmaceutically acceptable salts. The compounds of the formula (I) as defined above, or the pharmaceutically acceptable salts thereof, can be subsequently formulated with a pharmaceutically acceptable carrier or diluent to provide a pharmaceutical composition.

The synthesis of a compound of formula (I), according to the synthetic process described above, can be conducted in a stepwise manner, whereby each intermediate is isolated and purified by standard purification techniques, like, for example, column chromatography, before carrying out the subsequent reaction.

Alternatively, two or more steps of the synthetic sequence can be carried out in a so-called "one-pot" procedure, as known in the art, whereby only the compound resultant from the two or more steps is isolated and purified.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wien, Samuel H., —*Enantiomers, Racemates, and Resolutions*, John Wiley & Sons Inc., New York (N.Y.), 1981.

According to any variant of the process for preparing the compounds of the formula (I), the starting materials and any other reactants are known or easily prepared according to known methods or as described in the experimental part below.

For example, the compounds of the formula (II) can be prepared as described in the experimental part, Preparation D; the compounds of the formula (III) can be prepared as described in the experimental part, Preparation C; the compounds of the formula (VII) can be prepared as described in the experimental part, Preparation E and O; the compounds of the formula (XII) can be prepared as described in the experimental part, Preparation H; the compounds of the formula (XIV) can be prepared as described in the experimental part, Preparation K; the compounds of the formula (XV) can be prepared as described in the experimental part, Preparation L; the compounds of the formula (XIX) can be prepared as described in the experimental part, Preparation M; the compounds of the formula (V) are either commercially available or can be prepared with known methods or can be prepared as described in the experimental part, Preparation N; the compounds of the formula (XI) are commercially available.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of the formula (I) may be used sequentially with known anticancer agents when a combination formulation is inappropriate.

The compounds of the formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of the formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of the formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

General Purification and Analytical Methods

Thin-layer chromatography was performed on Merck silica gel 60 $F_{254}$ pre-coated plates. Column chromatography was conducted either under medium pressure on silica (Merck silica gel 40-63 µm) or performed by using a Biotage SP1 Flash Purification system with prepacked silica gel cartridges (Biotage or Varian). Components were visualized by UV light (X: 254 nm) and by iodine vapor. When necessary, compounds were purified by preparative HPLC on a Waters Symmetry C18 (19×50 mm, 5 µm) column or on a Waters X Terra RP 18 (30×150 mm, 5 µm) column using a Waters preparative HPLC 600 equipped with a 996 Waters PDA detector and a Micromass mod. ZMD single quadrupole mass spectrometer, electron spray ionization, positive mode. Method 1: Phase A 0.1% TFA/ACN 95/5; phase B: ACN/$H_2O$ 9515. Gradient from 10 to 90% B in 8 min, hold 90% B 2 min; flow rate 20 mL/min. Method 2: Phase A: 0.05% $NH_4OH$/ACN 9515; Phase B: ACN/$H_2O$ 9515. Gradient from 10 to 100% B in 8 min, hold 100% B 2 min. Flow rate 20 mL/min.

$^1$H-NMR spectra were recorded in DMSO-$d_6$ or $CDCl_3$ on a Varian Inova 400 spectrometer operating at 400.50 MHz for $^1$H and on a Varian Inova 500 spectrometer operating at 499.75 MHz. Residual solvent signal was used as reference (δ=2.50 or 7.27 ppm). Chemical shifts (δ) are reported in parts per million (ppm) and coupling constants (J) in Hz. The following abbreviations are used for multiplicities: s=singlet; br. s.=broad signal; d=doublet; t=triplet; m=multiplet; dd=doublet of doublets.

Electrospray (ESI) mass spectra were obtained on a Finnigan LCQ ion trap.

Unless otherwise specified, all final compounds were homogeneous (purity of not less than 95%), as determined by high-performance liquid chromatography (HPLC). HPLC-UV-MS analyses, used to assess compound purity, were carried out combining the ion trap MS instrument with HPLC system SSP4000 (Thermo Separation Products) equipped with an autosampler LC Pal (CTC Analytics) and UV6000LP diode array detector (UV detection 215-400 nm). Instrument control, data acquisition and processing were performed with the Xcalibur 1.2 software (Finnigan). HPLC chromatography was run at room temperature, and 1 mL/min flow rate, using a Waters X Terra RP 18 column (4.6×50 mm; 3.5 µm). Mobile phase A was ammonium acetate 5 mM buffer (pH 5.5 with acetic acid):acetonitrile 90:10, and mobile phase B was ammonium acetate 5 mM buffer (pH 5.5 with acetic acid):acetonitrile 10:90; the gradient was from 0 to 100% B in 7 minutes then hold 100% B for 2 minutes before requilibration.

ESI(+) high resolution mass spectra (HRMS) were obtained on a Waters Q-Tof Ultima directly connected with micro HPLC 1100 Agilent as previously described (Colombo, M.; Riccardi-Sirtori, F.; Rizzo, V.; *Rapid Commun. Mass Spectrom.* 2004, 18, 511-517).

In the examples below as well as throughout the application, the following abbreviations have the following meanings. If not defined, the terms have their generally accepted meanings.

ABBREVIATIONS

ACN acetonitrile
AcOH acetic acid
Boc tert-butyloxycarbonyl
n-BuLi n-butyllithium
$Cs_2CO_3$ cesium carbonate
CuCl copper(I) chloride
CuI copper(I) iodide
DCM dichloromethane
DIAD di-iso-propyl azadicarboxylate
DIPEA N,N-diisopropyethylamine
DMF N,N-dimethylformamide
DMSO dimethyl sulfoxide
eq equivalents
ESI electrospray ionization
EtOAc ethyl acetate
EDCl N-ethyl-N',N'-diisopropyl carbodiimide hydrochloride
$Et_2O$ diethyl ether
EtOH ethanol
g gram(s)
h hour(s)
HCl hydrochloric acid
HOBt 1-hydroxybenzotriazole
HOBLN$H_3$ 1H-benzotriazol-1-ol ammonium salt
HPLC high performance liquid chromatography
$K_2CO_3$ potassium carbonate
$K_3PO_4.3H_2O$ potassium phosphate trihydrate
KOH potassium hydroxide
$^t$BuOK potassium tert-butoxide
LDA lithium diisopropylamide
LiCl lithium chloride
LiHMDS lithium hexamethyldisilazide
LiOH.$H_2O$ lithium hydroxide monohydrate
M Molar
MeOH Methanol
MeN$H_2$ Methylamine
mg milligram(s)
min Minutes
µL microliter(s)
mL milliliter(s)
mmol millimole(s)
mol mol(s)

N Normal
NaCl sodium chloride
$Na_2CO_3$ sodium carbonate
$Na_2S_2O_3$ sodium thiosulfate
$Na_2SO_4$ sodium sulfate
NaH sodium hydride
$NaHCO_3$ sodium hydrogen carbonate
NaOH sodium hydroxide
NBS N-Bromosuccinimide
$NH_4Cl$ ammonium chloride
$NH_4OH$ ammonium hydroxide
$Pd(OAc)_2$ palladium(II)acetate
$Pd_2(dba)_3$ tris(dibenzylideneacetone)dipalladium(0)
$PdCl_2(PPh_3)_2$ bis(triphenylphosphine)-palladium(II) chloride
$PdCl_2(dppf)$ [1,1'-bis(diphenylphosphino)ferrocene] palladium(II)chloride
$Ph_3P$ Triphenylphosphine
SEM 2-(trimethylsilyl)ethoxymethyl
$SOCl_2$ thionyl chloride
TEA Triethylamine
TFA trifluoroacetic acid
THF Tetrahydrofurane Preparation A Methyl 2-chloro-5-(trifluoromethyl)benzoate

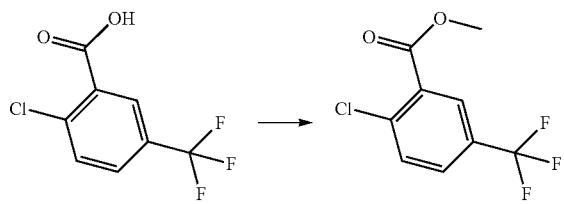

To a solution of 2-chloro-5-(trifluoromethyl)benzoic acid (8.96 g, 40 mmol) in MeOH (40 mL) sulfuric acid (96%, 4 mL) was added drop wise. The reaction mixture was refluxed for 4 h. The reaction mixture was cooled to room temperature, poured into saturated solution of $Na_2CO_3$ at 5° C. under stirring, and then extracted with EtOAc. The organic phase was washed with water, with aqueous brine, dried over $Na_2SO_4$, filtered and concentrated under reduced pressure to afford the title compound as an oil (8.79 g, 92%).

$^1$H NMR (400 MHz, DMSO-$d_6$) δ 8.15 (d, J=2.2 Hz, 1H), 7.97 (dd, J=2.2, 8.2 Hz, 1H), 7.85 (d, J=8.2 Hz, 1H), 3.90 (s, 3H).

According to this procedure, but starting from 2-methyl-5-(trifluoromethyl)benzoic acid, the following compound was prepared:

Methyl 2-methyl-5-(trifluoromethyl)benzoate $^1$H NMR (500 MHz, DMSO-$d_6$) δ 8.08 (s, 1H), 7.86 (dd, J=1.6, 7.9 Hz, 1H), 7.60 (d, J=7.9 Hz, 1H), 3.87 (s, 3H), 2.60 (s, 3H).

According to this procedure, but starting from 2-bromo-5-(trifluoromethyl)benzoic acid, the following compound was prepared:

Methyl 2-bromo-5-(trifluoromethyl)benzoate $^1$H NMR (400 MHz, DMSO-$d_6$) δ 8.10 (d, J=1.6 Hz, 1H), 8.02 (d, J=8.3 Hz, 1H), 7.85 (dd, J=2.1, 8.4 Hz, 1H), 3.89 (s, 3H).

Preparation B

Methyl 5-chloro-2-ethylbenzoate

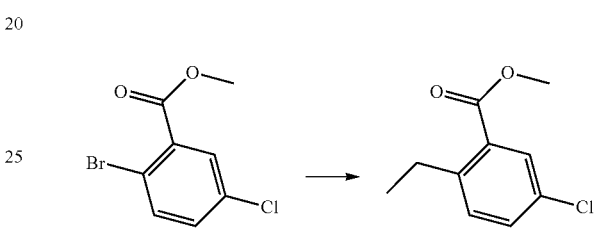

Into a 500 mL round bottom flask equipped with a stir bar, condenser and 3-way valve connected to argon and vacuum methyl 2-bromo-5-chlorobenzoate (15.0 g, 60 mmol), ethylboronic acid (5.3 g, 72 mmol), $K_3PO_4.3H_2O$ (48.0 g, 180 mmol), tricyclohexylphosphine (1.7 g, 6 mmol) and toluene (250 mL) and water (12 mL) were charged at room temperature. The resulting reaction mixture was degassed three times back filling with argon each time before being charged $Pd(OAc)_2$ (0.673 g, 3 mmol). The resulting reaction mixture was degassed four times back filling with argon each time and then warmed to 110° C. for 5 h. The reaction mixture was cooled to room temperature, filtered through a pad of Celite, washed with EtOAc and the filtrate was concentrated and then diluted with EtOAc (400 mL) and water (300 mL). The two layers were separated, and the aqueous layer was extracted with EtOAc (100 mL). The combined organic fractions were dried over $Na_2SO_4$, filtered and concentrated under reduced pressure. The residue was purified by flash chromatography (hexane/EtOAc 97/3) to afford the title compound (9.3 g, 78%).

$^1$H NMR (600 MHz, DMSO-$d_6$) δ 7.74 (d, J=2.4 Hz, 1H), 7.57 (dd, J=2.4, 8.4 Hz, 1H), 7.39 (d, J=8.2 Hz, 1H), 3.84 (s, 3H), 2.85 (q, J=7.4 Hz, 2H), 1.15 (t, J=7.4 Hz, 3H).

According to this procedure, but starting from methyl 2-bromo-5-(trifluoromethyl)benzoate, the following compound was prepared:

Methyl 2-ethyl-5-(trifluoromethyl)benzoate $^1$H NMR (600 MHz, DMSO-$d_6$) δ 8.04 (d, J=1.10 Hz, 1H), 7.88 (dd, J=1.5, 8.2 Hz, 1H), 7.62 (d, J=8.1 Hz, 1H), 3.87 (s, 3H), 2.97 (q, J=7.6 Hz, 2H), 1.18 (t, J=7.6 Hz, 3H).

Preparation C: Preparation of Compounds of Formula (III)

Bromo-2-(5-chloro-2-methylphenyl)-1-{[2-(trimethylsilyl)ethoxy]methyl}-1H-pyrrole-3-carbonitrile (III)

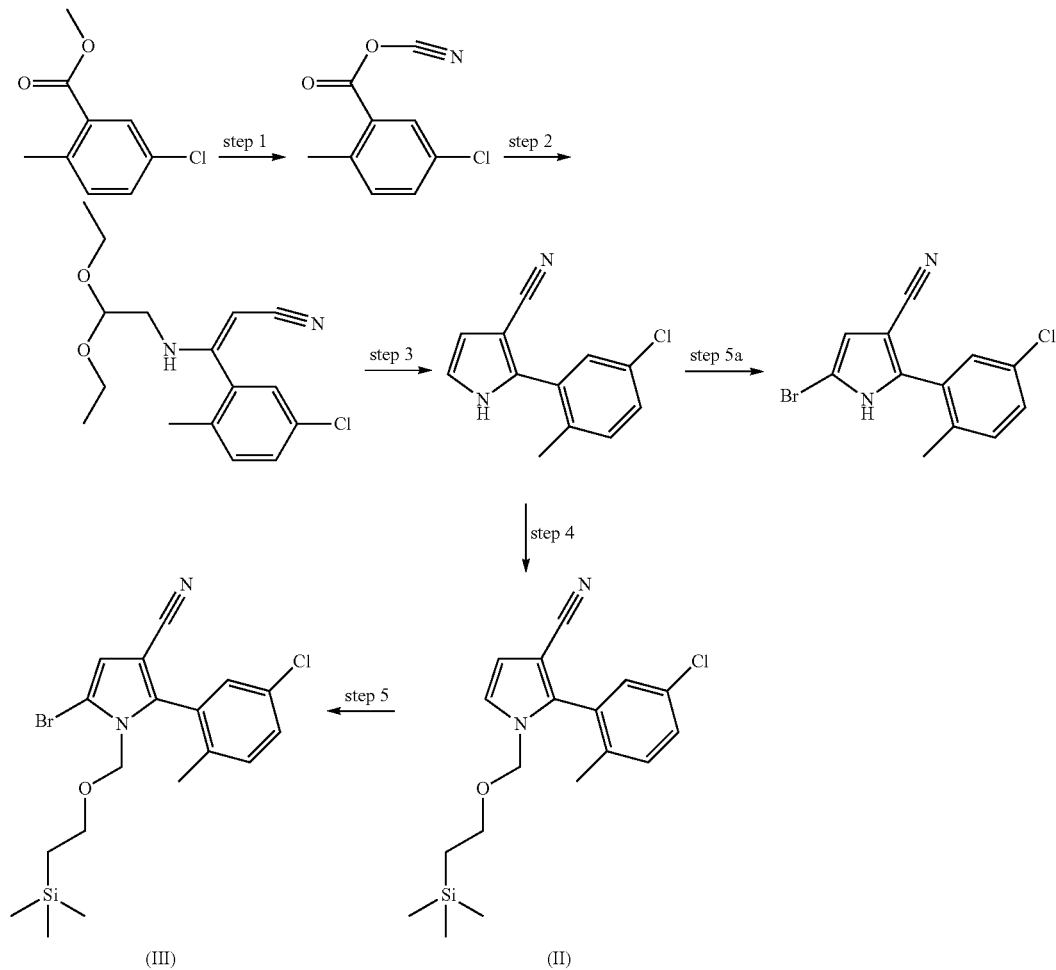

Step 1: 3-(5-Chloro-2-methylphenyl)-3-oxopropanenitrile

To a solution of LiHMDS (76 mL, 1M solution) in THF (70 mL) cooled to −78° C. was added ACN (4.1 mL, 79 mmol) drop wise. The solution was stirred at −78° C. for 1 h, and a solution of methyl 5-chloro-2-methylbenzoate (7.38 g, 40 mmol) in THF (20 mL) was added. The reaction mixture was left to warm to room temperature over 16 h. Then NH$_4$Cl (110 mL, 10% aqueous solution) was added, and the mixture was extracted with EtOAc (120 mL). The aqueous layer was further extracted with EtOAc (80 mL), dried over Na$_2$SO$_4$ and evaporated to dryness. The crude residue was purified by flash chromatography (hexane/EtOAc 85115) to give the title compound (6.2 g, 80%).

$^1$H NMR (400 MHz, DMSO-d$_6$) δ 7.88 (d, J=2.1 Hz, 1H), 7.57 (dd, J=2.1, 8.4 Hz, 1H), 7.29-7.47 (m, 1H), 4.69 (s, 2H), 2.41 (s, 3H).

Step 2: 3-(5-Chloro-2-methylphenyl)-3-[(2,2-diethoxyethyl)amino]prop-2-enenitrile A mixture of 3-(5-chloro-2-methylphenyl)-3-oxopropanenitrile (4.65 g, 24 mmol), 2-aminoacetaldehyde diethyl acetal (3.85 mL, 26.5 mmol) and toluene (150 mL) was stirred under reflux overnight under nitrogen atmosphere in the Dean-Stark apparatus. The mixture was evaporated in vacuo and used in the next step without further purification.

Step 3: 2-(5-Chloro-2-methylphenyl)-1H-pyrrole-3-carbonitrile

To TFA (20 mL) at 5° C. the crude 3-(5-chloro-2-methylphenyl)-3-[(2,2-diethoxyethyl)amino]prop-2-enenitrile dissolved in DCM (10 mL) was added. After stirring at room temperature for 30 min, the reaction mixture was concentrated and then diluted with EtOAc and a NaHCO$_3$ saturated solution. The organic layer was separated, washed with water and brine, dried over Na$_2$SO$_4$ and concentrated. Column chromatography on silica gel (EtOAc/hexane, gradient elution from 0% to 20%) afforded the title compound (2.31 g, 45%, 2 steps).

$^1$H NMR (400 MHz, DMSO-d$_6$) δ 11.99 (br. s., 1H), 7.42-7.47 (m, 1H), 7.39-7.42 (m, 1H), 7.38 (d, J=2.2 Hz, 1H), 7.04 (t, J=2.8 Hz, 1H), 6.59 (t, J=2.8 Hz, 1H), 2.26 (s, 3H).

According to this procedure, but starting from the suitable benzoate derivative, the following compounds were prepared:

2-(5-Chloro-2-ethylphenyl)-1H-pyrrole-3-carbonitrile $^1$H NMR (400 MHz, DMSO-$d_6$) δ 11.99 (br. s., 1H), 7.47-7.52 (m, 1H), 7.41-7.46 (m, 1H), 7.31-7.37 (m, 1H), 7.02 (t, J=2.81 Hz, 1H), 6.53-6.61 (m, 1H), 2.58 (q, J=7.53 Hz, 2H), 0.99 (t, J=7.51 Hz, 3H).

2-[2-Chloro-5-(trifluoromethyl)phenyl]-1H-pyrrole-3-carbonitrile $^1$H NMR (400 MHz, DMSO-$d_6$) δ 12.23 (br. s., 1H), 7.80-7.96 (m, 3H), 7.12 (t, J=2.81 Hz, 1H), 6.65 (t, J=2.69 Hz, 1H).

2-[2-Methyl-5-(trifluoromethyl)phenyl]-1H-pyrrole-3-carbonitrile $^1$H NMR (500 MHz, DMSO-$d_6$) δ 12.08 (br. s., 1H), 7.74 (d, J=7.96 Hz, 1H), 7.65 (s, 1H), 7.62 (d, J=8.24 Hz, 1H), 7.08 (t, J=2.75 Hz, 1H), 6.62 (t, J=2.61 Hz, 1H), 2.36-2.39 (m, 3H).

2-[2-Ethyl-5-(trifluoromethyl)phenyl]-1H-pyrrole-3-carbonitrile $^1$H NMR (600 MHz, DMSO-$d_6$) δ 12.05 (br. s., 1H), 7.79 (dd, J=1.46, 8.06 Hz, 1H), 7.66 (d, J=8.24 Hz, 1H), 7.61 (s, 1H), 7.06 (t, J=2.75 Hz, 1H), 6.61 (t, J=2.75 Hz, 1H), 2.69 (q, J=7.51 Hz, 1H), 2.07 (s, 1H), 1.11-1.52 (m, 1H), 1.04 (t, J=7.51 Hz, 1H).

2-Phenyl-1H-pyrrole-3-carbonitrile $^1$H NMR (600 MHz, DMSO-$d_6$) δ 12.15 (br. s., 1H), 7.94 (dd, J=1.28, 8.42 Hz, 2H), 7.76 (dd, J=1.28, 8.42 Hz, 2H), 7.49-7.54 (m, 2H), 7.36-7.42 (m, 1H), 7.02 (t, J=2.84 Hz, 1H), 6.58 (dd, J=2.38, 2.93 Hz, 1H).

Step 4: 2-(5-Chloro-2-methylphenyl)-1-{[2-(trimethylsilyl)ethoxy]methyl}-1H-pyrrole-3-carbonitrile (II)

NaH (60% dispersion in mineral oil, 0.452 g, 11.3 mmol) was added to a suspension of 2-(5-chloro-2-methylphenyl)-1H-pyrrole-3-carbonitrile (1.733 g, 8.0 mmol) in dry THF (25 mL) at 0° C. The reaction was kept at the same temperature for 20 min then 2-[(chloromethoxy)ethyl](trimethyl)silane (2.0 mL, 11.3 mmol) was added and the mixture was stirred at room temperature for 2 h. Saturated NaCl solution (30 mL) was added at 0° C. and the mixture was extracted with EtOAc (2×35 mL). The separated organic phase was dried over Na$_2$SO$_4$ and the solvent evaporated to afford the title compound (2.637 g, 95%).

$^1$H NMR (400 MHz, DMSO-$d_6$) δ 7.50 (dd, J=2.3, 8.3 Hz, 1H), 7.43 (d, J=8.3 Hz, 1H), 7.37 (d, J=2.3 Hz, 1H), 7.21 (d, J=3.0 Hz, 1H), 6.64 (d, J=3.0 Hz, 1H), 5.16 (d, J=10.8 Hz, 1H), 4.95 (d, J=10.8 Hz, 1H), 3.27-3.30 (m, 2H), 2.10 (s, 3H), 0.69-0.76 (m, 2H), −0.08 (s, 9H).

HRMS (ESI) m/z calcd for C$_{18}$H$_{23}$ClN$_2$OSi+H$^+$ 347.1341, found 347.1345.

Step 5: 5-Bromo-2-(5-chloro-2-methylphenyl)-1-{[2-(trimethylsilyl)ethoxy]methyl}-1H-pyrrole-3-carbonitrile To a solution of 2-(5-chloro-2-methylphenyl)-1-{[2-(trimethylsilyl)ethoxy]methyl}-1H-pyrrole-3-carbonitrile (2.5 g, 7.2 mmol) in MeOH/THF 2/1 (450 mL) was added NBS (1.281 g, 7.2 mmol) in three portions over 3 h at 5° C. The mixture was allowed to stir at room temperature after every addition. The mixture was evaporated in vacuo. Saturated NaCl solution was added and the mixture was extracted with EtOAc. The separated organic phase was dried over Na$_2$SO$_4$, the solvent evaporated and the crude was purified by flash chromatography (hexane/EtOAc 911) to afford the title compound (2.14 g, 70%).

$^1$H NMR (400 MHz, DMSO-$d_6$) δ 7.52-7.57 (m, 1H), 7.40-7.48 (m, 2H), 6.92 (s, 1H), 5.17 (d, J=11.2 Hz, 1H), 4.94 (d, J=11.2 Hz, 1H), 3.27-3.30 (m, 2H), 2.12 (s, 3H), 0.62-0.82 (m, 2H), −0.08 (s, 9H).

HRMS (ESI) m/z calcd for C$_{18}$H$_{22}$BrClN$_2$OSi+H$^+$ 425.0446, found 425.0441.

According to this procedure, but starting from the suitable substituted carbonitrile, the following compounds were prepared:

5-Bromo-2-(5-chloro-2-ethylphenyl)-1-{[2-(trimethylsilyl)ethoxy]methyl}-H-pyrrole-3-carbonitrile (III)

$^1$H NMR (600 MHz, DMSO-$d_6$) δ 7.59 (dd, J=2.4, 8.4 Hz, 1H), 7.47-7.51 (m, 1H), 7.40 (d, J=2.4 Hz, 1H), 6.91 (s, 1H), 5.15 (d, J=11.2 Hz, 1H), 4.89 (d, J=11.2 Hz, 1H), 2.40-2.47 (m, 1H), 2.29-2.36 (m, 1H), 1.05 (t, J=7.5 Hz, 3H), 0.65-0.78 (m, 2H), −0.07 (s, 9H).

HRMS (ESI) m/z calcd for C$_{19}$H$_{24}$BrClN$_2$OSi+Na$^+$ 439.0603, found 439.0600.

5-Bromo-2-[2-chloro-5-(trifluoromethyl)phenyl]-1-{[2-(trimethylsilyl)ethoxy]methyl}-1H-pyrrole-3-carbonitrile (III)

$^1$H NMR (400 MHz, DMSO-$d_6$) δ 8.03 (s, 1H), 7.93-8.01 (m, 2H), 6.98 (s, 1H), 5.23 (d, J=11.4 Hz, 1H), 5.06 (d, J=11.4 Hz, 1H), 3.27-3.30 (m, 2H), 0.61-0.77 (m, 2H), −0.11 (m, 9H).

HRMS (ESI) m/z calcd for C$_{18}$H$_{19}$BrClF$_3$N$_2$OSi+Na$^+$ 500.9983, found 500.9982.

5-Bromo-2-[2-methyl-5-(trifluoromethyl)phenyl]-1-{[2-(trimethylsilyl)ethoxy]methyl}-pyrrole-3-carbonitrile (III)

$^1$H NMR (600 MHz, DMSO-$d_6$) δ 7.80-7.90 (m, 1H), 7.73 (s, 1H), 7.68 (d, J=7.9 Hz, 1H), 6.94 (s, 1H), 5.15 (d, J=11.2 Hz, 1H), 4.93 (d, J=11.2 Hz, 1H), 3.28-3.30 (m, 2H), 2.22 (s, 3H), 0.62-0.75 (m, 2H), −0.10 (s, 9H).

HRMS (ESI) m/z calcd for C$_{19}$H$_{22}$BrF$_3$N$_2$OSi+Na$^+$ 481.0529, found 481.0531.

5-Bromo-2-[2-ethyl-5-(trifluoromethyl)phenyl]-1-{[2-(trimethylsilyl)ethoxy]methyl}-1H-pyrrole-3-carbonitrile (III)

$^1$H NMR (600 MHz, DMSO-$d_6$) δ 7.89 (dd, J=1.5, 8.2 Hz, 1H), 7.71 (d, J=8.1 Hz, 1H), 7.69 (s, 1H), 6.94 (s, 1H), 5.14 (d, J=11.2 Hz, 1H), 4.88 (d, J=11.2 Hz, 1H), 3.28-3.30 (m, 2H), 2.55-2.59 (m, 1H), 2.44 (qd, J=7.4, 14.7 Hz, 1H), 1.08-1.12 (m, 3H), 0.65-0.76 (m, 2H), −0.09 (s, 9H).

HRMS (ESI) m/z calcd for $C_{20}H_{24}BrF_3N_2OSi+Na^+$ 495.0685, found 495.0689.

5-Bromo-2-phenyl-1-([2-(trimethylsilyl)ethoxy]methyl)-1H-pyrrole-3-carbonitrile (III)

$^1$H NMR (600 MHz, DMSO-$d_6$) δ 7.51-7.63 (m, 5H), 6.91 (s, 1H), 5.23 (s, 2H), 3.34-3.38 (m, 2H), 0.71-0.78 (m, 2H), −0.08 (s, 9H).

HRMS (ESI) m/z calcd for $C_{17}H_{21}BrN_2OSi+H^+$ 377.0680, found 377.0685.

Step 5a: 5-Bromo-2-(chloro-2-methylphenyl)-1H-pyrrole-3-carbonitrile

To a solution of 2-(5-chloro-2-methylphenyl)-1H-pyrrole-3-carbonitrile (400 mg, 1.85 mmol) in ACN (20 mL) was added NBS (329 mg, 1.85 mmol) in two portions over 2 h at 5° C. The mixture was allowed to stir at room temperature after every addition. The mixture was evaporated in vacuo and the crude was purified by flash chromatography (hexane/EtOAc 9/1) to afford the title compound (379 mg, 69%).

$^1$H NMR (400 MHz, DMSO-$d_6$) δ 12.72 (br. s., 1H), 7.44-7.48 (m, 1H), 7.38-7.44 (m, 2H), 6.73 (s, 1H), 2.26 (s, 3H).

According to this procedure, but starting from 2-(5-chloro-2-ethylphenyl)-1H-pyrrole-3-carbonitrile, the following compound was prepared:

5-Bromo-2-(5-chloro-2-ethylphenyl)-1H-pyrrole-3-carbonitrile $^1$H NMR (400 MHz, DMSO-$d_6$) δ 12.73 (br. s., 1H), 7.51 (dd, J=2.20, 8.43 Hz, 1H), 7.44 (d, J=8.42 Hz, 1H), 7.39 (d, J=2.38 Hz, 1H), 6.72 (s, 1H), 2.58 (q, J=7.57 Hz, 2H), 1.02 (t, J=7.60 Hz, 3H).

Preparation D: Preparation of Compounds of Formula (II)

2-(5-Chloro-2-ethylphenyl)-1-(phenylsulfonyl)-H-pyrrole-3-carbonitrile (II)

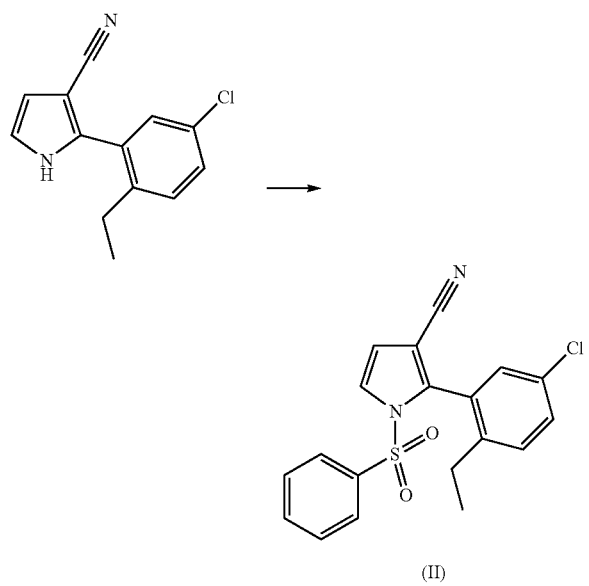

(II)

To a solution of 2-(5-chloro-2-ethylphenyl)-pyrrole-3-carbonitrile (1.26 g, 5.46 mmol) in DMF (13 mL) NaH (60% dispersion in oil, 262 mg, 6.55 mmol) was added at 5° C., under argon atmosphere. The reaction mixture was stirred for 1 h, then benzenesulfonyl chloride (0.766 mL, 6.01 mmol) was added dropwise. After 24 h the reaction mixture was added to water (50 mL) under stirring. EtOAc (75 mL) was added, the organic layer was separated and washed with water, brine, dried over $Na_2SO_4$, filtered, the solvent was evaporated under reduced pressure to give an oil, which was purified by Biotage SP1 Flash Chromatography (hexane/EtOAc 9/1) to afford the title compound (1.44 g, 71%).

$^1$H NMR (600 MHz, DMSO-$d_6$) δ 7.79-7.87 (m, 1H), 7.61 (dd, J=7.7, 8.4 Hz, 1H), 7.56 (dd, J=2.2, 8.4 Hz, 1H), 7.51 (dd, J=0.9, 8.4 Hz, 1H), 7.38 (d, J=8.4 Hz, 1H), 6.95 (d, J=3.6 Hz, 1H), 6.80 (d, J=2.2 Hz, 1H), 2.01 (q, J=7.6 Hz, 1H), 0.96 (t, J=7.6 Hz, 1H).

Preparation E: Preparation of Compounds of Formula (VII)

Ethyl 2-phenyl-1-(phenylsulfonyl)-1H-pyrrole-3-carboxylate (VII)

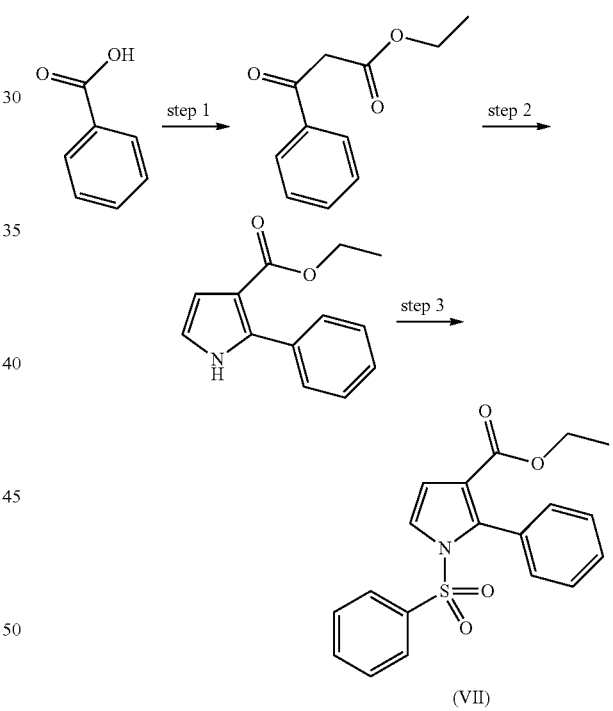

(VII)

Step 1: Ethyl 3-oxo-3-phenylpropanoate-1H-imidazole

Carbonyldiimidazole (7.31 g, 45 mmol) was added to a solution of benzoic acid (5.0 g, 41 mmol) in DMF (50 mL). The mixture was stirred at room temperature. After 2 h magnesium chloride (4.68 g, 49 mmol) and potassium monoethyl malonate (14 g, 82 mmol) were added. The mixture was heated to 100° C. under stirring until reaction was complete, then cooled to room temperature and slowly added to 750 mL of iced water affording the precipitation of a solid. The solid was recovered by filtration affording the title compound (8.66 g, 81.1%), which was used in the next step without further purification.

$^1$H NMR (600 MHz, DMSO-d$_6$) δ 11.99 (br. s., 1H), 7.71-7.81 (m, 2H), 7.28-7.39 (m, 3H), 5.24 (s, 2H), 4.00 (q, J=6.9 Hz, 2H), 1.16 (t, J=7.0 Hz, 3H).

Step 2: Ethyl 2-phenyl-1H-pyrrole-3-carboxylate

Acetyl chloride (4.17 g, 53.14 mmol) was added to a solution of 2,2-diethoxyethanamine (6.43 g, 48.3 mmol) and TEA (6.84 g, 67.62 mmol) in EtOAc (70 mL), at room temperature. After 1 h, EtOH (0.7 mL) was added. The resulting suspension was stirred for 1 h, and then filtered. EtOAc was removed by evaporation from the filtration liquors yielding N-(2,2-diethoxyethyl)acetamide as an oil, which was used without further purification in the next step. Ethyl 3-oxo-3-phenylpropanoate-1H-imidazole (8.66 g, 33.26 mmol) in TFA (10.6 mL) was treated with N-(2,2-diethoxyethyl)acetamide (48.3 mmol). The reaction mixture was heated for 60 min at 60° C., then TFA was removed by evaporation and the oily residue was dissolved in EtOAc, washed twice with water and a NaHCO$_3$ saturated solution. The organic layer was recovered and the solvent was evaporated yielding a dark oil. The oil was treated with EtOH (28 mL) and 2N NaOH (14 mL), the resulting reaction mixture was stirred at room temperature overnight. The solution was slowly added to iced water affording after filtration the title compound (6.2 g, 55.8%).

$^1$H NMR (600 MHz, DMSO-d$_6$) δ 11.60 (br. s., 1H), 7.53-7.61 (m, 2H), 7.38-7.43 (m, 2H), 7.31-7.36 (m, 1H), 6.84 (t, J=2.75 Hz, 1H), 6.53 (t, J=2.75 Hz, 1H), 4.10 (q, J=7.02 Hz, 2H), 1.17 (t, J=7.14 Hz, 3H).

Step 3: Ethyl 2-phenyl-1-(phenylsulfonyl)-1H-pyrrole-3-carboxylate

To a solution of ethyl 2-phenyl-1H-pyrrole-3-carboxylate (1.0 g, 4.65 mmol) in DMF (12 mL) NaH (60% dispersion in oil, 223 mg, 5.58 mmol) was added at 5° C., under argon atmosphere. The reaction mixture was stirred for 1 h, then benzenesulfonyl chloride (0.653 mL, 5.11 mmol) was added dropwise. After 2 h the reaction mixture was added to water and ice under stirring. EtOAc (150 mL) was added, the organic layer was separated and washed with water, brine, dried over Na$_2$SO$_4$, filtered, the solvent was evaporated under reduced pressure to give an oil, which was purified by Biotage SP1 Flash Chromatography (cyclohexane/EtOAc 9/1) to afford the title compound (1.24 g, 75%).

$^1$H NMR (600 MHz, DMSO-d$_6$) δ 7.70-7.75 (m, 1H), 7.62-7.65 (m, 1H), 7.50-7.55 (m, 2H), 7.40-7.43 (m, 1H), 7.37-7.39 (m, 2H), 7.24-7.30 (m, 2H), 6.90-6.98 (m, 2H), 6.72-6.76 (m, 1H), 3.88-3.94 (m, 2H), 0.82-0.96 (m, 3H).

Preparation F

5-Chloro-2-ethylaniline

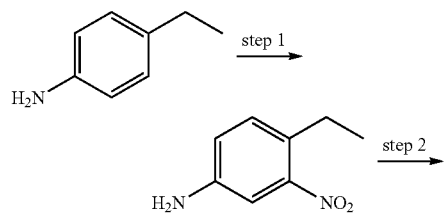

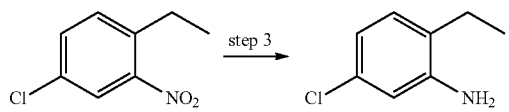

Step 1: 4-Ethyl-3-nitroaniline

4-Ethylaniline (10.3 mL, 82.5 mmol) was added drop wise to sulfuric acid (96%, 63 mL), cooled to 8° C., maintaining the temperature below 10° C. After the addition, the reaction mixture was cooled to −5° C., before the addition of a mixture of nitric acid (100%, 4 mL) and sulfuric acid (96%, 10 mL), keeping the temperature below 0° C. The reaction mixture was then stirred at the same temperature for 1 h. The reaction mixture was poured into ice (200 mL) and the precipitate filtered and washed with water. The solid was suspended with water (100 mL) and neutralized with NH$_4$OH (35%). The precipitate was filtered and dried in the oven to obtain a light-brown solid (10.0 g, 73%).

$^1$H NMR (400 MHz, DMSO-d$_6$) δ 7.11 (d, J=8.3 Hz, 1H), 7.04 (d, J=2.4 Hz, 1H), 6.81 (dd, J=2.4, 8.3 Hz, 1H), 5.53 (s, 2H), 2.63 (q, J=7.4 Hz, 2H), 1.11 (t, J=7.4 Hz, 3H).

Step 2: 4-Chloro-1-ethyl-2-nitrobenzene

A solution of sodium nitrite in water (4.2 g, 60 mmol, 5 M, 12 mL) was added drop wise to a cooled (5° C.) solution of 4-ethyl-3-nitroaniline (10 g, 60 mmol) in conc. HCl (200 mL) and the reaction mixture was stirred at the same temperature for 1.5 h. CuCl (9.5 g, 96 mmol) was then added and the solution was stirred at room temperature for 1 h and then at 80° C. for an additional hour. After cooling down the reaction mixture was extracted with DCM (3×100 mL) and the combined organic layers were dried over Na$_2$SO$_4$. The crude was then purified by flash chromatography (hexane/EtOAc 9/1) to obtain the title compound as a yellow oil (6.28 g, 56%).

$^1$H NMR (400 MHz, DMSO-d$_6$) δ 8.03 (d, J=2.3 Hz, 1H), 7.74 (dd, J=2.2, 8.3 Hz, 1H), 7.57 (d, J=8.4 Hz, 1H), 2.78 (q, J=7.4 Hz, 2H), 1.19 (t, J=7.4 Hz, 3H)

Step 3: 5-Chloro-2-ethylaniline

A solution of hydrazine hydrate (6.95 mL, 134.7 mmol) in methanol (50 mL) was added drop wise to a solution of 4-chloro-1-ethyl-2-nitrobenzene (6.25 g, 33.7 mmol) in methanol (120 mL), in the presence of iron (III) chloride (547 mg, 3.4 mmol) and activated charcoal (547 mg) and the reaction mixture was stirred under reflux for 14 h. The solids were removed by filtration through Celite, the filtrate concentrated and purified by flash chromatography (hexane/EtOAc 9/1) to obtain the title compound as a light-pink oil (5.09 g, 97%).

$^1$H NMR (400 MHz, DMSO-d$_6$) δ 6.89 (d, J=8.0 Hz, 1H), 6.62 (d, J=2.2 Hz, 1H), 6.47 (dd, J=2.2, 8.0 Hz, 1H), 5.12 (s, 2H), 2.39 (q, J=7.5 Hz, 2H), 1.09 (t, J=7.4 Hz, 3H).

Preparation G

2-Ethyl-5-(trifluoromethyl)aniline

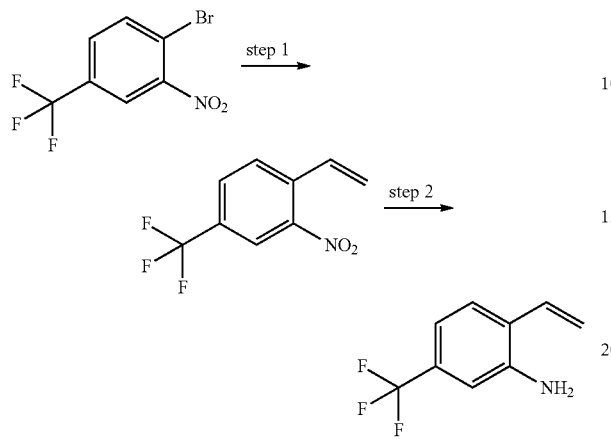

Step 1: 1-Ethenyl-2-nitro-4-(trifluoromethyl)benzene

1-Bromo-2-nitro-4-(trifluoromethyl)benzene (6.14 mL, 40.1 mmol) was dissolved in 2-propanol (200 mL). To this mixture TEA (19.8 mL, 140.3 mmol) and potassium vinyl trifluoroborate (6.44 g, 48.1 mmol) were added. The resulting reaction mixture was degassed three times back filling with argon each time before being charged $PdCl_2(dppf)$ (1.5 g, 2.0 mmol). The resulting reaction mixture was degassed four times back filling with argon each time and then warmed to reflux for 3 h. The reaction mixture was cooled to room temperature, filtered through a pad of Celite, washed with EtOAc, and the filtrate was concentrated and then diluted with EtOAc and water. The two layers were separated, and the aqueous layer was extracted with EtOAc. The combined organic fractions were washed with aqueous brine, dried over $Na_2SO_4$, filtered and concentrated under reduced pressure. The residue was purified by flash chromatography (hexane/EtOAc 9/1) to afford the title compound (5.6 g, 64%).

$^1$H NMR (600 MHz, DMSO-$d_6$) δ 8.34 (s, 1H), 8.09 (d, J=8.2 Hz, 1H), 8.05 (d, J=8.2 Hz, 1H), 7.03 (dd, J=11.1, 17.3 Hz, 1H), 6.07 (d, J=17.3 Hz, 1H), 5.68 (d, J=11.1 Hz, 1H).

Step 2: 2-Ethyl-5-(trifluoromethyl)aniline

1-Ethenyl-2-nitro-4-(trifluoromethyl)benzene (2.2 g, 10.13 mmol) dissolved in THF (150 mL) was shaked at room temperature under $H_2$ (40 psi) in the presence of 10% Pd/C (200 mg) for 8 h. The reaction mixture was filtered through a pad of Celite, washed with EtOAc, and the filtrate was concentrated. The residue was purified by flash chromatography (hexane/EtOAc 9/1) to afford the title compound (1.76 g, 92%).

$^1$H NMR (600 MHz, DMSO-$d_6$) δ 7.10 (d, J=7.7 Hz, 1H), 6.89 (d, J=1.5 Hz, 1H), 6.61-6.81 (d, J=7.7 Hz, 1H), 5.30 (s, 2H), 2.48 (q, J=7.5 Hz, 2H), 1.13 (t, J=7.5 Hz, 3H).

Preparation H: Preparation of Compounds of Formula (XII)

4-Bromo-1-(5-chloro-2-ethylphenyl)-1H-pyrrole-2-carbonitrile (XII)

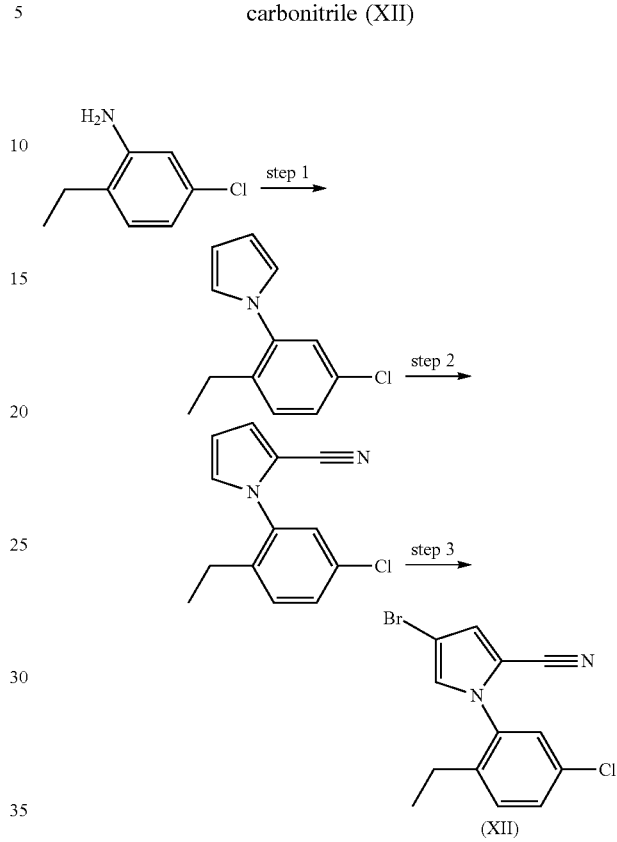

Step 1: 1-(5-Chloro-2-ethylphenyl)-1H-pyrrole

5-Chloro-2-ethylaniline (10.8 g, 69.44 mmol) and 2,5-dimethoxy-tetrahydrofuran (9.87 mL, 76.38 mmol) was refluxed for 3 h in AcOH (20 mL). The reaction mixture was evaporated and the residue was diluted in EtOAc, washed with water, $NaHCO_3$ saturated solution, brine, and then dried over $Na_2SO_4$. The solvent was evaporated and the crude was purified by Biotage SP1 Flash Chromatography (gradient elution from 0% to 15% of EtOAc in hexane) to afford the title compound (12.52 g, 88%).

$^1$H NMR (600 MHz, DMSO-$d_6$) δ 7.36-7.47 (m, 2H), 7.31 (d, J=1.3 Hz, 1H), 6.93 (t, J=2.1 Hz, 2H), 6.23 (t, J=2.1 Hz, 2H), 2.46 (q, J=7.5 Hz, 2H), 0.99 (t, J=7.5 Hz, 3H).

Step 2: 1-(5-Chloro-2-ethylphenyl)-1H-pyrrole-2-carbonitrile

To a solution of 1-(5-chloro-2-ethylphenyl)-1H-pyrrole (11.8 g, 57.56 mmol) in anhydrous ACN (150 ml) was added chlorosulfonyl isocyanate (5.32 mL, 61.11 mmol) drop wise at 0° C. The mixture was stirred at the same temperature for 30 min and then DMF (12 mL) was added to this mixture drop wise. After stirring at the same temperature for 1 h, the reaction mixture was poured into ice-water, stirred for 10 min and then diluted with EtOAc. The organic layer was isolated and the aqueous layer was extracted with EtOAc twice. The combined organic phases were dried over $Na_2SO_4$ and evaporated in vacuo. The crude was purified by Biotage SP1 Flash Chromatography (gradient elution from 0% to 15% of EtOAc in hexane) to give the title compound (10.62 g, 80%).

$^1$H NMR (600 MHz, DMSO-$d_6$) δ 7.57-7.62 (m, 1H), 7.51-7.55 (m, 2H), 7.39 (dd, J=1.5, 2.6 Hz, 1H), 7.19 (dd, J=1.5, 3.9 Hz, 1H), 6.44 (dd, J=2.7, 4.0 Hz, 1H), 2.33 (q, J=7.5 Hz, 2H), 1.00 (t, J=7.5 Hz, 3H).

Step 3: 4-Bromo-1-(5-chloro-2-ethylphenyl)-1H-pyrrole-2-carbonitrile

To a solution of 1-(5-chloro-2-ethylphenyl)-1H-pyrrole-2-carbonitrile (2.307 g, 10 mmol) in THF (50 mL) was added a solution of NBS (1.87 g, 10.5 mmol) in THF (50 mL). The mixture was allowed to stir at room temperature for 90 min and then a solution of NBS (356 mg, 2 mmol) in THF (10 mL) was added. The mixture was allowed to stir at room temperature for 90 min and then was evaporated in vacuo. Saturated NaCl solution was added and the mixture was extracted with EtOAc. The separated organic phase was dried over $Na_2SO_4$, the solvent evaporated and the crude was purified by Biotage SP1 Flash Chromatography (gradient elution from 0% to 15% of EtOAc in hexane) to afford the title compound (2.38 g, 77%).

$^1$H NMR (600 MHz, DMSO-$d_6$) δ 7.68 (d, J=1.8 Hz, 1H), 7.60-7.64 (m, 2H), 7.53 (d, J=8.8 Hz, 1H), 7.38 (d, J=1.6 Hz, 1H), 2.34 (q, J=7.3 Hz, 2H), 1.03 (t, J=7.3 Hz, 3H).

According to this procedure, but starting from the suitable aniline, the following compounds were prepared:

4-Bromo-1-(5-chloro-2-methylphenyl)-1H-pyrrole-2-carbonitrile (XII)

$^1$H NMR (400 MHz, DMSO-$d_6$) δ 7.66 (d, J=1.7 Hz, 1H), 7.63 (d, J=2.2 Hz, 1H), 7.55-7.59 (m, 1H), 7.50 (d, J=8.5 Hz, 1H), 7.38 (d, J=1.7 Hz, 1H), 2.06 (s, 1H).

4-Bromo-1-[2-chloro-5-(trifluoromethyl)phenyl]-1H-pyrrole-2-carbonitrile (XII)

$^1$H NMR (400 MHz, DMSO-$d_6$) δ 8.26 (s, 1H), 8.03 (d, J=0.7 Hz, 2H), 7.77 (d, J=1.8 Hz, 1H), 7.45 (d, J=1.7 Hz, 1H).

4-Bromo-1-[2-methyl-5-(trifluoromethyl)phenyl]-1H-pyrrole-2-carbonitrile (XII)

ESI (+) MS: m/z 330 (MH$^+$).

4-Bromo-1-[2-ethyl-5-(trifluoromethyl)phenyl]-1H-pyrrole-2-carbonitrile (XII)

$^1$H NMR (600 MHz, DMSO-$d_6$) δ 7.89-7.95 (m, 2H), 7.76 (d, J=7.9 Hz, 1H), 7.74 (d, J=1.6 Hz, 1H), 7.41 (d, J=1.6 Hz, 1H), 2.44 (q, J=7.3 Hz, 2H), 1.08 (t, J=7.3 Hz, 3H).

4-Bromo-1-phenyl-H-pyrrole-2-carbonitrile (XII)

ESI (+) MS: m/z 248 (MH$^+$).

Preparation I

4-Chloro-2-iodo-1-ethylbenzene

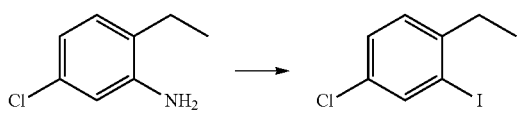

A mixture of 5-chloro-2-ethylaniline (3.35 g, 21.5 mmol), p-toluenesulfonic acid (12.29 g, 64.6 mmol) and water (2.15 mL) were ground in a mortar for few minutes, to obtain a homogeneous paste to which solid sodium nitrite (3.71 g, 53.8 mmol) was added and the paste ground for 10 min. Solid potassium iodide (8.94 g, 53.8 mmol) was added and the paste ground for 20 min. The paste was then dissolved in water (50 mL) and treated with sodium sulfite (10% aq. sol.), before being extracted with EtOAc (3×100 mL). The combined organic layers were dried over $Na_2SO_4$ and the crude was purified by flash chromatography (hexane) to obtain the title compound as a light-yellow oil (4.35 g, 76%).

$^1$H NMR (400 MHz, DMSO-$d_6$) δ 7.87 (d, J=2.2 Hz, 1H), 7.42 (dd, J=2.2, 8.30 Hz, 1H), 7.29-7.35 (m, 1H), 2.66 (q, J=7.5 Hz, 2H), 1.12 (t, J=7.5 Hz, 3H).

Preparation J

1-Ethyl-2-iodo-4-(trifluoromethyl)benzene

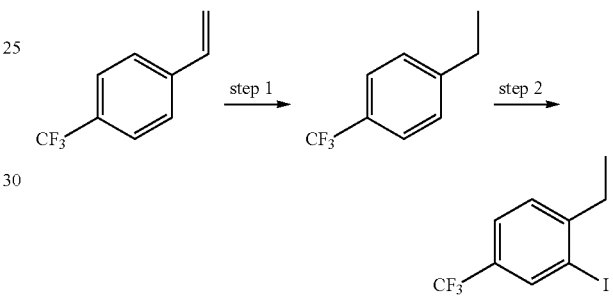

Step 1: 1-Ethyl-4-(trifluoromethyl)benzene

A solution of 1-ethenyl-4-(trifluoromethyl)benzene (1.72 mL, 11.6 mmol) in THF (60 mL) was stirred in the presence of Pd/C (10%, 400 mg), under a hydrogen atmosphere (45 psi) for 7 h. The solid was filtered through celite (washed with DCM) and the filtrate was carefully concentrated, keeping the temperature of the bath below 20° C. at 200 mmHg. The concentrated solution thus obtained was used in the next step without further manipulation.

$^1$H NMR (400 MHz, DMSO-$d_6$) δ 7.63 (d, J=7.9 Hz, 2H). 7.44 (d, J=7.9 Hz, 2H), 2.70 (q, J=7.1 Hz, 2H), 1.20 (t, J=7.6 Hz, 3H).

Step 2: 1-Ethyl-2-iodo-4-(trifluoromethyl)benzene

Sulfuric acid (96%, 1.9 mL) was added drop wise to a solution of sodium periodate (3.73 g, 17.4 mmol) and iodine (2.95 g, 11.6 mmol) in a mixture of acetic acid (8.45 mL) and acetic anhydride (4.23 mL) at 0° C., followed by the drop wise addition of 1-ethyl-4-(trifluoromethyl)benzene (2.0 g, 11.6 mmol). The reaction mixture was let warming up to room temperature while stirring for a period of 24 h. A solution of sodium metabisulfite (10%) was added to quench the remaining iodine and successively NaOH (35%) was added to reach pH=7. The aqueous layer was extracted with DCM (3×50 mL) and the combined organic layers were dried over $Na_2SO_4$. Once the solvent was removed, the crude was used without further purification in the next step.

¹H NMR (400 MHz, DMSO-d₆) δ 8.11 (dq, J=1.9, 0.7 Hz, 1H), 7.69-7.75 (m, 1H), 7.53 (d, J=8.0 Hz, 1H), 2.75 (q, J=7.5 Hz, 2H), 1.16 (t, J=7.51 Hz, 3H).

Preparation K: Preparation of Compounds of Formula (XIV)

4-(5-Chloro-2-methylphenyl)-1H-pyrrole-3-carbonitrile (XIV)

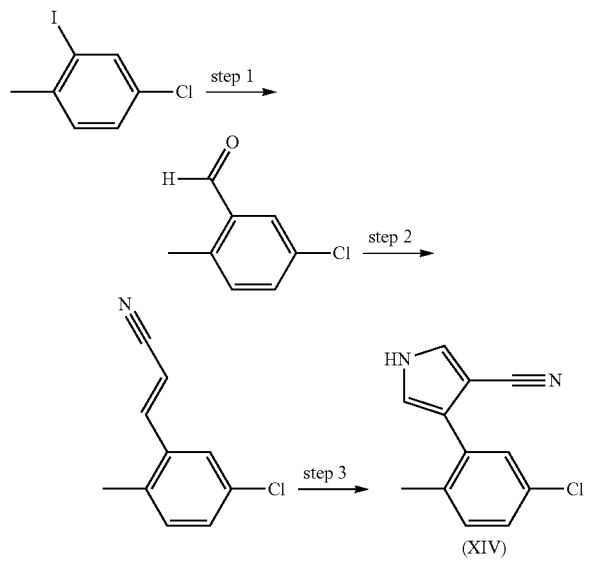

Step 1: 5-Chloro-2-methylbenzaldehyde

To a solution of 4-chloro-2-iodo-1-methylbenzene (5.0 g, 19.8 mmol) in THF (40 mL) n-BuLi (2.5 M in hexane, 8.72 mL, 21.8 mmol) was slowly added dropwise at −78° C. under argon. The mixture was stirred at −78° C. for 1 h, then DMF (7.7 mL, 99 mmol) was added, followed by warming to room temperature in 4 h and quenching with 1N HCl (5 mL). The reaction mixture was stirred overnight, diluted with 1N HCl (50 mL) and Et₂O, the organic phase was separated, washed with aqueous brine, dried over Na₂SO₄ and evaporated to give the title compound (3.14 g, 94%) as a yellow oil.

¹H NMR (600 MHz, DMSO-d₆) δ 10.17 (s, 1H), 7.80 (d, J=2.2 Hz, 1H), 7.60 (dd, J=2.4, 8.1 Hz, 1H), 7.37 (d, J=8.1 Hz, 1H), 2.57 (s, 3H).

Step 2: 3-(5-Chloro-2-methylphenyl)-acrylonitrile

To a suspension of NaH (60% dispersion in oil, 950 mg, 23.28 mmol) in dry THF (43 mL) a solution of diethyl cyanomethylphosphonate (3.67 ml, 23.28 mmol) in THF (17 mL) was added at 5° C. dropwise over 20 min, maintaining the reaction temperature below 10° C. The suspension was stirred at 5° C. for 60 min. A solution of 5-chloro-2-methyl-benzaldehyde (2.99 g, 19.4 mmol) in THF (30 mL) was added dropwise over 20 min, maintaining the reaction temperature below 10° C. The reaction mixture was allowed to warm to room temperature and stirred overnight. Water was added, the solvent was evaporated, the residue was partitioned between EtOAc and water. The aqueous layer was separated and extracted with EtOAc, the combined organic layers were washed with water, brine, dried over Na₂SO₄, filtered and the solvent was evaporated under reduced pressure to give the title compound (3.26 g, 95%) as a pale yellow oil.

Step 3: 4-(5-Chloro-2-methylphenyl)-1H-pyrrole-3-carbonitrile

To a suspension of NaH (60% dispersion in oil, 263 mg, 6.58 mmol) in dry THF (40 mL) a solution of 3-(5-chloro-2-methylphenyl)-acrylonitrile (970 mg, 15.48 mmol) and (p-toluenesulfonyl)methylisocyanide (1.28 g, 6.58 mmol) in THF (20 mL) was added at 5 C dropwise over 10 min, maintaining the reaction temperature below 5° C. The reaction mixture was allowed to warm to room temperature and stirred overnight Water was added, the solvent was evaporated, the residue was partitioned between DCM and water. The aqueous layer was separated and extracted with DCM, the combined organic layers were washed with water, brine, dried over Na₂SO₄, filtered, the solvent was evaporated under reduced pressure and the crude was purified by Biotage SP1 Flash Chromatography (hexane/EtOAc 7/3) to afford the title compound (497 mg, 42%).

¹H NMR (600 MHz, DMSO-d₆) δ 11.95 (br. s., 1H), 7.71 (s, 1H), 7.29-7.35 (m, 2H), 7.27 (d, J=2.2 Hz, 1H), 7.08 (d, J=1.5 Hz, 1H), 2.27 (s, 3H).

According to this procedure, but starting from the suitable substituted iodo-benzene, the following compounds were prepared:

4-(5 Chloro-2-ethylphenyl)-H-pyrrole-3-carbonitrile (XIV)

ESI (+) MS: m/z 231 (MH⁺).

4-[2-Chloro-5-(trifluoromethyl)phenyl]-1H-pyrrole-3-carbonitrile (XIV)

ESI (+) MS: m/z 271 (MH⁺).

4-[2-Methyl-5-(trifluoromethyl)phenyl]-1H-pyrrole-3-carbonitrile (XIV)

ESI (+) MS: m/z 251 (MH⁺).

4-[2-Ethyl-5-(trifluoromethyl)phenyl]-1H-pyrrole-3-carbonitrile (XIV)

ESI (+) MS: m/z 265 (MH⁺).

4-Phenyl-1H-pyrrole-3-carbonitrile (XIV)

ESI (+) MS: m/z 169 (MH⁺).

Preparation L: Preparation of Compounds of Formula (XV)

Ethyl 3-(chloro-2-methylphenyl)-1-(phenylsulfonyl)-1H-pyrrole-2-carboxylate (XV)

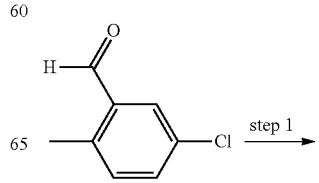

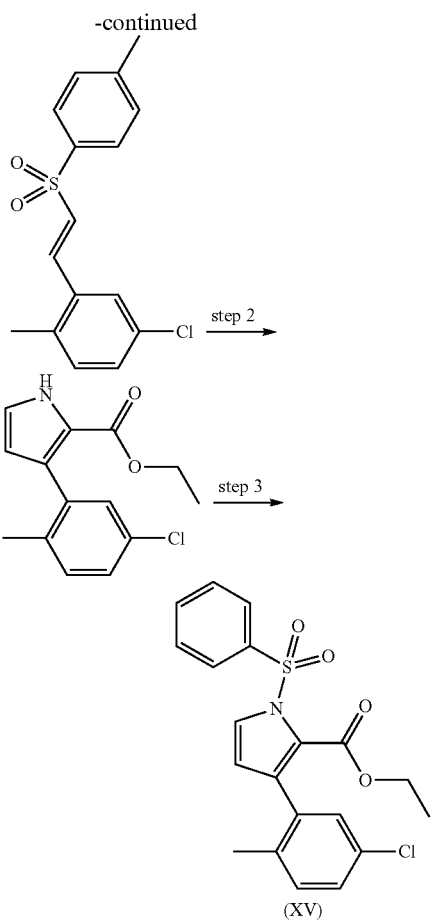

Step 1: (E)-2-(5-Chloro-2-methylphenyl)ethenyl 4-methylphenyl sulfone

To a solution of methyl-(4-methylphenyl)sulphone (6.74 g, 39.6 mmol) in THF (200 mL) n-BuLi (2.5 M in hexane, 34.8 mL, 87.12 mmol) was added dropwise at 0° C. under argon atmosphere. After stirring for 30 min at 0° C. diethyl chlorophosphate (5.70 mL, 39.6 mmol) in THF (30 mL) was slowly added dropwise. The reaction mixture was stirred at 0° C. for 30 min, then was cooled to −78° C., followed by addition of a solution of 5-chloro-2-methyl-benzaldehyde (6.1 g, 39.6 mmol) in THF (10 mL). After stirring at −78° C. for 1 h, the temperature of the reaction mixture was allowed to rise to room temperature. Water was added (50 mL) and the reaction mixture was concentrated under reduced pressure to give a precipitated that was filtered, washed with water and oven-dried under reduced pressure to afford the title compound as a beige solid (8.24 g, 68%).

$^1$H NMR (600 MHz, DMSO-$d_6$) δ 7.79-7.85 (m, 2H), 7.76 (d, J=8.2 Hz, 1H), 7.68-7.72 (m, 1H), 7.62-7.67 (m, 1H), 7.47 (d, J=8.0 Hz, 1H), 7.37-7.43 (m, 1H), 7.30-7.34 (m, 1H), 2.41 (s, 3H), 2.39 (s, 3H).

Step 2: Ethyl 3-(5-chloro-2-methylphenyl)-1H-pyrrole-2-carboxylate

To a suspension of NaH (60% dispersion in oil, 2.25 g, 56.19 mmol) in dry THF (140 mL) a solution of (E)-2-(5-chloro-2-methylphenyl)ethenyl 4-methylphenyl sulfone (8.18 g, 26.76 mmol) and ethyl isocyanoacetate (5.85 mL, 53.52 mmoL) in THF (200 mL) was added dropwise at room temperature over 1 h, under argon atmosphere. The reaction mixture was stirred for 2 h, then water and EtOAc were added. The organic layer was separated and washed with water, brine, dried over $Na_2SO_4$ filtered, the solvent was evaporated under reduced pressure to give a brown oil, which was purified by Biotage SP1 Flash Chromatography (hexane/EtOAc 9/1) to afford the title compound (3.44 g, 49%).

$^1$H NMR (600 MHz, DMSO-$d_6$) δ 11.90 (br. s., 1H), 7.19-7.28 (m, 2H), 7.13 (d, J=1.6 Hz, 1H), 7.02-7.08 (m, 1H), 6.14 (t, J=2.5 Hz, 1H), 4.06 (q, J=7.1 Hz, 2H), 2.08 (s, 3H), 1.05 (t, J=7.1 Hz, 1H).

Step 3: Ethyl 3-(5-chloro-2-methylphenyl)-1-(phenylsulfonyl)-1H-pyrrole-2-carboxylate To a solution of ethyl 3-(5-chloro-2-methylphenyl)-1H-pyrrole-2-carboxylate (526 mg, 2 mmol) in DMF (5 mL) NaH (60% dispersion in oil, 96 mg, 2.4 mmol) was added at 5° C., under argon atmosphere. The reaction mixture was stirred for 1 h, then benzenesulfonyl chloride (0.306 mL, 2.4 mmol) was added dropwise. After 2.5 h at room temperature the reaction mixture was added to water and ice under stirring. EtOAc was added, the organic layer was separated and washed with water, brine, dried over $Na_2SO_4$, filtered, the solvent was evaporated under reduced pressure to give an oil, which was purified by Biotage SP1 Flash Chromatography (hexane/EtOAc 9/1) to afford the title compound (783 mg, 97%).

$^1$H NMR (600 MHz, DMSO-$d_6$) δ 8.03 (dd, J=1.0, 8.3 Hz, 2H), 7.85 (d, J=3.3 Hz, 1H), 7.78-7.83 (m, 1H), 7.62-7.75 (m, 2H), 7.29-7.35 (m, 1H), 7.23-7.28 (m, 1H), 7.11 (d, J=2.2 Hz, 1H), 6.52 (d, J=3.3 Hz, 1H), 3.96 (q, J=7.1 Hz, 2H), 2.04 (s, 3H), 0.82 (t, J=7.0 Hz, 3H).

According to this procedure, but starting from the suitable substituted benzaldehyde, the following compounds were prepared:

Ethyl 3-(5-chloro 2-ethylphenyl)-1-phenylsulfonyl)-1H-pyrrole-2-carboxylate (XV)

$^1$H NMR (600 MHz, DMSO-$d_6$) δ 7.94-8.06 (m, 2H), 7.85 (d, J=3.30 Hz, 1H), 7.77-7.82 (m, 1H), 7.68-7.73 (m, 2H), 7.34-7.37 (m, 1H), 7.28-7.31 (m, 1H), 7.08 (d, J=2.38 Hz, 1H), 6.51 (d, J=3.30 Hz, 1H), 3.93 (q, J=7.08 Hz, 2H), 2.28-2.40 (m, 2H), 0.94 (t, J=7.60 Hz, 3H), 0.78 (t, J=7.05 Hz, 3H)

Ethyl 3-[2-chloro-5-(trifluoromethyl)phenyl]-1-(phenylsulfonyl)-1H-pyrrole-2-carboxylate (XV)

ESI (+) MS: m/z 458 (MH$^+$).

Ethyl 3-[2-methyl-5-(trifluoromethyl)phenyl]-1-(phenylsulfonyl)-1H-pyrrole-2-carboxylate (XV)

ESI (+) MS: m/z 438 (MH$^+$).

Ethyl 3-[2-ethyl-5-(trifluoromethyl)phenyl]-1-(phenylsulfonyl)-1H-pyrrole-2-carboxylate (XV)

$^1$H NMR (600 MHz, DMSO-$d_6$) δ 8.04 (dd, J=1.19, 8.52 Hz, 2H), 7.89 (d, J=3.11 Hz, 1H), 7.79-7.82 (m, 1H), 7.69-7.73 (m, 2H), 7.66 (d, J=8.06 Hz, 1H), 7.52 (d, J=8.06

Hz, 1H), 7.35 (s, 1H), 6.57 (d, J=3.30 Hz, 1H), 3.88 (q, J=7.02 Hz, 2H), 2.43-2.49 (m, 2H), 0.98 (t, J=7.51 Hz, 3H), 0.71 (t, J=7.14 Hz, 3H).

Ethyl 3-phenyl-1-(phenylsulfonyl)-1H-pyrrole-2-carboxylate (XV)

ESI (+) MS: m/z 356 (MH+).

Preparation M: Preparation of Compounds of Formula (XIX)

tert-Butyl 2-(5-chloro-2-methylphenyl)-4-iodo-1H-pyrrole-1-carboxylate (XIX)

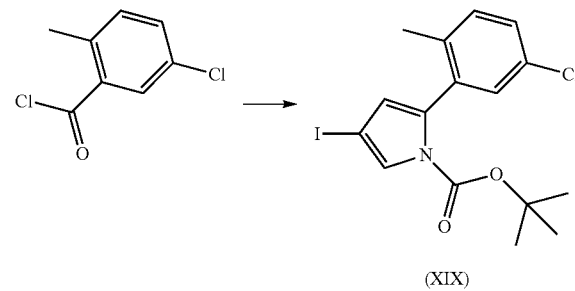

(XIX)

PdCl$_2$(PPh$_3$)$_2$ (70 mg, 0.10 mmol) and CuI (39 mg, 0.20 mmol) were placed under argon in a flame-dried screwcap vessel. Dry THF (25 mL) was added, and the mixture was degassed with argon. TEA (0.69 mL, 5.00 mmol), 5-chloro-2-methylbenzoyl chloride (945 mg, 5.00 mmol), and tert-butyl prop-2-ynylcarbamate (776 mg, 5.00 mmol) were successively added to the mixture which was then stirred at room temperature for 1 h. Sodium iodide (3.79 g, 25.0 mmol), toluene-4-sulfonic acid monohydrate (1.94 g, 10.0 mmol), and tert-butyl alcohol (5 mL) were successively added to the mixture, which was stirred at room temperature for 1 h. The reaction mixture was diluted with brine (50 mL), the phases were separated and the aqueous phase was extracted with DCM (3×25 mL). The combined organic layers were dried over Na$_2$SO$_4$. After removal of the solvents in vacuo, the residue was absorbed onto Celite and chromatographed on silica gel (hexane/EtOAc 95/5) to give the title compound (1.04 g, 50%) as a colorless solid.

$^1$H NMR (600 MHz, DMSO-d$_6$) δ 7.53 (d, J=1.71 Hz, 1H,), 7.42 (dd, J=8.09 Hz, 1H), 7.23 (dd, 1H), 7.20 (dd, 1H), 6.30 (d, J=1.71 Hz, 1H) 2.38 (s, 3H), 1.44 (s, 9H).

According to this procedure and using the suitable acyl chloride, the following compounds were prepared:

tert-Butyl 2-(5-chloro-2-ethylphenyl)-4-iodo-1H-pyrrole-1-carboxylate (XIX)

ESI (+) MS: m/z 432 (MH+).

tert-Butyl 2-[2-chloro-5-(trifluoromethyl)phenyl]-4-iodo-1H-pyrrole-1-carboxylate (XIX)

ESI (+) MS: m/z 472 (MH+).

tert-Butyl 2-[2-methyl-5-(trifluoromethyl)phenyl]-4-iodo-1H-pyrrole-1-carboxylate (XIX)

ESI (+) MS: m/z 452 (MH+).

tert-Butyl 2-[2-ethyl-5-(trifluoromethyl)phenyl]-4-iodo-1H-pyrrole-1-carboxylate (XIX)

ESI (+) MS: m/z 466 (MH+).

tert-Butyl 2-(phenyl)-4-iodo-1H-pyrrole-1-carboxylate (XIX)

ESI (+) MS: m/z 370 (MH+).

Preparation N: Preparation of Compounds of Formula (V)

4-Chloro-7-(4-methoxybenzyl)-6,7-dihydro-5H-pyrrolo[2,3-d]pyrimidine (V)

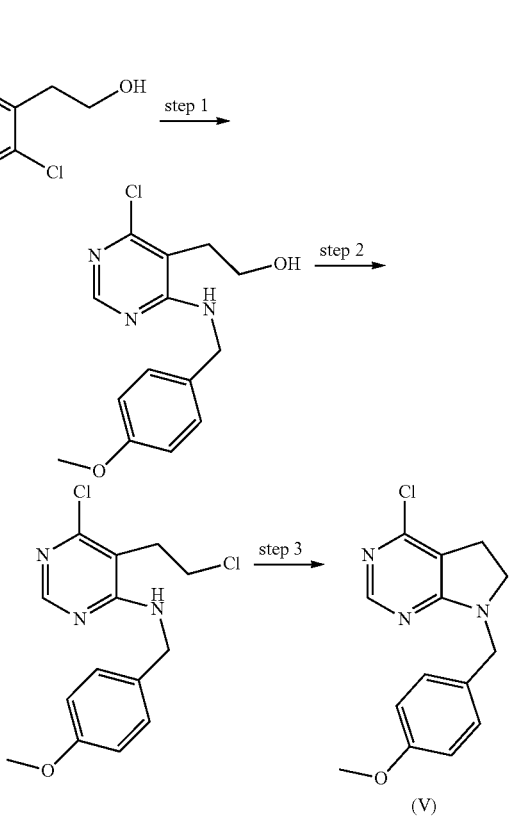

(V)

Step 1: 2-{4-Chloro-6-[(4-methoxybenzyl)amino]pyrimidin-5-yl}ethanol

To a solution of 2-(4,6-dichloropyrimidin-5-yl)ethanol (470 mg, 2.43 mmol) in EtOH (10 mL) DIPEA (592 μL, 2.9 mmol) and 4-methoxybenzylamine (380 μL, 3.40 mmol) were added. The solution was refluxed for 5 h. The solvent was removed in vacuo and the residue was diluted with EtOAc, washed with water, dried over Na$_2$SO$_4$, filtered and concentrated under reduced pressure to afford the title compound as an oil (520 mg, 73%).

$^1$H NMR (600 MHz, DMSO-d$_6$) δ 8.12 (s, 1H), 7.76 (t, J=5.7 Hz, 1H), 7.22 (d, J=8.6 Hz, 2H), 6.86 (d, J=8.6 Hz, 2H), 4.82 (t, J=5.2 Hz, 1H), 4.52 (d, J=5.8 Hz, 2H), 3.71 (s, 3H), 3.51-3.61 (m, 2H), 2.81 (t, J=6.8 Hz, 2H).

Step 2: 6-Chloro-5-(2-chloroethyl)-N-(4-methoxybenzyl)pyrimidin-4-amine

2-{4-Chloro-6-[(4-methoxybenzyl)amino]pyrimidin-5-yl}ethanol (293 mg, 1 mmol) in toluene (5 mL) was treated with SOCl$_2$ (145 µL, 2 mmol). The reaction mixture was refluxed 1 h and then concentrated to give the title compound as an oil. The crude product was used for the next reaction without purification.

$^1$H NMR (600 MHz, DMSO-d$_6$) δ 8.17 (s, 1H), 8.03 (t, J=5.59 Hz, 1H), 7.22 (d, J=8.6 Hz, 2H), 6.86 (d, J=8.6 Hz, 2H), 4.53 (d, J=5.8 Hz, 2H), 3.72 (t, J=7.3 Hz, 2H), 3.71 (s, 3H), 3.13 (t, J=7.3 Hz, 2H).

Step 3: 4-Chloro-7-(4-methoxybenzyl)-6,7-dihydro-5H-pyrrolo[2,3-d]pyrimidine To a solution of 6-chloro-5-(2-chloroethyl)-N-(4-methoxybenzyl)pyrimidin-4-amine in DMF (5 ml) K$_2$CO$_3$ (414 mg, 3 mmol) was added and then warmed to 110° C. for 2 h. The reaction mixture was diluted with water and extracted with EtOAc, dried over Na$_2$SO$_4$, filtered and concentrated under reduced pressure to obtain the title compound as an oil (261 mg, 95%).

$^1$H NMR (600 MHz, DMSO-d$_6$) δ 8.15 (s, 1H), 7.21 (d, J=8.6 Hz, 2H), 6.90 (d, J=8.6 Hz, 2H), 4.50 (s, 2H), 3.73 (s, 3H), 3.53 (t, J=8.7 Hz, 2H), 3.00 (t, J=8.7 Hz, 2H).

Preparation O: Preparation of Compounds of Formula (VII)

Methyl 2-(5-chloro-2-ethylphenyl)-1-(phenylsulfonyl)-1H-pyrrole-3-carboxylate (VII)

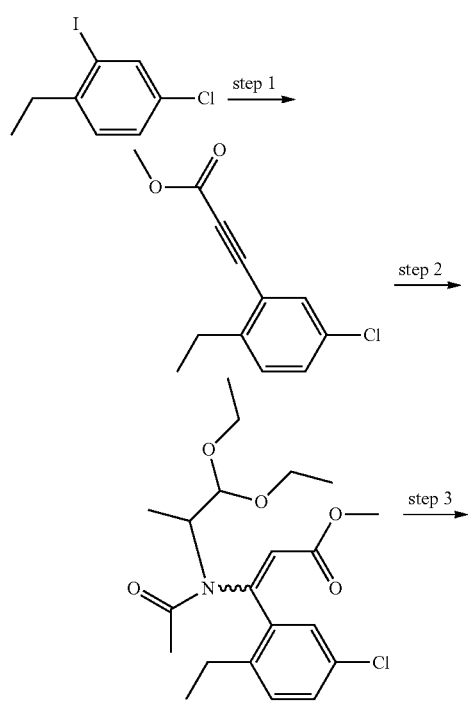

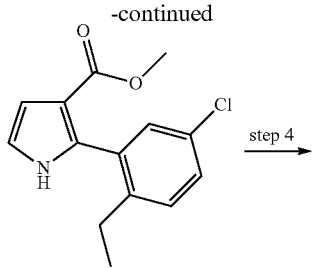

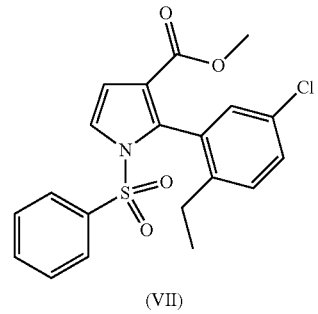

(VII)

Step 1: Methyl 3-(5-chloro-2-ethylphenyl)prop-2-ynoate

To a solution of 4-chloro-1-ethyl-2-iodo-benzene (2.66 g, 10 mmol) and methyl propiolate (1.79 mL, 20 mmol) in DMF (20 mL), Cu$_2$O (1.43 g, 10 mmol) was added. The reaction was heated to 110° C. (oil bath temperature) for 20 h with mechanical stirring. The reaction was filtered over a plug of celite, the plug was washed with EtOAc (100 mL) and the filtrate was washed first with water, then with brine. Drying over sodium sulfate of the organic phase, evaporation and purification of the crude by chromatography over silica gel (heptane/Et$_2$O 95/5) afforded the title compound as an oil (1.29 g, 58%).

$^1$H NMR (400 MHz, DMSO-d$_6$) δ 7.69 (d, J=2.3 Hz, 1H), 7.56 (dd, J=2.3, 8.4 Hz, 1H), 7.42 (d, J=8.4 Hz, 1H), 3.80 (s, 3H), 2.75 (q, J=7.6 Hz, 2H), 1.18 (t, J=7.57 Hz, 3H).

Step 2: Methyl 3-[acetyl(2,2-diethoxyethyl)amino]-3-(5-chloro-2-ethylphenyl)prop-2-enoate Methyl 3-(5-chloro-2-ethylphenyl)prop-2-ynoate (500 mg, 2.25 mmol) in DMF (4.5 mL) was treated with 2,2-diethoxyethanamine (0.368 mL, 2.48 mmol) and heated to 110° C. (oil bath temperature) for 18 h. The volatiles were evaporated under reduced pressure and the crude was heated under reflux in acetic anhydride (9 mL). After 10 h the reaction was completed and removal of the volatiles under reduced pressure afforded the title compound which was employed in the next step without further purification.

Step 3: Methyl 2-(5-chloro-2-ethylphenyl)-H-pyrrole-3-carboxylate

Methyl 3-[acetyl(2,2-diethoxyethyl)amino]-3-(5-chloro-2-ethylphenyl)prop-2-enoate (2.25 mmol) in DCM (0.350 mL) was added to magnesium chloride (43 mg, 0.45 mmol) in TFA (0.6 mL), heated to 65° C. (oil bath temperature). After 0.5 h the reaction was evaporated and the crude isolated by chromatography over silica gel (hexane:EtOAc 8:2) affording the title compound as a yellow crystalline solid (142 mg, 24%).

ESI (+) MS: m/z 264 (MH$^+$).

Step 4: Methyl 2-(5-chloro-2-ethylphenyl)-1-(phenylsulfonyl)-1H-pyrrole-3-carboxylate To a solution of methyl 2-(5-chloro-2-ethylphenyl)-1H-pyrrole-3-carboxylate (0.2 g, 0.76 mmol) in DMF (3 mL) NaH (60% dispersion in oil, 36 mg, 0.91 mmol) was added at 5° C., under argon atmosphere. The reaction mixture was stirred for 1 h, then benzenesulfonyl chloride (0.106 mL, 0.83 mmol) was added dropwise. After 2 h the reaction mixture was added to water and ice under stirring. EtOAc (30 mL) was added, the organic layer was separated and washed with water, brine, dried over $Na_2SO_4$, filtered, the solvent was evaporated under reduced pressure to give an oil, which was purified by Biotage SP1 Flash Chromatography (cyclohexane/EtOAc 9/1) to afford the title compound (248 mg, 81%).

ESI (−) MS: m/z 404 (MH$^+$).

Example 1

5-(6-Aminopyrimidin-4-yl)-2-(5-chloro-2-ethylphenyl)-H-pyrrole-3-carbonitrile (Compd 1)

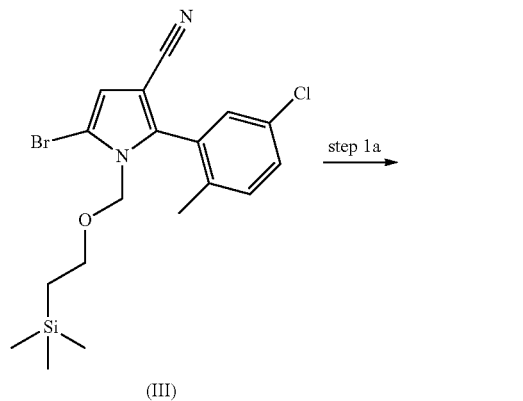

(III)

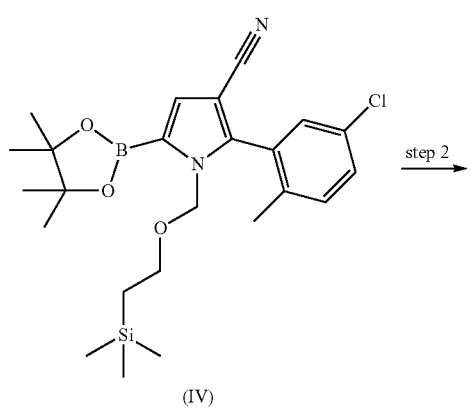

(IV)

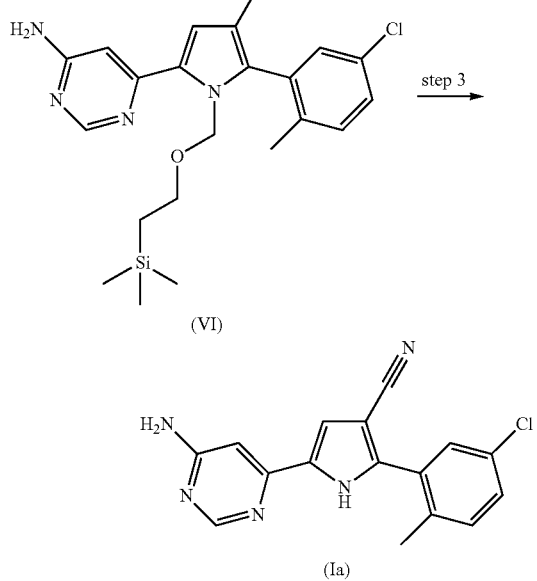

(VI)

(Ia)

Scheme A: Steps 1a, 2, 3

Step 1a: 2-(5-Chloro-2-methylphenyl)-5-(4,4,5,5-tetramethyl-1,3,2-dioxaborolan-2-yl)-1-{[2-(trimethylsilyl)ethoxy]methyl}-1H-pyrrole-3-carbonitrile (IV)

To a solution of 5-bromo-2-(5-chloro-2-methylphenyl)-1-{[2-(trimethylsilyl)ethoxy]methyl}-1H-pyrrole-3-carbonitrile (948 mg, 2.23 mmol) in THF (10 mL) 2-isopropoxy-4,4,5,5-tetramethyl-1,3,2-dioxyborolane (0.683 mL, 3.35 mmol) was added to the mixture at −78° C. under argon. n-BuLi (2.5 M in hexane, 1.95 mL, 5.025 mmol) was slowly added dropwise at −78° C. The mixture was stirred at −78° C. for 1 h. MeOH (1.5 mL) was added and the resultant mixture was stirred at room temperature after slowly raising the temperature. $NH_4Cl$ solution (10 mL) was added and the mixture was extracted with EtOAc (30 mL), washed with aqueous brine, dried over $Na_2SO_4$, filtered, concentrated under reduced pressure and used in the next step without further purification.

Step 2: 5-(6-Aminopyrimidin-4-yl)-2-chloro-2-methylphenyl)-1-{[2-(trimethylsilyl)ethoxy]methyl}-1H-pyrrole-3-carbonitrile (VI)

Into a 50 mL round bottom flask equipped with a stir bar, condenser and 3-way valve connected to argon and vacuum 2-(5-chloro-2-methylphenyl)-5-(4,4,5,5-tetramethyl-1,3,2-dioxaborolan-2-yl)-1-{[2-(trimethylsilyl)ethoxy]methyl}-1H-pyrrole-3-carbonitrile coming from the previous step, 6-iodopyrimidin-4-amine (740 mg, 3.35 mmol), 2M $Na_2CO_3$ (3.35 mL, 6.70 mmol) and dioxane (22 mL) were charged at room temperature. The resulting reaction mixture was degassed three times back filling with argon each time before being charged $PdCl_2(dppf)$ (182 mg, 0.223 mmol). The resulting reaction mixture was degassed four times back filling with argon each time and then warmed to 110° C. for 1 h. The reaction mixture was cooled to room temperature, filtered through a pad of Celite, washed with EtOAc, and the filtrate was concentrated and then diluted with EtOAc (30 mL) and water (10 mL). The two layers were separated, and the aqueous layer was extracted with EtOAc (25 mL). The combined organic fractions were washed with aqueous brine (2×20 mL), dried over $Na_2SO_4$, filtered and concentrated under reduced pressure. The residue was purified by Biotage SP1 Flash Chromatography (DCM/MeOH/7N $NH_3$ in MeOH 97/2/1) to afford the title compound (343 mg, 35%, 2 steps).

$^1$H NMR (400 MHz, DMSO-$d_6$) δ 8.40 (s, 1H), 7.52-7.58 (m, 1H), 7.39-7.51 (m, 2H), 7.15 (s, 1H), 7.01 (d, J=3.6 Hz, 3H), 6.69 (s, 1H), 5.78 (d, J=10.3 Hz, 1H), 5.40 (d, J=10.3 Hz, 1H), 3.02-3.17 (m, 2H), 2.14 (s, 3H), 0.53-0.63 (m, 1H), −0.18 (s, 9H).

HRMS (ESI) m/z calcd for $C_{22}H_{26}ClN_5OSi+H^+$ 440.1668, found 440.1671.

Step 3: 5-(6-Aminopyrimidin-4-yl)-2-(5-chloro-2-methylphenyl)-1H-pyrrole-3-carbonitrile TFA (1.4 mL) was added to a solution of 5-(6-aminopyrimidin-4-yl)-2-(5-chloro-2-methylphenyl)-1-{[2-(trimethylsilyl)ethoxy]methyl}-1H-pyrrole-3-carbonitrile (61 mg, 0.14 mmol) in dry DCM (2.8 mL) and stirred for 4 h at room temperature. After solvent removal, the residue was treated with EtOH (3 mL), 33% $NH_4OH$ (0.4 mL) and stirred for 0.5 h. The solvent was evaporated to dryness and the residue was purified by flash-chromatography (DCM/MeOH/7N $NH_3$ in MeOH 93/7/0.7) to afford the title compound as a solid (28 mg, 65%).

$^1$H NMR (600 MHz, DMSO-$d_6$) δ 12.71 (br. s., 1H), 8.36 (d, J=0.9 Hz, 1H), 7.48-7.53 (m, 1H), 7.44 (d, J=8.4 Hz, 1H), 7.41 (d, J=2.4 Hz, 1H), 7.22 (s, 1H), 6.89 (s, 2H), 6.73 (d, J=1.1 Hz, 1H), 2.14 (s, 3H).

According to this procedure, but using 6-chloro-N-methylpyrimidin-4-amine instead of 6-iodopyrimidin-4-amine in the step 2, the following compound was prepared:

2-(5-Chloro-2-methylphenyl-5-[6-(methylamino)pyrimidin-4-yl]-1H-pyrrole-3-carbonitrile (Compd 2)

ESI (+) MS: m/z 324 (MH$^+$).

According to this procedure, but using 4-chloro-7-{[2-(trimethylsilyl)ethoxy]methyl}-7H-pyrrolo[2,3-d]pyrimidine instead of 6-iodopyrimidin-4-amine in the step 2, the following compound was prepared:

2-(5-Chloro-2-methylphenyl)-5-(7H-pyrrolo[2,3]pyrimidin-4-yl)-1H-pyrrole-3-carbonitrile (Compd 3)

ESI (+) MS: m/z 334 (MH$^+$).

According to this procedure, but using 4-chloro-1-{[2-(trimethylsilyl)ethoxy]methyl}-1H-pyrrolo[2,3-b]pyridine instead of 6-iodopyrimidin-4-amine in the step 2, the following compound was prepared:

2-(5-Chloro-2-methylphenyl)-5-(1H-pyrrolo[2,3-b]pyridin-4-yl)-1H-pyrrole-3-carbonitrile (Compd 4)

$^1$H NMR (400 MHz, DMSO-$d_6$) δ 12.94 (br. s., 1H), 12.21 (br. s., 1H), 8.75 (s, 1H), 7.70 (br. s., 1H), 7.64 (dd, J=2.5, 3.4 Hz, 1H), 7.45-7.52 (m, 2H), 7.39-7.43 (m, 1H), 7.09 (dd, J=1.7, 3.5 Hz, 1H), 2.32 (s, 3H).

HRMS (ESI) m/z calcd for $C_{18}H_{12}ClN_5+H^+$ 334.0854, found 334.0860.

According to this procedure, but using 6-chloro-9-(4-methoxybenzyl)-9H-purine instead of 6-iodopyrimidin-4-amine in the step 2, the following compound was prepared:

2-(5-Chloro-2-methylphenyl)-5-(9H-purin-6-yl)-1H-pyrrole-3-carbonitrile (Compd 5)

ESI (+) MS: m/z 335 (MH$^+$).

According to this procedure, but using 4-chloro-1-{[2-(trimethylsilyl)ethoxy]methyl}-1H-pyrazolo[3,4-d]pyrimidine instead of 6-iodopyrimidin-4-amine in the step 2, the following compound was prepared:

2-(5-Chloro-2-methylphenyl)-5-(1H-pyrazolo[3,4-d]pyrimidin-4-yl)-1H-pyrrole-3-carbonitrile (Compd 6)

ESI (+) MS: m/z 335 (MH$^+$).

According to this procedure, but using 4-chloropyrrolo[2,1-f][1,2,4]triazine instead of 6-iodopyrimidin-4-amine in the step 2, the following compound was prepared:

2-(5-Chloro-2-methylphenyl)-5-(pyrrolo[2,1-f][1,2,4]triazin-4-yl)-1H-pyrrole-3-carbonitrile (Compd 7)

ESI (+) MS: m/z 334 (MH$^+$).

According to this procedure, but using 4-chloro-7-(4-methoxy-benzyl)-6,7-dihydro-5H-pyrrolo[2,3-d]pyrimidine instead of 6-iodopyrimidin-4-amine in the step 2, the following compound was prepared:

2-(5-Chloro-2-methylphenyl)-5-(6,7-dihydro-5H-pyrrolo[2,3-d]pyrimidin-4-yl)-1H-pyrrole-3-carbonitrile (Compd 8)

ESI (+) MS: m/z 336 (MH$^+$).

According to this procedure, but starting from 5-bromo-2-(5-chloro-2-ethylphenyl)-1-{[2-(trimethylsilyl)ethoxy]methyl}-1H-pyrrole-3-carbonitrile in the step 1a, the following compound was prepared:

5-(6-Aminopyrimidin-4-yl)-2-(5-chloro-2-ethylphenyl)-1H-pyrrole-3-carbonitrile (Compd 9)

$^1$H NMR (600 MHz, DMSO-$d_6$) δ 12.71 (br. s., 1H), 8.36 (d, J=0.9 Hz, 1H), 7.48-7.53 (m, 1H), 7.44 (d, J=8.4 Hz, 1H), 7.41 (d, J=2.4 Hz, 1H), 7.22 (s, 1H), 6.89 (s, 2H), 6.73 (d, J=1.1 Hz, 1H), 2.61 (q, J=7.6 Hz, 2H), 1.01 (t, J=7.6 Hz, 3H).

HRMS (ESI) calcd for $C_{17}H_{14}ClN_5+H^+$ 324.1011, found 324.1007.

According to this procedure, but starting from 5-bromo-2-(5-chloro-2-ethylphenyl)-1-{[2-(trimethylsilyl)ethoxy]methyl}-1H-pyrrole-3-carbonitrile in the step Ia and using 6-chloro-N-methylpyrimidin-4-amine instead of 6-iodopyrimidin-4-amine in the step 2, the following compound was prepared:

2-(5-Chloro-2-ethylphenyl)-5-[6-(methylamino)pyrimidin-4-yl]-1H-pyrrole-3-carbonitrile (Compd 10)

$^1$H NMR (600 MHz, DMSO-$d_6$) δ 12.78 (br. s., 1H), 8.54 (br. s., 1H), 8.19 (br. s., 1H), 7.52-7.61 (m, 1H), 7.42-7.52 (m, 3H), 6.90 (br. s., 1H), 2.89 (br. s., 3H), 2.61 (q, J=7.6 Hz, 2H), 1.01 (t, J=7.6 Hz, 3H).

HRMS (ESI) calcd for $C_{18}H_{16}ClN_5+H^+$ 338.1167, found 338.1169.

According to this procedure, but starting from 5-bromo-2-(5-chloro-2-ethylphenyl)-1-{[2-(trimethylsilyl)ethoxy]methyl}-1H-pyrrole-3-carbonitrile in the step 1a and using 4-chloro-7-{[2-(trimethylsilyl)ethoxy]methyl}-7H-pyrrolo[2,3-d]pyrimidine instead of 6-iodopyrimidin-4-amine in the step 2, the following compound was prepared:

2-(5-Chloro-2-ethylphenyl)-5-(7H-pyrrolo[2,3-d]pyrimidin-4-yl)-1H-pyrrole-3-carbonitrile (Compd 11)

$^1$H NMR (600 MHz, DMSO-d$_6$) δ 12.96 (br. s., 1H), 12.21 (br. s., 1H), 8.73 (s, 1H), 7.71 (s, 1H), 7.60-7.66 (m, 1H), 7.50-7.55 (m, 1H), 7.40-7.47 (m, 2H), 7.09 (d, J=2.0 Hz, 1H), 2.65 (q, J=7.5 Hz, 2H), 1.03 (t, J=7.5 Hz, 3H).

HRMS (ESI) calcd for $C_{19}H_{14}ClN_5+H^+$ 348.1011, found 348.1014.

According to this procedure, but starting from 5-bromo-2-(5-chloro-2-ethylphenyl)-1-{[2-(trimethylsilyl)ethoxy]methyl}-1H-pyrrole-3-carbonitrile in the step 1a and using 6-chloro-9-(4-methoxybenzyl)-9H-purine instead of 6-iodopyrimidin-4-amine in the step 2, the following compound was prepared:

2-(5-Chloro-2-ethylphenyl)-5-(9H-purin-6-yl)-1H-pyrrole-3-carbonitrile (Compd 12)

ESI (+) MS: m/z 349 (MH$^+$).

According to this procedure, but starting from 5-bromo-2-(5-chloro-2-ethylphenyl)-1-{[2-(trimethylsilyl)ethoxy]methyl}-1H-pyrrole-3-carbonitrile in the step 1a and using 4-chloro-1-{[2-(trimethylsilyl)ethoxy]methyl}-1H-pyrazolo[3,4-d]pyrimidine instead of 6-iodopyrimidin-4-amine in the step 2, the following compound was prepared:

2-(5-Chloro-2-ethylphenyl)-5-(1H-pyrazolo[3,4-d]pyrimidin-4-yl)-1H-pyrrole-3-carbonitrile (Compd 13)

ESI (+) MS: m/z 349 (MH$^+$).

According to this procedure, but starting from 5-bromo-2-(5-chloro-2-ethylphenyl)-1-{[2-(trimethylsilyl)ethoxy]methyl}-1H-pyrrole-3-carbonitrile in the step 1a and using 4-chloropyrrolo[2,1-f][1,2,4]triazine instead of 6-iodopyrimidin-4-amine in the step 2, the following compound was prepared:

2-(5-Chloro-2-ethylphenyl)-5-(pyrrolo[2,1-f][1,2,4]triazin-4-yl)-1H-pyrrole-3-carbonitrile (Compd 14)

ESI (+) MS: m/z 348 (MH$^+$).

According to this procedure, but starting from 5-bromo-2-(5-chloro-2-ethylphenyl)-1-{[2-(trimethylsilyl)ethoxy]methyl}-1H-pyrrole-3-carbonitrile in the step 1a and using 4-chloro-7-(4-methoxy-benzyl)-6,7-dihydro-5H-pyrrolo[2,3-d]pyrimidine instead of 6-iodopyrimidin-4-amine in the step 2, the following compound was prepared:

2-(5-Chloro-2-ethylphenyl-5-(6,7-dihydro-5H-pyrrolo[2,3-d]pyrimidin-4-yl)-1H-pyrrole-3-carbonitrile (Compd 15)

ESI (+) MS: m/z 350 (MH$^+$).

According to this procedure, but starting from 5-bromo-2-[2-chloro-5-(trifluoromethyl)phenyl]-1-{[2-(trimethylsilyl)ethoxy]methyl}-1H-pyrrole-3-carbonitrile in the step 1a, the following compound was prepared:

5-(6-Aminopyrimidin-4 yl)-2-[2-chloro-5-(trifluoromethyl)phenyl]-1H-pyrrole-3-carbonitrile (Compd 16)

$^1$H NMR (600 MHz, DMSO-d$_6$) δ 12.90 (br. s., 1H), 8.38 (d, J=1.1 Hz, 1H), 7.96 (s, 1H), 7.84-7.92 (m, 2H), 7.28 (s, 1H), 6.94 (s, 2H), 6.75 (d, J=1.28 Hz, 1H).

HRMS (ESI) calcd for $C_{16}H_9ClF_3N_5+H^+$ 364.0572, found 364.0572.

According to this procedure, but starting from 5-bromo-2-[2-chloro-5-(trifluoromethyl)phenyl]-1-{[2-(trimethylsilyl)ethoxy]methyl}-1H-pyrrole-3-carbonitrile in the step 1a and using 6-chloro-N-methylpyrimidin-4-amine instead of 6-iodopyrimidin-4-amine in the step 2, the following compound was prepared:

2-[2-Chloro-5-(trifluoromethyl)phenyl]-5-[6-(methylamino)pyrimidin-4-yl]-1H-pyrrole-3-carbonitrile (Compd 17)

$^1$H NMR (600 MHz, DMSO-d$_6$) δ 12.53-13.20 (m, 1H), 8.44 (br. s., 1H), 7.72-8.05 (m, 3H), 7.23-7.56 (m, 1H), 6.82 (br. s., 1H), 2.84 (d, J=3.5 Hz, 3H).

HRMS (ESI) calcd for $C_{17}H_{11}ClF_3N_5+H^+$ 378.0728, found 378.0732.

According to this procedure, but starting from 5-bromo-2-[2-chloro-5-(trifluoromethyl)phenyl]-1-{[2-(trimethylsilyl)ethoxy]methyl}-1H-pyrrole-3-carbonitrile in the step 1a and using 4-chloro-7-{[2-(trimethylsilyl)ethoxy]methyl}-7H-pyrrolo[2,3-d]pyrimidine instead of 6-iodopyrimidin-4-amine in the step 2, the following compound was prepared:

2-[2-Chloro-5-(trifluoromethyl)phenyl]-5-(7H-pyrrolo[2,3-d]pyrimidin-4-yl)-1H-pyrrole-3-carbonitrile (Compd 18)

ESI (+) MS: m/z 388 (MH$^+$).

According to this procedure, but starting from 5-bromo-2-[2-chloro-5-(trifluoromethyl)phenyl]-1-{[2-(trimethylsilyl)ethoxy]methyl}-1H-pyrrole-3-carbonitrile in the step 1a and using 6-chloro-9-(4-methoxybenzyl)-9H-purine instead of 6-iodopyrimidin-4-amine in the step 2, the following compound was prepared:

2-[2-Chloro-5-(trifluoromethyl)phenyl]-5-(9H-purin-8-yl-1H-pyrrole-3-carbonitrile (Compd 19)

ESI (+) MS: m/z 389 (MH$^+$).

According to this procedure, but starting from 5-bromo-2-[2-chloro-5-(trifluoromethyl)phenyl]-1-{[2-(trimethylsilyl)ethoxy]methyl}-1H-pyrrole-3-carbonitrile in the step 1a and using 4-chloro-1-{[2-(trimethylsilyl)ethoxy]methyl}-1H-pyrazolo[3,4-d]pyrimidine instead of 6-iodopyrimidin-4-amine in the step 2, the following compound was prepared:

2-[2-Chloro-5-(trifluoromethyl)phenyl]-5-(1H-pyrazolo[3,4-d]pyrimidin-4-yl)-1H-pyrrole-3-carbonitrile (Compd 20)

ESI (+) MS: m/z 389 (MH$^+$).

According to this procedure, but starting from 5-bromo-2-[2-chloro-5-(trifluoromethyl)phenyl]-1-{[2-(trimethylsilyl)ethoxy]methyl}-1H-pyrrole-3-carbonitrile in the step 1a and using 4-chloropyrrolo[2,1-f][1,2,4]triazine instead of 6-iodopyrimidin-4-amine in the step 2, the following compound was prepared:

2-[2-Chloro-5-(trifluoromethyl)phenyl]-5-(pyrrolo[2,1-f][1,2,4]triazin-4-yl)-1H-pyrrole-3-carbonitrile (Compd 21)

ESI (+) MS: m/z 388 (MH$^+$).

According to this procedure, but starting from 5-bromo-2-[2-chloro-5-(trifluoromethyl)phenyl]-1-{[2-(trimethylsilyl)ethoxy]methyl}-1H-pyrrole-3-carbonitrile in the step 1a and using 4-chloro-7-(4-methoxy-benzyl)-6,7-dihydro-5H-pyrrolo[2,3-d]pyrimidine instead of 6-iodopyrimidin-4-amine in the step 2, the following compound was prepared:

2-[2-Chloro-5-(trifluoromethyl)phenyl]-(6,7-dihydro-5H-pyrrolo[2,3-d]pyrimidin-4-yl)-1H-pyrrole-3-carbonitrile (Compd 22)

ESI (+) MS: m/z 390 (MH$^+$).

According to this procedure, but starting from 5-bromo-2-[2-methyl-5-(trifluoromethyl)phenyl]-1-{[2-(trimethylsilyl)ethoxy]methyl}-1H-pyrrole-3-carbonitrile in the step 1a, the following compound was prepared:

5-(6-Aminopyrimidin-4-yl)-2-[2-methyl-5-(fluromethyl)phenyl]-1H-pyrrole-3-carbonitrile (Compd 23)

$^1$H NMR (600 MHz, DMSO-d$_6$) δ 12.77 (br. s., 1H), 8.37 (d, J=0.9 Hz, 1H), 7.76 (d, J=8.0 Hz, 1H), 7.71 (s, 1H), 7.62 (d, J=8.0 Hz, 1H), 7.25 (s, 1H), 6.91 (s, 2H), 6.74 (d, J=1.1 Hz, 1H), 2.41 (s, 3H).

HRMS (ESI) calcd for C$_{17}$H$_{12}$F$_3$N$_5$+H$^+$ 344.1118, found 344.1116.

According to this procedure, but starting from 5-bromo-2-[2-methyl-5-(trifluoromethyl)phenyl]-1-{[2-(trimethylsilyl)ethoxy]methyl}-1H-pyrrole-3-carbonitrile in the step 1a and using 6-chloro-N-methylpyrimidin-4-amine instead of 6-iodopyrimidin-4-amine in the step 2, the following compound was prepared:

5-[6-(Methylamino)pyrimidin-4-yl]-2-[2-methyl-5-(trifluoromethyl)phenyl]-1H-pyrrole-3-carbonitrile (Compd 24)

$^1$H NMR (600 MHz, DMSO-d$_6$) δ 12.76 (br. s., 1H), 8.42 (br. a, 1H), 7.76 (d, J=7.9 Hz, 1H), 7.72 (s, 1H), 7.63 (d, J=7.9 Hz, 1H), 7.35 (br. s., 2H), 6.81 (br. s., 1H), 2.83 (d, J=4.21 Hz, 3H), 2.41 (s, 3H).

HRMS (ESI) calcd for C$_{18}$H$_{14}$F$_3$N$_5$+H$^+$ 358.1274, found 358.1271.

According to this procedure, but starting from 5-bromo-2-[2-methyl-5-(trifluoromethyl)phenyl]-1-{[2-(trimethylsilyl)ethoxy]methyl}-1H-pyrrole-3-carbonitrile in the step 1a and using 4-chloro-7-{[2-(trimethylsilyl)ethoxy]methyl}-7H-pyrrolo[2,3-d]pyrimidine instead of 6-iodopyrimidin-4-amine in the step 2, the following compound was prepared:

2-[2-Methyl-5-(trifluoromethyl)phenyl]-5-(7H-pyrrolo[2,3-d]pyrimidin-4-yl)-1H-pyrrole-3-carbonitrile (Compd 25)

ESI (+) MS: m/z 368 (MH$^+$).

According to this procedure, but starting from 5-bromo-2-[2-methyl-5-(trifluoromethyl)phenyl]-1-{[2-(trimethylsilyl)ethoxy]methyl}-1H-pyrrole-3-carbonitrile in the step 1a and using 4-chloropyrrolo[2,1-f][1,2,4]triazine instead of 6-iodopyrimidin-4-amine in the step 2, the following compound was prepared:

2-[2-Methyl-5-(trifluoromethyl)phenyl]-5-(pyrrolo[2,1-f][1,2,4]triazin-4-yl)-1H-pyrrole-3-carbonitrile (Compd 26)

ESI (+) MS: m/z 368 (MH$^+$).

According to this procedure, but starting from 5-bromo-2-[2-methyl-5-(trifluoromethyl)phenyl]-1-{[2-(trimethylsilyl)ethoxy]methyl}-1H-pyrrole-3-carbonitrile in the step 1a and using 4-chloro-7-(4-methoxy-benzyl)-6,7-dihydro-5H-pyrrolo[2,3-d]pyrimidine instead of 6-iodopyrimidin-4-amine in the step 2, the following compound was prepared:

2-[2-Methyl-5-(trifluoromethyl)phenyl]-5-(6,7-dihydro-5H-pyrrolo[2,3-d]pyrimidin-4-yl)-1H-pyrrole-3-carbonitrile (Compd 27)

ESI (+) MS: m/z 370 (MH$^+$).

According to this procedure, but starting from 5-bromo-2-[2-ethyl-5-(trifluoromethyl)phenyl]-1-{[2-(trimethylsilyl)ethoxy]methyl}-1H-pyrrole-3-carbonitrile in the step 1a, the following compound was prepared:

5-(6-Aminopyrimidin-4-yl)-2-[2-ethyl-5-(trifluoromethyl)phenyl]-1H-pyrrole-3-carbonitrile (Compd 28)

ESI (+) MS: m/z 358 (MH$^+$).

According to this procedure, but starting from 5-bromo-2-[2-ethyl-5-(trifluoromethyl)phenyl]-1-{[2-(trimethylsilyl)ethoxy]methyl}-1H-pyrrole-3-carbonitrile in the step 1a and using 6-chloro-N-methylpyrimidin-4-amine instead of 6-iodopyrimidin-4-amine in the step 2, the following compound was prepared:

5-[6-(Methylamino)pyrimidin-4-yl]-2-[2-ethyl-5-(trifluoromethyl)phenyl]-1H-pyrrole-3-carbonitrile (Compd 29)

ESI (+) MS: m/z 372 (MH$^+$).

According to this procedure, but starting from 5-bromo-2-[2-ethyl-5-(trifluoromethyl)phenyl]-1-{[2-(trimethylsilyl)ethoxy]methyl}-1H-pyrrole-3-carbonitrile in the step 1a and using 4-chloro-7-{[2-(trimethylsilyl)ethoxy]methyl}-7H-pyrrolo[2,3-d]pyrimidine instead of 6-iodopyrimidin-4-amine in the step 2, the following compound was prepared:

2-[2-Ethyl-5-(trifluoromethyl)phenyl]-5-(7H-pyrrolo[2,3-d]pyrimidin-4-yl)-1H-pyrrole-3-carbonitrile (Compd 30)

$^1$H NMR (600 MHz, DMSO-d$_6$) δ 13.05 (br. s., 1H), 12.22 (br. s., 1H), 8.74 (s, 1H), 7.82 (d, J=8.6 Hz, 1H), 7.74 (s, 1H), 7.72 (s, 1H), 7.67 (d, J=8.0 Hz, 1H), 7.62-7.66 (m, J=2.7 Hz, 1H), 7.10 (d, J=2.4 Hz, 1H), 2.76 (q, J=7.6 Hz, 2H), 1.08 (t, J=7.5 Hz, 3H).

ESI (+) MS: m/z 382 (MH$^+$).

According to this procedure, but starting from 5-bromo-2-[2-ethyl-5-(trifluoromethyl)phenyl]-1-{[2-(trimethylsilyl)ethoxy]methyl}-1H-pyrrole-3-carbonitrile in the step 1a and using 4-chloropyrrolo[2,1-f][1,2,4]triazine instead of 6-iodopyrimidin-4-amine in the step 2, the following compound was prepared:

2-[2-Ethyl-5-(trifluoromethyl)phenyl]-5-(pyrrolo[2,1-f][1,2,4]triazin-4-yl)-1H-pyrrole-3-carbonitrile (Compd 31)

ESI (+) MS: m/z 382 (MH+).

According to this procedure, but starting from 5-bromo-2-[2-ethyl-5-(trifluoromethyl)phenyl]-1-{[2-(trimethylsilyl)ethoxy]methyl}-1H-pyrrole-3-carbonitrile in the step 1a and using 4-chloro-7-(4-methoxy-benzyl)-6,7-dihydro-5H-pyrrolo[2,3-d]pyrimidine instead of 6-iodopyrimidin-4-amine in the step 2, the following compound was prepared:

5-(6,7-Dihydro-5H-pyrrolo[2,3-d]pyrimidin-4-yl)-2-[2-ethyl-5-(trifluoromethyl)phenyl]-1H-pyrrole-3-carbonitrile (Compd 32)

ESI (+) MS: m/z 384 (MH+).

According to this procedure, but starting from 5-bromo-2-phenyl-1-{[2-(trimethylsilyl)ethoxy]methyl}-1H-pyrrole-3-carbonitrile in the step 1a, the following compound was prepared:

5-(6-Aminopyrimidin-4-yl)-2-phenyl-1H-pyrrole-3-carbonitrile (Compd 33)

ESI (+) MS: m/z 262 (MH+).

According to this procedure, but starting from 5-bromo-2-phenyl-1-{[2-(trimethylsilyl)ethoxy]methyl}-1H-pyrrole-3-carbonitrile in the step 1a and using 6-chloro-N-methylpyrimidin-4-amine instead of 6-iodopyrimidin-4-amine in the step 2, the following compound was prepared:

5-[6-(Methylamino)pyrimidin-4-yl]-2-phenyl-1H-pyrrole-3-carbonitrile (Compd 34)

$^1$H NMR (600 MHz, DMSO-d$_6$) δ 12.64 (br. s., 1H), 8.54 (br. s., 1H), 7.79-7.88 (m, 1H), 7.57 (t, J=7.7 Hz, 1H), 7.47-7.51 (m, 1H), 7.35-7.41 (m, 1H), 6.93 (br. s., 1H), 2.90 (d, J=4.40 Hz, 3H).

HRMS (ESI) calcd for C$_{16}$H$_{13}$N$_5$+H+ 276.1244, found 276.1243.

According to this procedure, but starting from 5-bromo-2-phenyl-1-{[2-(trimethylsilyl)ethoxy]methyl}-1H-pyrrole-3-carbonitrile in the step 1a and using 4-chloro-7-{[2-(trimethylsilyl)ethoxy]methyl}-7H-pyrrolo[2,3-d]pyrimidine instead of 6-iodopyrimidin-4-amine in the step 2, the following compound was prepared:

2-Phenyl-5-(7H-pyrrolo[2,3-d]pyrimidin-4-yl)-1H-pyrrole-3-carbonitrile (Compd 35)

ESI (+) MS: m/z 286 (MH+).

According to this procedure, but starting from 5-bromo-2-phenyl-1-{[2-(trimethylsilyl)ethoxy]methyl}-1H-pyrrole-3-carbonitrile in the step 1a and using 4-chloropyrrolo[2,1-f][1,2,4]triazine instead of 6-iodopyrimidin-4-amine in the step 2, the following compound was prepared:

2-Phenyl-5-(pyrrolo[2,1-f][1,2,4]triazin-4-yl)-1H-pyrrole-3-carbonitrile (Compd 36)

ESI (+) MS: m/z 286 (MH+).

According to this procedure, but starting from 5-bromo-2-phenyl-1-{[2-(trimethylsilyl)ethoxy]methyl}-1H-pyrrole-3-carbonitrile in the step 1a and using 4-chloro-7-(4-methoxy-benzyl)-6,7-dihydro-5H-pyrrolo[2,3-d]pyrimidine instead of 6-iodopyrimidin-4-amine in the step 2, the following compound was prepared:

2-Phenyl-5-(pyrrolo[2,1-f][1,2,4]triazin-4-yl)-1H-pyrrole-3-carbonitrile (Compd 37)

ESI (+) MS: m/z 288 (MH+).

Example 2

5-(6-Aminopyrimidin-4-yl)-2-(5-chloro-2-ethylphenyl)-H-pyrrole-3-carbonitrile (Compd 9)

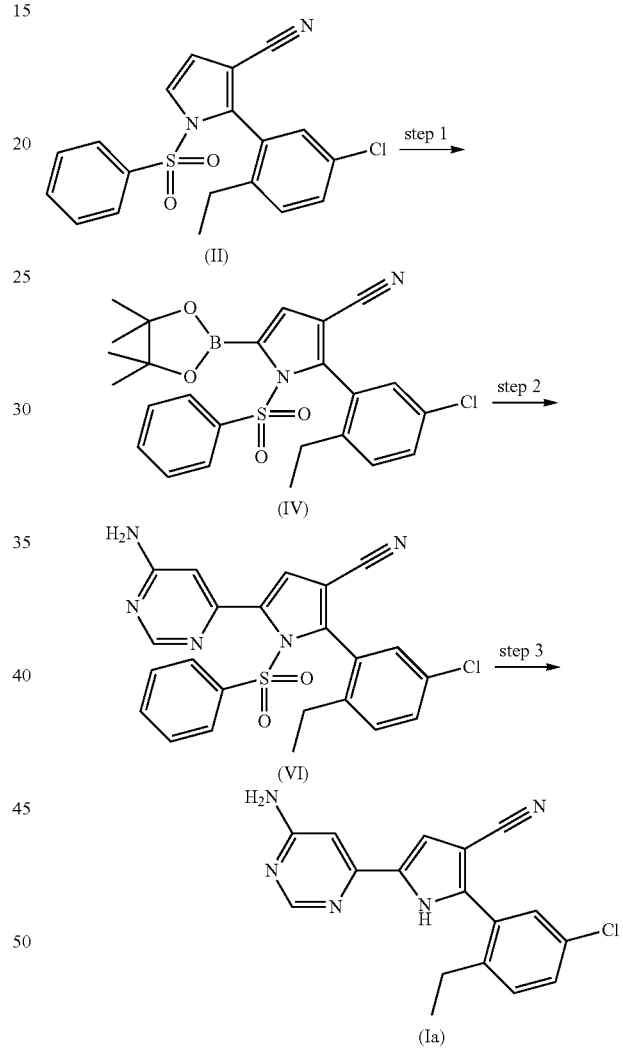

Scheme A: Steps 1, 2, 3

Step 1: 2-(5-Chloro-2-ethylphenyl)-1-(phenylsulfonyl)-5-(4,4,5,5-tetramethyl-1,3,2-dioxaborolan-2-yl)-1H-pyrrole-3-carbonitrile (IV)

To a solution of 2-(5-chloro-2-ethylphenyl)-1-(phenylsulfonyl)-1H-pyrrole-3-carbonitrile (1.02 g, 2.77 mmol) and 2-isopropoxy-4,4,5,5-tetramethyl-1,3,2-dioxyborolane (0.791 mL, 3.88 mmol) in THF (8.5 mL) LDA (2M in THF/heptane/ethylbenzene, 4.6 mL, 9.15 mmol) was slowly added dropwise at −78° C. under argon. After 50 min, MeOH (4 mL) was added, the temperature was allowed to rise and NH₄Cl solution (20 mL) was added drop wise at room temperature. The reaction was then diluted with water and extracted with Et₂O, dried over Na₂SO₄, filtered and the solvent was evaporated under reduced pressure to afford the title compound that was used without further purification.

Step 2: 5-(6-Aminopyrimidin-4-yl)-2-(chloro-2-ethylphenyl)-1-(phenylsulfonyl)-1H-pyrrole-3-carbonitrile (VI)

2-(5-Chloro-2-ethylphenyl)-1-(phenylsulfonyl)-5-(4,4,5,5-tetramethyl-1,3,2-dioxaborolan-2-yl)-1H-pyrrole-3-carbonitrile (2.77 mmol), 6-iodopyrimidin-4-amine (918 mg, 4.16 mmol), PdCl₂(dppf) (226 mg, 0.277 mmol) and Cs₂CO₃ (2.71 g, 8.31 mmol) were degassed and back filled with argon and then dissolved in dioxane (20 mL) and water (4 mL) under nitrogen. The reaction mixture was stirred at room temperature over night, then diluted with EtOAc, washed with aqueous brine, dried over Na₂SO₄, filtered and concentrated under reduced pressure. The residue was purified by Biotage SP1 Flash Chromatography (DCM/MeOH/NH₃ 7 N in MeOH 95/5/0.5) to afford the title compound (540 mg, 39%, 2 steps).

¹H NMR (600 MHz, DMSO-d₆) δ 8.45 (d, J=0.92 Hz, 1H), 7.82 (t, J=7.42 Hz, 1H), 7.71-7.78 (m, 1H), 7.59-7.63 (m, 1H), 7.56 (dd, J=2.29, 8.33 Hz, 1H), 7.39 (d, J=8.43 Hz, 1H), 7.11 (br. s., 1H), 7.09 (s, 1H), 6.83 (d, J=2.20 Hz, 1H), 6.64 (d, J=1.10 Hz, 1H), 2.03-2.24 (m, 2H), 1.01 (t, J=7.60 Hz, 3H).

HRMS (ESI) m/z calcd for $C_{23}H_{18}N_5O_2SCl+H^+$ 464.0943, found 464.0938.

Step 3: 5-(6-Aminopyrimidin-4-yl)-2-(5-chloro-2-ethylphenyl-1H-pyrrole-3-carbonitrile 5-(6-Aminopyrimidin-4-yl)-2-(5-chloro-2-ethylphenyl)-1-(phenylsulfonyl)-1H-pyrrole-3-carbonitrile (299 mg, 0.647 mmol) in THF (6.5 mL) was treated with LiOH.H₂O (109 mg, 2.59 mmol) in water (3 mL) and heated under reflux for two days. After cooling, the residue was diluted with water (20 mL) and washed with Et₂O (20 mL). The aqueous phase was slowly added to 1N HCl (7 mL) in iced water (70 mL) under stirring and the white solid was collected by filtration affording after drying at 50° C. under vacuum, the title compound (157 mg, 70%).

¹H NMR (600 MHz, DMSO-d₆) δ 12.71 (br. s., 1H), 8.36 (d, J=0.9 Hz, 1H), 7.48-7.53 (m, 1H), 7.44 (d, J=8.4 Hz, 1H), 7.41 (d, J=2.4 Hz, 1H), 7.22 (s, 1H), 6.89 (s, 2H), 6.73 (d, J=1.1 Hz, 1H), 2.61 (q, J=7.6 Hz, 2H), 1.01 (t, J=7.6 Hz, 3H).

HRMS (ESI) calcd for $C_{17}H_{14}ClN_5+H^+$ 324.1011, found 324.1007.

Example 3

5-(6-Aminopyrimidin-4-yl)-2-phenyl-1H-pyrrole-3-carboxamide (Compd 38)

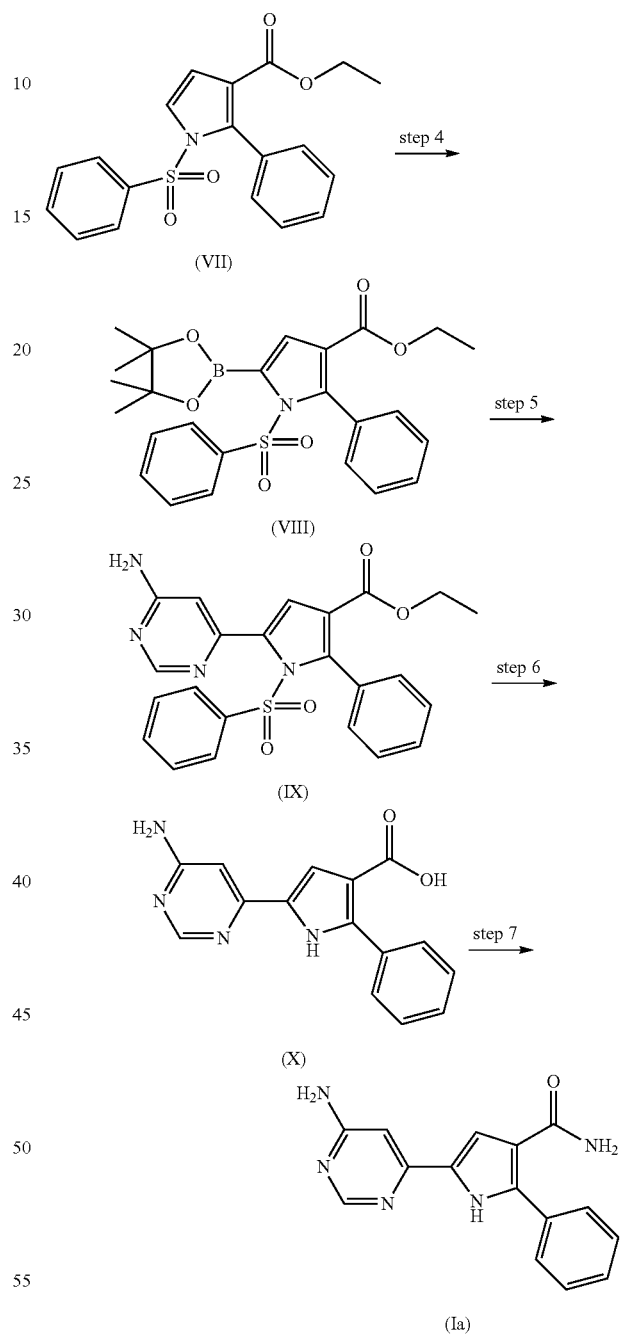

Scheme B: Steps 4, 5, 6, 7

Step 4: Ethyl 2-phenyl-1-(phenylsulfonyl)-5-(4,4,5,5-tetramethyl-1,3,2-dioxaborolan-2-yl)-1H-pyrrole-3-carboxylate (VIII)

To a solution of ethyl 2-phenyl-1-(phenylsulfonyl)-1H-pyrrole-3-carboxylate (440 mg, 1.24 mmol) and 2-isopropoxy-4,4,5,5-tetramethyl-1,3,2-dioxyborolane (0.303 mL, 1.2 mmol) in THF (1.9 mL) LDA (2M in THF/heptane/ethylbenzene, 1.61 mL, 3.22 mmol) was slowly added dropwise at −78° C. under argon. After 50 min, MeOH (1 mL) was added, the temperature was allowed to rise and $NH_4Cl$ solution (2 mL) was added drop wise at room temperature. The reaction was the diluted with water and extracted with $Et_2O$, dried over $Na_2SO_4$, filtered and the solvent was evaporated under reduced pressure to afford the title compound that was used without further purification.

Step 5: Ethyl 5-(6-aminopyrimidin-4-yl)-2-phenyl)-1-(phenylsulfonyl)-1H-pyrrole-3-carboxylate (IX)

Ethyl 2-phenyl-1-(phenylsulfonyl)-5-(4,4,5,5-tetramethyl-1,3,2-dioxaborolan-2-yl)-1H-pyrrole-3-carboxylate (1.24 mmol), 6-iodopyrimidin-4-amine (411 mg, 1.86 mmol), $PdCl_2(dppf)$ (101 mg, 0.124 mmol) and $Na_2CO_3$ (394 mg, 3.72 mmol) were degassed and back filled with argon and then dissolved in dioxane (12 mL) and water (1.9 mL) under nitrogen. The reaction mixture was stirred at room temperature over night, then diluted with EtOAc, washed with aqueous brine, dried over $Na_2SO_4$, filtered and concentrated under reduced pressure. The residue was purified by Biotage SP1 Flash Chromatography (DCM/MeOH/$NH_3$ 7 N in MeOH 95/5/0.5) to afford the title compound (240 mg, 43%, 2 steps).

$^1$H NMR (600 MHz, DMSO-$d_6$) δ 8.42 (d, J=1.1 Hz, 1H), 7.72 (quin, J=4.3 Hz, 1H), 7.48-7.53 (m, 4H), 7.37-7.44 (m, 1H), 7.26 (t, J=7.7 Hz, 2H), 7.00 (s, 2H), 6.96 (dd, J=1.2, 8.1 Hz, 2H), 6.82-6.86 (m, 1H), 6.67-6.70 (m, 1H), 3.95 (q, J=7.0 Hz, 2H), 0.87-1.01 (m, 3H).

HRMS (ESI) m/z calcd for $C_{23}H_{20}N_4O_4S+H^+$ 449.1278, found 449.1273.

Step 6: 5-(6-Aminopyrimidin-4-yl)-2-phenyl-1H-pyrrole-3-carboxylic Acid (X)

Ethyl 5-(6-aminopyrimidin-4-yl)-2-phenyl)-1-(phenylsulfonyl)-1H-pyrrole-3-carboxylate (290 mg, 0.647 mmol) in THF (6.5 mL) was treated with LiOH.$H_2O$ (109 mg, 2.59 mmol) in water (3 mL) and heated under reflux for two days. After cooling, the residue was diluted with water (20 mL) and washed with $Et_2O$ (20 mL). The aqueous phase was slowly added to 1N HCl (7 mL) in iced water (70 mL) under stirring and the white solid was collected by filtration affording, after drying at 50° C. under vacuum, the title compound (153 mg, 85%).

$^1$H NMR (600 MHz, DMSO-$d_6$) δ 12.42 (br. s., 1H), 12.10 (br. s., 1H), 8.53 (br. s., 1H), 7.63 (d, J=6.8 Hz, 2H), 7.39-7.48 (m, 4H), 7.25-7.34 (m, 1H), 6.94 (br. s., 1H).

HRMS (ESI) m/z calcd for $C_{15}H_{12}N_4O_2+H^+$ 281.1033, found 281.1033.

Step 7: 5-(6-Aminopyrimidin-4-yl)-2-phenyl-1H-pyrrole-3-carboxamide

A solution of 5-(6-aminopyrimidin-4-yl)-2-phenyl-1H-pyrrole-3-carboxylic acid (40 mg, 0.143 mmol) in DMF (0.5 mL) and DIPEA (99 µL, 0.571 mmol) was stirred at 0° C. EDCl (55 mg, 0.286 mmol) and HOBT.$NH_3$ (44 mg, 0.286 mmol) were added and the reaction mixture was stirred over night at room temperature. The reaction was diluted with saturated solution of $NaHCO_3$ (20 mL), extracted with EtOAc (50 mL), dried over $Na_2SO_4$, filtered. The solvent was evaporated under reduced pressure and the crude was purified by Biotage SP1 Flash Chromatography (DCM/MeOH/$NH_3$ 7 N in MeOH 9/1/0.1) to afford the title compound (35 mg, 89%).

$^1$H NMR (600 MHz, DMSO-$d_6$) δ 11.77 (br. s., 1H), 8.33 (s, 1H), 7.64 (d, J=7.1 Hz, 2H), 7.35-7.40 (m, 2H), 7.28-7.34 (m, 2H), 7.19 (s, 1H), 6.79 (br. s., 1H), 6.76 (s, 2H), 6.73 (d, J=1.1 Hz, 1H).

HRMS (ESI) m/z calcd for $C_{15}H_{13}N_5O+H^+$ 280.1193, found 280.1196.

According to this procedure, but using 6-chloro-N-methylpyrimidin-4-amine instead of 6-iodopyrimidin-4-amine in the step 5, the following compound was prepared:

5-[6-(Methylamino)pyrimidin-4-yl]-2-phenyl-1H-pyrrole-3-carboxamide (Compd 39)

$^1$H NMR (600 MHz, DMSO-$d_6$) δ 11.77 (br. s., 1H), 8.36 (br. s., 1H), 7.62-7.65 (m, 2H), 7.37-7.42 (m, 2H), 7.32-7.36 (m, 1H), 7.30 (br. s., 1H), 7.26 (br. s., 1H), 7.18 (br. s., 1H), 6.80 (br. s., 2H), 2.82 (d, J=4.58 Hz, 3H).

HRMS (ESI) calcd for $C_{16}H_{15}N_5O+H^+$ 294.1350, found 294.1350.

According to this procedure, but using 4-chloropyrrolo[2,1-f][1,2,4]triazine instead of 6-iodopyrimidin-4-amine in the step 5, the following compound was prepared:

2-Phenyl-5-(pyrrolo[2,1-f][1,2,4]triazin-4-yl)-1H-pyrrole-3-carboxamide (Compd 40)

ESI (+) MS: m/z 304 (MH$^+$).

According to this procedure, but using methylamine in the step 7, the following compound was prepared:

5-(6-Aminopyrimidin-4-yl)-2-phenyl-N-methyl-1H-pyrrole-3-carboxamide (Compd 41)

$^1$H NMR (600 MHz, DMSO-$d_6$) δ 11.77 (br. s., 1H), 8.33 (d, J=0.9 Hz, 1H), 7.83 (q, J=4.2 Hz, 1H), 7.60-7.67 (m, 2H), 7.35-7.40 (m, 2H), 7.28-7.34 (m, 1H), 7.14 (s, 1H), 6.76 (s, 2H), 6.73 (d, J=1.1 Hz, 1H), 2.67 (d, J=4.6 Hz, 3H).

HRMS (ESI) m/z calcd for $C_{16}H_{15}N_5O+H^+$ 294.1350, found 294.1348.

According to this procedure, but using 6-chloro-N-methylpyrimidin-4-amine instead of 6-iodopyrimidin-4-amine in the step 5 and methylamine in the step 7, the following compound was prepared:

N-methyl-5-[6-(methylamino)pyrimidin-4-yl]-2-phenyl-1H-pyrrole-3-carboxamide (Compd 42)

$^1$H NMR (600 MHz, DMSO-$d_6$) δ 11.78 (br. s., 1H), 8.37 (br. s., 1H), 7.83 (d, J=4.58 Hz, 1H), 7.59-7.66 (m, 2H), 7.37-7.41 (m, 2H), 7.33 (d, J=7.33 Hz, 1H), 7.21 (br. s., 2H), 6.81 (br. s., 1H), 2.83 (d, J=4.58 Hz, 3H), 2.67 (d, J=4.58 Hz, 3H).

HRMS (ESI) m/z calcd for $C_{17}H_{17}N_5O+H^+$ 308.1506, found 308.1501.

According to this procedure, but using 4-chloropyrrolo[2,1-f][1,2,4]triazine instead of 6-iodopyrimidin-4-amine in the step 5 and methylamine in the step 7, the following compound was prepared:

N-methyl-2-phenyl-5-(pyrrolo[2,1-f][1,2,4]triazin-4-yl)-1H-pyrrole-3-carboxamide (Compd 43)

ESI (+) MS: m/z 318 (MH$^+$).

Example 4

4-(6-Aminopyrimidin-4-yl)-1-(5-chloro-2-methylphenyl)-H-pyrrole-2-carbonitrile (Compd 44)

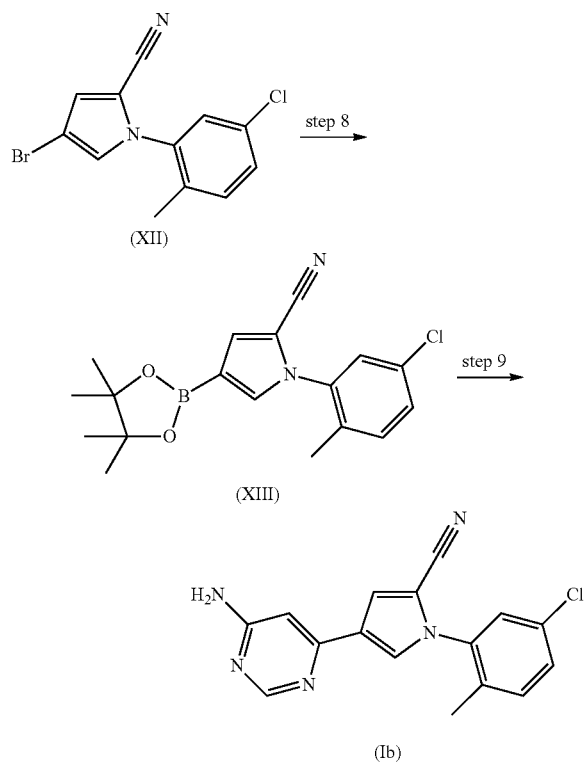

Scheme C: Steps 8, 9

Step 8: 1-(5-Chloro-2-methylphenyl)-4-(4,4,5,5-tetramethyl-1,3,2-dioxaborolan-2-yl)-1H-pyrrole-2-carbonitrile (XIII)

To a solution of 4-bromo-1-(5-chloro-2-methylphenyl)-1H-pyrrole-2-carbonitrile (591 mg, 2.0 mmol) in THF (10 mL) 2-isopropoxy-4,4,5,5-tetramethyl-1,3,2-dioxyborolane (0.446 mL, 2.2 mmol) was added to the mixture at −78° C. under argon. n-BuLi (2.5M in hexane, 0.88 mL, 2.2 mmol) was slowly added dropwise at −78° C. The mixture was stirred at −78° C. for 1 h. MeOH (1.0 mL) was added and the resultant mixture was stirred at room temperature after slowly raising the temperature. NH$_4$Cl solution (10 mL) was added and the mixture was extracted with EtOAc (3×30 mL), washed with aqueous brine, dried over Na$_2$SO$_4$, distilled under reduced pressure and used in the next step without further purification.

$^1$H NMR (600 MHz, DMSO-d$_6$) δ 7.59 (d, J=1.5 Hz, 1H), 7.52-7.57 (m, 2H), 7.44-7.50 (m, 1H), 7.32 (d, J=1.5 Hz, 1H), 2.03 (s, 3H), 1.27 (s, 12H).

Step 9: 4-(6-Aminopyrimidin-4-yl)-1-(5-chloro-2-methylphenyl)-1H-pyrrole-2-carbonitrile Into a 50 mL round bottom flask equipped with a stir bar, condenser and 3-way valve connected to argon and vacuum 1-(5-chloro-2-methylphenyl)-4-(4,4,5,5-tetramethyl-1,3,2-dioxaborolan-2-yl)-1H-pyrrole-2-carbonitrile coming from the previous step, 6-iodopyrimidin-4-amine (663 mg, 3.0 mmol), 2M Na$_2$CO$_3$ (3.0 mL, 6.0 mmol) and dioxane (20 mL) were charged at room temperature. The resulting reaction mixture was degassed three times back filling with argon each time before being charged PdCl$_2$(dppf) (163 mg, 0.2 mmol). The resulting reaction mixture was degassed four times back filling with argon each time and then warmed to 110° C. for 1 h. The reaction mixture was cooled to room temperature, filtered through a pad of Celite, washed with EtOAc, and the filtrate was concentrated and then diluted with EtOAc and water. The two layers were separated, and the aqueous layer was extracted with EtOAc. The combined organic fractions were washed with aqueous brine, dried over Na$_2$SO$_4$, filtered and concentrated under reduced pressure. The residue was purified by Biotage SP1 Flash Chromatography (DCM/MeOH/7N NH$_3$ in MeOH 95/50.5) to afford the title compound (291 mg, 47%, 2 steps).

$^1$H NMR (400 MHz, DMSO-d$_6$) δ 8.33 (d, J=0.98 Hz, 1H), 7.96 (d, J=1.7 Hz, 1H), 7.64-7.69 (m, 2H), 7.55-7.61 (m, 1H), 7.50-7.54 (m, 1H), 6.81 (s, 2H), 6.65 (d, J=1.1 Hz, 1H), 2.10 (s, 3H).

HRMS (ESI) m/z calcd for C$_{16}$H$_{12}$ClN$_5$+H$^+$ 310.0854, found 310.0858.

According to this procedure, but using 6-chloro-N-methylpyrimidin-4-amine instead of 6-iodopyrimidin-4-amine in the step 9, the following compound was prepared:

1-(5-Chloro-2-methylphenyl)-4-[6-(methylamino)pyrimidin-4-yl]-1H-pyrrole-2-carbonitrile (Compd 45)

$^1$H NMR (600 MHz, DMSO-d$_6$) δ 8.38 (br. s., 1H), 8.01 (br. s., 1H), 7.71 (br. s., 1H), 7.66 (d, J=2.0 Hz, 1H), 7.58 (dd, J=2.2, 8.4 Hz, 1H), 7.52 (d, J=8.4 Hz, 1H), 7.25 (br. s., 1H), 6.72 (br. s., 1H), 2.82 (d, J=4.4 Hz, 3H), 2.10 (s, 3H).

HRMS (ESI) m/z calcd for C$_{17}$H$_{14}$ClN$_5$+H$^+$ 324.1011, found 324.1014.

According to this procedure, but using 4-chloropyrrolo[2,1-f][1,2,4]triazine instead of 6-iodopyrimidin-4-amine in the step 9, the following compound was prepared:

1-(5-Chloro-2-methylphenyl)-4-(pyrrolo[2,1-f][1,2,4]triazin-4-yl)-1H-pyrrole-2-carbonitrile (Compd 46)

$^1$H NMR (600 MHz, DMSO-d$_6$) δ 8.52 (s, 1H), 8.49 (d, J=1.6 Hz, 1H), 8.11 (dd, J=1.3, 2.6 Hz, 1H), 8.07 (d, J=1.8 Hz, 1H), 7.77 (d, J=2.3, 1H), 7.62 (dd, J=2.3, 8.3 Hz, 1H), 7.56 (d, J=8.3 Hz, 1H), 7.50 (dd, J=1.3, 4.8 Hz, 1H), 7.03-7.09 (m, 1H), 2.14 (s, 3H).

HRMS (ESI) m/z calcd for C$_{18}$H$_{12}$ClN$_5$+H$^+$ 334.0854, found 334.0851.

According to this procedure, but starting from 4-bromo-1-(5-chloro-2-ethylphenyl)-1H-pyrrole-2-carbonitrile in the step 8, the following compound was prepared:

4-(6-Aminopyrimidin-4-yl)-1-(5-chloro-2-ethylphenyl)-1H-pyrrole-2-carbonitrile (Compd 47)

$^1$H NMR (600 MHz, DMSO-d$_6$) δ 8.33 (s, 1H), 7.97 (d, J=1.5 Hz, 1H), 7.65 (s, 1H), 7.61-7.64 (m, 1H), 7.55 (d, J=8.4 Hz, 1H), 6.81 (s, 2H), 6.65 (s, 1H) 2.39 (q, J=7.3 Hz, 2H), 1.04 (t, J=7.3 Hz, 3H).

HRMS (ESI) calcd for C$_{17}$H$_{14}$ClN$_5$+H$^+$ 324.1011, found 324.1006.

According to this procedure, but starting from 4-bromo-1-(5-chloro-2-ethylphenyl)-1H-pyrrole-2-carbonitrile in the step 8 and using 6-chloro-N-methylpyrimidin-4-amine instead of 6-iodopyrimidin-4-amine in the step 9, the following compound was prepared:

1-(5-Chloro-2-ethylphenyl)-4-[6-(methylamino)pyrimidin-4-yl]-1H-pyrrole-2-carbonitrile (Compd 48)

$^1$H NMR (600 MHz, DMSO-$d_6$) δ 8.38 (br. s., 1H), 8.02 (br. s., 1H), 7.71 (br. s., 1H), 7.66 (d, J=2.0 Hz, 1H), 7.63 (dd, J=2.2, 8.4 Hz, 1H), 7.56 (d, J=8.4 Hz, 1H), 7.25 (br. s., 1H), 6.72 (br. s., 1H), 2.82 (d, J=4.4 Hz, 3H), 2.39 (q, J=7.33 Hz, 2H), 1.04 (t, J=7.3 Hz, 3H).

HRMS (ESI) calcd for $C_{18}H_{16}ClN_5$+H$^+$ 338.1167, found 338.1164.

According to this procedure, but starting from 4-bromo-1-(5-chloro-2-ethylphenyl)-1H-pyrrole-2-carbonitrile in the step 8 and using 4-chloropyrrolo[2,1-f][1,2,4]triazine instead of 6-iodopyrimidin-4-amine in the step 9, the following compound was prepared:

1-(5-Cloro-2-ethylphenyl)-4-(pyrrolo[2,1-f][1,2,4]triazin-4-yl)-1H-pyrrole-2-carbonitrile (Compd 49)

$^1$H NMR (600 MHz, DMSO-$d_6$) δ 8.52 (s, 1H), 8.51 (d, J=1.8 Hz, 1H), 8.11 (dd, J=1.3, 2.6 Hz, 1H), 8.07 (d, J=1.6 Hz, 1H), 7.77 (d, J=2.2 Hz, 1H), 7.67 (dd, J=2.2, 8.4 Hz, 1H), 7.59 (d, J=8.4 Hz, 1H), 7.49 (d, J=4.8 Hz, 1H), 7.06 (dd, J=2.6, 4.8 Hz, 1H), 2.39-2.46 (q, J=7.1 Hz, 2H), 1.06 (t, J=7.6 Hz, 3H).

HRMS (ESI) calcd for $C_{19}H_{14}ClN_5$+H$^+$ 348.1011, found 348.1008.

According to this procedure, but starting from 4-bromo-1-[2-chloro-5-(trifluoromethyl)phenyl]-1H-pyrrole-2-carbonitrile in the step 8, the following compound was prepared:

4-(6-Aminopyrimidin-4-yl)-1-[2-chloro-5-(trifluoromethyl)phenyl]-H-pyrrole-2-carbonitrile (Compd 50)

$^1$H NMR (600 MHz, DMSO-$d_6$) δ 8.34 (d, J=0.9 Hz, 1H), 8.27 (s, 1H), 8.07 (d, J=1.8 Hz, 1H), 7.94-8.06 (m, 2H), 7.72 (d, J=1.6 Hz, 1H), 6.84 (br. s., 2H), 6.67 (d, J=1.1 Hz, 1H).

HRMS (ESI) calcd for $C_{16}H_9ClF_3N_5$+H$^+$ 364.0572, found 364.0577.

According to this procedure, but starting from 4-bromo-1-[2-chloro-5-(trifluoromethyl)phenyl]-1H-pyrrole-2-carbonitrile in the step 8 and using 6-chloro-N-methylpyrimidin-4-amine instead of 6-iodopyrimidin-4-amine in the step 9, the following compound was prepared:

1-[2-Chloro-5-(trifluoromethyl)phenyl]4-[6-(methylamino)pyrimidin-4-yl]-1H-pyrrole-2-carbonitrile (Compd 51)

$^1$H NMR (600 MHz, DMSO-$d_6$) δ 8.39 (br. s., 1H), 8.26 (br. s., 1H), 8.10 (br. s., 1H), 8.03 (br. s., 2H), 7.77 (br. s., 1H), 7.28 (br. s., 1H), 6.73 (br. s., 1H), 2.82 (d, J=4.4 Hz, 3H).

HRMS (ESI) calcd for $C_{17}H_{11}ClF_3N_5$+H$^+$ 378.0728, found 378.0733.

According to this procedure, but starting from 4-bromo-1-[2-chloro-5-(trifluoromethyl)phenyl]-1H-pyrrole-2-carbonitrile in the step 8 and using 4-chloropyrrolo[2,1-f][1,2,4]triazine instead of 6-iodopyrimidin-4-amine in the step 9, the following compound was prepared:

1-[2-Chloro-5-(trifluoromethyl)phenyl]-4-(pyrrolo[2,1-f][1,2,4]triazin-4-yl)-1H-pyrrole-2-carbonitrile (Compd 52)

$^1$H NMR (600 MHz, DMSO-$d_6$) δ 8.62 (d, J=1.6 Hz, 1H), 8.54 (s, 1H), 8.40 (s, 1H), 8.10-8.14 (m, 2H), 8.08 (br. s., 2H), 7.45-7.50 (m, 1H), 7.08 (dd, J=2.56, 4.58 Hz, 1H).

HRMS (ESI) calcd for $C_{18}H_9ClF_3N_5$+H$^+$ 388.0572, found 388.0566.

According to this procedure, but starting from 4-bromo-1-[2-methyl-5-(trifluoromethyl)phenyl]-1H-pyrrole-2-carbonitrile in the step 8, the following compound was prepared:

4-(6-Aminopyrimidin-4-yl)-1-[2-methyl-5-(trifluoromethyl)phenyl]-1H-pyrrole-2-carbonitrile (Compd 53)

ESI (+) MS: m/z 344 (MH$^+$).

According to this procedure, but starting from 4-bromo-1-[2-methyl-5-(trifluoromethyl)phenyl]-1H-pyrrole-2-carbonitrile in the step 8 and using 6-chloro-N-methylpyrimidin-4-amine instead of 6-iodopyrimidin-4-amine in the step 9, the following compound was prepared:

4-[6-(Methylamino)pyrimidin-4-yl]-1-[2-methyl-5-(trifluoromethyl)phenyl]-1H-pyrrole-2-carbonitrile (Compd 54)

ESI (+) MS: m/z 358 (MH$^+$).

According to this procedure, but starting from 4-bromo-1-[2-methyl-5-(trifluoromethyl)phenyl]-1H-pyrrole-2-carbonitrile in the step 8 and using 4-chloropyrrolo[2,1-f][1,2,4]triazine instead of 6-iodopyrimidin-4-amine in the step 9, the following compound was prepared:

1-[2-Methyl-5-(trifluoromethyl)phenyl]-4-(pyrrolo[2,1-f][1,2,4]triazin-4-yl)-1H-pyrrole-2-carbonitrile (Compd 55)

ESI (+) MS: m/z 368 (MH$^+$).

According to this procedure, but starting from 4-bromo-1-[2-ethyl-5-(trifluoromethyl)phenyl]-1H-pyrrole-2-carbonitrile in the step 8, the following compound was prepared:

4-(6-Aminopyrimidin-4-yl)-1-[2-ethyl-5-(trifluoromethyl)phenyl]-1H-pyrrole-2-carbonitrile (Compd 56)

$^1$H NMR (600 MHz, DMSO-$d_6$) δ 8.31-8.36 (m, 1H), 8.03 (d, J=1.65 Hz, 1H), 7.87-7.96 (m, 2H), 7.78 (d, J=8.61 Hz, 1H), 7.68 (d, J=1.65 Hz, 1H), 6.82 (s, 2H), 6.66 (d, J=1.10 Hz, 1H), 2.52 (q, J=7.3 Hz, 2H), 1.08 (t, J=7.3 Hz, 3H).

HRMS (ESI) calcd for $C_{18}H_{14}F_3N_5$+H$^+$ 358.1274, found 358.1279.

According to this procedure, but starting from 4-bromo-1-[2-ethyl-5-(trifluoromethyl)phenyl]-1H-pyrrole-2-carbonitrile in the step 8 and using 6-chloro-N-methylpyrimidin-4-amine instead of 6-iodopyrimidin-4-amine in the step 9, the following compound was prepared:

1-[2-Ethyl-5-(trifluoromethyl)phenyl]-4-[6-(methyl-amino)pyrimidin-4-yl]-1H-pyrrole-2-carbonitrile (Compd 57)

ESI (+) MS: m/z 372 (MH+).

According to this procedure, but starting from 4-bromo-1-[2-ethyl-5-(trifluoromethyl)phenyl]-1H-pyrrole-2-carbonitrile in the step 8 and using 4-chloropyrrolo[2,1-f][1,2,4]triazine instead of 6-iodopyrimidin-4-amine in the step 9, the following compound was prepared:

1-[2-Ethyl-5-(trifluoromethyl)phenyl]-4-(pyrrolo[2,1-f][1,2,4]triazin-4-yl)-H-pyrrole-2-carbonitrile (Compd 58)

ESI (+) MS: m/z 382 (MH+).

According to this procedure, but starting from 4-bromo-1-phenyl-1H-pyrrole-2-carbonitrile in the step 8, the following compound was prepared:

4-(6-Aminopyrimidin-4-yl)-1-phenyl-1H-pyrrole-2-carbonitrile (Compd 59)

ESI (+) MS: m/z 262 (MH+).

According to this procedure, but starting from 4-bromo-1-phenyl-1H-pyrrole-2-carbonitrile in the step 8 and using 6-chloro-N-methylpyrimidin-4-amine instead of 6-iodopyrimidin-4-amine in the step 9, the following compound was prepared:

1-Phenyl-4-[6-methylamino)pyrimidin-4-yl]-1H-pyrrole-2-carbonitrile (Compd 60)

ESI (+) MS: m/z 276 (MH+).

According to this procedure, but starting from 4-bromo-1-phenyl-1H-pyrrole-2-carbonitrile in the step 8 and using 4-chloropyrrolo[2,1-j][1,2,4]triazine instead of 6-iodopyrimidin-4-amine in the step 9, the following compound was prepared:

1-Phenyl-4-(pyrrolo[2,1-f][1,2,4]triazin-4-yl)-1H-pyrrole-2-carbonitrile (Compd 61)

ESI (+) MS: m/z 286 (MH+).

Example 5

1-[2-Chloro-5-(trifluoromethyl)phenyl]-4-(9H-purin-6-yl)-1H-pyrrole-2-carbonitrile (Compd 62)

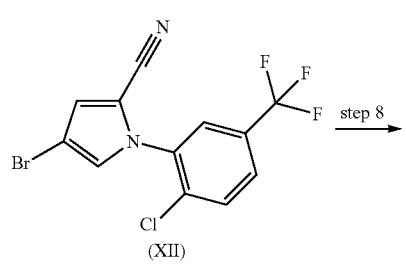

(XII)

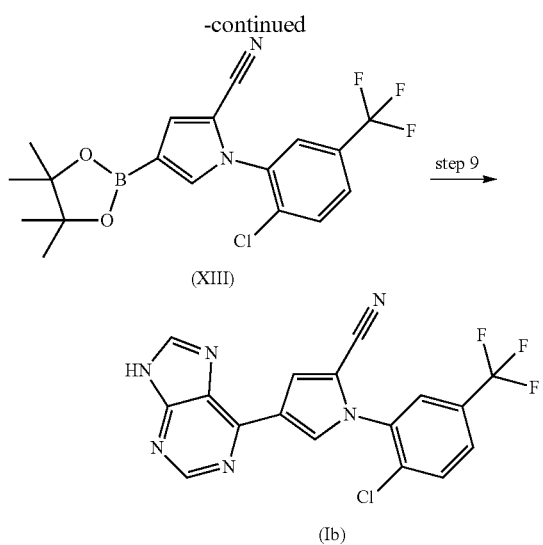

Scheme C: Steps 8, 9

Step 8: 1-[2-Chloro-5-(trifluoromethyl)phenyl]-4-(4,4,5,5-tetramethyl-1,3,2-dioxaborolan-2-yl)-1H-pyrrole-2-carbonitrile (XIII)

To a solution of 4-bromo-1-[2-chloro-5-(trifluoromethyl)phenyl]-1H-pyrrole-2-carbonitrile (349 mg, 1.0 mmol) in THF (4 mL) 2-isopropoxy-4,4,5,5-tetramethyl-1,3,2-dioxyborolane (0.230 mL, 1.1 mmol) was added to the mixture at −78° C. under argon, n-BuLi (2.5M in hexane, 0.440 mL, 1.1 mmol) was slowly added dropwise at −78° C. The mixture was stirred at −78° C. for 1 h. MeOH (0.5 mL) was added and the resultant mixture was stirred at room temperature after slowly raising the temperature. NH$_4$Cl solution (5 mL) was added and the mixture was diluted with water and extracted with EtOAc (30 mL), washed with aqueous brine, dried over Na$_2$SO$_4$, distilled under reduced pressure and used in the next step without further purification.

$^1$H NMR (600 MHz, DMSO-d$_6$) δ 7.59 (d, J=1.5 Hz, 1H), 7.52-7.57 (m, 2H), 7.44-7.50 (m, 1H), 7.32 (d, J=1.5 Hz, 1H), 2.03 (s, 3H), 1.27 (s, 12H).

Step 9: 1-[2-Chloro-5-(trifluoromethyl)phenyl]-4-(9H-purin-6-yl)-1H-pyrrole-2-carbonitrile Into a 50 mL round bottom flask equipped with a stir bar, condenser and 3-way valve connected to argon and vacuum 1-[2-chloro-5-(trifluoromethyl)phenyl]-4-(4,4,5,5-tetramethyl-1,3,2-dioxaborolan-2-yl)-1H-pyrrole-2-carbo  nitrile coming from the previous step, 6-chloro-9-(4-methoxybenzyl)-9H-purine (412 mg, 1.5 mmol), 2M Na$_2$CO$_3$ (1.5 mL, 3.0 mmol) and dioxane (8 mL) were charged at room temperature. The resulting reaction mixture was degassed three times back filling with argon each time before being charged PdCl$_2$(dppf) (81.6 mg, 0.1 mmol). The resulting reaction mixture was degassed four times back filling with argon each time and then warmed to 110° C. for 2 h. The reaction mixture was cooled to room temperature, filtered through a pad of Celite, washed with EtOAc, and the filtrate was concentrated and then diluted with EtOAc and water. The two layers were separated, and the aqueous layer was extracted with EtOAc. The combined organic fractions were washed with aqueous brine, dried over Na$_2$SO$_4$, filtered and concentrated under reduced pressure. The residue was purified by Biotage SP1 Flash Chromatography (gradient elution from 30% to 50% of EtOAc in hexane) to afford 1-[2-chloro-5-(trifluoromethyl)phenyl]-4-[9-(4-methoxybenzyl)-9H-purin-6-yl]-1H-pyrrole-2-carbonitrile (178 mg, 35%, 2 steps).

$^1$H NMR (600 MHz, DMSO-d$_6$) δ 8.87 (s, 1H), 8.72 (s, 1H), 8.54 (d, J=1.65 Hz, 1H), 8.33 (s, 1H), 8.15 (d, J=1.5 Hz, 1H), 7.97-8.05 (m, 2H), 7.33 (d, J=8.8 Hz, 2H), 6.88 (d, J=8.8 Hz, 2H), 5.42 (s, 2H), 3.69 (s, 3H).

HRMS (ESI) m/z calcd for C$_{25}$H$_{16}$ClF$_3$N$_6$+H$^+$ 509.1099, found 509.1100.

A solution of 1-[2-chloro-5-(trifluoromethyl)phenyl]-4-[9-(4-methoxybenzyl)-9H-purin-6-yl]-1H-pyrrole-2-carbonitrile (60 mg, 0.12 mmol) in TFA (1.0 mL) was stirred for 5 h at 70° C. The solution was concentrated and then was diluted with DCM and washed with saturated solution of NaHCO$_3$. The combined organic fractions were washed with aqueous brine, dried over Na$_2$SO$_4$, filtered and concentrated under reduced pressure. The residue was crystallized from Et$_2$O to afford the title compound (33 mg, 72%).

$^1$H NMR (600 MHz, DMSO-d$_6$) δ 13.50 ((br. s., 1H), 8.85 (s, 1H), 8.59 (br. s., 1H), 8.56 (d, J=1.5 Hz, 1H), 8.36 (s, 1H), 8.18 (d, J=1.5 Hz, 1H), 7.98-8.11 (m, 2H).

HRMS (ESI) m/z calcd for C$_{17}$H$_8$ClF$_3$N$_6$+H$^+$ 389.0524, found 389.0527.

According to this procedure, but starting from 4-bromo-1-(5-chloro-2-methylphenyl)-1H-pyrrole-2-carbonitrile in the step 8 and using 4-chloro-7-{[2-(trimethylsilyl)ethoxy]methyl}-7H-pyrrolo[2,3-d]pyrimidine instead of 6-chloro-9-(4-methoxybenzyl)-9H-purine in the step 9, the following compound was prepared:

1-(5-Chloro-2-methylphenyl)-4-(7H-pyrrolo[2,3-d]pyrimidin-4-yl)-1H-pyrrole-2-carbonitrile (Compd 63)

$^1$H NMR (400 MHz, DMSO-d$_6$) δ 12.13 (br. s., 1H), 8.72 (br. s., 1H), 8.32 (d, J=1.7 Hz, 1H), 8.01 (d, J=1.7 Hz, 1H), 7.72 (d, J=2.2 Hz, 1H), 7.51-7.65 (m, 3H), 7.09 (dd, J=1.6, 3.6 Hz, 1H), 2.14 (s, 3H).

HRMS (ESI) m/z calcd for C$_{18}$H$_{12}$ClN$_5$+H$^+$ 334.0854, found 334.0859.

According to this procedure, but starting from 4-bromo-1-(5-chloro-2-methylphenyl)-1H-pyrrole-2-carbonitrile in the step 8 and using 4-chloro-1-{[2-(trimethylsilyl)ethoxy]methyl}-1H-pyrrolo[2,3-b]pyridine instead of 6-chloro-9-(4-methoxybenzyl)-9H-purine in the step 9, the following compound was prepared:

1-(5-Chloro-2-methylphenyl)-4-(1H-pyrrolo[2,3-b]pyrimidin-4-yl)-1H-pyrrole-2-carbonitrile (Compd 64)

ESI (+) MS: m/z 333 (MH$^+$).

According to this procedure, but starting from 4-bromo-1-(5-chloro-2-methylphenyl)-1H-pyrrole-2-carbonitrile in the step 8, the following compound was prepared:

1-(5-Chloro-2-methylphenyl)-4-(9H-purin-6-yl)-H-pyrrole-2-carbonitrile (Compd 65)

ESI (+) MS: m/z 335 (MH$^+$).

According to this procedure, but starting from 4-bromo-1-(5-chloro-2-methylphenyl)-1H-pyrrole-2-carbonitrile in the step 8 using 4-chloro-1-{[2-(trimethylsilyl)ethoxy]methyl}-1H-pyrazolo[3,4-d]pyrimidine instead of 6-chloro-9-(4-methoxybenzyl)-9H-purine in the step 9, the following compound was prepared:

1-(5-Chloro-2-methylphenyl)-4-(1H-pyrazolo[3,4-d]pyrimidin-4-yl)-1H-pyrrole-2-carbonitrile (Compd 66)

ESI (+) MS: m/z 335 (MH$^+$).

According to this procedure, but starting from 4-bromo-1-(5-chloro-2-methylphenyl)-1H-pyrrole-2-carbonitrile in the step 8 using 4-chloro-7-(4-methoxybenzyl)-6,7-dihydro-5H-pyrrolo[2,3-d]pyrimidine instead of 6-chloro-9-(4-methoxybenzyl)-9H-purine in the step 9, the following compound was prepared:

1-(5-Chloro-2-methylphenyl)-4-(6,7-dihydro-5H-pyrrolo[2,3-d]pyrimidin-4-yl)-1H-pyrrole-2-carbonitrile (Compd 67)

ESI (+) MS: m/z 336 (MH$^+$).

According to this procedure, but starting from 4-bromo-1-(5-chloro-2-ethylphenyl)-1H-pyrrole-2-carbonitrile in the step 8 and using 4-chloro-7-{[2-(trimethylsilyl)ethoxy]methyl}-7H-pyrrolo[2,3-d]pyrimidine in the step 9 instead of 6-chloro-9-(4-methoxybenzyl)-9H-purine, the following compound was prepared:

1-(5-Chloro-2-ethylphenyl)-4-(7H-pyrrolo[2,3-d]pyrimidin-4-yl)-1H-pyrrole-2-carbonitrile (Compd 68)

$^1$H NMR (600 MHz, DMSO-d$_6$) δ 12.13 (br. s., 1H), 8.72 (s, 1H), 8.33 (d, J=1.8 Hz, 1H), 8.01 (d, J=1.65 Hz, 1H), 7.73 (d, J=2.2 Hz, 1H), 7.63-7.67 (m, 1H), 7.56-7.61 (m, 3H), 7.08 (dd, J=1.6, 3.6 Hz, 1H), 2.43 (q, J=7.3 Hz, 2H), 1.06 (t, J=7.5 Hz, 3H).

HRMS (ESI) calcd for C$_{19}$H$_{14}$ClN$_5$+H$^+$ 348.1011, found 348.1014.

According to this procedure, but starting from 4-bromo-1-(5-chloro-2-ethylphenyl)-1H-pyrrole-2-carbonitrile in the step 8, the following compound was prepared:

1-(5-Chloro-2-ethylphenyl)-4-(H-purin-6-yl)-1H-pyrrole-2-carbonitrile (Compd 69)

ESI (+) MS: m/z 349 (MH$^+$).

According to this procedure, but starting from 4-bromo-1-(5-chloro-2-ethylphenyl)-1H-pyrrole-2-carbonitrile in the step 8 and using 4-chloro-1-{[2-(trimethylsilyl)ethoxy]methyl}-1H-pyrazolo[3,4-d]pyrimidine instead of 6-chloro-9-(4-methoxybenzyl)-9H-purine in the step 9, the following compound was prepared:

1-(5-Chloro-2-ethylphenyl)-4-(1H-pyrazolo[3,4-d]pyrimidin-4-yl)-1H-pyrrole-2-carbonitrile (Compd 70)

ESI (+) MS: m/z 349 (MH$^+$).

According to this procedure, but starting from 4-bromo-1-(5-chloro-2-ethylphenyl)-1H-pyrrole-2-carbonitrile in the step 8 and using 4-chloro-7-(4-methoxybenzyl)-6,7-dihydro-5H-pyrrolo[2,3-d]pyrimidine instead of 6-chloro-9-(4-methoxybenzyl)-9H-purine in the step 9, the following compound was prepared:

1-(5-Chloro-2-ethylphenyl(6,7-dihydro-5H-pyrrolo [2,3-d]pyrimidin-4-yl)-1H-pyrrole-2-carbonitrile (Compd 71)

ESI (+) MS: m/z 350 (MH+).

According to this procedure, but using 4-chloro-7-{[2-(trimethylsilyl)ethoxy]methyl}-7H-pyrrolo[2,3-d]pyrimidine instead of 6-chloro-9-(4-methoxybenzyl)-9H-purine in the step 9, the following compound was prepared:

1-[2-Chloro-5-(trifluoromethyl)phenyl]4-(7H-pyrrolo[2,3-d]pyrimidin-4-yl)-H-pyrrole-2-carbonitrile (Compd 72)

$^1$H NMR (400 MHz, DMSO-d$_6$) δ 12.15 (br. s., 1H), 8.73 (s, 1H), 8.45 (d, J=1.7 Hz, 1H), 8.36 (d, J=0.8 Hz, 1H), 8.03-8.09 (m, 3H), 7.61 (dd, J=2.4, 3.5 Hz, 1H), 7.07 (dd, J=1.7, 3.6 Hz, 1H).

HRMS (ESI) calcd for $C_{18}H_{19}ClF_3N_5+H^+$ 388.0572, found 388.0575.

According to this procedure, but using 4-chloro-1-{[2-(trimethylsilyl)ethoxy]methyl}-1H-pyrazolo[3,4-d]pyrimidine instead of 6-chloro-9-(4-methoxybenzyl)-9H-purine in the step 9, the following compound was prepared:

1-[2-Chloro-5-(trifluoromethyl)phenyl]-4-(1H-pyrazolo[3,4-d]pyrimidin-4-yl)-1H-pyrrole-2-carbonitrile (Compd 73)

ESI (+) MS: m/z 389 (MH+).

According to this procedure, but using 4-chloro-7-(4-methoxybenzyl)-6,7-dihydro-5H-pyrrolo[2,3-d]pyrimidine instead of 6-chloro-9-(4-methoxybenzyl)-9H-purine in the step 9, the following compound was prepared:

1-[2-Chloro-5-(trifluoromethyl)phenyl]-4-(6,7-dihydro-H-pyrrolo[2,3-d]pyrimidin-4-yl)-1H-pyrrole-2-carbonitrile (Compd 74)

ESI (+) MS: m/z 390 (MH+).

According to this procedure, but starting from 4-bromo-1-[2-methyl-5-(trifluoromethyl)phenyl]-1H-pyrrole-2-carbonitrile in the step 8 and using 4-chloro-7-{[2-(trimethylsilyl)ethoxy]methyl}-7H-pyrrolo[2,3-d]pyrimidine instead of 6-chloro-9-(4-methoxybenzyl)-9H-purine in the step 9, the following compound was prepared:

1-[2-Methyl-5-(trifluoromethyl)phenyl]-4-(7-pyrrolo[2,3-d]pyrimidin-4-yl)-1H-pyrrole-2-carbonitrile (Compd 75)

ESI (+) MS: m/z 368 (MH+).

According to this procedure, but starting from 4-bromo-1-[2-methyl-5-(trifluoromethyl)phenyl]-1H-pyrrole-2-carbonitrile in the step 8, the following compound was prepared:

1-[2-Methyl-5-(trifluoromethyl)phenyl]-4-(9H-purin-6-yl)-1H-pyrrole-2-carbonitrile (Compd 76)

ESI (+) MS: m/z 369 (MH+).

According to this procedure, but starting from 4-bromo-1-[2-methyl-5-(trifluoromethyl)phenyl]-1H-pyrrole-2-carbonitrile in the step 8 and using 4-chloro-1-{[2-(trimethylsilyl)ethoxy]methyl}-1H-pyrazolo[3,4-d]pyrimidine instead of 6-chloro-9-(4-methoxybenzyl)-9H-purine in the step 9, the following compound was prepared:

1-[2-Methyl-5-(trifluoromethyl)phenyl]-4-(1H-pyrazolo[3,4-d]pyrimidin-4-yl)-1H-pyrrole-2-carbonitrile (Compd 77)

ESI (+) MS: m/z 369 (MH+).

According to this procedure, but starting from 4-bromo-1-[2-methyl-5-(trifluoromethyl)phenyl]-1H-pyrrole-2-carbonitrile in the step 8 and using 4-chloro-7-(4-methoxybenzyl)-6,7-dihydro-5H-pyrrolo[2,3-d]pyrimidine instead of 6-chloro-9-(4-methoxybenzyl)-9H-purine in the step 9, the following compound was prepared:

1-[2-Methyl-5-(trifluoromethyl)phenyl]-4-(6,7-dihydro-5H-pyrrolo[2,3-d]pyrimidin-4-yl)-1H-pyrrole-2-carbonitrile (Compd 78)

ESI (+) MS: m/z 370 (MH+).

According to this procedure, but starting from 4-bromo-1-[2-ethyl-5-(trifluoromethyl)phenyl]-1H-pyrrole-2-carbonitrile in the step 8 and using 4-chloro-7-{[2-(trimethylsilyl)ethoxy]methyl}-7H-pyrrolo[2,3-d]pyrimidine instead of 6-chloro-9-(4-methoxybenzyl)-9H-purine in the step 9, the following compound was prepared:

1-[2-Ethyl-5-(trifluoromethyl)phenyl]-4-(7H-pyrrolo[2,3-d]pyrimidin-4-yl)-1H-pyrrole-2-carbonitrile (Compd 79)

ESI (+) MS: m/z 382 (MH+).

According to this procedure, but starting from 4-bromo-1-[2-ethyl-5-(trifluoromethyl)phenyl]-1H-pyrrole-2-carbonitrile in the step 8, the following compound was prepared:

1-[2-Ethyl-5-(trifluoromethyl)phenyl]-4-(9H-purin-6-yl)-1H-pyrrole-2-carbonitrile (Compd 80)

ESI (+) MS: m/z 383 (MH+).

According to this procedure, but starting from 4-bromo-1-[2-ethyl-5-(trifluoromethyl)phenyl]-1H-pyrrole-2-carbonitrile in the step 8 and using 4-chloro-1-{[2-(trimethylsilyl)ethoxy]methyl}-1H-pyrazolo[3,4-d]pyrimidine instead of 6-chloro-9-(4-methoxybenzyl)-9H-purine in the step 9, the following compound was prepared:

1-[2-Ethyl-5-(trifluoromethyl)phenyl]-4-(1H-pyrazolo[3,4-d]pyrimidin-4-yl)-1H-pyrrole-2-carbonitrile (Compd 81)

ESI (+) MS: m/z 383 (MH+).

According to this procedure, but starting from 4-bromo-1-[2-ethyl-5-(trifluoromethyl)phenyl]-1H-pyrrole-2-carbonitrile in the step 8 and using 4-chloro-7-(4-methoxybenzyl)-6,7-dihydro-5H-pyrrolo[2,3-d]pyrimidine instead of 6-chloro-9-(4-methoxybenzyl)-9H-purine in the step 9, the following compound was prepared:

1-[2-Ethyl-5-(trifluoromethyl)phenyl]-4-(6,7-dihydro-5H-pyrrolo[2,3-d]pyrimidin-4-yl)-1H-pyrrole-2-carbonitrile (Compd 82)

ESI (+) MS: m/z 384 (MH+).

According to this procedure, but starting from 4-bromo-1-phenyl-1H-pyrrole-2-carbonitrile in the step 8 and using 4-chloro-7-{[2-(trimethylsilyl)ethoxy]methyl}-7H-pyrrolo

[2,3-d]pyrimidine instead of 6-chloro-9-(4-methoxybenzyl)-9H-purine in the step 9, the following compound was prepared:

1-Phenyl-4-(7H-pyrrolo[2,3-d]pyrimidin-4-yl)-1H-pyrrole-2-carbonitrile (Compd 83)

ESI (+) MS: m/z 286 (MH+).

According to this procedure, but starting from 4-bromo-1-phenyl-1H-pyrrole-2-carbonitrile in the step 8, the following compound was prepared:

1-Phenyl-4-(9H-purin-6-yl)-1H-pyrrole-2-carbonitrile (Compd 84)

ESI (+) MS: m/z 287 (MH+).

According to this procedure, but starting from 4-bromo-1-phenyl-1H-pyrrole-2-carbonitrile in the step 8 and using 4-chloro-1-{[2-(trimethylsilyl)ethoxy]methyl}-1H-pyrazolo[3,4-d]pyrimidine instead of 6-chloro-9-(4-methoxybenzyl)-9H-purine in the step 9, the following compound was prepared:

1-Phenyl-4-(1H-pyrazolo[3,4-d]pyrimidin-4-yl)-1H-pyrrole-2-carbonitrile (Compd 85)

ESI (+) MS: mm/z 287 (MH+).

According to this procedure, but starting from 4-bromo-1-phenyl-1H-pyrrole-2-carbonitrile in the step 8 and using 4-chloro-7-(4-methoxybenzyl)-6,7-dihydro-5H-pyrrolo[2,3-d]pyrimidine instead of 6-chloro-9-(4-methoxybenzyl)-9H-purine in the step 9, the following compound was prepared:

1-Phenyl-4-(6,7-dihydro-5H-pyrrolo[2,3-d]pyrimidin-4-yl)-1H-pyrrole-2-carbonitrile (Compd 86)

ESI (+) MS: m/z 288 (MH+).

Example 6

1-(6-Aminopyrimidin-4-yl)-4-(5-chloro-2-methylphenyl)-H-pyrrole-3-carbonitrile (Compd 87)

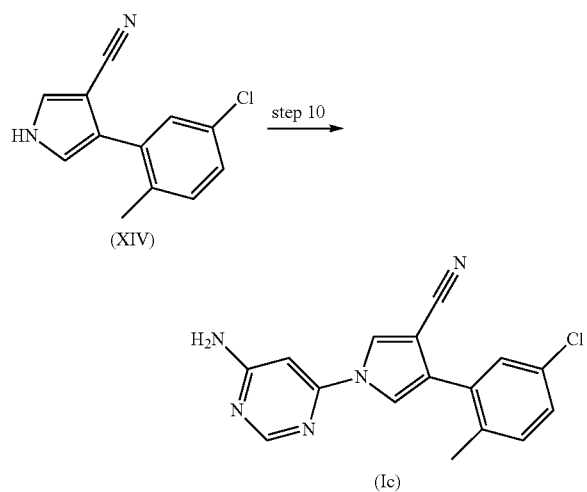

Scheme D: Step 10

To a suspension of NaH (60% dispersion in oil, 60 mg, 1.5 mmol) in dry THF (4 mL) a solution of 4-(5-chloro-2-methylphenyl)-1H-pyrrole-3-carbonitrile (216 mg, 1 mmol) in THF (4 mL) was added at 5° C. dropwise over 20 min, maintaining the reaction temperature below 10° C. The suspension was stirred at 5° C. for 60 min. A solution of 4,6-dichloropyrimidine (179 mg, 1.2 mmol) in THF (4 mL) was added dropwise over 10 min, maintaining the reaction temperature below 10° C. The reaction mixture was allowed to warm to room temperature and stirred overnight. The reaction mixture was poured into a solution of NH$_4$Cl and extracted with EtOAc (2×30 mL). The combined organic layers were washed with water, brine, dried over Na$_2$SO$_4$, filtered and the solvent was evaporated under reduced pressure. The residue was purified by Biotage SP1 Flash Chromatography (hexane/EtOAc 8/2) to afford 4-(5-chloro-2-methylphenyl)-1-(6-chloropyrimidin-4-yl)-1H-pyrrole-3-carbonitrile (203 mg, 62%).

$^1$H NMR (600 MHz, DMSO-d$_6$) δ 9.01 (d, J=0.9 Hz, 1H), 8.77 (d, J=2.4 Hz, 1H), 8.28 (d, J=0.9 Hz, 1H), 8.11 (d, J=2.2 Hz, 1H), 7.36-7.44 (m, 3H), 2.33 (s, 3H).

HRMS (ESI) m/z calcd for C$_{16}$H$_{10}$Cl$_2$N$_4$+Na+ 351.0175, found 351.0172.

4-(5-Chloro-2-methylphenyl)-1-(6-chloropyrimidin-4-yl)-1H-pyrrole-3-carbonitrile (100 mg, 0.30 mmol) was treated with c. NH$_4$OH (4 mL) in a closed vessel at 130° C. for 1 h in a microwave apparatus. After cooling, the precipitate was collected, washed with water to give the title compound (82 mg, 88%).

$^1$H NMR (600 MHz, DMSO-d$_6$) δ 8.52 (d, J=2.2 Hz, 1H), 8.35 (s, 1H), 7.85 (d, J=2.4 Hz, 1H), 7.33-7.46 (m, 3H), 7.24 (s, 2H), 6.66 (d, J=0.7 Hz, 1H), 2.32 (s, 3H).

HRMS (ESI) m/calcd for C$_{16}$H$_{12}$ClN$_5$+H+ 310.0854, found 310.0852.

According to this step, but using methylamine instead of NH$_4$OH, the following compound was prepared:

4-(5-Chloro-2-methylphenyl)-1-[6-(methylamino)pyrimidin-4-yl]-1H-pyrrole-3-carbonitrile (Compd 88)

$^1$H NMR (600 MHz, DMSO-d$_6$) δ 8.79 (d, J=2.2 Hz, 1H), 8.10 (d, J=2.2 Hz, 1H), 7.45 (s, 1H), 7.41 (s, 2H), 2.32 (s, 3H).

HRMS (ESI) m/calcd for C$_{17}$H$_{14}$ClN$_5$+H+ 324.1011, found 324.1013.

According to this procedure, but starting from 4-(5-chloro-2-ethylphenyl)-1H-pyrrole-3-carbonitrile, the following compound was prepared:

1-(6-Aminopyrimidin-4-yl)-4-(5-chloro-2-ethylphenyl)-1H-pyrrole-3-carbonitrile (Compd 89)

ESI (+) MS: m/z 324 (MH+).

According to this procedure, but starting from 4-(5-chloro-2-ethylphenyl)-1H-pyrrole-3-carbonitrile and using methylamine instead of NH$_4$OH, the following compound was prepared:

4-(5-Chloro-2-ethylphenyl)-1-[6-(methylamino)pyrimidin-4-yl]-1H-pyrrole-3-carbonitrile (Compd 90)

HRMS (ESI) calcd for C$_{18}$H$_{16}$ClN$_5$+H+ 338.1167, found 338.1169.

According to this procedure, but starting from 4-[2-chloro-5-(trifluoromethyl)phenyl]-1H-pyrrole-3-carbonitrile, the following compound was prepared:

1-(6-Aminopyrimidin-4-yl)-4-[2-chloro-5-(trifluoromethyl)phenyl]1H-pyrrole-3-carbonitrile (Compd 91)

HRMS (ESI) calcd for $C_{16}H_9ClF_3N_5+H^+$ 364.0572, found 364.0575.

According to this procedure, but starting from 4-[2-chloro-5-(trifluoromethyl)phenyl]-1H-pyrrole-3-carbonitrile and using methylamine instead of NH$_4$OH, the following compound was prepared:

4-[2-Chloro-5-(trifluoromethyl)phenyl]-1-[6-(methylamino)pyrimidin-4-yl]-1H-pyrrole-3-carbonitrile (Compd 92)

HRMS (ESI) calcd for $C_{17}H_{11}ClF_3N_5+H^+$ 378.0728, found 378.0731.

According to this procedure, but starting from 4-[2-methyl-5-(trifluoromethyl)phenyl]-1H-pyrrole-3-carbonitrile, the following compound was prepared:

1-(6-Aminopyrimidin-4-yl)-4-[2-methyl-5-(trifluoromethyl)phenyl]-1H-pyrrole-3-carbonitrile (Compd 93)

ESI (+) MS: m/z 344 (MH$^+$).

According to this procedure, but starting from 4-[2-methyl-5-(trifluoromethyl)phenyl]-1H-pyrrole-3-carbonitrile and using methylamine instead of NH$_4$OH, the following compound was prepared:

1-[6-(Methylamino)pyrimidin-4-yl]-4-[2-methyl-5-(trifluoromethyl)phenyl]-1H-pyrrole-2-carbonitrile (Compd 94)

ESI (+) MS: m/z 358 (MH$^+$).

According to this procedure, but starting from 4-[2-ethyl-5-(trifluoromethyl)phenyl]-1H-pyrrole-3-carbonitrile, the following compound was prepared:

1-(6-Aminopyrimidin-4-yl)-4-[2-ethyl-trifluoromethyl)phenyl]-1H-pyrrole-3-carbonitrile (Compd 95)

HRMS (ESI) calcd for $C_{18}H_{14}F_3N_5+H^+$ 358.1274, found 358.1270.

According to this procedure, but starting from 4-[2-ethyl-5-(trifluoromethyl)phenyl]-1H-pyrrole-3-carbonitrile and using methylamine instead of NH$_4$OH, the following compound was prepared:

4-[2-Ethyl-5-(trifluoromethyl)phenyl]-1-[6-(methylamino)pyrimidin-4-yl]-1H-pyrrole-3-carbonitrile (Compd 96)

ESI (+) MS: m/z 372 (MH$^+$).

According to this procedure, but starting from 4-phenyl-1H-pyrrole-3-carbonitrile, the following compound was prepared:

1-(6-Aminopyrimidin-4-yl)-4-phenyl-1H-pyrrole-2-carbonitrile (Compd 97)

ESI (+) MS: m/z 262 (MH$^+$).

According to this procedure, but starting from 4-phenyl-1H-pyrrole-3-carbonitrile and using methylamine instead of NH$_4$OH, the following compound was prepared:

1-[6-(Methylamino)pyrimidin-4-yl]-4-phenyl-1H-pyrrole-3-carbonitrile (Compd 98)

ESI (+) MS: m/z 276 (MH$^+$).

Example 7

4-(5-Chloro-2-methylphenyl)-1-(pyrrolo[2,1-f][1,2,4]triazin-4-yl)-1H-pyrrole-3-carbonitrile (Compd 99)

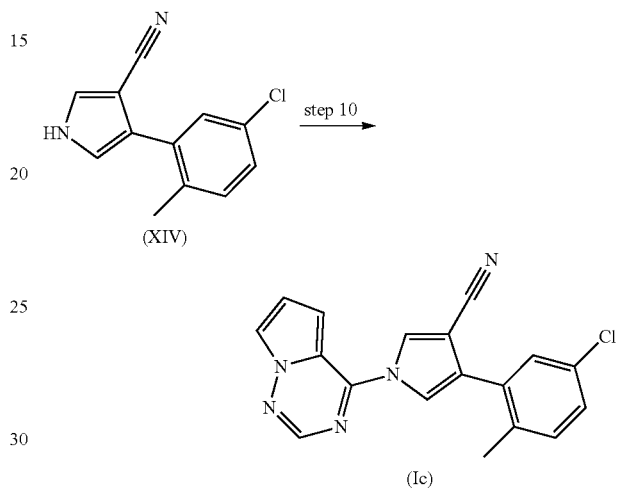

Scheme D: Step 10

To a suspension of NaH (60% dispersion in oil, 60 mg, 1.5 mmol) in dry THF (4 mL) a solution of 4-(5-chloro-2-methylphenyl)-1H-pyrrole-3-carbonitrile (216 mg, 1 mmol) in THF (4 mL) was added at 5° C. dropwise over 20 min, maintaining the reaction temperature below 10° C. The suspension was stirred at 5° C. for 60 min. 4-Chloropyrrolo[2,1-f][1,2,4]triazine (183 mg, 1.2 mmol) was added and the reaction was stirred under reflux for 2 h. The reaction mixture was poured into a solution of NH$_4$Cl and extracted with EtOAc (2×30 mL). The combined organic layers were washed with water, brine, dried over Na$_2$SO$_4$, filtered and the solvent was evaporated under reduced pressure. The residue was purified by Biotage SP1 Flash Chromatography (hexane/EtOAc 85/15) to afford the title compound (183 mg, 55%).

$^1$H NMR (600 MHz, DMSO-d$_6$) δ 8.81 (d, J=2.38 Hz, 1H), 8.54 (s, 1H), 8.32 (dd, J=1.19, 2.66 Hz, 1H), 8.09 (d, J=2.38 Hz, 1H), 7.59 (dd, J=1.28, 4.76 Hz, 1H), 7.44-7.46 (m, 1H), 7.41 (d, J=1.28 Hz, 2H), 7.19 (dd, J=2.56, 4.76 Hz, 1H), 2.35 (s, 3H).

HRMS (ESI) calcd for $C_{18}H_{12}ClN_5+H^+$ 334.0854, found 334.0858.

According to this procedure the following compounds were prepared:

4-(5-Chloro-2-ethylphenyl)-1-(pyrrolo[2,1-f][1,2,4]triazin-4-yl)-1H-pyrrole-3-carbonitrile (Compd 100)

HRMS (ESI) calcd for $C_{19}H_{14}ClN_5+H^+$ 348.1011, found 348.1013.

4-[2-Chloro-5-(trifluoromethyl)phenyl]-1-(pyrrolo[2,1-f][1,2,4]triazin-4-yl)-1H-pyrrole-3-carbonitrile (Compd 101)

HRMS (ESI) calcd for $C_{18}H_9ClF_3N_5+H^+$ 388.0572, found 388.0568.

4-[2-Methyl-5-(trifluoromethyl)phenyl]-1-(pyrrolo[2,1-f][1,2,4]triazin-4-yl)-1H-pyrrole-3-carbonitrile (Compd 102)

ESI (+) MS: m/z 368 (MH⁺).

4-[2-Ethyl-5-(trifluoromethyl)phenyl]-1-(pyrrolo[2,1-f][1,2,4]triazin-4-yl)-1H-pyrrole-2-carbonitrile (Compd 103)

ESI (+) MS: m/z 382 (MH⁺).

4-Phenyl-1-(pyrrolo[2,1-f][1,2,4]triazin-4-yl)-1H-pyrrole-2-carbonitrile (Compd 104)

ESI (+) MS: mm/z 286 (MH⁺).

Example 8

4-(5-Chloro-2-methylphenyl)-1-(7H-pyrrolo[2,3-d]pyrimidin-4-yl)-1H-pyrrole-3-carbonitrile (Compd 105)

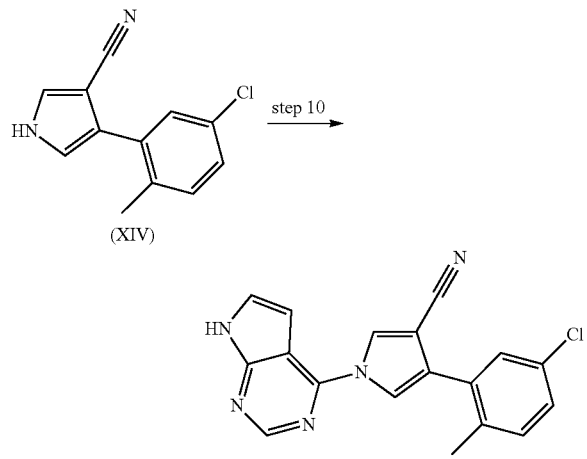

Scheme D: Step 10

4-Chloro-7-{[2-(trimethylsilyl)ethoxy]methyl}-7H-pyrrolo[2,3-d]pyrimidine (157 mg, 0.55 mmol), Cs₂CO₃ (223 mg, 0.69 mmol), 4-(5-chloro-2-methylphenyl)-1H-pyrrole-3-carbonitrile (100 mg, 0.46 mmol) and dry toluene (2.5 mL) were charged at room temperature. The resulting reaction mixture was degassed three times back filling with argon each time before being charged Pd₂(dba)₃ (10 mg, 0.011 mmol) and tri-tert-butylphosphine (23 μL, 0.023 mmol, 1.0M in toluene). The resulting reaction mixture was degassed four times back filling with argon each time and then warmed to 100° C. for 6 h. The reaction mixture was concentrated and purified by Biotage SP1 Flash Chromatography (gradient elution from 10% to 20% of EtOAc in hexane) to afford 4-(5-chloro-2-methylphenyl)-1-(7-{[2-(trimethylsilyl)ethoxy]methyl}-7H-pyrrolo[2,3-d]pyrimidin-4-yl)-1H-pyrrole-3-carbonitrile (110 mg, 51%).

¹H NMR (600 MHz, DMSO-d₆) δ 8.80 (s, 1H), 8.79 (d, J=2.2 Hz, 1H), 8.10 (d, J=2.2 Hz, 1H), 7.94 (d, J=3.8 Hz, 1H), 7.45 (s, 1H), 7.41 (s, 2H), 7.26 (d, J=3.8 Hz, 1H), 5.69 (s, 2H), 3.56 (t, J=8.0 Hz, 2H), 2.36 (s, 3H), 0.85 (t, J=8.0 Hz, 2H), −0.09 (s, 9H).

HRMS (ESI) m/z calcd for $C_{24}H_{26}ClN_5OSi+H^+$ 464.1668, found 464.1665.

TFA (2.1 mL) was added to a solution of 4-(5-chloro-2-methylphenyl)-1-(7-{[2-(trimethylsilyl)ethoxy]methyl}-7H-pyrrolo[2,3-d]pyrimidin-4-yl)-1H-pyrrole-3-carbonitrile (100 mg, 0.21 mmol) in dry DCM (4.2 mL) and stirred for 5 h at room temperature. After solvent removal, the residue was treated with EtOH 96% (6 mL), 33% NH₄OH (0.5 mL) and stirred for 1 h at room temperature. The precipitate was filtered and washed with EtOH to afford the title compound as a white solid (57 mg, 79%).

¹H NMR (600 MHz, DMSO-d₆) δ 12.57 (br. s., 1H), 8.74 (d, J=2.2 Hz, 1H), 8.69 (s, 1H), 8.06 (d, J=2.4 Hz, 1H), 7.73 (d, J=3.5 Hz, 1H), 7.31-7.44 (m, 3H), 7.12 (d, J=3.5 Hz, 1H), 2.33 (s, 3H).

HRMS (ESI) m/z calcd for $C_{18}H_{12}ClN_5+H^+$ 334.0854, found 334.0858.

According to this procedure, but using 4-chloro-1-{[2-(trimethylsilyl)ethoxy]methyl}-1H-pyrrolo[2,3-b]pyridine instead of 4-chloro-7-{[2-(trimethylsilyl)ethoxy]methyl}-7H-pyrrolo[2,3-d]pyrimidine, the following compound was prepared:

4-(5-Chloro-2-methylphenyl)-1-(1H-pyrrolo[2,3-b]pyrimidin-4-yl)-1H-pyrrole-3-carbonitrile (Compd 106)

ESI (+) MS: m/z 333 (MH⁺).

According to this procedure, but using 6-chloro-9-(4-methoxybenzyl)-9H-purine instead of 4-chloro-7-{[2-(trimethylsilyl)ethoxy]methyl}-7H-pyrrolo[2,3-d]pyrimidine, the following compound was prepared:

4-(5-Chloro-2-methylphenyl)-1-(9H-purin-6-yl)-1H-pyrrole-3-carbonitrile (Compd 107)

ESI (+) MS: m/z 335 (MH⁺).

According to this procedure, but using 4-chloro-1-{[2-(trimethylsilyl)ethoxy]methyl}-1H-pyrazolo[3,4-d]pyrimidine instead of 4-chloro-7-{[2-(trimethylsilyl)ethoxy]methyl}-7H-pyrrolo[2,3-d]pyrimidine, the following compound was prepared:

4-(5-Chloro-2-methylphenyl)-1-(1H-pyrazolo[3,4-d]pyrimidin-4-yl)-1H-pyrrole-3-carbonitrile (Compd 108)

ESI (+) MS: m/z 335 (MH⁺).

According to this procedure, but using 4-chloro-7-(4-methoxy-benzyl)-6,7-dihydro-5H-pyrrolo[2,3-d]pyrimidine instead of 4-chloro-7-{[2-(trimethylsilyl)ethoxy]methyl}-7H-pyrrolo[2,3-d]pyrimidine, the following compound was prepared:

4-(5-Chloro-2-methylphenyl)-1-(6,7-dihydro-5H-pyrrolo[2,3-d]pyrimidin-4-yl)-1H-pyrrole-3-carbonitrile (Compd 109)

ESI (+) MS: m/z 336 (MH$^+$).

According to this procedure, but starting from 4-(5-chloro-2-ethylphenyl)-1H-pyrrole-3-carbonitrile, the following compound was prepared:

4-(5-Chloro-2-ethylphenyl-1-(7H-pyrrolo[2,3-d]pyrimidin-4-yl)-1H-pyrrole-3-carbonitrile (Compd 110)

HRMS (ESI) calcd for $C_{19}H_{14}ClN_5$+H$^+$ 348.1011, found 348.1015.

According to this procedure, but starting from 4-(5-chloro-2-ethylphenyl)-1H-pyrrole-3-carbonitrile and using 4-chloro-7-(4-methoxy-benzyl)-6,7-dihydro-5H-pyrrolo[2,3-d]pyrimidine instead of 4-chloro-7-{[2-(trimethylsilyl)ethoxy]methyl}-7H-pyrrolo[2,3-d]pyrimidine, the following compound was prepared:

4-(5-Chloro-2-ethylphenyl)-1-(6,7-dihydro-5H-pyrrolo[2,3-d]pyrimidin-4-yl)-1H-pyrrole-3-carbonitrile (Compd 111)

ESI (+) MS: m/z 350 (MH$^+$).

According to this procedure, but starting from 4-[2-chloro-5-(trifluoromethyl)phenyl]-1H-pyrrole-3-carbonitrile, the following compound was prepared:

4-[2-Chloro-5-(trifluoromethyl)phenyl]-1-(7H-pyrrolo[2,3-d]pyrimidin-4-yl)-1H-pyrrole-3-carbonitrile (Compd 112)

HRMS (ESI) calcd for $C_{18}H_9ClF_3N_5$+H$^+$ 388.0572, found 388.0575.

According to this procedure, but starting from 4-[2-chloro-5-(trifluoromethyl)phenyl]-1H-pyrrole-3-carbonitrile and using 4-chloro-7-(4-methoxy-benzyl)-6,7-dihydro-5H-pyrrolo[2,3-d]pyrimidine instead of 4-chloro-7-{[2-(trimethylsilyl)ethoxy]methyl}-7H-pyrrolo[2,3-d]pyrimidine, the following compound was prepared:

4-[2-Chloro-5-(trifluoromethyl)phenyl]-1-(6,7-dihydro-5H-pyrrolo[2,3-d]pyrimidin-4-yl)-1H-pyrrole-3-carbonitrile (Compd 113)

ESI (+) MS: m/z 390 (MH$^+$).

According to this procedure, but starting from 4-[2-methyl-5-(trifluoromethyl)phenyl]-1H-pyrrole-3-carbonitrile, the following compound was prepared:

4-[2-Methyl-5-(trifluoromethyl)phenyl]-1-(7H-pyrrolo[2,3-d]pyrimidin-4-yl)-1H-pyrrole-3-carbonitrile (Compd 114)

ESI (+) MS: m/z 368 (MH$^+$).

According to this procedure, but starting from 4-[2-methyl-5-(trifluoromethyl)phenyl]-1H-pyrrole-3-carbonitrile and using 4-chloro-7-(4-methoxy-benzyl)-6,7-dihydro-5H-pyrrolo[2,3-d]pyrimidine instead of 4-chloro-7-{[2-(trimethylsilyl)ethoxy]methyl}-7H-pyrrolo[2,3-d]pyrimidine, the following compound was prepared:

4-[2-Methyl-5-(trifluoromethyl)phenyl]-1-(6,7-dihydro-5H-pyrrolo[2,3-d]pyrimidin-4-yl)-H-pyrrole-3-carbonitrile (Compd 115)

ESI (+) MS: m/z 370 (MH$^+$).

According to this procedure, but starting from 4-[2-ethyl-5-(trifluoromethyl)phenyl]-1H-pyrrole-3-carbonitrile, the following compound was prepared:

4-[2-Ethyl-5-(trifluoromethyl)phenyl]-1-(7H-pyrrolo[2,3-d]pyrimidin-4-yl)-1H-pyrrole-3-carbonitrile (Compd 116)

ESI (+) MS: m/z 382 (MH$^+$).

According to this procedure, but starting from 4-[2-ethyl-5-(trifluoromethyl)phenyl]-1H-pyrrole-3-carbonitrile and using 4-chloro-7-(4-methoxy-benzyl)-6,7-dihydro-5H-pyrrolo[2,3-d]pyrimidine instead of 4-chloro-7-{[2-(trimethylsilyl)ethoxy]methyl}-7H-pyrrolo[2,3-d]pyrimidine, the following compound was prepared:

4-[2-Ethyl-5-(trifluoromethyl)phenyl]-1-(6,7-dihydro-5H-pyrrolo[2,3-d]pyrimidin-4-yl)-1H-pyrrole-3-carbonitrile (Compd 117)

ESI (+) MS: m/z 384 (MH$^+$).

According to this procedure, but starting from 4-phenyl-1H-pyrrole-3-carbonitrile, the following compound was prepared:

4-Phenyl-17H-pyrrolo[2,3-d]pyrimidin-4-yl)-1H-pyrrole-2-carbonitrile (Compd 118)

ESI (+) MS: m/z 286 (MH$^+$).

According to this procedure, but starting from 4-phenyl-1H-pyrrole-3-carbonitrile and using 4-chloro-7-(4-methoxy-benzyl)-6,7-dihydro-5H-pyrrolo[2,3-d]pyrimidine instead of 4-chloro-7-{[2-(trimethylsilyl)ethoxy]methyl}-7H-pyrrolo[2,3-d]pyrimidine, the following compound was prepared:

4-Phenyl-1-(6,7-dihydro-5H-pyrrolo[2,3-d]pyrimidin-4-yl)-1H-pyrrole-3-carbonitrile (Compd 119)

ESI (+) MS: m/z 288 (MH$^+$).

Example 9

5-(6-Aminopyrimidin-4-yl)-3-(5-chloro-2-methylphenyl)-H-pyrrole-2-carboxamide (Compd 120)

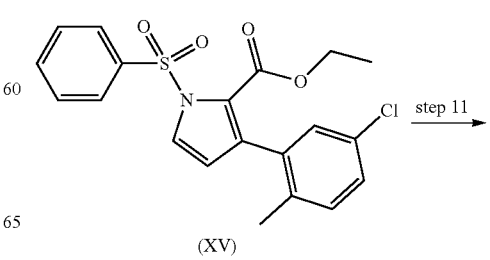

(XV)

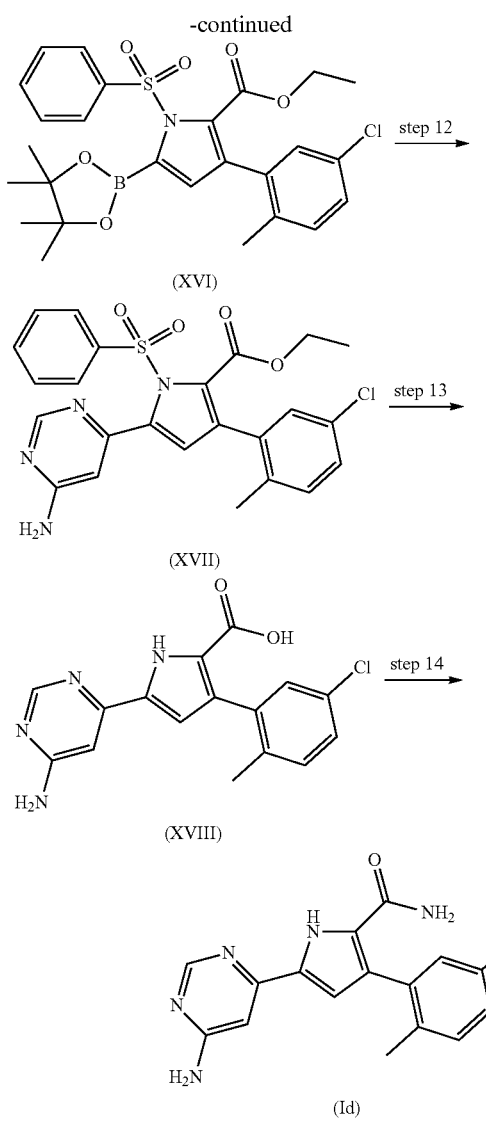

Scheme E: Steps 11, 12, 13, 14

Step 11: Ethyl 3-(5-chloro-2-methylphenyl)-1-(phenylsulfonyl)-5-(4,4,5,5-tetramethyl-1,3,2-dioxaborolan-2-yl)-1H-pyrrole-2-carboxylate (XVI)

To a solution of ethyl 3-(5-chloro-2-methylphenyl)-1-(phenylsulfonyl)-1H-pyrrole-2-carboxylate (403 mg, 1.0 mmol) in THF (5 mL) LDA (2M in THF/heptane/ethylbenzene, 0.55 mL, 1.1 mmol) was slowly added dropwise at −78° C. under argon. After 30 min, 2-isopropoxy-4,4,5,5-tetramethyl-1,3,2-dioxyborolane (0.230 mL, 1.1 mmol) was added to the mixture at −78° C. and stirred for 1 h. MeOH (0.5 mL) was added and the resultant mixture was stirred at room temperature after slowly raising the temperature, diluted with water and extracted with EtOAc (30 mL×3), dried over Na$_2$SO$_4$, filtered and the solvent was evaporated under reduced pressure to afford the title compound that was used without further purification.

Step 12: Ethyl 5-(6-aminopyrimidin-4-yl)-3-(5-chloro-2-methylphenyl)-1-phenylsulfonyl-1H-pyrrole-2-carboxylate (XVII)

Ethyl 3-(5-chloro-2-methylphenyl)-1-(phenylsulfonyl)-5-(4,4,5,5-tetramethyl-1,3,2-dioxaborolan-2-yl)-1H-pyrrole-2-carboxylate, 6-iodopyrimidin-4-amine (221 mg, 1 mmol) and Na$_2$CO$_3$ (318 mg, 3 mmol) were dissolved in dioxane/water (3/1, 10 mL). The resulting reaction mixture was degassed three times back filling with argon each time before being charged PdCl$_2$(dppf) (81 mg, 0.1 mmol). The resulting reaction mixture was degassed four times back filling with argon each time and then warmed to 110° C. for 30 min. The reaction mixture was cooled to room temperature, filtered through a pad of Celite, washed with EtOAc. The filtrate was concentrated and then diluted with EtOAc, washed with aqueous brine, dried over Na$_2$SO$_4$, filtered and concentrated under reduced pressure. The residue was purified by by Biotage SP1 Flash Chromatography (DCM/MeOH/7N NH$_3$ in MeOH 98/2/0.2) to afford the title compound (198 mg, 40%).

$^1$H NMR (600 MHz, DMSO-d$_6$) δ 8.23-8.30 (m, 3H), 7.77-7.83 (m, 1H), 7.66-7.73 (m, 2H), 7.33-7.37 (m, 1H), 7.29-7.32 (m, 1H), 7.17 (d, J=2.20 Hz, 1H), 7.04 (s, 2H), 6.76 (s, 1H), 6.63 (d, J=0.92 Hz, 1H), 3.99-4.10 (m, 2H), 2.11 (s, 3H), 0.90 (t, J=7.11 Hz, 3H).

HRMS (ESI) m/z calcd for C$_{24}$H$_{21}$ClN$_4$O$_4$S+H$^+$ 497.1045, found 497.1049.

According to this step, but using (4-chloro-7H-pyrrolo[2,3-d]pyrimidin-7-yl)methyl 2,2-dimethylpropanoate instead of 6-iodopyrimidin-4-amine, the following compound was prepared:

Ethyl 3-(5-chloro-2-methylphenyl)-5-(7-{[(2,2-dimethylpropanoyl)oxy]methyl}-7H-pyrrolo[2,3-d]pyrimidin-4-yl)-1-(phenylsulfonyl)-1H-pyrrole-2-carboxylate (XVII)

$^1$H NMR (600 MHz, DMSO-d$_6$) δ 8.78 (s, 1H), 8.35 (dd, J=1.19, 8.52 Hz, 2H), 7.80-7.85 (m, 2H), 7.70-7.78 (m, 2H), 7.35-7.40 (m, 1H), 7.32-7.34 (m, 1H), 7.31 (d, J=2.20 Hz, 1H), 7.09 (s, 1H), 6.88 (d, J=3.66 Hz, 1H), 6.27 (s, 2H), 4.09 (q, J=7.14 Hz, 2H), 2.17 (s, 3H), 1.11 (s, 9H), 0.92 (t, J=7.05 Hz, 3H).

According to this procedure, but starting from 3-(5-chloro-2-ethylphenyl)-1-(phenylsulfonyl)-1H-pyrrole-2-carboxylate, the following compound was prepared:

Ethyl 5-(6-aminopyrimidin-4-yl)-3-(5-chloro-2-ethylphenyl)-1-(phenylsulfonyl)-1H-pyrrole-2-carboxylate (XVII)

ESI (+) MS: m/z 511 (MH$^+$).

According to this procedure, but starting from 3-(5-chloro-2-ethylphenyl)-1-(phenylsulfonyl)-1H-pyrrole-2-carboxylate and using 4-chloro-7H-pyrrolo[2,3-d]pyrimidin-7-yl)methyl 2,2-dimethylpropanoate instead of 6-iodopyrimidin-4-amine, the following compound was prepared:

Ethyl 3-(5-chloro-2-ethylphenyl)-5-(7-{[(2,2-dimethylpropanoyl)oxy]methyl}-7H-pyrrolo[2,3-d]pyrimidin-4-yl)-1-(phenylsulfonyl)-1H-pyrrole-2-carboxylate (XVII)

$^1$H NMR (600 MHz, DMSO-d$_6$) δ 8.79 (s, 1H), 8.33 (dd, J=1.01, 8.52 Hz, 2H), 7.80-7.85 (m, 2H), 7.70-7.78 (m, 2H), 7.39-7.44 (m, 1H), 7.31-7.38 (m, 1H), 7.27 (d, J=2.20 Hz, 1H), 7.09 (s, 1H), 6.83 (d, J=3.66 Hz, 1H), 6.27 (s, 2H), 3.99-4.10 (m, 2H), 1.11 (s, 9H), 1.02-1.07 (m, 3H), 0.88 (t, J=7.14 Hz, 3H).

According to this procedure, but starting from ethyl 3-[2-ethyl-5-(trifluoromethyl)phenyl]-1-(phenylsulfonyl)-1H-pyrrole-2-carboxylate, the following compound was prepared:

Ethyl 5-(6-aminopyrimidin-4-yl)-3-[2-ethyl-5-(trifluoromethyl)phenyl]-1H-pyrrole-2-carboxylate (XVII)

ESI (+) MS: m/z 545 (MH$^+$).

According to this procedure, but starting from ethyl 3-[2-ethyl-5-(trifluoromethyl)phenyl]-1-(phenylsulfonyl)-1H-pyrrole-2-carboxylate and using (4-chloro-7H-pyrrolo[2,3-d]pyrimidin-7-yl)methyl 2,2-dimethylpropanoate instead of 6-iodopyrimidin-4-amine, the following compound was prepared:

Ethyl 3-[2-ethyl-5-(trifluoromethyl)phenyl]-5-(7-{[(2,2-dimethylpropanoyl)oxy]methyl}-7H-pyrrolo[2,3-d]pyrimidin-4-yl)-1-(phenylsulfonyl)-1H-pyrrole-2-carboxylate (XVII)

$^1$H NMR (600 MHz, DMSO-d$_6$) δ 8.79 (s, 1H), 8.28-8.45 (m, 2H), 7.81-7.87 (m, 2H), 7.73-7.78 (m, 2H), 7.72 (d, J=8.0 Hz, 1H), 7.58 (d, J=8.0 Hz, 1H), 7.54 (s, 1H), 7.14 (s, 1H), 6.84 (d, J=3.6 Hz, 1H), 6.27 (s, 2H), 4.02 (q, J=6.9 Hz, 2H), 2.61 (q, J=7.6 Hz, 2H), 1.11 (s, 9H), 1.06-1.10 (m, 3H), 0.81 (t, J=7.0 Hz, 3H).

Step 13: 5-(6-Aminopyrimidin-4-yl)-3-(5-chloro-2-methylphenyl)-1H-pyrrole-2-carboxylic Acid (XVIII)

Ethyl 5-(6-aminopyrimidin-4-yl)-3-(5-chloro-2-methylphenyl)-1-(phenylsulfonyl)-1H-pyrrole-2-carboxylate (80 mg, 0.161 mmol) in THF (0.5 mL) was treated with LiOH.H$_2$O (27 mg, 0.644 mmol) at 150° C. in the microwave apparatus for 15 min. After cooling, the residue was concentrated, treated with 1N HCl (300 µL), neutralized with saturated solution of sodium hydrogen carbonate, the resulting precipitate was collected by filtration to afford the title compound (52 mg, 98%).

ESI (+) MS: m/z 329 (MH$^+$).

According to this step the following compounds were prepared:

5-(6-Aminopyrimidin-4-yl)-3-(5-chloro-2-ethylphenyl)-1H-pyrrole-2-carboxylic Acid (XVIII)

ESI (+) MS: m/z 343 (MH$^+$).

5-(6-Aminopyrimidin-4-yl)-3-[2-ethyl-5-(trifluoromethyl)phenyl]-1H-pyrrole-2-carboxylic Acid (XVIII)

ESI (+) MS: m/z 377 (MH$^+$).

3-(5-Chloro-2-methylphenyl)-5-(7H-pyrrol[2,3-d]pyrimidin-4-yl)-1H-pyrrole-2-carboxylic Acid (XVIII)

ESI (+) MS: m/z 353 (MH$^+$).

3-(5-Chloro-2-ethylphenyl)-5-(7H-pyrrolo[2,3-d]pyrimidin-4-yl)-1H-pyrrole-2-carboxylic Acid (XVIII)

$^1$H NMR (600 MHz, DMSO-d$_6$) δ 12.42-12.89 (m, 1H), 12.24 (br. s., 1H), 11.39 (br. S., 1H), 8.79 (s, 1H), 7.62 (dd, J=2.47, 3.39 Hz, 1H), 7.29-7.36 (m, 1H), 7.25 (d, J=2.01 Hz, 1H), 7.19 (s, 1H), 7.01 (dd, J=1.65, 3.48 Hz, 1H), 2.52-2.56 (m, 2H), 1.00-1.05 (m, 3H).

3-[2-Ethyl-5-(trifluoromethyl)phenyl]-5-(7H-pyrrolo[2,3-d]pyrimidin-4-yl)-1H-pyrrole-2-carboxylic Acid (XVIII)

ESI (+) MS: mm/z 401 (MH$^+$).

Step 14: 5-(6-Aminopyrimidin-4-yl)-3-(5-chloro-2-methylphenyl)-1H-pyrrole-2-carboxamide A solution of 5-(6-aminopyrimidin-4-yl)-3-(5-chloro-2-methylphenyl)-1H-pyrrole-2-carboxylic acid (52 mg, 0.158 mmol) in DMF (1.0 mL) and DIPEA (55 µL, 0.634 mmol) was stirred at 0° C. EDCl (60 mg, 0.317 mmol) and HOBT.NH$_3$ (48 mg, 0.317 mmol) were added and the reaction mixture was stirred for 3 h at room temperature. The mixture was diluted with saturated solution of sodium hydrogen carbonate at 5° C., stirred for 30 min, the resulting precipitate was collected by filtration to afford the title compound (42 mg, 80%).

$^1$H NMR (600 MHz, DMSO-d$_6$) δ 11.83 (br. s., 1H), 8.39 (s, 1H), 7.38 (br. s., 1H), 7.21-7.27 (m, 2H), 7.15 (s, 1H), 7.08 (br. s., 1H), 6.85 (s, 2H), 6.74 (s, 1H), 6.67 (s, 1H), 2.10 (s, 3H).

HRMS (ESI) m/z calcd for C$_{16}$H$_{14}$ClN$_5$O+H$^+$ 328.0960, found 328.0955.

According to this step the following compounds were prepared:

5-(6-Aminopyrimidin-4-yl)-3-(5-chloro-2-ethylphenyl)-1H-pyrrole-2-carboxamide (Compd 121)

ESI (+) MS: m/z 342 (MH$^+$).

5-(6-Aminopyrimidin-4-yl)-3-[2-ethyl-5-(trifluoromethyl)phenyl]-1H-pyrrole-2-carboxamide (Compd 122)

ESI (+) MS: m/z 376 (MH$^+$).

3-(5-Chloro-2-methylphenyl)-5-(7H-pyrrolo[2,3-d]pyrimidin-4-yl)-1H-pyrrole-2-carboxamide (Compd 123)

$^1$H NMR (600 MHz, DMSO-d$_6$) δ 12.16 (br. s., 1H), 12.04 (br. s., 1H), 8.78 (s, 1H), 7.63-7.76 (m, 1H), 7.58 (dd, J=2.38, 3.48 Hz, 1H), 7.24-7.27 (m, 2H), 7.22 (d, J=1.28 Hz, 1H), 7.14-7.18 (m, 1H), 7.12 (s, 1H), 7.01 (dd, J=1.74, 3.57 Hz, 1H), 2.14 (s, 3H).

HRMS (ESI) m/z calcd for C$_{18}$H$_{14}$ClN$_5$O+H$^+$ 352.0960, found 352.0961.

3-(5-Chloro-2-ethylphenyl)-5-(7H-pyrrolo[2,3-d]pyrimidin-4-yl)-1H-pyrrole-2-carboxamide (Compd 124)

$^1$H NMR (600 MHz, DMSO-d$_6$) δ 12.17 (br. s., 1H), 12.03 (br. s., 1H), 8.78 (s, 1H), 7.64 (br. s., 1H), 7.58 (dd,

J=2.38, 3.48 Hz, 1H), 7.26-7.33 (m, 2H), 7.19 (d, J=2.02 Hz, 1H), 7.14 (br. s., 1H), 7.12 (d, J=2.20 Hz, 1H), 6.99 (dd, J=1.83, 3.66 Hz, 1H), 1.01 (t, J=7.51 Hz, 3H).

HRMS (ESI) m/z calcd for $C_{19}H_{16}ClN_5O+H^+$ 366.1116, found 366.1111.

3-[2-Ethyl-5-(trifluoromethyl)phenyl]-5-(7-pyrrolo[2,3-d]pyrimidin-4-yl)-1H-pyrrole-2-carboxamide (Compd 125)

$^1$H NMR (600 MHz, DMSO-$d_6$) δ 12.17 (br. s., 1H), 12.14 (br. s., 1H), 8.79 (s, 1H), 7.79 (br. s., 1H), 7.60 (dd, J=1.28, 8.06 Hz, 1H), 7.58 (dd, J=2.56, 3.48 Hz, 1H), 7.49 (d, J=8.06 Hz, 1H), 7.45 (d, J=1.28 Hz, 1H), 7.17 (d, J=1.65 Hz, 1H), 7.13 (br. s., 1H), 7.01 (dd, J=1.74, 3.57 Hz, 1H), 2.60 (q, J=7.51 Hz, 2H), 1.05 (t, J=7.51 Hz, 3H).

HRMS (ESI) m/z calcd for $C_{20}H_{16}F_3N_5O+H^+$ 400.1380, found 400.1380.

According to this step, but using methylamine, the following compounds were prepared:

5-(6-Aminopyrimidin-4-yl)-N-methy-3-(5-chloro-2-methylphenyl)-1H-pyrrole-2-carboxamide (Compd 126)

ESI (+) MS: m/z 342 (MH$^+$).

5-(6-Aminopyrimidin-4-yl)-N-methyl-3-chloro-2-ethylphenyl)-1H-pyrrole-2-carboxamide (Compd 127)

ESI (+) MS: m/z 356 (MH$^+$).

5-(6-Aminopyrimidin-4-yl)-N-methyl-3-[2-ethyl-5-(trifluoromethyl)phenyl]-1H-pyrrole-2-carboxamide (Compd 128)

ESI (+) MS: m/z 390 (MH$^+$).

3-(5-Chloro-2-methylphenyl)-N-methyl-5-(7H-pyrrolo[2,3-d]pyrimidin-4-yl)-1H-pyrrole-2-carboxamide (Compd 129)

$^1$H NMR (600 MHz, DMSO-$d_6$) δ 12.16 (br. s., 1H), 12.03 (br. s., 1H), 8.77 (s, 1H), 8.29 (q, J=4.15 Hz, 1H), 7.58 (dd, J=2.47, 3.39 Hz, 1H), 7.22-7.28 (m, 2H), 7.21 (d, J=1.65 Hz, 1H), 7.13 (d, J=2.01 Hz, 1H), 7.01 (dd, J=1.65, 3.48 Hz, 1H), 2.70 (d, J=4.58 Hz, 3H), 2.13 (s, 3H).

HRMS (ESI) m/z calcd for $C_{19}H_{16}ClN_5O+H^+$ 366.1116, found 366.1119.

3-(5-Chloro-2-ethylphenyl)-N-methyl-5-(7H-pyrrolo[2,3-d]pyrimidin-4-yl)-1H-pyrrole-2-carboxamide (Compd 130)

$^1$H NMR (600 MHz, DMSO-$d_6$) δ 12.16 (br. s., 1H), 12.03 (br. s., 1H), 8.78 (s, 1H), 8.27 (q, J=4.33 Hz, 1H), 7.57 (dd, J=2.38, 3.48 Hz, 1H), 7.29-7.32 (m, 1H), 7.26-7.28 (m, 1H), 7.17 (d, J=2.20 Hz, 1H), 7.13 (d, J=2.20 Hz, 1H), 6.99 (dd, J=1.65, 3.66 Hz, 1H), 2.69 (d, J=4.58 Hz, 3H), 2.45-2.48 (m, 1H), 1.00 (t, J=7.60 Hz, 3H).

HRMS (ESI) m/z calcd for $C_{20}H_{18}ClN_5O+H^+$ 380.1273, found 380.1272.

3-[2-Ethyl-5-(trifluoromethyl)phenyl]-N-methyl-5-(7H-pyrrolo[2,3-d]pyrimidin-4-yl)-1H-pyrrole-2-carboxamide (Compd 131)

$^1$H NMR (600 MHz, DMSO-$d_6$) δ 12.16 (br. s., 1H), 12.12 (br. s., 1H), 8.78 (s, 1H), 8.38 (q, J=4.03 Hz, 1H), 7.59 (dd, J=1.37, 8.15 Hz, 1H), 7.57 (dd, J=2.47, 3.39 Hz, 1H), 7.49 (d, J=8.06 Hz, 1H), 7.44 (d, J=1.10 Hz, 1H), 7.17 (d, J=1.65 Hz, 1H), 7.01 (dd, J=1.74, 3.57 Hz, 1H), 2.69 (d, J=4.40 Hz, 3H), 2.58 (q, J=7.51 Hz, 2H), 1.04 (t, J=7.60 Hz, 3H).

HRMS (ESI) m/z calcd for $C_{21}H_{18}F_3N_5O+H^+$ 414.1536, found 414.1534.

According to this procedure, but using 6-chloro-N-methylpyrimidin-4-amine instead of 6-iodopyrimidin-4-amine in the step 12, the following compound was prepared:

3-(5-Chloro-2-methylphenyl)-5-[6-(methylamino)pyrimidin-4-yl]-1H-pyrrole-2-carboxamide (Compd 132)

ESI (+) MS: m/z 342 (MH$^+$).

According to this procedure, but using 4-chloropyrrolo[2,1-J][1,2,4]triazine instead of 6-iodopyrimidin-4-amine in the step 12, the following compound was prepared:

3-(5-Chloro-2-methylphenyl)-5-(pyrrolo[2,1-f][1,2,4]triazin-4-yl)-1H-pyrrole-2-carboxamide (Compd 133)

ESI (+) MS: m/z 352 (MH$^+$).

According to this procedure, but using 4-chloro-7-(4-methoxy-benzyl)-6,7-dihydro-5H-pyrrolo[2,3-d]pyrimidine instead of 6-iodopyrimidin-4-amine in the step 12 and removing the 4-methoxy-benzyl protecting group with TFA in DCM, the following compound was prepared: 3-(5-Chloro-2-methylphenyl)-5-(6,7-dihydro-5H-pyrrolo[2,3-d]pyrimidin-4-yl)-1H-pyrrole-2-carboxamide (Compd 134)

ESI (+) MS: m/z 354 (MH$^+$).

According to this procedure, but starting from ethyl 3-(5-chloro-2-ethylphenyl)-1-(phenylsulfonyl)-1H-pyrrole-2-carboxylate in the step 11 and using 6-chloro-N-methylpyrimidin-4-amine instead of 6-iodopyrimidin-4-amine in the step 12, the following compound was prepared:

3-(5-Chloro-2-ethylphenyl)-5-[6-(methylamino)pyrimidin-4-yl]-1H-pyrrole-2-carboxamide (Compd 135)

ESI (+) MS: m/z 356 (MH$^+$).

According to this procedure, but starting from ethyl 3-(5-chloro-2-ethylphenyl)-1-(phenylsulfonyl)-1H-pyrrole-2-carboxylate in the step 11 and using 4-chloropyrrolo[2,1-f][1,2,4]triazine instead of 6-iodopyrimidin-4-amine in the step 12, the following compound was prepared:

3-(5-Chloro-2-ethylphenyl)-5-(pyrrolo[2,1-f][1,2,4]triazin-4-yl)-1H-pyrrole-2-carboxamide (Compd 136)

ESI (+) MS: m/z 366 (MH$^+$).

According to this procedure, but starting from ethyl 3-(5-chloro-2-ethylphenyl)-1-(phenylsulfonyl)-1H-pyrrole-2-carboxylate in the step 11, using 4-chloro-7-(4-methoxy-benzyl)-6,7-dihydro-5H-pyrrolo[2,3-d]pyrimidine instead of 6-iodopyrimidin-4-amine in the step 12 and removing the 4-methoxy-benzyl protecting group with TFA in DCM, the following compound was prepared:

3-(5-Chloro-2-ethylphenyl)-5-(6,7-dihydro-5H-pyrrolo[2,3-d]pyrimidin-4-yl)-1H-pyrrole-2-carboxamide (Compd 137)

ESI (+) MS: m/z 368 (MH+).
According to this procedure, but starting from ethyl 3-[2-chloro-5-(trifluoromethyl)phenyl]-1-(phenylsulfonyl)-1H-pyrrole-2-carboxylate in the step 11, the following compound was prepared:

5-(6-Aminopyrimidin-4-yl)-3-[2-chloro-5-(trifluoromethyl)phenyl]-1H-pyrrole-2-carboxamide (Compd 138)

ESI (+) MS: m/z 382 (MH+).
According to this procedure, but starting from ethyl 3-[2-chloro-5-(trifluoromethyl)phenyl]-1-(phenylsulfonyl)-1H-pyrrole-2-carboxylate in the step 11 and using 6-chloro-N-methylpyrimidin-4-amine instead of 6-iodopyrimidin-4-amine in the step 12, the following compound was prepared:

3-[2-Chloro-5-(fluoromethyl)phenyl]-5-[6-(methylamino)pyrimidin-4-yl]-1H-pyrrole-2-carboxamide (Compd 139)

ESI (+) MS: m/z 396 (MH+).
According to this procedure, but starting from ethyl 3-[2-chloro-5-(trifluoromethyl)phenyl]-1-(phenylsulfonyl)-1H-pyrrole-2-carboxylate in the step 11 and using 4-chloro-7H-pyrrolo[2,3-d]pyrimidin-7-yl)methyl 2,2-dimethylpropanoate instead of 6-iodopyrimidin-4-amine in the step 12, the following compound was prepared:

3-[2-Chloro-5-(trifluoromethyl)phenyl]-7H-pyrrolo[2,3-d]pyrimidin-4-yl)-1H-pyrrole-2-carboxamide (Compd 140)

ESI (+) MS: m/z 406 (MH+).
According to this procedure, but starting from ethyl 3-[2-chloro-5-(trifluoromethyl)phenyl]-1-(phenylsulfonyl)-1H-pyrrole-2-carboxylate in the step 11 and using 4-chloropyrrolo[2,1-f][1,2,4]triazine instead of 6-iodopyrimidin-4-amine in the step 12, the following compound was prepared:

3-[2-Chloro-5-(trifluormethyl)phenyl]-5-(pyrrolo[2,1-f][1,2,4]triazin-4-yl)-1H-pyrrole-2-carboxamide (Compd 141)

ESI (+) MS: m/z 406 (MH+).
According to this procedure, but starting from ethyl 3-[2-chloro-5-(trifluoromethyl)phenyl]-1-(phenylsulfonyl)-1H-pyrrole-2-carboxylate in the step 11, using 4-chloro-7-(4-methoxy-benzyl)-6,7-dihydro-5H-pyrrolo[2,3-d]pyrimidine instead of 6-iodopyrimidin-4-amine in the step 12 and removing the 4-methoxy-benzyl protecting group with TFA in DCM, the following compound was prepared:

3-[2-Chloro-5-(trifluoromethyl)phenyl]-5-(6,7-dihydro-5H pyrrolo[2,3-d]pyrimidin-4-yl)-1H-pyrrole-2-carboxamide (Compd 142)

ESI (+) MS: m/z 408 (MH+).
According to this procedure, but starting from ethyl 3-[2-methyl-5-(trifluoromethyl)phenyl]-1-(phenylsulfonyl)-1H-pyrrole-2-carboxylate in the step 11, the following compound was prepared:

5-[6-Aminopyrimidin-4-yl]-3-[2-methyl-5-(trifluormethyl)phenyl]-1H-pyrrole-2-carboxamide (Compd 143)

ESI (+) MS: m/z 362 (MH+).
According to this procedure, but starting from ethyl 3-[2-methyl-5-(trifluoromethyl)phenyl]-1-(phenylsulfonyl)-1H-pyrrole-2-carboxylate in the step 11 and using 6-chloro-N-methylpyrimidin-4-amine instead of 6-iodopyrimidin-4-amine in the step 12, the following compound was prepared:

5-[6-(Methylamino)pyrimidin-4-yl]-3-[2-methyl-5-(trifluoromethyl)phenyl]-1H-pyrrole-2-carboxamide (Compd 144)

ESI (+) MS: m/z 376 (MH+).
According to this procedure, but starting from ethyl 3-[2-methyl-5-(trifluoromethyl)phenyl]-1-(phenylsulfonyl)-1H-pyrrole-2-carboxylate in the step 11 and using 4-chloro-7H-pyrrolo[2,3-d]pyrimidin-7-yl)methyl 2,2-dimethylpropanoate instead of 6-iodopyrimidin-4-amine in the step 12, the following compound was prepared:

3-[2-Methyl-5-(trifluoromethyl)phenyl]-5-(7H-pyrrolo[2,3-d]pyrimidin-4-yl)-1H-pyrrole-2-carboxamide (Compd 145)

ESI (+) MS: m/z 386 (MH+).
According to this procedure, but starting from ethyl 3-[2-methyl-5-(trifluoromethyl)phenyl]-1-(phenylsulfonyl)-1H-pyrrole-2-carboxylate in the step 11 and using 4-chloropyrrolo[2,1-f][1,2,4]triazine instead of 6-iodopyrimidin-4-amine in the step 12, the following compound was prepared:

3-[2-Methyl-5-(trifluoromethyl)phenyl]-5-(pyrrolo[2,1-f][1,2,4]triazin-4-yl)-1H-pyrrole-2-carboxamide (Compd 146)

ESI (+) MS: m/z 386 (MH+).
According to this procedure, but starting from ethyl 3-[2-methyl-5-(trifluoromethyl)phenyl]-1-(phenylsulfonyl)-1H-pyrrole-2-carboxylate in the step 11, using 4-chloro-7-(4-methoxy-benzyl)-6,7-dihydro-5H-pyrrolo[2,3-d]pyrimidine instead of 6-iodopyrimidin-4-amine in the step 12 and removing the 4-methoxy-benzyl protecting group with TFA in DCM, the following compound was prepared:

3-[2-Methyl-5-(trifluoromethyl)phenyl]-5-(6,7-dihydro-5H-pyrrolo[2,3-d]pyrimidin-4-yl)-1H-pyrrole-2-carboxamide (Compd 147)

ESI (+) MS: m/z 388 (MH+).
According to this procedure, but starting from ethyl 3-[2-ethyl-5-(trifluoromethyl)phenyl]-1-(phenylsulfonyl)-1H-pyrrole-2-carboxylate in the step 11, using 6-chloro-N-methylpyrimidin-4-amine instead of 6-iodopyrimidin-4-amine in the step 12, the following compound was prepared:

3-[2-Ethyl-5-(trifluoromethyl)phenyl]-5-[6-(methylamino)pyrimidin-4-yl]-1H-pyrrole-2-carboxamide (Compd 148)

ESI (+) MS: m/z 390 (MH+).
According to this procedure, but starting from ethyl 3-[2-ethyl-5-(trifluoromethyl)phenyl]-1-(phenylsulfonyl)-1H-pyrrole-2-carboxylate in the step 11 and using 4-chloropyrrolo[2,1-f][1,2,4]triazine instead of 6-iodopyrimidin-4-amine in the step 12, the following compound was prepared:

3-[2-Ethyl-5-(trifluoromethyl)phenyl]-5-(pyrrolo[2,1-f][1,2,4]triazin-4-yl)-1H-pyrrole-2-carboxamide (Compd 149)

ESI (+) MS: m/z 400 (MH+).

According to this procedure, but starting from ethyl 3-[2-ethyl-5-(trifluoromethyl)phenyl]-1-(phenylsulfonyl)-1H-pyrrole-2-carboxylate in the step 11, using 4-chloro-7-(4-methoxy-benzyl)-6,7-dihydro-5H-pyrrolo[2,3-d]pyrimidine instead of 6-iodopyrimidin-4-amine in the step 12 and removing the 4-methoxy-benzyl protecting group with TFA in DCM, the following compound was prepared:

3-[2-Ethyl-5-(trifluoromethyl)phenyl]-5-(6,7-dihydro-5H-pyrrolo[2,3-d]pyrimidin-4-yl)-1H-pyrrole-2-carboxamide (Compd 150)

ESI (+) MS: m/z 402 (MH+).

According to this procedure, but starting from ethyl 3-phenyl-1-(phenylsulfonyl)-1H-pyrrole-2-carboxylate in the step 11, the following compound was prepared:

5-(6-Aminopyrimidin-4-yl)-3-phenyl-1H-pyrrole-2-carboxamide (Compd 151)

ESI (+) MS: m/z 280 (MH+).

According to this procedure, but starting from ethyl 3-phenyl-1-(phenylsulfonyl)-1H-pyrrole-2-carboxylate in the step 11 and using 6-chloro-N-methylpyrimidin-4-amine instead of 6-iodopyrimidin-4-amine in the step 12, the following compound was prepared:

5-[6-(Methylamino)pyrimidin-4-yl]-3-phenyl-1H-pyrrole-2-carboxamide (Compd 152)

ESI (+) MS: m/z 294 (MH+).

According to this procedure, but starting from ethyl 3-phenyl-1-(phenylsulfonyl)-1H-pyrrole-2-carboxylate in the step 11 and using 4-chloro-7H-pyrrolo[2,3-d]pyrimidin-7-yl)methyl 2,2-dimethylpropanoate instead of 6-iodopyrimidin-4-amine in the step 12, the following compound was prepared:

3-Phenyl-5-(7H-pyrrolo[2,3-d]pyrimidin-4-yl)-1H-pyrrole-2-carboxamide (Compd 153)

ESI (+) MS: m/z 304 (MH+).

According to this procedure, but starting from ethyl 3-phenyl-1-(phenylsulfonyl)-1H-pyrrole-2-carboxylate in the step 11 and using 4-chloropyrrolo[2,1-f][1,2,4]triazine instead of 6-iodopyrimidin-4-amine in the step 12, the following compound was prepared:

3-Phenyl-5-(pyrrolo[2,1-f][1,2,4]triazin-4-yl)-1H-pyrrole-2-carboxamide (Compd 154)

ESI (+) MS: m/z 304 (MH+).

According to this procedure, but starting from ethyl 3-phenyl-1-(phenylsulfonyl)-1H-pyrrole-2-carboxylate in the step 11, using 4-chloro-7-(4-methoxy-benzyl)-6,7-dihydro-5H-pyrrolo[2,3-d]pyrimidine instead of 6-iodopyrimidin-4-amine in the step 12 and removing the 4-methoxy-benzyl protecting group with TFA in DCM, the following compound was prepared:

5-(6,7-Dihydro-5H-pyrrolo[2,3-d]pyrimidin-4-yl)-3-phenyl-1H-pyrrole-2-carboxamide (Compd 155)

ESI (+) MS: m/z 306 (MH+).

According to this procedure, but using 6-chloro-N-methylpyrimidin-4-amine instead of 6-iodopyrimidin-4-amine in the step 12 and methylamine in the step 14, the following compound was prepared:

3-(5-Chloro-2-methylphenyl)-N-methyl-5-[6-(methylamino pyrimidin-4-yl]-1H-pyrrole-2-carboxamide (Compd 156)

ESI (+) MS: m/z 356 (MH+).

According to this procedure, but using 4-chloropyrrolo[2,1-f][1,2,4]triazine instead of 6-iodopyrimidin-4-amine in the step 12 and methylamine in the step 14, the following compound was prepared:

3-(5-Chloro-2-methylphenyl)-N-methyl-5-(pyrrolo[2,1-f][1,2,4]triazin-4-yl)-1H-pyrrole-2-carboxamide (Compd 157)

ESI (+) MS: m/z 366 (MH+).

According to this procedure, but using 4-chloro-7-(4-methoxy-benzyl)-6,7-dihydro-5H-pyrrolo[2,3-d]pyrimidine instead of 6-iodopyrimidin-4-amine in the step 12 and methylamine in the step 14 and removing the 4-methoxy-benzyl protecting group with TFA in DCM, the following compound was prepared:

3-(5-Chloro-2-methylphenyl 6,7-dihydro-5H-pyrrolo[2,3-d]pyrimidin-4-yl)-N-methyl-1H-pyrrole-2-carboxamide (Compd 158)

ESI (+) MS: m/z 368 (MH+).

According to this procedure, but starting from ethyl 3-(5-chloro-2-ethylphenyl)-1-(phenylsulfonyl)-1H-pyrrole-2-carboxylate in the step 11, using 6-chloro-N-methylpyrimidin-4-amine instead of 6-iodopyrimidin-4-amine in the step 12 and methylamine in the step 14, the following compound was prepared:

3-(5-Chloro-2-ethylphenyl)-N-ethyl-5-[6-(methylamino)pyrimidin-4-yl]-1H-pyrrole-2-carboxamide (Compd 159)

ESI (+) MS: m/z 368 (MH+).

According to this procedure, but starting from ethyl 3-(5-chloro-2-ethylphenyl)-1-(phenylsulfonyl)-1H-pyrrole-2-carboxylate in the step 11, using 4-chloropyrrolo[2,1-f][1,2,4]triazine instead of 6-iodopyrimidin-4-amine in the step 12 and methylamine in the step 14, the following compound was prepared:

3-(5-Chloro-2-ethylphenyl)-N-methyl-5-(pyrrolo[2,1-f][1,2,4]triazin-4-yl)-1H-pyrrole-2-carboxamide (Compd 160)

ESI (+) MS: m/z 380 (MH+).

According to this procedure, but starting from ethyl 3-(5-chloro-2-ethylphenyl)-1-(phenylsulfonyl)-1H-pyrrole-2-carboxylate in the step 11, using 4-chloro-7-(4-methoxybenzyl)-6,7-dihydro-5H-pyrrolo[2,3-d]pyrimidine instead of 6-iodopyrimidin-4-amine in the step 12 and methylamine in the step 14 and removing the 4-methoxy-benzyl protecting group with TFA in DCM, the following compound was prepared:

3-(5-Chloro-2-ethylphenyl-5-(6,7-dihydro-5H-pyrrolo[2,3-d]pyrimidin-4-yl)-N-methyl-1H-pyrrole-2-carboxamide (Compd 161)

ESI (+) MS: m/z 382 (MH+).

According to this procedure, but starting from ethyl 3-[2-chloro-5-(trifluoromethyl)phenyl]-1-(phenylsulfonyl)-1H-pyrrole-2-carboxylate in the step 11 and using methylamine in the step 14, the following compound was prepared:

5-(6-Aminopyrimidin-4-yl)-3-[2-chloro-5-(trifluoromethyl)phenyl]-N-methyl-1H-pyrrole-2-carboxamide (Compd 162)

ESI (+) MS: m/z 396 (MH+).

According to this procedure, but starting from ethyl 3-[2-chloro-5-(trifluoromethyl)phenyl]-1-(phenylsulfonyl)-1H-pyrrole-2-carboxylate in the step 11, using 6-chloro-N-methylpyrimidin-4-amine instead of 6-iodopyrimidin-4-amine in the step 12 and methylamine in the step 14, the following compound was prepared:

3-[2-Chloro-5-(trifluoromethyl)phenyl]-N-methyl-5-[6-(methylamino)pyrimidin-4-yl]-1H-pyrrole-2-carboxamide (Compd 163)

ESI (+) MS: m/z 410 (MH+).

According to this procedure, but starting from ethyl 3-[2-chloro-5-(trifluoromethyl)phenyl]-1-(phenylsulfonyl)-1H-pyrrole-2-carboxylate in the step 11, using 4-chloro-7H-pyrrolo[2,3-d]pyrimidin-7-yl)methyl 2,2-dimethylpropanoate instead of 6-iodopyrimidin-4-amine in the step 12 and methylamine in the step 14, the following compound was prepared:

3-[2-Chloro-5-(trifluoromethyl)phenyl]-N-methyl-5-(H-pyrrolo[2,3-d]pyrimidin-4-yl)-H-pyrrole-2-carboxamide (Compd 164)

ESI (+) MS: m/z 420 (MH+).

According to this procedure, but starting from ethyl 3-[2-chloro-5-(trifluoromethyl)phenyl]-1-(phenylsulfonyl)-1H-pyrrole-2-carboxylate in the step 11, using 4-chloropyrrolo[2,1-f][1,2,4]triazine instead of 6-iodopyrimidin-4-amine in the step 12 and methylamine in the step 14, the following compound was prepared:

3-[2-Chloro-5-(trifluoromethyl)phenyl]-N-methyl-5-(pyrrolo[2,1-f][1,2,4]triazin-4-yl)-1H-pyrrole-2-carboxamide (Compd 165)

ESI (+) MS: m/z 420 (MH+).

According to this procedure, but starting from ethyl 3-[2-chloro-5-(trifluoromethyl)phenyl]-1-(phenylsulfonyl)-1H-pyrrole-2-carboxylate in the step 11, using 4-chloro-7-(4-methoxy-benzyl)-6,7-dihydro-5H-pyrrolo[2,3-d]pyrimidine instead of 6-iodopyrimidin-4-amine in the step 12 and methylamine in the step 14 and removing the 4-methoxy-benzyl protecting group with TFA in DCM, the following compound was prepared:

3-[2-Chloro-5-(trifluormethyl)phenyl]-5-(6,7-dihydro-H-pyrrolo[2,3-d]pyrimidin-4-yl)-N-methyl-1H-pyrrole-2-carboxamide (Compd 166)

ESI (+) MS: m/z 422 (MH+).

According to this procedure, but starting from ethyl 3-[2-methyl-5-(trifluoromethyl)phenyl]-1-(phenylsulfonyl)-1H-pyrrole-2-carboxylate in the step 11 and using methylamine in the step 14, the following compound was prepared:

5-(6-Aminopyrimidin-4-yl)-N-methy-3-[2-methyl-5-(trifluoromethyl)phenyl]-1H-pyrrole-2-carboxamide (Compd 167)

ESI (+) MS: m/z 390 (MH+).

According to this procedure, but starting from ethyl 3-[2-methyl-5-(trifluoromethyl)phenyl]-1-(phenylsulfonyl)-1H-pyrrole-2-carboxylate in the step 11, using 6-chloro-N-methylpyrimidin-4-amine instead of 6-iodopyrimidin-4-amine in the step 12 and methylamine in the step 14, the following compound was prepared:

N-Methyl-5-[6-(methylamino)pyrimidin-4-yl]-3-[2-methyl-5-(trifluoromethyl)phenyl]-1H-pyrrole-2-carboxamide (Compd 168)

ESI (+) MS: m/z 404 (MH+).

According to this procedure, but starting from ethyl 3-[2-methyl-5-(trifluoromethyl)phenyl]-1-(phenylsulfonyl)-1H-pyrrole-2-carboxylate in the step 11, using 4-chloro-7H-pyrrolo[2,3-d]pyrimidin-7-yl)methyl 2,2-dimethylpropanoate instead of 6-iodopyrimidin-4-amine in the step 12 and methylamine in the step 14, the following compound was prepared:

N-methyl-3-[2-methyl-5-(trifluoromethyl)phenyl]-5-(7H-pyrrolo[2,3-d]pyrimidin-4-yl)-1H-pyrrole-2-carboxamide (Compd 169)

ESI (+) MS: m/z 400 (MH+).

According to this procedure, but starting from ethyl 3-[2-methyl-5-(trifluoromethyl)phenyl]-1-(phenylsulfonyl)-1H-pyrrole-2-carboxylate in the step 11, using 4-chloropyrrolo[2,1-f][1,2,4]triazine instead of 6-iodopyrimidin-4-amine in the step 12 and methylamine in the step 14, the following compound was prepared:

N-Methyl-3-[2-methyl-5-(trifluoromethyl)phenyl]-5-(pyrrolo[2,1-f][1,2,4]triazin-4-yl)-1H-pyrrole-2-carboxamide (Compd 170)

ESI (+) MS: m/z 400 (MH+).

According to this procedure, but starting from ethyl 3-[2-methyl-5-(trifluoromethyl)phenyl]-1-(phenylsulfonyl)-1H-pyrrole-2-carboxylate in the step 11, using 4-chloro-7-(4-methoxy-benzyl)-6,7-dihydro-5H-pyrrolo[2,3-d]pyrimidine instead of 6-iodopyrimidin-4-amine in the step 12 and methylamine in the step 14 and removing the 4-methoxy-benzyl protecting group with TFA in DCM, the following compound was prepared:

3-[2-Methyl-5-(trifluoromethyl)phenyl]-5-(6,7-di-hydro-5H-pyrrolo[2,3-d]pyrimidin-4-yl)-N-methyl-1H-pyrrole-2-carboxamide (Compd 171)

ESI (+) MS: m/z 402 (MH+).

According to this procedure, but starting from ethyl 3-[2-ethyl-5-(trifluoromethyl)phenyl]-1-(phenylsulfonyl)-1H-pyrrole-2-carboxylate in the step 11, using 6-chloro-N-methylpyrimidin-4-amine instead of 6-iodopyrimidin-4-amine in the step 12 and methylamine in the step 14, the following compound was prepared:

3-[2-Ethyl-5-(trifluoromethyl)phenyl]-N-methyl-5-[6-methylamino)pyrimidin-4-yl]-1H-pyrrole-2-carboxamide (Compd 172)

ESI (+) MS: m/z 404 (MH+).

According to this procedure, but starting from ethyl 3-[2-ethyl-5-(trifluoromethyl)phenyl]-1-(phenylsulfonyl)-1H-pyrrole-2-carboxylate in the step 11, using 4-chloropyrrolo[2,1-f][1,2,4]triazine instead of 6-iodopyrimidin-4-amine in the step 12 and methylamine in the step 14, the following compound was prepared:

3-[2-Ethyl-5-(trifluoromethyl)phenyl]-N-methyl-5-(pyrrolo[2,1-f][1,2,4]triazin-4-yl)-1H-pyrrole-2-carboxamide (Compd 173)

ESI (+) MS: m/z 414 (MH+).

According to this procedure, but starting from ethyl 3-[2-ethyl-5-(trifluoromethyl)phenyl]-1-(phenylsulfonyl)-1H-pyrrole-2-carboxylate in the step 11, using 4-chloro-7-(4-methoxy-benzyl)-6,7-dihydro-5H-pyrrolo[2,3-d]pyrimidine instead of 6-iodopyrimidin-4-amine in the step 12 and methylamine in the step 14 and removing the 4-methoxy-benzyl protecting group with TFA in DCM, the following compound was prepared:

3-[2-Ethyl-5-(trifluoromethyl)phenyl]-5-(6,7-di-hydro-5H-pyrrolo[2,3-d]pyrimidin-4-yl)-N-methyl-1H-pyrrole-2-carboxamide (Compd 174)

ESI (+) MS: m/z 416 (MH+).

According to this procedure, but starting from ethyl 3-phenyl-1-(phenylsulfonyl)-1H-pyrrole-2-carboxylate in the step 11 and methylamine in the step 14, the following compound was prepared:

5-(6-Aminopyrimidin-4-yl)-N-methyl-3-phenyl-1H-pyrrole-2-carboxamide (Compd 175)

ESI (+) MS: m/z 294 (MH+).

According to this procedure, but starting from ethyl 3-phenyl-1-(phenylsulfonyl)-1H-pyrrole-2-carboxylate in the step 11, using 6-chloro-N-methylpyrimidin-4-amine instead of 6-iodopyrimidin-4-amine in the step 12 and methylamine in the step 14, the following compound was prepared:

5-[6-(Methylamino)pyrimidin-4-yl]-N-methyl-3-phenyl-1H-pyrrole-2-carboxamide (Compd 176)

ESI (+) MS: m/z 306 (MH+).

According to this procedure, but starting from ethyl 3-phenyl-1-(phenylsulfonyl)-1H-pyrrole-2-carboxylate in the step 11, using 4-chloro-7H-pyrrolo[2,3-d]pyrimidin-7-yl)methyl 2,2-dimethylpropanoate instead of 6-iodopyrimidin-4-amine in the step 12 and methylamine in the step 14, the following compound was prepared:

N-methyl-3-phenyl-5-(7H-pyrrolo[2,3-d]pyrimidin-4-yl)-1H-pyrrole-2-carboxamide (Compd 177)

ESI (+) MS: m/z 318 (MH+).

According to this procedure, but starting from ethyl 3-phenyl-1-(phenylsulfonyl)-1H-pyrrole-2-carboxylate in the step 11, using 4-chloropyrrolo[2,1-f][1,2,4]triazine instead of 6-iodopyrimidin-4-amine in the step 12 and methylamine in the step 14, the following compound was prepared:

N-methyl-3-phenyl-5-(pyrrolo[2,1-f][1,2,4]triazin-4-yl)-1H-pyrrole-2-carboxamide (Compd 178)

ESI (+) MS: m/z 318 (MH+).

According to this procedure, but starting from ethyl 3-phenyl-1-(phenylsulfonyl)-1H-pyrrole-2-carboxylate in the step 11, using 4-chloro-7-(4-methoxy-benzyl)-6,7-dihydro-5H-pyrrolo[2,3-d]pyrimidine instead of 6-iodopyrimidin-4-amine in the step 12 and methylamine in the step 14 and removing the 4-methoxy-benzyl protecting group with TFA in DCM, the following compound was prepared:

5-(6,7-Dihydro-5H-pyrrolo[2,3-d]pyrimidin-4-yl)-N-methyl-3-phenyl-1H-pyrrole-2-carboxamide (Compd 179)

ESI (+) MS: m/z 320 (MH+).

Example 10

4-(6-Aminopyrimidin-4-yl)-2-(5-chloro-2-methyl-phenyl)-N-methyl-1H-pyrrole-1-carboxamide (Compd 180)

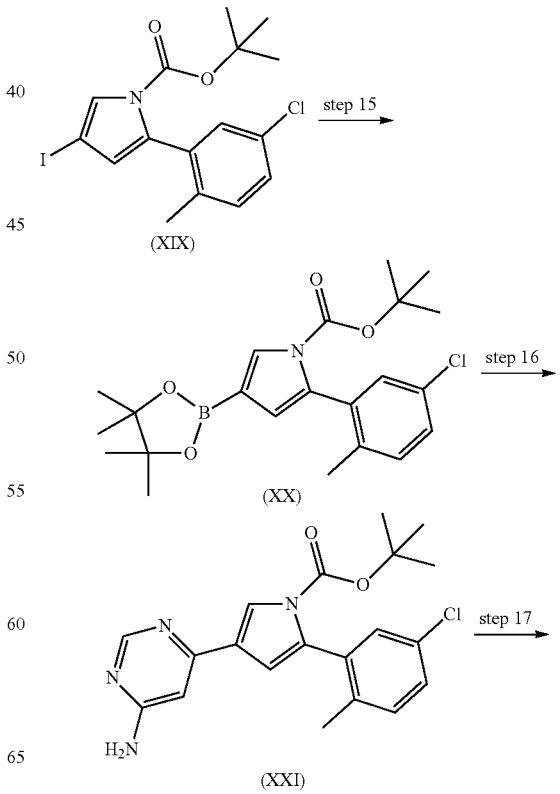

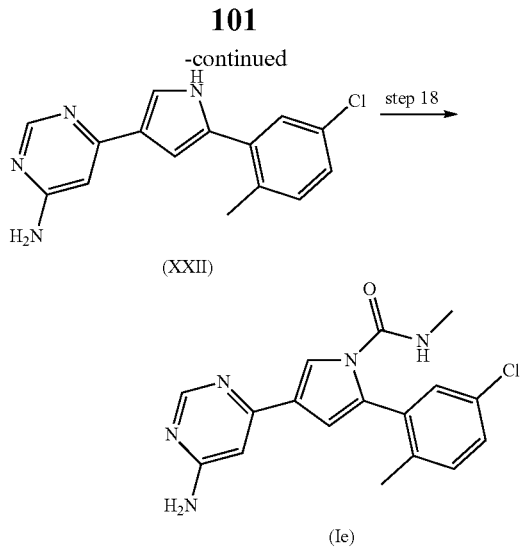

(XXII)

(Ie)

Scheme F: Steps 15, 16, 17, 18

Step 15: tert-Butyl 2-(5-chloro-2-methylphenyl)-4-(4,4,5,5-tetramethyl-1,3,2-dioxaborolan-2-yl)-1H-pyrrole-1-carboxylate (XX)

tert-Butyl 2-(5-chloro-2-methylphenyl)-4-iodo-1H-pyrrole-1-carboxylate (442 mg, 1.06 mmol) and 4,4,5,5-tetramethyl-2-(propan-2-yloxy)-1,3,2-dioxaborolane (217 mg, 1.16 mmol) in dry THF (1.6 mL), under argon at −78° C. was treated with n-BuLi (2M in hexane, 0.58 mL, 1.6 mmol) and the reaction mixture was stirred at −78° C. After 2 h, MeOH (1 mL) was added, the temperature was allowed to rise and NH$_4$Cl solution (2 mL) was added drop wise at room temperature. The solution was diluted with diethyl ether and washed in sequence with water and brine. The organic layer was dried over anhydrous Na$_2$SO$_4$ and evaporated to afford the title compound, which was used without further purification in the following reaction.

Step 16: tert-Butyl 4-(6-aminopyrimidin-4-yl)-2-(5-chloro-2-methylphenyl)-1H-pyrrole-1-carboxylate (XXI)

The crude tert-butyl 2-(5-chloro-2-methylphenyl)-4-(4,4,5,5-tetramethyl-1,3,2-dioxaborolan-2-yl)-1H-pyrrole-1-carboxylate (392 mg, 0.94 mmol), Na$_2$CO$_3$ (250 mg, 2.36 mmol), PdCl$_2$(dppf) (77 mg, 0.094 mmol) and 6-iodopyrimidin-4-amine (311 mg, 1.41 mmol) were degassed and purged with argon and suspended in degassed 1,4-dioxane (3 mL) and water (1 mL). The reaction mixture was heated to 110° C. (oil bath temperature) for 2 h. The solution was diluted with EtOAc and washed with water. After drying over anhydrous Na$_2$SO$_4$, the organic layer was evaporated. The crude was purified by chromatography on silica gel (hexane/EtOAc 8:2) providing the title compound (220 mg, 58%).

$^1$H NMR (600 MHz, DMSO-d$_6$) δ 8.55 (s, 1H), 7.79 (s, 1H), 7.41 (d, 1H), 7.29 (d, 1H), 7.16 (m, 1H), 6.98 (s, 1H), 6.66 (s, 1H), 2.30 (s, 3H), 1.44 (s, 9H).

Step 17: 6-[5-(5-Chloro-2-methylphenyl)-1H-pyrrol-3-yl]pyrimidin-4-amine (XXII)

tert-Butyl 4-(6-aminopyrimidin-4-yl)-2-(5-chloro-2-methylphenyl)-1H-pyrrole-1-carboxylate (210 mg, 0.55 mmol) in DCM (11 mL) was treated with TFA (5.5 mL). The reaction mixture was stirred at room temperature for 3 days. The volatiles were evaporated and the solid obtained was suspended with EtOH and treated with ammonium hydroxide 30% until pH 9-10. The solution was diluted with EtOAc and washed first with 10% ammonium hydroxide then with brine and, after drying over anhydrous Na$_2$SO$_4$, the organic layer was evaporated leaving the title compound that was employed in the following step without further purification.

$^1$H NMR (600 MHz, DMSO-d$_6$) δ 8.46 (s, 1H), 7.41 (m, 1H), 7.40 (m, 1H), 7.23 (m, 1H), 7.16 (m, 1H), 6.83 (s, 1H), 6.29 (s, 1H), 2.23 (s, 3H).

Step 18: 4-(8-Aminopyrimidin-4-yl)-2-(5-chloro-2-methylphenyl)-N-methy-1H-pyrrole-1-carboxamide To a solution of triphosgene (97.5 mg, 0.325 mmol) in DCM (7 mL) was added a solution of 6-[5-(5-chloro-2-methylphenyl)-1H-pyrrol-3-yl]pyrimidin-4-amine (156 mg, 0.55 mmol) in DCM (10 mL) followed by DIPEA (373 μL, 2.15 mmol). After 3 h, a solution of methylamine (2M in tetrahydrofuran, 430 μL, 0.86 mmol) and DIPEA (97 μL, 0.56 mmol) in DCM (4 mL) was added. The reaction was stirred overnight at room temperature. The solution was washed with brine, the organic phase was dried over Na$_2$SO$_4$ and concentrated. The crude was purified by flash chromatography (DCM/MeOH 90/10) to afford the title compound (120 mg, 64%, 2 steps).

$^1$H NMR (600 MHz, DMSO-d$_6$) δ 8.45 (s, 1H), 7.40 (m, 1H), 8.05 (s, 1H), 7.40 (m, 1H), 7.30 (m, 1H), 6.90 (s, 1H), 6.58 (s, 1H), 2.78 (s, 3H), 2.22 (s, 3H).

According to this procedure, but using 6-chloro-N-methylpyrimidin-4-amine instead of 6-iodopyrimidin-4-amine in the step 16, the following compound was prepared:

2-(5-Chloro-2-methylphenyl)-N-methyl-4-[6-(methylamino)pyrimidin-4-yl]-1H-pyrrole-1-carboxamide (Compd 181)

ESI (+) MS: m/z 356 (MH$^+$).

According to this procedure, but using 4-chloro-7H-pyrrolo[2,3-d]pyrimidin-7-yl)methyl 2,2-dimethylpropanoate instead of 6-iodopyrimidin-4-amine in the step 16 and removing the 2,2-dimethylpropanoyl protecting group with LiOH.H$_2$O in THF/water at room temperature, the following compound was prepared:

2-(5-Chloro-2-methylphenyl-N-methyl-4-(7H-pyrrolo[2,3-d]pyrimidin-4-yl)-1H-pyrrole-1-carboxamide (Compd 182)

ESI (+) MS: m/z 366 (MH$^+$).

According to this procedure, but starting from tert-butyl 2-(5-chloro-2-ethylphenyl)-4-iodo-1H-pyrrole-1-carboxylate the following compound was prepared:

4-(6-Aminopyrimidin-4-yl)-2-(chloro-2-ethylphenyl)-N-methyl-1H-pyrrole-1-carboxamide (Compd 183)

ESI (+) MS: m/z 356 (MH$^+$).

According to this procedure, but starting from tert-butyl 2-(5-chloro-2-ethylphenyl)-4-iodo-1H-pyrrole-1-carboxylate and using 6-chloro-N-methylpyrimidin-4-amine instead of 6-iodopyrimidin-4-amine in the step 16, the following compound was prepared:

2-(5-Chloro-2-ethylphenylmethyl-4-[6-(methylamino)pyrimidin-4-yl]-1H-pyrrole-1-carboxamide (Compd 184)

ESI (+) MS: m/z 370 (MH+).

According to this procedure, but starting from tert-butyl 2-(5-chloro-2-ethylphenyl)-4-iodo-1H-pyrrole-1-carboxylate, using 4-chloro-7H-pyrrolo[2,3-d]pyrimidin-7-yl)methyl 2,2-dimethylpropanoate instead of 6-iodopyrimidin-4-amine in the step 16 and removing the 2,2-dimethylpropanoyl protecting group with $LiOH \cdot H_2O$ in THF/water at room temperature, the following compound was prepared:

2-(5-Chloro-2-ethylphenyl)-N-methyl-4-(7H-pyrrolo[2,3-d]pyrimidin-4-yl)-1H-pyrrole-1-carboxamide (Compd 185)

ESI (+) MS: m/z 380 (MH+).

According to this procedure, but starting from tert-butyl 2-[2-ethyl-5-(trifluoromethyl)phenyl]-4-iodo-1H-pyrrole-1-carboxylate the following compound was prepared:

4-(8-Aminopyrimidin-4-yl)-2-[2-ethyl-5-(trifluoromethyl)phenyl]-N-methyl-1H-pyrrole-1-carboxamide (Compd 186)

ESI (+) MS: m/z 390 (MH+).

According to this procedure, but starting from tert-butyl 2-[2-ethyl-5-(trifluoromethyl)phenyl]-4-iodo-1H-pyrrole-1-carboxylate and using 6-chloro-N-methylpyrimidin-4-amine instead of 6-iodopyrimidin-4-amine in the step 16, the following compound was prepared:

2-[2-Ethyl-5-(trifluoromethyl)phenyl]-N-methyl-4-[6-(methylamino)pyrimidin-4-yl]-1H-pyrrole-1-carboxamide (Compd 187)

ESI (+) MS: m/z 404 (MH+).

According to this procedure, but starting from tert-butyl 2-[2-ethyl-5-(trifluoromethyl)phenyl]-4-iodo-1H-pyrrole-1-carboxylate, using 4-chloro-7H-pyrrolo[2,3-d]pyrimidin-7-yl)methyl 2,2-dimethylpropanoate instead of 6-iodopyrimidin-4-amine in the step 16 and removing the 2,2-dimethylpropanoyl protecting group with $LiOH \cdot H_2O$ in THF/water at room temperature, the following compound was prepared:

2-[2-Ethyl-5-(trifluoromethyl)phenyl]-N-methyl-4-(7H-pyrrolo[2,3-d]pyrimidin-4-yl)-1H-pyrrole-1-carboxamide (Compd 188)

ESI (+) MS: m/z 414 (MH+).

Example 11

5-(6-Aminopyrimidin-4-yl)-2-(chloro-2-methylphenyl)-H-pyrrole-3-carboxamide (Compd 189)

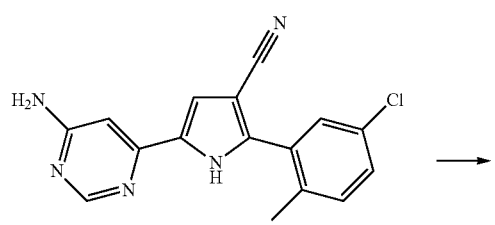

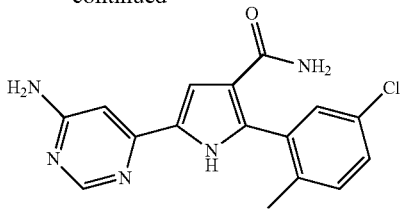

Conv.1

To a solution of 5-(6-aminopyrimidin-4-yl)-2-(5-chloro-2-methylphenyl)-1H-pyrrole-3-carbonitrile (59 mg, 0.19 mmol) in TFA (0.90 mL) were sequentially added water (0.11 mL) and 96% sulfuric acid (0.22 mL) under efficient stirring. The mixture was allowed to stir for 5 h at 70° C. and then was diluted by drop wise addition of water (1.5 mL). The reaction mixture was made basic (pH 10-12) by adding 30% aqueous ammonia under stirring. The precipitated solid was collected by filtration, washed with water and finally dried in a vacuum oven at 50° C. affording the title compound as an off-white solid (42 mg, 68%).

$^1$H NMR (400 MHz, DMSO-$d_6$) δ 11.91 (br. s., 1H), 8.31 (d, J=0.8 Hz, 1H), 7.30-7.36 (m, 1H), 7.23-7.30 (m, 3H), 7.22 (br. s., 1H), 6.76 (s, 2H), 6.70 (br. s., 1H), 6.66 (d, J=1.1 Hz, 1H), 2.12 (s, 3H).

HRMS (ESI) m/z calcd for $C_{16}H_{14}ClN_5O+H^+$ 328.0960, found 328.0964.

The above procedure was employed, starting from the suitable carbonitrile derivative, to synthesize the following compounds:

2-(5-Chloro-2-methylphenyl)-5-[6-(methylamino)pyrimidin-4-yl]-1H-pyrrole-3-carboxamide (Compd 190)

$^1$H NMR (400 MHz, DMSO-$d_6$) δ 11.91 (br. s., 1H), 8.35 (s, 1H), 7.10-7.39 (m, 5H), 6.52-6.78 (m, 2H), 2.81 (d, J=4.5 Hz, 3H), 2.12 (m, 3H).

HRMS (ESI) m/z calcd for $C_{17}H_{16}ClN_5O+H^+$ 342.1116, found 342.1112.

2-(5-Chloro-2-methylphenyl)-5-(7H-pyrrolo[2,3-d]pyrimidin-4-yl)-1H-pyrrole-3-carboxamide (Compd 191)

$^1$H NMR (400 MHz, DMSO-$d_6$) δ 12.16 (br. s., 1H), 12.08 (br. s., 1H), 8.66 (s, 1H), 7.71 (s, 1H), 7.61 (dd, J=2.5, 3.3 Hz, 1H), 7.47 (br. s., 1H), 7.29-7.36 (m, 1H), 7.21-7.28 (m, 1H), 7.11 (dd, J=1.6, 3.5 Hz, 1H), 6.79 (br. s., 1H), 2.14 (s, 3H).

HRMS (ESI) m/z calcd for $C_{18}H_{14}ClN_5O+H^+$ 352.0960, found 352.0962.

2-(5-Chloro-2-methylphenyl)-5-(1H-pyrrolo[2,3-b]pyridimin-4-yl)-1H-pyrrole-3-carboxamide (Compd 192)

$^1$H NMR (400 MHz, DMSO-$d_6$) δ 11.85 (br. s., 1H), 11.65 (br. s., 1H), 8.16 (d, J=5.0 Hz, 1H), 7.53 (d, J=3.3 Hz, 1H), 7.44 (s, 2H), 7.39 (d, J=5.1 Hz, 1H), 7.27-7.38 (m, 4H), 7.02 (d, J=3.5 Hz, 1H), 6.74 (br. s., 1H), 2.17 (s, 3H).

HRMS (ESI) m/z calcd for $C_{19}H_{15}ClN_4O+H^+$ 351.1007, found 351.1011.

2-(5-Chloro-2-methylphenyl)-5-(9H-purin-6-yl)-H-pyrrole-3-carboxamide (Compd 193)

$^1$H NMR (500 MHz, DMSO-d$_6$) δ 12.21 (br. s., 1H), 8.78 (s, 1H), 8.59 (s, 1H), 7.99 (d, J=2.20 Hz, 1H), 7.33-7.38 (m, 1H), 7.21-7.33 (m, 3H), 6.82 (br. s., 1H), 2.16 (s, 3H).
HRMS (ESI) m/z calcd for C$_{17}$H$_{13}$ClN$_6$O+H$^+$ 353.0912, found 353.0917.

2-(5-Chloro-2-methylphenyl)-5-(1H-pyrazolo[3,4-d]pyrimidin-4-yl)-1H-pyrrol-3-carboxamide (Compd 194)

$^1$H NMR (400 MHz, DMSO-d$_6$) δ 14.00 (s, 1H), 12.47 (br. s., 1H), 8.82 (s, 1H), 8.78 (s, 1H), 7.93-7.98 (m, 1H), 7.49 (br. s., 1H), 7.22-7.39 (m, 3H), 6.90 (br. s., 1H), 2.14 (s, 3H).
HRMS (ESI) m/z calcd for C$_{17}$H$_{13}$ClN$_6$O+H$^+$ 353.0912, found 353.0914.

2-(5-Chloro-2-methylphenyl)-5-(pyrrolo[2,1-f][1,2,4]triazin-4-yl)-1H-pyrrole-3-carboxamide (Compd 195)

$^1$H NMR (600 MHz, DMSO-d$_6$) δ 11.67 (s, 1H), 8.41 (s, 1H), 8.02 (dd, J=1.3, 2.5 Hz, 1H), 7.91 (s, 1H), 7.54 (br. s., 1H), 7.47 (dd, J=1.3, 4.7 Hz, 1H), 7.27-7.37 (m, 1H), 7.16-7.27 (m, 2H), 7.05 (dd, J=2.5, 4.6 Hz, 1H), 6.85 (br. s., 1H), 2.10 (s, 3H).
HRMS (ESI) m/z calcd for C$_{18}$H$_{14}$ClN$_5$O+H$^+$ 352.0960, found 352.0955.

2-(5-Chloro-2-methylphenyl-5-(6,7-dihydro-5H-pyrrolo[2,3-d]pyrimidin-4-yl)-1H-pyrrole-3-carboxamide (Compd 196)

ESI (+) MS: m/z 354 (MH$^+$).

5-(6-Aminopyrimidin-4-yl)-2-(5-chloro-2-ethylphenyl)-1H-pyrrole-3-carboxamide (compd 197)

$^1$H NMR (600 MHz, DMSO-d$_6$) δ 11.94 (br. s., 1H), 8.31 (d, J=0.9 Hz, 1H), 7.37 (dd, J=2.4, 8.2 Hz, 1H), 7.30 (d, J=8.2 Hz, 1H), 7.28 (s, 1H), 7.21 (d, J=2.4 Hz, 1H), 7.16 (br. s., 1H), 6.76 (s, 1H), 6.68 (br. s., 1H), 6.66 (d, J=1.1 Hz, 1H), 2.46 (q, J=7.7 Hz, 2H), 0.96 (t, J=7.6 Hz, 3H).
HRMS (ESI) calcd for C$_{17}$H$_{16}$ClN$_5$O+H$^+$ 342.1116, found 342.1119.

2-(5-Chloro-2-ethylphenyl)-5-[6-(methylamino)pyrimidin-4-yl]-1H-pyrrole-3-carboxamide (Compd 198)

$^1$H NMR (600 MHz, DMSO-d$_6$) δ 11.94 (br. s., 1H), 8.35 (br. s., 1H), 7.39 (dd, J=2.3, 8.3 Hz, 1H), 7.34 (br. s., 1H), 7.31 (d, J=8.2 Hz, 1H), 7.23 (d, J=2.0 Hz, 1H), 7.17 (br. s., 2H), 6.73 (br. s., 1H), 6.68 (br. s., 1H), 2.80 (br. s., 3H), 2.46 (q, J=7.6 Hz, 2H), 0.97 (t, J=7.6 Hz, 3H).
HRMS (ESI) calcd for C$_{16}$H$_{15}$ClN$_5$O+H$^+$ 356.1273, found 356.1273.

2-(5-Chloro-2-ethylphenyl)-5-(7H-pyrrolo[2,3-d]pyrimidin-4-yl)-1H-pyrrole-3-carboxamide (Compd 199)

$^1$H NMR (600 MHz, DMSO-d$_6$) δ 12.17 (br. s., 1H), 12.08 (br. s., 1H), 8.65 (s, 1H), 7.71 (s, 1H), 7.61 (dd, J=2.2, 3.3 Hz, 1H), 7.42 (br. s., 1H), 7.37 (dd, J=2.3, 8.4 Hz, 1H), 7.29 (d, J=8.4 Hz, 1H), 7.23 (d, J=2.3 Hz, 1H), 7.00-7.14 (m, 1H), 6.76 (br. s., 1H), 2.45 (q, J=7.5 Hz, 2H), 0.98 (t, J=7.5 Hz, 3H).
HRMS (ESI) calcd for C$_{19}$H$_{16}$ClN$_5$O+H$^+$ 366.1116, found 366.1116.

2-(5-Chloro-2-ethylphenyl)-5-(9H-purin-6-yl)-1H-pyrrole-3-carboxamide (Compd 200)

ESI (+) MS: m/z 367 (MH$^+$).

2-(5-Chloro-2-ethylphenyl)-5-(1H-pyrazolo[3,4-d]pyrimidin-4-yl)-1H-pyrrole-3-carboxamide (Compd 201)

ESI (+) MS: m/z 367 (MH$^+$).

2-(5-Chloro-2-ethylphenyl)-5-(pyrrolo[2,1-f][1,2,4]triazin-4-yl)-1H-pyrrole-3-carboxamide (Compd 202)

ESI (+) MS: m/z 366 (MH$^+$).

2-(5-Chloro-2-ethylphenyl)-5-(6,7-dihydro-5H-pyrrolo[2,3-d]pyrimidin-4-yl)-1H-pyrrole-3-carboxamide (Compd 203)

ESI (+) MS: m/z 368 (MH$^+$).

5-(6-Aminopyrimidin-4-yl)-2-[2-chloro-5-(trifluoromethyl)phenyl]-1H-pyrrole-3-carboxamide (Compd 204)

$^1$H NMR (600 MHz, DMSO-d$_6$) δ 12.17 (br. s., 1H), 8.34 (s, 1H), 7.65-7.81 (m, 3H), 7.43 (br. s., 1H), 7.31 (s, 1H), 6.89 (br. s., 2H), 6.76 (br. s., 1H), 6.66 (s, 1H).
HRMS (ESI) calcd for C$_{16}$H$_{11}$ClF$_3$N$_5$O+H$^+$ 382.0677, found 382.0674.

2-[2-Chloro-5-(trifluoromethyl)phenyl]-5-[6-(methylamino)pyrimidin-4-yl]-1H-pyrrole-3-carboxamide (Compd 205)

$^1$H NMR (400 MHz, DMSO-d$_6$) δ 12.13 (br. s., 1H), 8.38 (s, 1H), 7.62-7.87 (m, 3H), 7.40 (br. s., 1H), 7.34 (br. s., 1H), 7.26 (br. s., 1H), 6.74 (br. s., 1H), 6.70 (s, 1H), 2.82 (d, J=4.39 Hz, 3H).
HRMS (ESI) calcd for C$_{17}$H$_{13}$ClF$_3$N$_5$O+H$^+$ 396.0834, found 396.0831.

2-[2-Chloro-5-(trifluoromethyl)phenyl]-5-(7H-pyrrolo[2,3-d]pyrimidin-4-yl)-1H-pyrrole-3-carboxamide (Compd 206)

HRMS (ESI) calcd for C$_{18}$H$_{11}$ClF$_3$N$_5$O+H$^+$ 406.0677, found 406.0679.

2-[2-Chloro-5-(trifluoromethyl)phenyl]-5-(9H-purin-6-yl)-1H-pyrrole-3-carboxamide (Compd 207)

$^1$H NMR (500 MHz, DMSO-d$_6$) δ 12.51 (br. s., 1H), 8.80 (s, 1H), 8.60 (s, 1H), 8.03 (d, J=1.9 Hz, 1H), 7.68-7.81 (m, 3H), 7.56 (br. s., 1H), 6.83 (br. s., 1H).
HRMS (ESI) calcd for C$_{17}$H$_{10}$ClF$_3$N$_6$O+H$^+$ 407.0630, found 407.0625.

2-[2-Chloro-5-(trifluoromethyl)phenyl]-5-(1H-pyrazolo[3,4-d]pyrimidin-4-yl)-1H-pyrrole-3-carboxamide (Compd 208)

$^1$H NMR (500 MHz, DMSO-d$_6$) δ 14.08 (br. s., 1H), 12.74 (br. s., 1H), 8.86 (s, 1H), 8.79 (s, 1H), 8.01 (s, 1H), 7.69-7.82 (m, 3H), 7.62 (br. s., 1H), 6.97 (br. s., 1H).
HRMS (ESI) calcd for C$_{17}$H$_{10}$ClF$_3$N$_6$O+H$^+$ 407.0630, found 407.0627.

2-[2-Chloro-5-(trifluoromethyl)phenyl]-5-(pyrrolo[2,1-f][1,2,4]triazin-4-yl)-1H-pyrrole-3-carboxamide (Compd 209)

ESI (+) MS: m/z 406 (MH$^+$).

2-[2-Chloro-5-(trifluoromethyl)phenyl]-5-(6,7-dihydro-5H-pyrrolo[2,3-d]pyrimidin-4-yl)-1H-pyrrole-3-carboxamide (Compd 210)

ESI (+) MS: m/z 408 (MH$^+$).

5-(6-Aminopyrimidin-4-yl)-2-[2-methyl-5-(trifluoromethyl)phenyl]-1H-pyrrole-3-carboxamide (Compd 211)

$^1$H NMR (600 MHz, DMSO-d$_6$) δ 12.00 (br. s., 1H), 8.32 (d, J=0.9 Hz, 1H), 7.61 (d, J=8.1 Hz, 1H), 7.51 (s, 1H), 7.47 (d, J=7.9 Hz, 1H), 7.32 (br. s., 1H), 7.30 (s, 1H), 6.78 (br. s., 1H), 6.72 (br. s., 1H), 6.66 (d, J=1.1 Hz, 1H), 2.23 (s, 3H).
HRMS (ESI) calcd for C$_{17}$H$_{14}$F$_3$N$_5$O+H$^+$ 362.1223, found 362.1223.

5-[6-(Methylamino)pyrimidin-4-yl]-2-[2-methyl-5-(trifluoromethyl)phenyl]-1H-pyrrole-3-carboxamide (Compd 212)

$^1$H NMR (600 MHz, DMSO-d$_6$) δ 11.96 (br. s., 1H), 8.34 (br. s., 1H), 7.60 (d, J=8.2 Hz, 1H), 7.50 (s, 1H), 7.44-7.48 (m, 1H), 7.33 (br. s., 1H), 7.29 (br. s., 1H), 7.20 (br. s., 1H), 6.70 (br. s., 2H), 2.78 (br. s., 3H), 2.20 (s, 3H).
HRMS (ESI) calcd for C$_{16}$H$_{16}$F$_3$N$_5$O+H$^+$ 376.1380, found 376.1380.

2-[2-Methyl-5-(trifluoromethyl)phenyl]-(7H-pyrrolo[2,3-d]pyrimidin-4-yl)-1H-pyrrole-3-carboxamide (Compd 213)

$^1$H NMR (600 MHz, DMSO-d$_6$) δ 12.27 (br. s., 1H), 12.10 (br. s., 1H), 8.67 (s, 1H), 7.75 (s, 1H), 7.58-7.64 (m, 2H), 7.55 (br. s., 1H), 7.54 (s, 1H), 7.47 (d, J=8.1 Hz, 1H), 7.12 (d, J=2.6 Hz, 1H), 6.81 (br. s., 1H), 2.25 (s, 3H).
HRMS (ESI) calcd for C$_{19}$H$_{14}$F$_3$N$_5$O+H$^+$ 386.1223, found 386.1223.

2-[2-Methyl-5-(trifluoromethyl)phenyl]-5-(9H-purin-6-yl)-1H-pyrrole-3-carboxamide (Compd 214)

ESI (+) MS: m/z 387 (MH$^+$).

2-[2-Methyl-5-(rifluoromethyl)phenyl]-5-(1H-pyrazolo[3,4-d]pyrimidin-4-yl)-1H-pyrrole-3-carboxamide (Compd 215)

ESI (+) MS: m/z 387 (MH$^+$).

2-[2-Methyl-5-(trifluoromethyl)phenyl]-5-(pyrrolo[2,1-f][1,2,4]triazin-4-yl)-1H-pyrrole-3-carboxamide (Compd 216)

ESI (+) MS: m/z 386 (MH$^+$).

2-[2-Methyl-5-(trifluoromethyl)phenyl]-5-(6,7-dihydro-5H-pyrrolo[2,3-d]pyrimidin-4-yl)-1H-pyrrole-3-carboxamide (Compd 217)

ESI (+) MS: m/z 388 (MH$^+$).

5-(6-Aminopyrimidin-4-yl)-2-[2-ethyl-5-(trifluoromethyl)phenyl]-1H-pyrrole-3-carboxamide (Compd 218)

$^1$H NMR (600 MHz, DMSO-d$_6$) δ 12.00 (br. s., 1H), 8.31 (d, J=1.10 Hz, 1H), 7.64-7.68 (m, 1H), 7.51 (d, J=8.06 Hz, 1H), 7.47 (s, 1H), 7.31 (s, 1H), 7.28 (br. s., 1H), 6.77 (br. s., 2H), 6.68 (br. s., 1H), 6.66 (d, J=1.10 Hz, 1H), 2.56 (q, J=7.63 Hz, 2H), 1.00 (t, J=7.63 Hz, 3H).
HRMS (ESI) calcd for C$_{18}$H$_{16}$F$_3$N$_5$O+H$^+$ 376.1380, found 376.1382.

2-[2-Ethyl-5-(trifluoromethyl)phenyl]-5-[6-(methylamino)pyrimidin-4-yl]-1H-pyrrole-3-carboxamide (Compd 219)

$^1$H NMR (600 MHz, DMSO-d$_6$) δ 12.00 (br. s., 1H), 8.35 (br. s., 1H), 7.68 (d, J=7.51 Hz, 1H), 7.52 (d, J=8.24 Hz, 1H), 7.49 (s, 1H), 7.36 (br. s., 1H), 7.27 (br. s., 1H), 7.20 (br. s., 1H), 6.70 (br. s., 1H), 6.68 (br. s., 1H), 2.81 (br. s., 3H), 2.56 (q, J=7.60 Hz, 2H), 1.01 (t, J=7.60 Hz, 3H).
HRMS (ESI) calcd for C$_{19}$H$_{18}$F$_3$N$_5$O+H$^+$ 390.1536, found 390.1538.

2-[2-Ethyl-5-(trifluoromethyl)phenyl]-5-(7H-pyrrolo[2,3-d]pyrimidin-4-yl)-1H-pyrrole-3-carboxamide (Compd 220)

$^1$H NMR (600 MHz, DMSO-d$_6$) δ 12.27 (br. s., 1H), 12.09 (br. s., 1H), 8.66 (s, 1H), 7.75 (d, J=0.55 Hz, 1H), 7.66 (dd, J=1.28, 8.24 Hz, 1H), 7.62 (d, J=3.11 Hz, 1H), 7.44-7.55 (m, 2H), 7.12 (d, J=3.48 Hz, 1H), 6.78 (br. s., 1H), 2.59 (q, J=7.61 Hz, 2H), 1.02 (t, J=7.61 Hz, 3H).
HRMS (ESI) calcd for C$_{20}$H$_{16}$F$_3$N$_5$O+H$^+$ 400.1380, found 400.1385.

2-[2-Ethyl-5-(trifluoromethyl)phenyl]-5-(9H-purin-6-yl)-1H-pyrrole-3-carboxamide (Compd 221)

ESI (+) MS: m/z 401 (MH$^+$).

2-[2-Ethyl-5-(trifluoromethyl)phenyl]-5-(1H-pyrazolo[3,4-d]pyrimidin-4-yl)-1H-pyrrole-3-carboxamide (Compd 222)

ESI (+) MS: m/z 401 (MH$^+$).

2-[2-Ethyl-5-(trifluoromethyl)phenyl]-5-(pyrrolo[2,1-f][1,2,4]triazin-4-yl)-1H-pyrrole-3-carboxamide (Compd 223)

ESI (+) MS: m/z 400 (MH$^+$).

2-[2-Ethyl-5-(trifluoromethyl)phenyl]-5-(6,7-dihydro-5-pyrrolo[2,3-d]pyrimidin-4-yl)-H-pyrrole-3-carboxamide (Compd 224)

ESI (+) MS: m/z 402 (MH$^+$).

2-Phenyl-5-(7H-pyrrolo[2,3-d]pyrimidin-4-yl)-H-pyrrole-3-carboxamide (Compd 225)

$^1$H NMR (600 MHz, DMSO-d$_6$) δ 12.09 (br. s., 1H), 11.99 (br. s., 1H), 8.70 (s, 1H), 7.66-7.73 (m, 2H), 7.59-7.62 (m, 2H), 7.53 (br. s., 1H), 7.36-7.41 (m, 2H), 7.30-7.35 (m, 1H), 7.09 (dd, J=1.74, 3.57 Hz, 1H), 6.87 (br. s., 1H).
HRMS (ESI) calcd for C$_{17}$H$_{13}$N$_5$O+H$^+$ 304.1193, found 304.1188.

5-(6,7-Dihydro-5H-pyrrolo[2,3-d]pyrimidin-4-yl)-2-phenyl-1H-pyrrole-3-carboxamide (Compd 226)

ESI (+) MS: m/z 306 (MH$^+$).

Example 12

4-(6-Aminopyrimidin-4-yl)-1-(5-chloro-2-methylphenyl)-H-pyrrole-2-carboxamide (Compd 227)

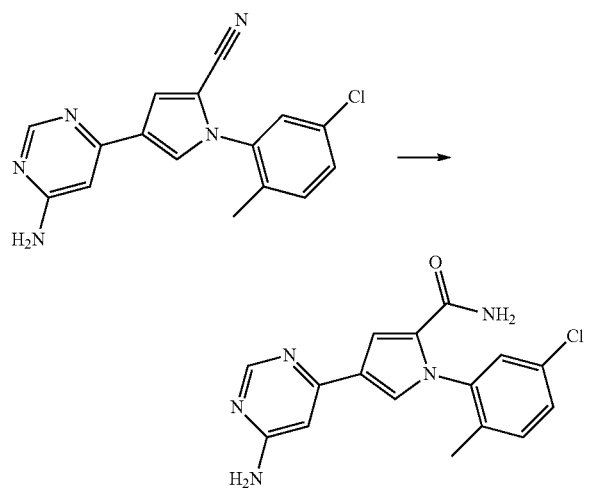

Conv.1
To a solution of 4-(6-aminopyrimidin-4-yl)-1-(5-chloro-2-methylphenyl)-1H-pyrrole-2-carbonitrile (32 mg, 0.103 mmol) in TFA (0.512 mL) were sequentially added water (64 μL) and 95% sulfuric acid (128 μL) under efficient stirring. The mixture was allowed to stir for 4 h at 70° C. and then was diluted by drop wise addition of water (1.5 mL). The reaction mixture was made basic (pH 10-12) by adding 30% aqueous ammonia under stirring. The precipitated solid was collected by filtration, washed with water and finally dried in a vacuum oven at 50° C. affording the title compound as an off-white solid (18 mg, 53%).
$^1$H NMR (400 MHz, DMSO-d$_6$) δ 8.30 (d, J=1.0 Hz, 1H), 7.69 ((br. s., 1H), 7.45-7.51 (m, 2H), 7.36-7.40 (m, 1H), 7.27-7.35 (m, 2H), 6.92 (br. s., 1H), 6.71 (s, 2H), 6.57 (d, J=1.1 Hz, 1H), 1.94 (s, 3H).
HRMS (ESI) calcd for C$_{16}$H$_{14}$ClN$_5$O+H$^+$ 328.0960, found 328.0958.

The above procedure was employed, starting from the suitable carbonitrile derivative, to synthesize the following compounds:

1-(5-Chloro-2-methylphenyl)-4-[6-(methylamino)pyrimidin-4-yl]-1H-pyrrole-2-carboxamide (Compd 228)

$^1$H NMR (600 MHz, DMSO-d$_6$) δ 8.35 (br. s., 1H), 7.70 (br. s., 1H), 7.51 (br. s., 1H), 7.35-7.40 (m, 1H), 7.26-7.35 (m, 2H), 7.15 (br. s., 1H), 6.92 (br. s., 1H), 6.62 (s, 1H), 2.81 (d, J=3.8 Hz, 3H), 1.94 (s, 3H).
HRMS (ESI) m/z calcd for C$_{17}$H$_{16}$ClN$_5$O+H$^+$ 342.1116, found 342.1120.

1-(5-Chloro-2-methylphenyl)-4-(7H-pyrrolo[2,3-d]pyrimidin-4-yl)-1H-pyrrole-2-carboxamide (Compd 229)

$^1$H NMR (400 MHz, DMSO-d$_6$) δ 12.16 (br. s., 1H), 12.08 (br. s., 1H), 8.66 (s, 1H), 7.71 (s, 1H), 7.61 (dd, J=2.5, 3.3 Hz, 1H), 7.47 (br. s., 1H), 7.29-7.36 (m, 1H), 7.21-7.28 (m, 1H), 7.11 (dd, J=1.6, 3.5 Hz, 1H), 6.79 (br. s., 1H), 2.14 (s, 3H).
HRMS (ESI) m/z calcd for C$_{18}$H$_{14}$ClN$_5$O+H$^+$ 352.0960, found 352.0962.

1-(5-Chloro-2-methylphenyl)-4-(1H-pyrrolo[2,3-b]pyridin-4-yl)-1H-pyrrole-2-carboxamide (Compd 230)

ESI (+) MS: m/z 351 (MH$^+$).

1-(5-Chloro-2-methylphenyl)-4-(9H-purin-6-yl)-1H-pyrrole-2-carboxamide (Compd 231)

ESI (+) MS: m/z 353 (MH$^+$).

1-(5-Chloro-2-methylphenyl)-4-(1H-pyrazolo[3,4-d]pyrimidin-4-yl)-1H-pyrrole-2-carboxamide (Compd 232)

$^1$H NMR (400 MHz, DMSO-d$_6$) δ 13.97 (s, 1H), 8.85 (s, 1H), 8.80 (s, 1H), 8.06 (d, J=1.8 Hz, 1H), 7.95 (d, J=1.8 Hz, 1H), 7.85 (br. s., 1H), 7.41-7.45 (m, 1H), 7.40 (d, J=2.0 Hz, 1H), 7.36 (d, J=8.2 Hz, 1H), 7.06 (br. s., 1H), 1.98 (s, 3H).
HRMS (ESI) m/z calcd for C$_{17}$H$_{13}$ClN$_6$O+H$^+$ 353.0912, found 353.0911.

1-(5-Chloro-2-methylphenyl)-4-(pyrrolo[2,1-f][1,2,4]triazin-4-yl)-1H-pyrrole-2-carboxamide (Compd 233)

$^1$H NMR (600 MHz, DMSO-d$_6$) δ 8.46 (s, 1H), 8.05 (dd, J=1.3, 2.5 Hz, 1H), 8.02 (d, J=1.8 Hz, 1H), 7.90 (d, J=1.8 Hz, 1H), 7.88 (br. s., 1H), 7.48 (dd, J=1.1, 4.6 Hz, 1H), 7.41-7.45 (m, 1H), 7.40 (d, J=2.0 Hz, 1H), 7.36 (d, J=8.4 Hz, 1H), 7.06 (br. s., 1H), 7.02 (dd, J=2.5, 4.6 Hz, 1H), 1.97 (s, 3H).
HRMS (ESI) m/z calcd for C$_{18}$H$_{14}$ClN$_5$O+H$^+$ 352.0960, found 352.0956.

1-(5-Chloro-2-methylphenyl)-4-(6,7-dihydro-5H-pyrrolo[2,3-d]pyrimidin-4-yl)-1H-pyrrole-2-carboxamide (Compd 234)

$^1$H NMR (600 MHz, DMSO-d$_6$) δ 8.16 (s, 1H), 7.75 (br. s., 1H), 7.54 (d, J=1.6 Hz, 1H), 7.36-7.42 (m, 1H), 7.34 (d,

J=1.6 Hz, 1H), 7.32 (d, J=8.4 Hz, 1H), 7.30 (d, J=2.0 Hz, 2H), 6.92 (br. s., 1H), 3.59 (t, J=8.6 Hz, 2H), 3.20 (t, J=8.6 Hz, 2H), 1.94 (s, 3H).

HRMS (ESI) m/z calcd for $C_{18}H_{16}ClN_5O+H^+$ 354.1116, found 354.1116.

4-(6-Aminopyrimidin-4-yl)-1-(5-chloro-2-ethylphenyl)-1H-pyrrole-2-carboxamide (Compd 235)

$^1$H NMR (600 MHz, DMSO-d$_6$) δ 8.30 (d, J=1.0 Hz, 1H), 7.71 (br. s., 1H), 7.49 (d, J=1.8 Hz, 1H), 7.47 (d, J=1.8 Hz, 1H), 7.40-7.45 (m, 1H), 7.33-7.38 (m, 1H), 7.29 (d, J=2.2 Hz, 1H), 6.91 (br. s., 1H), 6.71 (s, 2H), 6.57 (d, J=1.1 Hz, 1H), 2.25 (dq, J=0.73, 7.53 Hz, 1H), 0.97 (t, J=7.63 Hz, 3H).

HRMS (ESI) calcd for $C_{17}H_{16}ClN_5O+H^+$ 342.1116, found 342.1120.

1-(Chloro-2-ethylphenyl)-4-[6-(methylamino)pyrimidin-4-yl]-1H-pyrrole-2-carboxamide (Compd 236)

$^1$H NMR (600 MHz, DMSO-d$_6$) δ 8.35 (br. s., 1H), 7.69 (br. s., 1H), 7.57 (br. s., 1H), 7.51 (br. s., 1H), 7.43 (dd, J=2.3, 8.3 Hz, 1H), 7.36 (d, J=8.2 Hz, 1H), 7.30 (d, J=2.2 Hz, 1H), 7.15 (br. s., 1H), 6.91 (br. s., 1H), 6.62 (s, 1H), 2.81 (d, J=4.0 Hz, 3H), 2.25 (dq, J=2.5, 7.5 Hz, 2H), 0.98 (t, J=7.6 Hz, 3H).

HRMS (ESI) calcd for $C_{18}H_{15}ClN_5O+H^+$ 356.1273, found 356.1269.

1-(5-Chloro-2-ethylphenyl-4-(7H-pyrrolo[2,3-d]pyrimidin-4-yl)-1H-pyrrole-2-carboxamide (Compd 237)

$^1$H NMR (600 MHz, DMSO-d$_6$) δ 12.03 (br. s., 1H), 8.66 (s, 1H), 7.87 (d, J=1.8 Hz, 1H), 7.83 (d, J=1.6 Hz, 2H), 7.55 (dd, J=2.6, 3.5 Hz, 1H), 7.45 (dd, J=2.2, 8.4 Hz, 1H), 7.38 (d, J=8.4 Hz, 1H), 7.36 (d, J=2.2 Hz, 1H), 7.07 (dd, J=1.6, 3.5 Hz, 1H), 6.96 (br. s., 1H), 2.29 (dq, J=2.5, 7.5 Hz, 2H), 1.00 (t, J=7.5 Hz, 3H).

HRMS (ESI) calcd for $C_{19}H_{16}ClN_5O+H^+$ 366.1116, found 366.1117.

1-(5-Chloro-2-ethylphenyl)-4-(9H-purin-6-yl)-1H-pyrrole-2-carboxamide (Compd 238)

ESI (+) MS: m/z 367 (MH$^+$).

1-(5-Chloro-2-ethylphenyl)-4-(1H-pyrazolo[3,4-d]pyrimidin-4-yl)-1H-pyrrole-2-carboxamide (Compd 239)

ESI (+) MS: m/z 367 (MH$^+$).

1-(5-Chloro-2-ethylphenyl)-4-(pyrrolo[2,1-f][1,2,4]triazin-4-yl)-1H-pyrrole-2-carboxamide (Compd 240)

$^1$H NMR (600 MHz, DMSO-d$_6$) δ 8.46 (s, 1H), 7.98-8.10 (m, 2H), 7.90 (d, J=1.8 Hz, 1H), 7.88 (br. s., 1H), 7.44-7.51 (m, 2H), 7.34-7.41 (m, 2H), 7.04 (br. s., 1H), 7.02 (dd, J=2.6, 4.6 Hz, 1H), 2.21-2.34 (m, 2H), 1.00 (t, J=7.5 Hz, 3H).

HRMS (ESI) calcd for $C_{19}H_{16}ClN_5O+H^+$ 366.1116, found 366.1117.

1-(5-Chloro-2-ethylphenyl)-4-(6,7-dihydro-5H-pyrrolo[2,3-d]pyrimidin-4-yl)-1H-pyrrole-2-carboxamide (Compd 241)

$^1$H NMR (600 MHz, DMSO-d$_6$) δ 8.41 (br. s., 1H), 7.81 (br. s., 1H), 7.60 (br. s., 1H), 7.44-7.52 (m, 2H), 7.39 (d, J=8.4 Hz, 1H), 7.32 (d, J=2.2 Hz, 1H), 7.09 (s, 1H), 3.79 (br. s., 2H), 2.18-2.32 (m, 2H), 0.98 (t, J=7.6 Hz, 3H).

HRMS (ESI) calcd for $C_{19}H_{16}ClN_5O+H^+$ 368.1273, found 368.1276.

4-(6-Aminopyrimidin-4-yl)-1-[2-chloro-5-(trifluoromethyl)phenyl]-1H-pyrrole-2-carboxamide (Compd 242)

$^1$H NMR (600 MHz, DMSO-d$_6$) δ 8.31 (d, J=1.1 Hz, 1H), 7.87 (s, 1H), 7.81-7.84 (m, 2H), 7.79 (br. s., 1H), 7.63 (d, J=1.6 Hz, 1H), 7.53 (d, J=1.6 Hz, 1H), 6.96 (br. s., 1H), 6.75 (br. s., 2H), 6.59 (d, J=1.1 Hz, 1H).

HRMS (ESI) calcd for $C_{16}H_{11}ClF_3N_5O+H^+$ 382.0677, found 382.0681.

1-[2-Chloro-5-(trifluoromethyl)phenyl]-4-[6-(methylamino)pyrimidin-4-yl]-1H-pyrrole-2-carboxamide (Compd 243)

$^1$H NMR (600 MHz, DMSO-d$_6$) δ 8.36 (br. s., 1H), 7.88 (s, 1H), 7.80-7.84 (m, 1H), 7.76 (br. s., 1H), 7.60 (br. s., 1H), 7.57 (br. s., 1H), 7.19 (br. s., 1H), 6.96 (br. s., 1H), 6.63 (s, 1H), 2.81 (d, J=3.5 Hz, 3H).

HRMS (ESI) calcd for $C_{17}H_{13}ClF_3N_5O+H^+$ 396.0834, found 396.0836.

1-[2-Chloro-5-(trifluoromethyl)phenyl]-4-(7H-pyrrolo[2,3-d]pyrimidin-4-yl)-1H-pyrrole-2-carboxamide (Compd 244)

$^1$H NMR (600 MHz, DMSO-d$_6$) δ 12.07 (br. s., 1H), 8.68 (s, 1H), 7.99 (d, J=1.6 Hz, 1H), 7.92-7.97 (m, 2H), 7.91 (br. s., 1H), 7.78-7.87 (m, 2H), 7.57 (dd, J=2.5, 3.3 Hz, 1H), 7.08 (dd, J=1.6, 3.6 Hz, 1H), 7.04 (br. s., 1H).

HRMS (ESI) calcd for $C_{18}H_{11}ClF_3N_5O+H^+$ 406.0677, found 406.0680.

1-[2-Chloro-5-(trifluoromethyl)phenyl]-4-(9H-purin-6-yl)-1H-pyrrole-2-carboxamide (Compd 245)

$^1$H NMR (500 MHz, DMSO-d$_6$) δ 12.51 (br. s., 1H), 8.80 (s, 1H), 8.60 (s, 1H), 8.03 (d, J=1.9 Hz, 1H), 7.68-7.81 (m, 3H), 7.56 (br. s., 1H), 6.83 (br. s., 1H).

HRMS (ESI) calcd for $C_{17}H_{10}ClF_3N_5O+H^+$ 407.0630, found 407.0630.

1-[2-Chloro-5-(trifluoromethyl)phenyl]-4-(1H-pyrazolo[3,4-d]pyrimidin-4-yl)-1H-pyrrole-2-carboxamide (Compd 246)

$^1$H NMR (500 MHz, DMSO-d$_6$) δ 14.02 (s, 1H), 8.87 (s, 1H), 8.80 (s, 1H), 8.23 (d, J=1.4 Hz, 1H), 8.00 (s, 2H), 7.92 (br. s., 1H), 7.81-7.89 (m, 2H), 7.12 (br. s., 1H).

HRMS (ESI) calcd for $C_{17}H_{10}ClF_3N_6O+H^+$ 407.0630, found 407.0627.

1-[2-Chloro-5-(trifluoromethyl)phenyl]-4-(pyrrolo[2,1-f][1,2,4]triazin-4-yl)-1H-pyrrole-2-carboxamide (Compd 247)

$^1$H NMR (500 MHz, DMSO-d$_6$) δ 8.48 (d, J=2.0 Hz, 1H), 8.19 (d, J=1.6 Hz, 1H), 8.06 (d, J=1.1 Hz, 1H), 7.98 (s, 1H), 7.96 (d, J=1.6 Hz, 1H), 7.94 (br. s., 1H), 7.82-7.88 (m, 2H), 7.46-7.49 (m, 1H), 7.09 (br. s., 1H), 7.04 (dd, J=2.4, 4.4 Hz, 1H).
HRMS (ESI) calcd for C$_{17}$H$_{10}$ClF$_3$N$_6$O+H$^+$ 406.0677, found 406.0674.

1-[2-Chloro-5-(trifluoromethyl)phenyl]-4-(6,7-dihydro-5H-pyrrolo[2,3-d]pyrimidin-4-yl)-1H-pyrrole-2-carboxamide (Compd 248)

ESI (+) MS: m/z 408 (MH$^+$).

4-(6-Aminopyrimidin-4-yl)-1-[2-methyl-5-(trifluoromethyl)phenyl]-pyrrole-2-carboxamide (Compd 249)

ESI (+) MS: m/z 362 (MH$^+$).

4-[6-(Methylamino)pyrimidin-4-yl]-1-[2-methyl-5-(trifluoromethyl)phenyl]-1H-pyrrole-2-carboxamide (Compd 250)

ESI (+) MS: m/z 376 (MH$^+$).

1-[2-Methyl-5-(trifluoromethyl)phenyl]-4-(7H-pyrrolo[2,3-d]pyrimidin-4 yl)-1H-pyrrole-2-carboxamide (Compd 251)

ESI (+) MS: m/z 386 (MH$^+$).

1-[2-Methyl-5-(trifluoromethyl)phenyl]-(9H-purin-6-yl)-1H-pyrrole-2-carboxamide (Compd 252)

ESI (+) MS: m/z 387 (MH$^+$).

1-[2-Methyl-5-(trifluoromethyl)phenyl]-4-(1H-pyrazolo[3,4-d]pyrimidin-4-yl)-1H-pyrrole-2-carboxamide (Compd 253)

ESI (+) MS: m/z 387 (MH$^+$).

1-[2-Methy-5-(trifluormethyl)phenyl]-4-(pyrrolo[2,1-f][1,2,4]triazin-4-yl)-1H-pyrrole-2-carboxamide (Compd 254)

ESI (+) MS: m/z 386 (MH$^+$).

4-(6,7-Dihydro-5H-pyrrolo[2,3-d]pyrimidin-4-yl)-1-[2-methyl-5-(trifluoromethyl)phenyl]-1H-pyrrole-2-carboxamide (Compd 255)

ESI (+) MS: m/z 388 (MH$^+$).

4-(6-Aminopyrimidin-4 yl)-1-[2-ethyl-5-(trifluoromethyl)phenyl]-1H-pyrrole-2-carboxamide (Compd 256)

$^1$H NMR (600 MHz, DMSO-d$_6$) δ 8.36 (br. s., 1H), 7.77 (br. s., 1H), 7.74 (dd, J=1.28, 7.88 Hz, 1H), 7.57-7.64 (m, 2H), 7.55 (s, 1H), 7.51 (d, J=1.83 Hz, 1H), 6.95 (br. s., 3H), 6.61 (s, 1H), 2.29-2.38 (m, 2H), 1.02 (t, J=7.60 Hz, 3H).
HRMS (ESI) calcd for C$_{18}$H$_{16}$F$_3$N$_5$O+H$^+$ 376.1380, found 376.1383.

1-[2-Ethyl-5-(trifluoromethyl)phenyl]-4-[6-(methylamino)pyrimidin-4-yl]-1H-pyrrole-2-carboxamide (Compd 257)

ESI (+) MS: m/z 390 (MH$^+$).

1-[2-Ethyl-5-(trifluoromethyl)phenyl]-4-(7H-pyrrolo[2,3-d]pyrimidin-4-yl)-1H-pyrrole-2-carboxamide (Compd 258)

ESI (+) MS: m/z 400 (MH$^+$).

1-[2-Ethyl-5-(trifluoromethyl)phenyl]-4-(H-purin-6-yl)-1H-pyrrole-2-carboxamide (compd 259)

ESI (+) MS: m/z 401 (MH$^+$).

1-[2-Ethyl-5-(trifluoromethyl)phenyl]-4-(1H-pyrazolo[3,4-d]pyrimidin-4-yl)-1H-pyrrole-2-carboxamide (Compd 260)

ESI (+) MS: m/z 401 (MH$^+$).

1-[2-Ethyl-5-(trifluoromethyl)phenyl]-4-(pyrrolo[2,1-f][1,2,4]triazin-4-yl)-1H-pyrrole-2-carboxamide (Compd 261)

ESI (+) MS: m/z 400 (MH$^+$).

4-(6,7-Dihydro-5H-pyrrolo[2,3-d]pyrimidin-4-yl)-1-[2-ethyl-5-(trifluoromethyl)phenyl]-1H-pyrrole-2-carboxamide (Compd 262)

ESI (+) MS: m/z 402 (MH$^+$).

4-(6-Aminopyrimidin-4-yl)-1-phenyl-1H-pyrrole-2-carboxamide (Compd 263)

ESI (+) MS: m/z 280 (MH$^+$).

4-[6-(Methylamino)pyrimidin-4-yl]-1-phenyl-1H-pyrrole-2-carboxamide (Compd 264)

ESI (+) MS: m/z 294 (MH$^+$).

1-Phenyl-4-(7H-pyrrolo[2,3-d]pyrimidin-4-yl)-1H-pyrrole-2-carboxamide (Compd 265)

ESI (+) MS: m/z 304 (MH$^+$).

1-Phenyl-4-(pyrrolo[2,1-f][1,2,4]triazin-4-yl)-1H-pyrrole-2-carboxamide (Compd 266)

ESI (+) MS: m/z 304 (MH$^+$).

4-(6,7-Dihydro-5H-pyrrolo[2,3-d]pyrimidin-4-yl)-1-phenyl-1H-pyrrole-2-carboxamide (Compd 267)

ESI (+) MS: m/z 306 (MH$^+$).

Example 13

1-(6-Aminopyrimidin-4-yl)-4-(5-chloro-2-ethylphenyl)-1H-pyrrole-3-arboxamide (Compd 268)

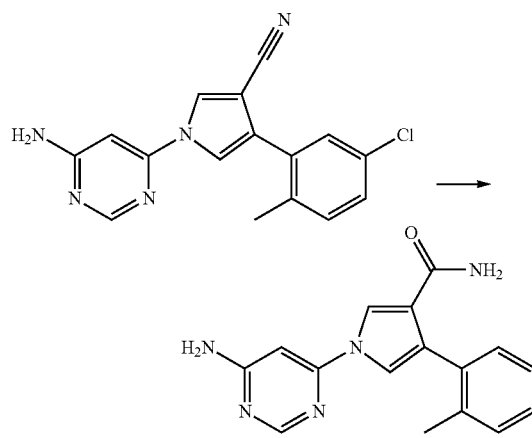

Conv.1

To a solution of 1-(6-aminopyrimidin-4-yl)-4-(5-chloro-2-methylphenyl)-1H-pyrrole-3-carbonitrile (80 mg, 0.258 mmol) in TFA (1.3 mL) were sequentially added water (0.16 mL) and 95% sulfuric acid (0.32 mL) under efficient stirring. The mixture was allowed to stir for 8 h at 70° C. and then was diluted by drop wise addition of water (2.0 mL). The reaction mixture was made basic (pH 10-12) by adding 30% aqueous ammonia under stirring. The precipitated solid was collected by filtration, washed with water and finally dried in a vacuum oven at 50° C. Purification by flash chromatography (DCM/MeOH 95/5) afforded the title compound (47 mg, 55%).

$^1$H NMR (600 MHz, DMSO-d$_6$) δ 8.32 (d, J=1.0 Hz, 1H), 8.25 (d, J=2.4 Hz, 1H), 7.49 ((d, J=2.4 Hz, 1H), 7.34 (br. s., 1H), 7.19-7.26 (m, 2H), 7.18 (d, J=2.2 Hz, 1H), 7.10 (s, 2H), 6.84 (br. s., 1H), 6.56 (d, J=1.0 Hz, 1H), 2.13 (s, 3H).

HRMS (ESI) calcd for C$_{16}$H$_{14}$ClN$_5$O+H$^+$ 328.0960, found 328.0962.

The above procedure was employed to synthesize the following compounds:

4-(5-Chloro-2-methylphenyl)-1-[6-(methylamino)pyrimidin-4-yl]-1H-pyrrole-3-carboxamide (Compd 269)

$^1$H NMR (600 MHz, DMSO-d$_6$) δ 8.35 (br. s., 2H), 7.73 (br. s., 1H), 7.43-7.56 (m, 1H), 7.32 (br. s., 1H), 7.24-7.26 (m, 2H), 7.21 (s, 1H), 7.19 (d, J=1.6 Hz, 1H), 6.84 (br. s., 1H), 6.63 (br. s., 1H), 2.85 (br. s., 3H), 2.11-2.15 (s, 3H).

HRMS (ESI) calcd for C$_{17}$H$_{16}$ClN$_5$O+H+342.1116, found 342.1112.

4-(5-Chloro-2-methylphenyl)-1-(7H-pyrrolo[2,3-d]pyrimidin-4-yl)-1H-pyrrole-3-carboxamide (Compd 270)

$^1$H NMR (600 MHz, DMSO-d$_6$) δ 12.47 (br. s., 1H), 8.66 (s, 1H), 8.47 (d, J=2.2 Hz, 1H), 7.78 (d, J=2.2 Hz, 1H), 7.71 (br. s., 1H), 7.61 (br. s., 1H), 7.21-7.29 (m, 3H), 7.17 (d, J=3.3 Hz, 1H), 6.91 (br. s., 1H), 2.17 (s, 3H).

HRMS (ESI) calcd for C$_{18}$H$_{14}$ClN$_5$O+H$^+$ 352.0960, found 352.0960.

4-(5-Chloro-2-methylphenyl)-1-(1H-pyrrolo[2,3-b]pyridin-4-yl)-1H-pyrrole-3-carboxamide (Compd 271)

ESI (+) MS: m/z 351 (MH$^+$).

4-(5-Chloro-2-methylphenyl)-1-(9H-purin-6-yl)-H-pyrrole-3-carboxamide (Compd 272)

ESI (+) MS: m/z 353 (MH$^+$).

4-(5-Chloro-2-methylphenyl)-1-1H-pyrazolo[3,4-d]pyrimidin-4-yl)-1H-pyrrole-3-carboxamide (Compd 273)

HRMS (ESI) m/z calcd for C$_{17}$H$_{13}$ClN$_6$O+H$^+$ 353.0912, found 353.0909.

4-(5-Chloro-2-methylphenyl)-1-(pyrrolo[2,1-f][1,2,4]triazin-4-yl)-1H-pyrrole-3-carboxamide (Compd 274)

$^1$H NMR (600 MHz, DMSO-d$_6$) δ 8.48 (s, 1H), 8.46 (d, J=2.2 Hz, 1H), 8.25 (d, J=1.3 Hz, 1H), 7.80 (d, J=2.2 Hz, 1H), 7.68 (br. s., 1H), 7.62 (d. J=4.2 Hz, 1H), 7.26-7.29 (m, 1H), 7.21-7.26 (m, 2H), 7.15 (dd, J=2.7, 4.6 Hz, 1H), 7.00 (br. s., 1H), 2.16 (s, 3H).

HRMS (ESI) calcd for C$_{18}$H$_{14}$ClN$_5$O+H$^+$ 352.0960, found 352.0960.

4-(5-Chloro-2-methylphenyl)-6,7-dihydro-5H-pyrrolo[2,3-d]pyrimidin-4-yl)-1H-pyrrole-3-carboxamide (Compd 275)

HRMS (ESI) m/z calcd for C$_{18}$H$_{16}$ClN$_5$O+H$^+$ 354.1116, found 354.1120.

4-(6-Aminopyrimidin-4-yl)-1-(5-chloro-2-ethylphenyl)-1H-pyrrole-3-carboxamide (Compd 276)

HRMS (ESI) calcd for C$_{17}$H$_{16}$ClN$_5$O+H+342.1116, found 342.1113.

4-(5-Chloro-2-ethylphenyl)-1-[6-(methylamino)pyrimidin-4-yl]-1H-pyrrole-3-carboxamide (Compd 277)

HRMS (ESI) calcd for C$_{18}$H$_{15}$ClN$_5$O+H$^+$ 356.1273, found 356.1267.

4-(5-Chloro-2-ethylphenyl)-1-(7H-pyrrolo[2,3-d]pyrimidin-4-yl)-1H-pyrrole-3-carboxamide (Compd 278)

HRMS (ESI) calcd for C$_{19}$H$_{16}$ClN$_5$O+H$^+$ 366.1116, found 366.1119.

4-(5-Chloro-2-ethylphenyl)-1-(pyrrolo[2,1-f][1,2,4]triazin-4-yl)-1H-pyrrole-3-carboxamide (Compd 279)

HRMS (ESI) calcd for C$_{19}$H$_{16}$ClN$_5$O+H$^+$ 366.1116, found 366.1111.

4-(5-Chloro-2-ethylphenyl)-1-(6,7-dihydro-5H-pyrrolo[2,3-d]pyrimidin-4-yl)-1H-pyrrole-3-carboxamide (Compd 280)

HRMS (ESI) calcd for $C_{19}H_{18}ClN_5O+H^+$ 368.1273, found 368.1277.

1-(6-Aminopyrimidin-4-yl)-4-[2-chloro-5-(trifluoromethyl)phenyl]-1H-pyrrol-3-carboxamide (Compd 281)

HRMS (ESI) calcd for $C_{16}H_{11}ClF_3N_5O+H^+$ 382.0677, found 382.0681.

4-[2-Chloro-5-(trifluoromethyl)phenyl]-1-[6-(methylamino)pyrimidin-4-yl]-1H-pyrrole-3-carboxamide (Compd 282)

HRMS (ESI) calcd for $C_{17}H_{13}ClF_3N_5O+H^+$ 396.0834, found 396.0838.

4-[2-Chloro-5-(trifluoromethyl)phenyl]-1-(7H-pyrrolo[2,3-d]pyrimidin-4-yl)-1H-pyrrole-3-carboxamide (Compd 283)

HRMS (ESI) calcd for $C_{18}H_{11}ClF_3N_5O+H^+$ 406.0677, found 406.0674.

4-[2-Chloro-5-(trifluoromethyl)phenyl]-1-(pyrrolo[2,1-f][1,2,4]triazin-4-yl)-1H-pyrrole-3-carboxamide (Compd 284)

HRMS (ESI) calcd for $C_{17}H_{10}ClF_3N_6O+H^+$ 406.0677, found 406.0676.

4-[2-Chloro-5-(trifluoromethyl)phenyl]-1-(6,7-dihydro-5H-pyrrolo[2,3-d]pyrimidin-4-yl-1H-pyrrole-3-carboxamide (Compd 285)

ESI (+) MS: m/z 408 (MH$^+$).

1-(6-Aminopyrimidin-4-yl)-4-[2-methyl-5-(trifluoromethyl)phenyl]-1H-pyrrole-3-carboxamide (Compd 286)

ESI (+) MS: m/z 362 (MH$^+$).

1-[6-(Methylamino)pyrimidin-4-yl]-4-[2-methyl-5-(trifluoromethyl)phenyl]-1H-pyrrole-3-carboxamide (Compd 287)

ESI (+) MS: m/z 376 (MH$^+$).

4[2-Methyl-5-(trifluoromethyl)phenyl]-1-(7H-pyrrolo[2,3-d]pyrimidin-4-yl)-1H-pyrrole-3-carboxamide (Compd 288)

ESI (+) MS: m/z 386 (MH$^+$).

4-[2-Methyl-5-(trifluormethyl)phenyl]-1-(pyrrolo[2,1-f][1,2,4]triazin-4-yl)-1H-pyrrole-3-carboxamide (Compd 289)

ESI (+) MS: m/z 386 (MH$^+$).

1-(6,7-Dihydro-5H-pyrrolo[2,3-d]pyridimin-4-yl)-4-[2-methyl-5-(trifluoromethyl)phenyl]-1H-pyrrole-3-carboxamide (Compd 290)

ESI (+) MS: m/z 388 (MH$^+$).

1-(6-Aminopyrimidin-4-yl)-4-[2-ethyl-5-(trifluoromethyl)phenyl]-1H-pyrrole-3-carboxamide (Compd 291)

HRMS (ESI) calcd for $C_{18}H_{16}F_3N_5O+H^+$ 376.1380, found 376.1385.

4-[2-Ethyl-5-(trifluoromethyl)phenyl]-1-[6-(methylamino)pyrimidin-4-yl]-1H-pyrrole-3-carboxamide (Compd 292)

ESI (+) MS: m/z 390 (MH$^+$).

4-[2-Ethyl-5-(trifluoromethyl)phenyl]-1-(7H-pyrrolo[2,3-d]pyrimidin-4-yl)-1H-pyrrole-3-carboxamide (Compd 293)

ESI (+) MS: m/z 400 (MH$^+$).

4-[2-Ethyl-5-(trifluoromethyl)phenyl]-1-(pyrrolo[2,1-f][1,2,4]triazin-4-yl)-1H-pyrrole-3-carboxamide (Compd 294)

ESI (+) MS: m/z 400 (M$^+$).

1-(6,7-Dihydro-5H-pyrrolo[2,3-d]pyrimidin-4-yl)-4-[2-ethyl-5-(trifluoromethyl)phenyl]-1H-pyrrole-3-carboxamide (Compd 295)

ESI (+) MS: m/z 402 (MH$^+$).

1-(6-Aminopyrimidin-4-yl)-4-phenyl-1H-pyrrole-3-carboxamide (Compd 296)

ESI (+) MS: m/z 280 (MH$^+$).

1-[6-(Methylamino)pyrimidin-4-yl]-4-phenyl-1H-pyrrole-3-carboxamide (Compd 297)

ESI (+) MS: m/z 294 (MH$^+$).

4-Phenyl-1-(7H-pyrrolo[2,3-d]pyrimidin-4-yl)-1H-pyrrolo-3-carboxamide (Compd 298)

ESI (+) MS: m/z 304 (MH$^+$).

4-Phenyl-1-(pyrrolo[2,1-f][1,2,4]triazin-4-yl)-1H-pyrrole-3-carboxamide (Compd 299)

ESI (+) MS: m/z 304 (MH$^+$).

1-(6,7-Dihydro-5H-pyrrolo[2,3-d]pyrimidin-4-yl)-4-phenyl-1H-pyrrole-3-carboxamide (Compd 300)

ESI (+) MS: m/z 306 (MH$^+$).

Example 14

5-(6-Aminopyrimidin-4-yl)-2-(5-chloro-2-ethylphenyl)-N-methyl-1H-pyrrole-3-carboxamide (Compd 301)

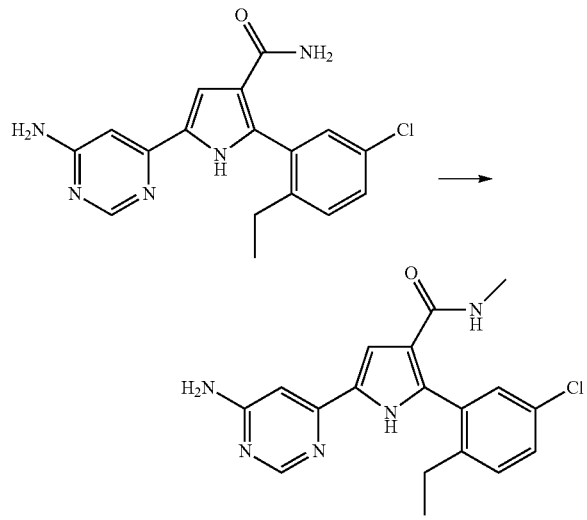

Conv.2

A solution of 5-(6-aminopyrimidin-4-yl)-2-(5-chloro-2-ethylphenyl)-1H-pyrrole-3-carboxamide (341 mg, 1.0 mmol) in DMF (0.3 mL) and THF (6 mL) was treated with di-tert-butyl dicarbonate (1.309 g, 6 mmol) and DMAP (15.8 mg, 0.13 mmol). After 3 h at room temperature, the reaction mixture was diluted with water and extracted with EtOAc. The combined organic layers were washed with brine, dried over $Na_2SO_4$, filtered and the solvent was evaporated under reduced pressure. The residue dissolved in THF (2 mL) was treated with methyl amine (2M in THF, 2 mL, 4 mmol) and stirred overnight at room temperature. The reaction mixture was concentrated, dissolved in DCM (5 mL) and treated with TFA (5 mL). After 3 h at room temperature, the reaction mixture was concentrated, diluted with EtOAc, washed with 10% ammonia. The organic phase was separated, washed with aqueous brine, dried over $Na_2SO_4$, filtered and the solvent was evaporated under reduced pressure. Purification by flash chromatography (DCM/MeOH/7 N $NH_3$ in MeOH 98/2/0.2) afforded the title compound (220 mg, 62%).

$^1$H NMR (600 MHz, DMSO-$d_6$) δ 11.93 (br. s., 1H), 8.30 (d, J=1.10 Hz, 1H), 7.74 (q, J=4.21 Hz, 1H), 7.37 (dd, J=2.29, 8.33 Hz, 1H), 7.29 (d, J=8.24 Hz, 1H), 7.25 (s, 1H), 7.20 (d, J=2.38 Hz, 1H), 6.76 (br. s., 2H), 6.66 (d, J=1.10 Hz, 1H), 2.61 (d, J=4.58 Hz, 3H), 2.44 (q, J=7.63 Hz, 2H), 0.95 (t, J=7.51 Hz, 3H).

HRMS (ESI) m/z calcd for $C_{18}H_{18}ClN_5O+H^+$ 356.1273, found 356.1272.

The above procedure was employed to synthesize the following compounds:

2-(5-Chloro-2-ethylphenyl)-N-methyl-5-[6-(methylamino)pyrimidin-4-yl]-1H-pyrrole-3-carboxamide (Compd 302)

$^1$H NMR (600 MHz, DMSO-$d_6$) δ 11.96 (br. s., 1H), 8.36 (br. s., 1H), 7.75 (d, J=4.76 Hz, 1H), 7.39 (dd, J=1.92, 8.15 Hz, 1H), 7.31 (d, J=8.24 Hz, 2H), 7.23 (d, J=1.65 Hz, 2H), 6.74 (br. s., 1H), 2.81 (br. s., 3H), 2.61 (d, J=4.58 Hz, 4H), 2.44 (q, J=7.63 Hz, 2H), 0.96 (t, J=7.60 Hz, 3H).

HRMS (ESI) m/z calcd for $C_{19}H_{20}ClN_5O+H^+$ 370.1429, found 370.1432.

2-(5-Chloro-2-ethylphenyl)-N-methyl-5-(7H-pyrrolo[2,3-d]pyrimidin-4-yl)-1H-pyrrole-3-carboxamide (Compd 303)

$^1$H NMR (600 MHz, DMSO-$d_6$) δ 12.18 (br. s., 1H), 12.09 (br. s., 1H), 8.66 (s, 1H), 7.93 (q, J=4.21 Hz, 1H), 7.68 (d, J=1.10 Hz, 1H), 7.60-7.64 (in, J=2.93 Hz. 1H), 7.36 (dd, J=2.29, 8.33 Hz, 1H), 7.29 (d, J=8.24 Hz, 1H), 7.22 (d, J=2.20 Hz, 1H), 7.07 (d, J=3.30 Hz, 1H), 2.67 (d, J=4.58 Hz, 3H), 2.46 (q, J=7.57 Hz, 2H), 0.97 (t, J=7.60 Hz, 3H).

HRMS (ESI) m/z calcd for $C_{20}H_{18}ClN_5O+H^+$ 380.1273, found 380.1275.

2-(5-Chloro-2-ethylphenyl)-N-methyl-5-(pyrrolo[2,1-f][1,2,4]triazin-4-yl)-1H-pyrrole-3-carboxamide (Compd 304)

ESI (+) MS: m/z 380 (MH$^+$).

2-(5-Chloro-2-ethylphenyl)-5-(6,7-dihydro-5H-pyrrolo[2,3-d]pyridimin-4-yl)-N-methy-1H-pyrrole-3-carboxamide (Compd 305)

ESI (+) MS: m/z 382 (MH$^+$).

5-(6-Aminopyrimidin-4-yl)-2-(5-chloro-2-methylphenyl)-N-methyl-1H-pyrrole-3-carboxamide (Compd 306)

ESI (+) MS: m/z 342 (MH$^+$).

2-(5-Chloro-2-methylphenyl)-N-methyl-5-[6-(methylamino)pyrimidin-4-yl]-1H-pyrrole-3-carboxamide (Compd 307)

ESI (+) MS: m/z 364 (MH$^+$).

2-(5-Chloro-2-methylphenyl)-N-methyl-5-(7H-pyrrolo[2,3-d]pyrimidin-4-yl)-1H-pyrrole-3-carboxamide (Compd 308)

ESI (+) MS: m/z 366 (MH$^+$).

2-(5-Chloro-2-methylphenyl)-N-methyl-5-(pyrrolo[2,1-f][1,2,4]triazin-4-yl)-1H-pyrrole-3-carboxamide (Compd 309)

ESI (+) MS: m/z 366 (MH$^+$).

2-(5-Chloro-2-methylphenyl)-5-(6,7-dihydro-5H-pyrrolo[2,3-d]pyrimidin-4-yl)-N-methy-1H-pyrrole-3-carboxamide (Compd 310)

ESI (+) MS: m/z 382 (MH$^+$).

5-(6-Aminopyrimidin-4-yl)-N-methyl-2-[2-chloro-5-(trifluoromethyl)phenyl]-1H-pyrrole-3-carboxamide (Compd 311)

ESI (+) MS: m/z 396 (M$^+$).

N-Methyl-5-[6-(methylamino)pyrimidin-4-yl]-2-[2-chloro-5-(trifluoromethyl)phenyl]-1H-pyrrole-3-carboxamide (Compd 312)

ESI (+) MS: m/z 410 (M+).

2-[2-Chloro-5-(trifluoromethyl)phenyl]-N-methyl-5-(7H-pyrrolo[2,3-d]pyrimidin-4-yl)-1H-pyrrole-3-carboxamide (Compd 313)

ESI (+) MS: m/z 420 (MH+).

2-[2-Chloro-5-(trifluoromethyl)phenyl]-N-methyl-5-(pyrrolo[2,1-f][1,2,4]triazin-4-yl)-1H-pyrrole-3-carboxamide (Compd 314)

ESI (+) MS: m/z 420 (MH+).

2-[2-Chloro-5-(trifluoromethyl)phenyl]-5-(6,7-dihydro-5H-pyrrolo[2,3-d]pyrimidin-4-yl)-N-methyl-1H-pyrrole-3-carboxamide (Compd 315)

ESI (+) MS: m/z 422 (MH+).

5-(6-Aminopyrimidin-4-yl)-N-methy-2-[2-methyl-5-(trifluoromethyl)phenyl]-1H-pyrrole-3-carboxamide (Compd 316)

$^1$H NMR (600 MHz, DMSO-$d_6$) δ 12.00 (br. s., 1H), 8.32 (d, J=1.10 Hz, 1H), 7.85 (q, J=4.40 Hz, 1H), 7.58-7.63 (m, 1H), 7.51 (s, 1H), 7.47 (d, J=8.24 Hz, 1H), 7.28 (d, J=1.10 Hz, 1H), 6.79 (s, 2H), 6.66 (d, J=1.10 Hz, 1H), 2.61 (d, J=4.52 Hz, 3H), 2.20 (s, 3H)
HRMS (ESI) m/z calcd for $C_{18}H_{16}F_3N_5O+H^+$ 376.1380, found 376.1384.

N-Methyl-5-[6-(methylamino)pyrimidin-4-yl]-2-[2-methyl-5-(trifluoromethyl)phenyl]-1H-pyrrole-3-carboxamide (Compd 317)

$^1$H NMR (600 MHz, DMSO-$d_6$) δ 11.99 (br. s., 1H), 8.36 (br. s., 1H), 7.84 (q, J=4.85 Hz, 1H), 7.63 (d, J=7.88 Hz, 1H), 7.53 (s, 1H), 7.44-7.50 (m, 1H), 7.33 (br, s., 1H), 7.22 (br. s., 1H), 6.72 (br. s., 1H), 2.81 (br. s., 3H), 2.62 (d, J=4.71 Hz, 3H), 2.21 (s, 3H)
HRMS (ESI) m/z calcd for $C_{19}H_{18}F_3N_5O+H^+$ 390.1536, found 390.1531.

2-[2-Methyl-5-(trifluoromethyl)phenyl]-N-methyl-5-(7H-pyrrolo[2,3-d]pyrimidin-4-yl)-1H-pyrrole-3-carboxamide (Compd 318)

$^1$H NMR (600 MHz, DMSO-$d_6$) δ 12.27 (br. s., 1H), 12.11 (br. s., 1H), 8.67 (s, 1H), 8.01 (q, J=4.46 Hz, 1H), 7.71 (d, J=1.28 Hz, 1H), 7.64 (dd, J=2.56, 3.48 Hz, 1H), 7.61 (dd, J=1.37, 8.15 Hz, 1H), 7.54 (s, 1H), 7.46 (d, J=7.88 Hz, 1H), 7.09 (dd, J=1.83, 3.48 Hz, 1H), 2.69 (d, J=4.40 Hz, 3H), 2.23 (s, 3H)
HRMS (ESI) m/z calcd for $C_{20}H_{16}F_3N_5O+H^+$ 400.1380, found 400.1382.

2-[2-Methyl-5-(trifluoromethyl)phenyl]-N-methyl-5-(pyrrolo[2,1-f][1,2,4]triazin-4-yl)-1H-pyrrole-3-carboxamide (Compd 319)

ESI (+) MS: m/z 400 (MH+).

2-[2-Methyl-5-(trifluoromethyl)phenyl]-5-(6,7-dihydro-5H-pyrrolo[2,3-d]pyrimidin-4-yl)-N-ethyl-1H-pyrrole-3-carboxamide (Compd 320)

ESI (+) MS: m/z 402 (MH+).

5-(6-Aminopyrimidin-4-yl)-2-[2-ethyl-5-(trifluoromethyl)phenyl]-N-methyl-1H-pyrrole-3-carboxamide (Compd 321)

$^1$H NMR (600 MHz, DMSO-$d_6$) δ 12.01 (br. s., 1H), 8.31 (d, J=1.10 Hz, 1H), 7.82 (q, J=4.52 Hz, 1H), 7.66 (dd, J=1.56, 8.15 Hz, 1H), 7.50 (d, J=8.24 Hz, 1H), 7.47 (s, 1H), 7.28 (s, 1H), 6.78 (s, 2H), 6.66 (d, J=1.10 Hz, 1H), 2.61 (d, J=4.58 Hz, 3H), 2.54 (q, J=7.57 Hz, 2H), 0.99 (t, J=7.60 Hz, 3H).
HRMS (ESI) m/z calcd for $C_{19}H_{18}F_3N_5O+H^+$ 390.1536, found 390.1541.

2-[2-Ethyl-5-(trifluoromethyl)phenyl]-N-methyl-5-[6-(methylamino)pyrimidin-4-yl]-1H-pyrrole-3-carboxamide (Compd 322)

$^1$H NMR (600 MHz, DMSO-$d_6$) δ 12.00 (br. s., 1H), 8.35 (br. s., 1H), 7.83 (d, J=4.58 Hz, 1H), 7.68 (d, J=8.24 Hz, 1H), 7.52 (d, J=8.24 Hz, 1H), 7.49 (s, 1H), 7.33 (br. s., 1H), 7.20 (br. s., 1H), 6.72 (br. s., 1H), 2.81 (br. s., 3H), 2.61 (d, J=4.58 Hz, 3H), 2.55 (q, J=7.63 Hz, 2H), 1.00 (t, J=7.60 Hz, 3H)
HRMS (ESI) m/calcd for $C_{20}H_{20}F_3N_5O+H^+$ 404.1693, found 404.1698.

2-[2-Ethyl-5-(trifluoromethyl)phenyl]-N-methyl-5-(7H-pyrrolo[2,3-d]pyrimidin-4-yl)-1H-pyrrole-3-carboxamide (Compd 323)

$^1$H NMR (600 MHz, DMSO-$d_6$) δ 12.27 (br. s., 1H), 12.11 (br. s., 1H), 8.66 (s, 1H), 7.99 (q, J=4.40 Hz, 1H), 7.72 (s, 1H), 7.66 (dd, J=1.56, 7.97 Hz, 1H), 7.63-7.64 (m, 1H), 7.51 (br. s., 1H), 7.49 (br. s., 1H), 7.08 (dd, J=1.83, 3.48 Hz, 1H), 2.68 (s, 3H), 2.57 (q, J=7.51 Hz, 2H), 1.01 (t, J=7.60 Hz, 3H)
HRMS (ESI) m/calcd for $C_{21}H_{18}F_3N_5O+H^+$ 414.1536, found 414.1534.

2-[2-Ethyl-5-(trifluoromethyl)phenyl]-N-methyl-5-(pyrrolo[2,1-f][1,2,4]triazin-4-yl)-1H-pyrrole-3-carboxamide (Compd 324)

ESI (+) MS: m/z 414 (MH+).

2-[2-Ethyl-5-(trifluoromethyl)phenyl]-5-(6,7-dihydro-5H-pyrrolo[2,3-d]pyrimidin-4-yl)-N-methyl-1H-pyrrole-3-carboxamide (Compd 325)

ESI (+) MS: m/z 416 (MH+).

N-methyl-2-phenyl-5-(7H-pyrrolo[2,3-d]pyrimidin-4-yl)-1H-pyrrole-3-carboxamide (compd 326)

$^1$H NMR (600 MHz, DMSO-$d_6$) δ 12.10 (br. s., 1H), 11.99 (br. s., 1H), 8.70 (s, 1H), 7.99 (q, J=4.76 Hz, 1H), 7.66-7.73 (m, 2H), 7.61 (dd, J=2.38, 3.48 Hz, 1H), 7.55 (s, 1H), 7.36-7.40 (m, 2H), 7.30-7.34 (m, 1H), 7.06 (dd, J=1.74, 3.57 Hz, 1H), 2.73 (d, J=4.58 Hz, 3H)
HRMS (ESI) m/calcd for $C_{18}H_{15}N_5O+H^+$ 318.1350, found 318.1350.

5-(6,7-Dihydro-5H-pyrrolo[2,3-d]pyrimidin-4-yl)-N-methyl-2-phenyl-1H-pyrrole-3-carboxamide (Compd 327)

ESI (+) MS: m/z 320 (MH+).

Example 15

5-(6-Aminopyrimidin-4-yl)-2-(5-chloro-2-methylphenyl)-1-methyl-1H-pyrrole-3-carboxamide (Compd 328)

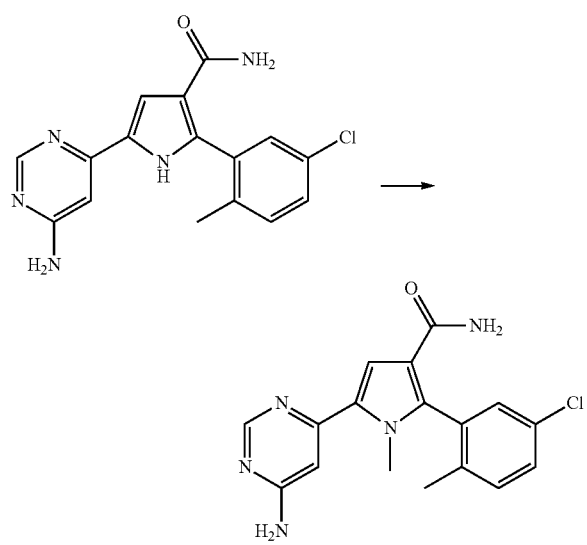

Conv.3

To a solution of 5-(6-aminopyrimidin-4-yl)-2-(5-chloro-2-methylphenyl)-1H-pyrrole-3-carboxamide (98 mg, 0.3 mmol) in DMF (1 mL), $Cs_2CO_3$ (107 mg, 0.33 mmol) and MeI (28 µL, 0.43 mmol) were added. The mixture was stirred at room temperature for 3 h, then the solvent was removed. To the residue EtOAc and water were added, the layers were separated, the aqueous layer was extracted with EtOAc and the combined organic layers were washed with water, dried over $Na_2SO_4$, filtered and concentrated. The crude material was purified by flash chromatography (DCM/MeOH/$NH_3$ in MeOH 95/5/0.5) affording the title compound (43 mg, 42%).

ESI (+) MS: m/z 342 (MH+).

According to this procedure, but using iodo ethane, the following compound was prepared:

5-(6-Aminopyrimidin-4-yl)-2-(5-chloro-2-methylphenyl)-1-ethyl-1H-pyrrole-3-carboxamide (Compd 329)

ESI (+) MS: m/z 366 (MH+).

According to this procedure, but using 2,2,2-trifluoroethyl trifluoromethanesulfonate, the following compound was prepared:

5-(6-Aminopyrimidin-4-yl)-2-(5-chloro-2-methylphenyl)-1-(2,2,2-trifluoroethyl)-1H-pyrrole-3-carboxamide (Compd 330)

ESI (+) MS: m/z 410 (MH+).

According to this procedure, but using 2-(2-iodoethoxy)tetrahydro-2H-pyran and removing the tetrahydro-2H-pyran-2-yl protecting group with conc. HCl in EtOH, the following compound was prepared:

5-(6-Aminopyrimidin-4-yl)-2-(5-chloro-2-methylphenyl)-1-(2-hydroxyethyl)-1H-pyrrole-3-carboxamide (Compd 331)

ESI (+) MS: m/z 372 (MH+).

According to this procedure, but starting from 5-(6-aminopyrimidin-4-yl)-3-(5-chloro-2-methylphenyl)-1H-pyrrole-2-carboxamide, the following compound was prepared:

5-(6-Aminopyrimidin-4-yl)-3-(5-chloro-2-methylphenyl)-1-methyl-1H-pyrrole-2-carboxamide (Compd 332)

ESI (+) MS: m/z 342 (MH+).

According to this procedure, but starting from 5-(6-aminopyrimidin-4-yl)-3-(5-chloro-2-methylphenyl)-1H-pyrrole-2-carboxamide and using iodo ethane, the following compound was prepared:

5-(6-Aminopyrimidin-4-yl)-3-(5-chloro-2-methylphenyl)-1-ethyl-1H-pyrrole-2-carboxamide (Compd 333)

ESI (+) MS: m/z 366 (MH+).

According to this procedure, but starting from 5-(6-aminopyrimidin-4-yl)-3-(5-chloro-2-methylphenyl)-1H-pyrrole-2-carboxamide and using 2,2,2-trifluoroethyl trifluoromethanesulfonate, the following compound was prepared:

5-(6-Aminopyrimidin-4-yl)-3-(chloro-2-methylphenyl)-1-(2,2,2-trifluoroethyl)-1H-pyrrole-2-carboxamide (Compd 334)

ESI (+) MS: m/z 410 (MH+).

According to this procedure, but starting from 5-(6-aminopyrimidin-4-yl)-3-(5-chloro-2-methylphenyl)-1H-pyrrole-2-carboxamide and using 2-(2-iodoethoxy)tetrahydro-2H-pyran and removing the tetrahydro-2H-pyran-2-yl protecting group with with conc. HCl in EtOH, the following compound was prepared:

5-(6-Aminopyrimidin-4-yl)-3-(5-chloro-2-methylphenyl)-1-(2-hydroxyethyl)-1H-pyrrole-2-carboxamide (Compd 335)

ESI (+) MS: m/z 372 (MH+).

Pharmacology

Biochemical Assay for Inhibitors of JAK Kinase Activity

General Principle—

Specific JAK2, JAK1 or JAK3 peptide substrates are trans-phosphorylated by JAK kinases in the presence of ATP traced with 33P-γ-ATP. At the end of the phosphorylation reaction, the unreacted ATP, cold and radioactive, is captured by an excess of dowex ion exchange resin that eventually settles by gravity to the bottom of the reaction plate.

The supernatant is subsequently withdrawn and transferred into a counting plate that is then evaluated by β-counting.

Dowex Resin Preparation—

500 g of wet resin (SIGMA, custom prepared resin DOWEX 1×8 200-400 mesh, 2.5 Kg) are weighed out and diluted 2 to 1 in 150 mM sodium formate, pH 3.00. The resin is allowed to settle down overnight and then the supernatant is discarded. After three washes as above over a couple of days, the resin is allowed to settle and two volumes (with respect to the resin volume) of 150 mM sodium formate buffer are added.

Kinase Buffer (KB)—

Kinase buffer was composed of 50 mM HEPES pH 7.5 containing 10 mM $MgCl_2$, 2.5 mM DTT, 10 μM $Na_3VO_4$ and 0.2 mg/mL BSA.

JAK2 Specific Assay Conditions

Enzyme—

Assays were performed with the commercially available JAK2 kinase domain (Invitrogen, Eugene, Oreg.) that showed a linear kinetic without prephosphorylation.

Assay Conditions—

The JAK2 kinase assay was run with a final enzyme concentration of 1 nM, in the presence of 60 μM ATP, 3 nM 33P-γ-ATP and 64 μM of substrate BioDBn*306 (Aminoacid sequence: LPLDKDYYVVREPGQ—SEQ ID NO: 1). The peptidic substrate was purchased from American Peptide Company (Sunnyvale, Calif.).

JAK1 Specific Assay Conditions

Enzyme—

Assays were performed with the JAK1 kinase domain (residues 861-1152 of the 1154 amino acid long full-length sequence, accession number P23458 of UniProtKBISwiss-Prot database).

The JAK1 kinase domain was preactivated with ATP for 1 h at 28° C. in order to obtain a linear kinetic.

Assay Conditions—

The JAK1 kinase assay was run with a final pre activated enzyme concentration of 2.5 nM, in the presence of 100 μM ATP, 2 nM 33P-γ-ATP and 154 μM of substrate Bio-DBn*333 (Aminoacid sequence: KKHTDDGYMPM-SPGVA—SEQ ID NO: 2). The peptidic substrate was purchased from American Peptide Company (Sunnyvale, Calif.).

JAK3 Specific Assay Conditions

Enzyme—

Assays were performed with the JAK3 kinase domain (residues 781-1124 of the 1124 amino acid long full-length sequence, accession number P52333 of UniProtKB/Swiss-Prot database) that showed a linear kinetic without prephosphorylation.

Assay Conditions—

The JAK3 kinase assay was run with a final enzyme concentration of 1 nM, in the presence of 22 μM ATP, 1 nM 33P-γ-ATP and 40 μM of substrate BioDBn*306 (Aminoacid sequence: LPLDKDYYVVREPGQ—SEQ ID NO: 1). The peptidic substrate was purchased from American Peptide Company (Sunnyvale, Calif.).

TYK2 Specific Assay Conditions

Enzyme—

Assays were performed with the TYK2 kinase domain (residues 833-1187 of the 1187 amino acid long full-length sequence, accession number P29597 of UniProtKB/Swiss-Prot database) that showed a linear kinetic without prephosphorylation.

Assay Conditions—

The TYK2 kinase assay was run with a final enzyme concentration of 3 nM, in the presence of 31 μM ATP, 0.8 nM 33P-γ-ATP and 71 μM of substrate BioDBn*333 (Aminoacid sequence: KKHTDDGYMPMSPGVA—SEQ ID NO: 2). The peptidic substrate was purchased from American Peptide Company (Sunnyvale, Calif.).

Cell Proliferation

Cell Lines:

the JAK2 dependent human megakaryoblastic leukemia cell line SET-2 (DSMZ, Braunschweig GERMANY), and JAK2 independent human chronic myelogenous leukaemia cell line K562 (ECACC, Wiltshire, UK) were cultured in RPMI-1640 medium-Glutamax (Gibco BRL, Gaithersburg, Md., USA), supplemented with 10% fetal bovine serum (FBS) at 37° C. and 5% $CO_2$. The IL-2 dependent human T lymphoma cell line DERL-7 (DSMZ, Braunschweig GERMANY) was used to test the activity of compounds in cells on JAK1/JAK3 kinases activated by IL-2. The DERL-7 cell lines were cultured in RPMI-1640 medium-Glutamax (Gibco BRL, Gaithersburg, Md., USA), supplemented with 20% FBS and 20 ng/ml of human IL-2 (Sigma-Aldrich, St Louis, Mo., USA).

Cell Proliferation Assay:

Approximately $5\times10^3$ cells were plated into 384 microtiter plate wells in 50 μL of growth media with different concentrations of inhibitors. The cells were incubated at 37° C. and 5% $CO_2$ for 72 hours, than the plates were processed using CellTiter-Glo assay (Promega, Madison, Wis., USA) following the manufacturer's instruction. Briefly 25 μL/well reagent solution are added to each wells and after 5 minutes shacking micro-plates are read by Envision luminometer (PerkinElmer, Waltham, Mass., USA).

Data Fitting—

Data are analyzed by Symix Assay Explorer software (Symix Technologies Inc.) that provides sigmoidal fitting algorithm of the 8 points dilutions curves for $IC_{50}$ determination.

In Vivo Model

Acute megakaryoblastic leukemia cell line SET-2 ($10^7$ cells) was inoculated s.c. in 5-6 weeks old female severe combined immunodeficient (SCID) mice (Charles River) previously exposed to gamma-irradiation (200 Rads of whole body gamma-irradiation). Mice bearing a palpable tumor (100-200 $mm^3$) were treated with vehicle (0.5% Methocel) or a compound of formula (I) for 10 days, bid. Tumor dimensions were measured regularly using Vernier calipers and tumor growth inhibition (TGI) was calculated.

In biochemical assays, the compounds of formula (I) tested as described above demonstrate a remarkably potent JAK inhibitory activity. See, as an example, the following Table A wherein is reported experimental data ($IC_{50}$) of the compounds of the invention obtained for representative enzymes of JAK (i.e. JAK1 and JAK2) family kinases.

In cellular assays, the compounds of formula (I) tested as described above show higher activity in JAK2 dependent SET-2 cell line in comparison to JAK2 independent K562 cell line (see Table A).

TABLE A

| Compd Number | Compound name | IC$_{50}$ μM | | | |
|---|---|---|---|---|---|
| | | JAK1 | JAK2 | SET-2 | K-562 |
| 9 | 5-(6-Aminopyrimidin-4-yl)-2-(5-chloro-2-ethylphenyl)-1H-pyrrole-3-carbonitrile | 0.141 | 0.023 | 1.27 | 7.23 |
| 47 | 4-(6-aminopyrimidin-4-yl)-1-(5-chloro-2-ethylphenyl)-1H-pyrrole-2-carbonitrile | 0.869 | 0.066 | 3.07 | >10 |
| 63 | 1-(5-Chloro-2-methylphenyl)-4-(7H-pyrrolo[2,3-d]pyrimidin-4-yl)-1H-pyrrole-2-carbonitrile | 0.015 | 0.004 | 1.38 | 1.89 |
| 68 | 1-(5-Chloro-2-ethylphenyl)-4-(7H-pyrrolo[2,3-d]pyrimidin-4-yl)-1H-pyrrole-2-carbonitrile | 0.014 | 0.006 | 0.34 | 4.13 |
| 72 | 1-[2-Chloro-5-(trifluoromethyl)phenyl]-4-(7H-pyrrolo[2,3-d]pyrimidin-4-yl)-1H-pyrrole-2-carbonitrile | 0.017 | 0.007 | 0.51 | 6.61 |
| 123 | 3-(5-Chloro-2-methylphenyl)-5-(7H-pyrrolo[2,3-d]pyrimidin-4-yl)-1H-pyrrole-2-carboxamide | 0.033 | 0.005 | 0.46 | 3.76 |
| 124 | 3-(5-Chloro-2-ethylphenyl)-5-(7H-pyrrolo[2,3-d]pyrimidin-4-yl)-1H-pyrrole-2-carboxamide | 0.018 | 0.004 | 0.33 | 9.66 |
| 125 | 3-[2-Ethyl-5-(trifluoromethyl)phenyl]-5-(7H-pyrrolo[2,3-d]pyrimidin-4-yl)-1H-pyrrole-2-carboxamide | 0.019 | 0.006 | 0.30 | >10 |
| 129 | 3-(5-Chloro-2-methylphenyl)-N-methyl-5-(7H-pyrrolo[2,3-d]pyrimidin-4-yl)-1H-pyrrole-2-carboxamide | 0.038 | 0.009 | 0.69 | >10 |
| 130 | 3-(5-Chloro-2-ethylphenyl)-N-methyl-5-(7H-pyrrolo[2,3-d]pyrimidin-4-yl)-1H-pyrrole-2-carboxamide | 0.011 | 0.003 | 0.40 | >10 |
| 131 | 3-[2-Ethyl-5-(trifluoromethyl)phenyl]-N-methyl-5-(7H-pyrrolo[2,3-d]pyrimidin-4-yl)-1H-pyrrole-2-carboxamide | 0.025 | 0.009 | 0.48 | 2.80 |
| 189 | 5-(6-Aminopyrimidin-4-yl)-2-(5-chloro-2-methylphenyl)-1H-pyrrole-3-carboxamide | 0.139 | 0.019 | 0.89 | >10 |
| 190 | 2-(5-Chloro-2-methylphenyl)-5-[6-(methylamino)pyrimidin-4-yl]-1H-pyrrole-3-carboxamide | 0.052 | 0.022 | 0.75 | >10 |
| 191 | 2-(5-Chloro-2-methylphenyl)-5-(7H-pyrrolo[2,3-d]pyrimidin-4-yl)-1H-pyrrole-3-carboxamide | 0.020 | 0.001 | 0.69 | >10 |
| 192 | 2-(5-Chloro-2-methylphenyl)-5-(1H-pyrrolo[2,3-b]pyridin-4-yl)-1H-pyrrole-3-carboxamide | 0.111 | 0.013 | 0.86 | >10 |
| 197 | 5-(6-Aminopyrimidin-4-yl)-2-(5-chloro-2-ethylphenyl)-1H-pyrrole-3-carboxamide | 0.008 | 0.001 | 0.15 | >10 |
| 198 | 2-(5-Chloro-2-ethylphenyl)-5-[6-(methylamino)pyrimidin-4-yl]-1H-pyrrole-3-carboxamide | 0.008 | 0.002 | 0.19 | >10 |
| 199 | 2-(5-Chloro-2-ethylphenyl)-5-(7H-pyrrolo[2,3-d]pyrimidin-4-yl)-1H-pyrrole-3-carboxamide | 0.007 | 0.001 | 0.10 | >10 |
| 204 | 5-(6-Aminopyrimidin-4-yl)-2-[2-chloro-5-(trifluoromethyl)phenyl]-1H-pyrrole-3-carboxamide | 0.167 | 0.012 | 0.45 | >10 |
| 205 | 2-[2-Chloro-5-(trifluoromethyl)phenyl]-5-[6-(methylamino)pyrimidin-4-yl]-1H-pyrrole-3-carboxamide | 0.104 | 0.019 | 0.65 | >10 |
| 206 | 2-[2-Chloro-5-(trifluoromethyl)phenyl]-5-(7H-pyrrolo[2,3-d]pyrimidin-4-yl)-1H-pyrrole-3-carboxamide | 0.140 | 0.019 | 0.70 | >10 |
| 211 | 5-(6-Aminopyrimidin-4-yl)-2-[2-methyl-5-(trifluoromethyl)phenyl]-1H-pyrrole-3-carboxamide | 0.108 | 0.011 | 0.59 | >10 |
| 212 | 5-[6-(Methylamino)pyrimidin-4-yl]-2-[2-methyl-5-(trifluoromethyl)phenyl]-1H-pyrrole-3-carboxamide | 0.048 | 0.021 | 0.46 | >10 |
| 213 | 2-[2-Methyl-5-(trifluoromethyl)phenyl]-5-(7H-pyrrolo[2,3-d]pyrimidin-4-yl)-1H-pyrrole-3-carboxamide | 0.027 | 0.008 | 0.29 | >10 |
| 218 | 5-(6-Aminopyrimidin-4-yl)-2-[2-ethyl-5-(trifluoromethyl)phenyl]-1H-pyrrole-3-carboxamide | 0.033 | 0.004 | 0.26 | 6.24 |
| 219 | 2-[2-Ethyl-5-(trifluoromethyl)phenyl]-5-[6-(methylamino)pyrimidin-4-yl]-1H-pyrrole-3-carboxamide | 0.014 | 0.004 | 0.27 | >10 |
| 220 | 2-[2-Ethyl-5-(trifluoromethyl)phenyl]-5-(7H-pyrrolo[2,3-d]pyrimidin-4-yl)-1H-pyrrole-3-carboxamide | 0.019 | 0.002 | 0.15 | 6.87 |
| 227 | 4-(6-aminopyrimidin-4-yl)-1-(5-chloro-2-methylphenyl)-1H-pyrrole-2-carboxamide | 0.595 | 0.073 | 2.36 | >10 |
| 229 | 1-(5-Chloro-2-methylphenyl)-4-(7H-pyrrolo[2,3-d]pyrimidin-4-yl)-1H-pyrrole-2-carboxamide | 0.003 | 0.001 | 0.08 | >10 |
| 232 | 1-(5-chloro-2-methylphenyl)-4-(1H-pyrazolo[3,4-d]pyrimidin-4-yl)-1H-pyrrole-2-carboxamide | 0.315 | 0.033 | 1.68 | >10 |

TABLE A-continued

| Compd Number | Compound name | IC$_{50}$ μM JAK1 | JAK2 | SET-2 | K-562 |
|---|---|---|---|---|---|
| 233 | 1-(5-chloro-2-methylphenyl)-4-(pyrrolo[2,1-f][1,2,4]triazin-4-yl)-1H-pyrrole-2-carboxamide | 0.396 | 0.068 | 1.92 | >10 |
| 234 | 1-(5-Chloro-2-methylphenyl)-4-(6,7-dihydro-5H-pyrrolo[2,3-d]pyrimidin-4-yl)-1H-pyrrole-2-carboxamide | 0.008 | 0.006 | 0.26 | >10 |
| 235 | 4-(6-Aminopyrimidin-4-yl)-1-(5-chloro-2-ethylphenyl)-1H-pyrrole-2-carboxamide | 0.079 | 0.008 | 0.40 | >10 |
| 236 | 1-(5-Chloro-2-ethylphenyl)-4-[6-(methylamino)pyrimidin-4-yl]-1H-pyrrole-2-carboxamide | 0.093 | 0.012 | 0.50 | >10 |
| 237 | 1-(5-Chloro-2-ethylphenyl)-4-(7H-pyrrolo[2,3-d]pyrimidin-4-yl)-1H-pyrrole-2-carboxamide | 0.001 | 0.001 | 0.03 | >10 |
| 240 | 1-(5-Chloro-2-ethylphenyl)-4-(pyrrolo[2,1-f][1,2,4]triazin-4-yl)-1H-pyrrole-2-carboxamide | 0.134 | 0.020 | 0.66 | >10 |
| 241 | 1-(5-Chloro-2-ethylphenyl)-4-(6,7-dihydro-5H-pyrrolo[2,3-d]pyrimidin-4-yl)-1H-pyrrole-2-carboxamide | 0.008 | 0.005 | 0.31 | >10 |
| 242 | 4-(6-Aminopyrimidin-4-yl)-1-[2-chloro-5-(trifluoromethyl)phenyl]-1H-pyrrole-2-carboxamide | 1.083 | 0.071 | 1.57 | >10 |
| 244 | 1-[2-Chloro-5-(trifluoromethyl)phenyl]-4-(7H-pyrrolo[2,3-d]pyrimidin-4-yl)-1H-pyrrole-2-carboxamide | 0.004 | 0.001 | 0.06 | 7.23 |
| 245 | 1-[2-Chloro-5-(trifluoromethyl)phenyl]-4-(9H-purin-6-yl)-1H-pyrrole-2-carboxamide | 0.386 | 0.027 | 1.23 | >10 |
| 246 | 1-[2-Chloro-5-(trifluoromethyl)phenyl]-4-(1H-pyrazolo[3,4-d]pyrimidin-4-yl)-1H-pyrrole-2-carboxamide | 0.212 | 0.018 | 1.20 | 3.49 |
| 247 | 1-[2-chloro-5-(trifluoromethyl)phenyl]-4-(pyrrolo[2,1-f][1,2,4]triazin-4-yl)-1H-pyrrole-2-carboxamide | 0.991 | 0.085 | 2.34 | >10 |
| 256 | 4-(6-Aminopyrimidin-4-yl)-1-[2-ethyl-5-(trifluoromethyl)phenyl]-1H-pyrrole-2-carboxamide | 0.053 | 0.006 | 0.62 | >10 |
| 270 | 4-(5-Chloro-2-methylphenyl)-1-(7H-pyrrolo[2,3-d]pyrimidin-4-yl)-1H-pyrrole-3-carboxamide | 0.085 | 0.017 | 0.55 | 1.89 |
| 301 | 5-(6-Aminopyrimidin-4-yl)-2-(5-chloro-2-ethylphenyl)-N-methyl-1H-pyrrole-3-carboxamide | 0.019 | 0.005 | 0.29 | 4.13 |
| 302 | 2-(5-Chloro-2-ethylphenyl)-N-methyl-5-[6-(methylamino)pyrimidin-4-yl]-1H-pyrrole-3-carboxamide | 0.001 | 0.001 | 0.13 | 6.61 |
| 303 | 2-(5-Chloro-2-ethylphenyl)-N-methyl-5-(7H-pyrrolo[2,3-d]pyrimidin-4-yl)-1H-pyrrole-3-carboxamide | 0.006 | 0.001 | 0.14 | 3.76 |
| 318 | 2-[2-Methyl-5-(trifluoromethyl)phenyl]-N-methyl-5-(7H-pyrrolo[2,3-d]pyrimidin-4-yl)-1H-pyrrole-3-carboxamide | 0.063 | 0.025 | 0.35 | >10 |
| 321 | 5-(6-Aminopyrimidin-4-yl)-2-[2-ethyl-5-(trifluoromethyl)phenyl]-N-methyl-1H-pyrrole-3-carboxamide | 0.009 | 0.003 | 0.25 | >10 |
| 322 | 2-[2-Ethyl-5-(trifluoromethyl)phenyl]-N-methyl-5-[6-(methylamino)pyrimidin-4-yl]-1H-pyrrole-3-carboxamide | 0.013 | 0.004 | 0.22 | 2.80 |
| 323 | 2-[2-Ethyl-5-(trifluoromethyl)phenyl]-N-methyl-5-(7H-pyrrolo[2,3-d]pyrimidin-4-yl)-1H-pyrrole-3-carboxamide | 0.006 | 0.003 | 0.22 | >10 |

In biochemical assays, the compounds of formula (I) tested as described above demonstrate a remarkably potent TYK2 inhibitory activity. See, as an example, the following Table B wherein is reported experimental data (IC$_{50}$) of the compounds of the invention obtained for TYK2 kinase (see Table B).

TABLE B

| Compd Number | Compound name | TYK2 IC$_{50}$ μM |
|---|---|---|
| 63 | 1-(5-Chloro-2-methylphenyl)-4-(7H-pyrrolo[2,3-d]pyrimidin-4-yl)-1H-pyrrole-2-carbonitrile | 0.013 |

TABLE B-continued

| Compd Number | Compound name | |
|---|---|---|
| 68 | 1-(5-Chloro-2-ethylphenyl)-4-(7H-pyrrolo[2,3-d]pyrimidin-4-yl)-1H-pyrrole-2-carbonitrile | 0.012 |
| 72 | 1-[2-Chloro-5-(trifluoromethyl)phenyl]-4-(7H-pyrrolo[2,3-d]pyrimidin-4-yl)-1H-pyrrole-2-carbonitrile | 0.038 |
| 123 | 3-(5-Chloro-2-methylphenyl)-5-(7H-pyrrolo[2,3-d]pyrimidin-4-yl)-1H-pyrrole-2-carboxamide | 0.023 |
| 124 | 3-(5-Chloro-2-ethylphenyl)-5-(7H-pyrrolo[2,3-d]pyrimidin-4-yl)-1H-pyrrole-2-carboxamide | 0.009 |
| 125 | 3-[2-Ethyl-5-(trifluoromethyl)phenyl]-5-(7H-pyrrolo[2,3-d]pyrimidin-4-yl)-1H-pyrrole-2-carboxamide | 0.032 |
| 129 | 3-(5-Chloro-2-methylphenyl)-N-methyl-5-(7H-pyrrolo[2,3-d]pyrimidin-4-yl)-1H-pyrrole-2-carboxamide | 0.070 |
| 130 | 3-(5-Chloro-2-ethylphenyl)-N-methyl-5-(7H-pyrrolo[2,3-d]pyrimidin-4-yl)-1H-pyrrole-2-carboxamide | 0.007 |
| 131 | 3-[2-Ethyl-5-(trifluoromethyl)phenyl]-N-methyl-5-(7H-pyrrolo[2,3-d]pyrimidin-4-yl)-1H-pyrrole-2-carboxamide | 0.087 |
| 190 | 2-(5-Chloro-2-methylphenyl)-5-[6-(methylamino)pyrimidin-4-yl]-1H-pyrrole-3-carboxamide | 0.094 |
| 191 | 2-(5-Chloro-2-methylphenyl)-5-(7H-pyrrolo[2,3-d]pyrimidin-4-yl)-1H-pyrrole-3-carboxamide | 0.007 |
| 192 | 2-(5-Chloro-2-methylphenyl)-5-(1H-pyrrolo[2,3-b]pyridin-4-yl)-1H-pyrrole-3-carboxamide | 0.051 |
| 197 | 5-(6-Aminopyrimidin-4-yl)-2-(5-chloro-2-ethylphenyl)-1H-pyrrole-3-carboxamide | 0.010 |
| 198 | 2-(5-Chloro-2-ethylphenyl)-5-[6-(methylamino)pyrimidin-4-yl]-1H-pyrrole-3-carboxamide | 0.023 |
| 199 | 2-(5-Chloro-2-ethylphenyl)-5-(7H-pyrrolo[2,3-d]pyrimidin-4-yl)-1H-pyrrole-3-carboxamide | 0.003 |
| 213 | 2-[2-Methyl-5-(trifluoromethyl)phenyl]-5-(7H-pyrrolo[2,3-d]pyrimidin-4-yl)-1H-pyrrole-3-carboxamide | 0.073 |
| 218 | 5-(6-Aminopyrimidin-4-yl)-2-[2-ethyl-5-(trifluoromethyl)phenyl]-1H-pyrrole-3-carboxamide | 0.054 |
| 219 | 2-[2-Ethyl-5-(trifluoromethyl)phenyl]-5-[6-(methylamino)pyrimidin-4-yl]-1H-pyrrole-3-carboxamide | 0.046 |
| 220 | 2-[2-Ethyl-5-(trifluoromethyl)phenyl]-5-(7H-pyrrolo[2,3-d]pyrimidin-4-yl)-1H-pyrrole-3-carboxamide | 0.020 |
| 229 | 1-(5-Chloro-2-methylphenyl)-4-(7H-pyrrolo[2,3-d]pyrimidin-4-yl)-1H-pyrrole-2-carboxamide | 0.002 |
| 232 | 1-(5-Chloro-2-methylphenyl)-4-(1H-pyrazolo[3,4-d]pyrimidin-4-yl)-1H-pyrrole-2-carboxamide | 0.069 |
| 233 | 1-(5-Chloro-2-methylphenyl)-4-(pyrrolo[2,1-f][1,2,4]triazin-4-yl)-1H-pyrrole-2-carboxamide | 0.123 |
| 234 | 1-(5-Chloro-2-methylphenyl)-4-(6,7-dihydro-5H-pyrrolo[2,3-d]pyrimidin-4-yl)-1H-pyrrole-2-carboxamide | 0.008 |
| 235 | 4-(6-Aminopyrimidin-4-yl)-1-(5-chloro-2-ethylphenyl)-1H-pyrrole-2-carboxamide | 0.032 |
| 236 | 1-(5-Chloro-2-ethylphenyl)-4-[6-(methylamino)pyrimidin-4-yl]-1H-pyrrole-2-carboxamide | 0.048 |
| 237 | 1-(5-Chloro-2-ethylphenyl)-4-(7H-pyrrolo[2,3-d]pyrimidin-4-yl)-1H-pyrrole-2-carboxamide | 0.001 |
| 240 | 1-(5-Chloro-2-ethylphenyl)-4-(pyrrolo[2,1-f][1,2,4]triazin-4-yl)-1H-pyrrole-2-carboxamide | 0.027 |
| 241 | 1-(5-Chloro-2-ethylphenyl)-4-(6,7-dihydro-5H-pyrrolo[2,3-d]pyrimidin-4-yl)-1H-pyrrole-2-carboxamide | 0.016 |
| 244 | 1-[2-Chloro-5-(trifluoromethyl)phenyl]-4-(7H-pyrrolo[2,3-d]pyrimidin-4-yl)-1H-pyrrole-2-carboxamide | 0.003 |
| 246 | 1-[2-Chloro-5-(trifluoromethyl)phenyl]-4-(1H-pyrazolo[3,4-d]pyrimidin-4-yl)-1H-pyrrole-2-carboxamide | 0.058 |
| 256 | 4-(6-Aminopyrimidin-4-yl)-1-[2-ethyl-5-(trifluoromethyl)phenyl]-1H-pyrrole-2-carboxamide | 0.031 |
| 270 | 4-(5-Chloro-2-methylphenyl)-1-(7H-pyrrolo[2,3-d]pyrimidin-4-yl)-1H-pyrrole-3-carboxamide | 0.043 |
| 301 | 5-(6-Aminopyrimidin-4-yl)-2-(5-chloro-2-ethylphenyl)-N-methyl-1H-pyrrole-3-carboxamide | 0.088 |
| 302 | 2-(5-Chloro-2-ethylphenyl)-N-methyl-5-[6-(methylamino)pyrimidin-4-yl]-1H-pyrrole-3-carboxamide | 0.010 |
| 303 | 2-(5-Chloro-2-ethylphenyl)-N-methyl-5-(7H-pyrrolo[2,3-d]pyrimidin-4-yl)-1H-pyrrole-3-carboxamide | 0.012 |
| 321 | 5-(6-Aminopyrimidin-4-yl)-2-[2-ethyl-5-(trifluoromethyl)phenyl]-N-methyl-1H-pyrrole-3-carboxamide | 0.038 |
| 323 | 2-[2-Ethyl-5-(trifluoromethyl)phenyl]-N-methyl-5-(7H-pyrrolo[2,3-d]pyrimidin-4-yl)-1H-pyrrole-3-carboxamide | 0.022 |
| | | DERL7 IC$_{50}$ μM |
| 10 | 2-(5-Chloro-2-ethylphenyl)-5-[6-(methylamino)pyrimidin-4-yl]-1H-pyrrole-3-carbonitrile | 0.780 |

TABLE B-continued

| Compd Number | Compound name | |
|---|---|---|
| 68 | 1-(5-Chloro-2-ethylphenyl)-4-(7H-pyrrolo[2,3-d]pyrimidin-4-yl)-1H-pyrrole-2-carbonitrile | 0.332 |
| 124 | 3-(5-Chloro-2-ethylphenyl)-5-(7H-pyrrolo[2,3-d]pyrimidin-4-yl)-1H-pyrrole-2-carboxamide | 1.071 |
| 125 | 3-[2-Ethyl-5-(trifluoromethyl)phenyl]-5-(7H-pyrrolo[2,3-d]pyrimidin-4-yl)-1H-pyrrole-2-carboxamide | 1.075 |
| 130 | 3-(5-Chloro-2-ethylphenyl)-N-methyl-5-(7H-pyrrolo[2,3-d]pyrimidin-4-yl)-1H-pyrrole-2-carboxamide | 1.599 |
| 197 | 5-(6-Aminopyrimidin-4-yl)-2-(5-chloro-2-ethylphenyl)-1H-pyrrole-3-carboxamide | 0.257 |
| 198 | 2-(5-Chloro-2-ethylphenyl)-5-[6-(methylamino)pyrimidin-4-yl]-1H-pyrrole-3-carboxamide | 0.170 |
| 199 | 2-(5-Chloro-2-ethylphenyl)-5-(7H-pyrrolo[2,3-d]pyrimidin-4-yl)-1H-pyrrole-3-carboxamide | 0.194 |
| 219 | 2-[2-Ethyl-5-(trifluoromethyl)phenyl]-5-[6-(methylamino)pyrimidin-4-yl]-1H-pyrrole-3-carboxamide | 0.392 |
| 220 | 2-[2-Ethyl-5-(trifluoromethyl)phenyl]-5-(7H-pyrrolo[2,3-d]pyrimidin-4-yl)-1H-pyrrole-3-carboxamide | 0.591 |
| 229 | 1-(5-Chloro-2-methylphenyl)-4-(7H-pyrrolo[2,3-d]pyrimidin-4-yl)-1H-pyrrole-2-carboxamide | 0.463 |
| 234 | 1-(5-Chloro-2-methylphenyl)-4-(6,7-dihydro-5H-pyrrolo[2,3-d]pyrimidin-4-yl)-1H-pyrrole-2-carboxamide | 0.208 |
| 237 | 1-(5-Chloro-2-ethylphenyl)-4-(7H-pyrrolo[2,3-d]pyrimidin-4-yl)-1H-pyrrole-2-carboxamide | 0.018 |
| 241 | 1-(5-Chloro-2-ethylphenyl)-4-(6,7-dihydro-5H-pyrrolo[2,3-d]pyrimidin-4-yl)-1H-pyrrole-2-carboxamide | 1.296 |
| 244 | 1-[2-Chloro-5-(trifluoromethyl)phenyl]-4-(7H-pyrrolo[2,3-d]pyrimidin-4-yl)-1H-pyrrole-2-carboxamide | 0.146 |
| 270 | 4-(5-Chloro-2-methylphenyl)-1-(7H-pyrrolo[2,3-d]pyrimidin-4-yl)-1H-pyrrole-3-carboxamide | 1.794 |
| 302 | 2-(5-Chloro-2-ethylphenyl)-N-methyl-5-[6-(methylamino)pyrimidin-4-yl]-1H-pyrrole-3-carboxamide | 0.469 |
| 321 | 5-(6-Aminopyrimidin-4-yl)-2-[2-ethyl-5-(trifluoromethyl)phenyl]-N-methyl-1H-pyrrole-3-carboxamide | 0.548 |
| 322 | 2-[2-Ethyl-5-(trifluoromethyl)phenyl]-N-methyl-5-[6-(methylamino)pyrimidin-4-yl]-1H-pyrrole-3-carboxamide | 0.246 |
| 323 | 2-[2-Ethyl-5-(trifluoromethyl)phenyl]-N-methyl-5-(7H-pyrrolo[2,3-d]pyrimidin-4-yl)-1H-pyrrole-3-carboxamide | 0.510 |

In cellular assays, the compounds of formula (I) tested as described above show high activity in JAK1/3 dependent human T lymphoma cell line DERL-7 (see Table C).

So far, the novel compounds of the invention are endowed with a potent JAK and TYK2 inhibitory activity and are thus particularly advantageous, in therapy, against cancer and metastasis, cell proliferative disorders, viral infections, immune disorders, neurodegenerative disorders, cardiovascular diseases and bone related diseases.

The invention claimed is:
1. A compound of formula (I):

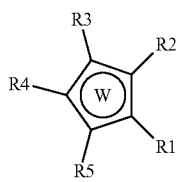

(I)

wherein:
Ring W is a pyrrole;
R1 is a substituted aryl;
R2 is CN or CONR6R7 wherein R6 and R7 are independently hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, aryl-alkyl, heteroaryl, heteroaryl-alkyl, heterocyclyl and heterocyclyl-alkyl, or R6 and R7, taken together with the nitrogen atom to which they are bonded, may form an optionally substituted 5 to 7 membered heterocyclyl group optionally containing one additional heteroatom selected from N, O and S;
R3 is hydrogen, halo or an optionally substituted group selected from straight or branched $C_1$-$C_6$ alkyl, $C_3$-$C_7$ cycloalkyl, cycloalkyl-alkyl, heterocyclyl and heterocyclyl-alkyl;
R4 is an optionally substituted heteroaryl group selected from

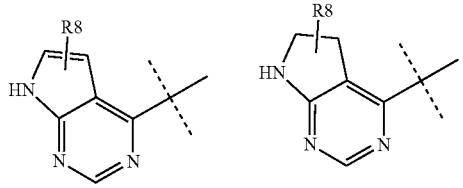

wherein:
R8 is hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, aryl-alkyl, heteroaryl, heteroaryl-alkyl, heterocyclyl and heterocyclyl-alkyl, COR9, CONR10R11 and SO$_2$R12,
wherein:
R9 is a group optionally substituted selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, aryl-alkyl, heteroaryl, heteroaryl-alkyl, heterocyclyl and heterocyclyl-alkyl;
R10 and R11 are independently hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, aryl-alkyl, heteroaryl, heteroaryl-alkyl, heterocyclyl and heterocyclyl-alkyl, or R10 and R11, taken together with the nitrogen atom to which they are bonded, may form an optionally substituted 5 to 7 membered heterocyclyl group optionally containing one additional heteroatom selected from N, O and S;
R12 is a group optionally substituted selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, aryl-alkyl, heteroaryl, heteroaryl-alkyl, heterocyclyl and heterocyclyl-alkyl;
R5 is hydrogen, halo or an optionally substituted group selected from straight or branched $C_1$-$C_6$ alkyl, $C_3$-$C_7$ cycloalkyl, cycloalkyl-alkyl, heterocyclyl and heterocyclyl-alkyl;
or a pharmaceutically acceptable salt thereof.
2. A compound of the formula (I), as defined in claim 1, wherein R2 is CN.
3. A compound of the formula (I), as defined in claim 1, wherein R2 is CONR6R7, wherein R6 and R7 are as defined in claim 1.
4. A compound or a pharmaceutically acceptable salt thereof which is selected from the group consisting of:
1-(5-Chloro-2-methylphenyl)-4-(7H-pyrrolo[2,3-d]pyrimidin-4-yl)-1H-pyrrole-2-carbonitrile (compd 63);
1-(5-Chloro-2-ethylphenyl)-4-(7H-pyrrolo[2,3-d]pyrimidin-4-yl)-1H-pyrrole-2-carbonitrile (compd 68);
1-[2-Chloro-5-(trifluoromethyl)phenyl]-4-(7H-pyrrolo[2,3-d]pyrimidin-4-yl)-1H-pyrrole-2-carbonitrile (compd 72);
3-(5-Chloro-2-methylphenyl)-5-(7H-pyrrolo[2,3-d]pyrimidin-4-yl)-1H-pyrrole-2-carboxamide (compd 123);
3-(5-Chloro-2-ethylphenyl)-5-(7H-pyrrolo[2,3-d]pyrimidin-4-yl)-1H-pyrrole-2-carboxamide (compd 124);
3-[2-Ethyl-5-(trifluoromethyl)phenyl]-5-(7H-pyrrolo[2,3-d]pyrimidin-4-yl)-1H-pyrrole-2-carboxamide (compd 125);
3-(5-Chloro-2-methylphenyl)-N-methyl-5-(7H-pyrrolo[2,3-d]pyrimidin-4-yl)-1H-pyrrole-2-carboxamide (compd 129);
3-(5-Chloro-2-ethylphenyl)-N-methyl-5-(7H-pyrrolo[2,3-d]pyrimidin-4-yl)-1H-pyrrole-2-carboxamide (compd 130);
3-[2-Ethyl-5-(trifluoromethyl)phenyl]-N-methyl-5-(7H-pyrrolo[2,3-d]pyrimidin-4-yl)-1H-pyrrole-2-carboxamide (compd 131);
2-(5-Chloro-2-methylphenyl)-5-(7H-pyrrolo[2,3-d]pyrimidin-4-yl)-1H-pyrrole-3-carboxamide (compd 191);

2-(5-Chloro-2-ethylphenyl)-5-(7H-pyrrolo[2,3-d]pyrimidin-4-yl)-1H-pyrrole-3-carboxamide (compd 199);
2-[2-Chloro-5-(trifluoromethyl)phenyl]-5-(7H-pyrrolo[2,3-d]pyrimidin-4-yl)-1H-pyrrole-3-carboxamide (compd 206);
2-[2-Methyl-5-(trifluoromethyl)phenyl]-5-(7H-pyrrolo[2,3-d]pyrimidin-4-yl)-1H-pyrrole-3-carboxamide (compd 213);
2-[2-Ethyl-5-(trifluoromethyl)phenyl]-5-(7H-pyrrolo[2,3-d]pyrimidin-4-yl)-1H-pyrrole-3-carboxamide (compd 220);
1-(5-Chloro-2-methylphenyl)-4-(7H-pyrrolo[2,3-d]pyrimidin-4-yl)-1H-pyrrole-2-carboxamide (compd 229);
1-(5-Chloro-2-methylphenyl)-4-(6,7-dihydro-5H-pyrrolo[2,3-d]pyrimidin-4-yl)-1H-pyrrole-2-carboxamide (compd 234);
1-(5-Chloro-2-ethylphenyl)-4-(7H-pyrrolo[2,3-d]pyrimidin-4-yl)-1H-pyrrole-2-carboxamide (compd 237);
1-(5-Chloro-2-ethylphenyl)-4-(6,7-dihydro-5H-pyrrolo[2,3-d]pyrimidin-4-yl)-1H-pyrrole-2-carboxamide (compd 241);
1-[2-Chloro-5-(trifluoromethyl)phenyl]-4-(7H-pyrrolo[2,3-d]pyrimidin-4-yl)-1H-pyrrole-2-carboxamide (compd 244);
4-(5-Chloro-2-methylphenyl)-1-(7H-pyrrolo[2,3-d]pyrimidin-4-yl)-1H-pyrrole-3-carboxamide (compd 270);
2-(5-Chloro-2-ethylphenyl)-N-methyl-5-(7H-pyrrolo[2,3-d]pyrimidin-4-yl)-1H-pyrrole-3-carboxamide (compd 303);
2-[2-Methyl-5-(trifluoromethyl)phenyl]-N-methyl-5-(7H-pyrrolo[2,3-d]pyrimidin-4-yl)-1H-pyrrole-3-carboxamide (compd 318); and
2-[2-Ethyl-5-(trifluoromethyl)phenyl]-N-methyl-5-(7H-pyrrolo[2,3-]pyrimidin-4-yl)-1H-pyrrole-3-carboxamide (compd 323).

5. A process for preparing a compound of formula (I) as defined in claim 1 or the pharmaceutically acceptable salts thereof wherein the process comprises:

Step 1: reaction of a compound of formula (II)

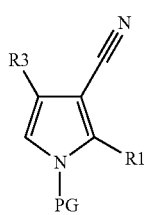

(II)

wherein R1 and R3 are as defined in claim 1 and PG is a protecting group being benzenesulfonyl with 2-isopropoxy-4,4,5,5-tetramethyl-1,3,2-dioxyborolane;

alternatively:

Step 1a: reaction of a halo compound of formula (III)

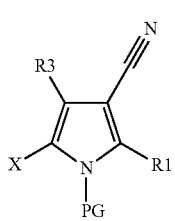

(III)

wherein R1 and R3 are as defined in claim 1, X is halogen, and PG is a protecting group being 2-(trimethylsilyl)ethoxymethyl or tert-butyloxycarbonyl, with 2-isopropoxy-4,4,5,5-tetramethyl-1,3,2-dioxyborolane;

Step 2: metal-catalyzed coupling reaction of the resultant compound of formula (IV)

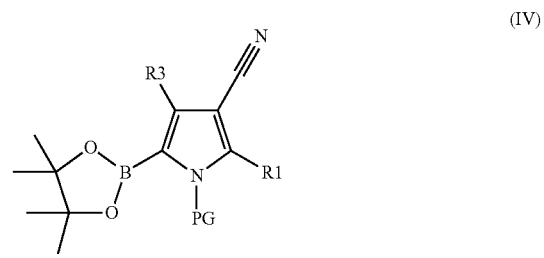

(IV)

wherein R1 and R3 are as defined in claim 1 and PG is a protecting group being 2-(trimethylsilyl)ethoxymethyl, tert-butyloxycarbonyl, or benzenesulfonyl with a halo compound of formula (V)

R4-x  (V)

wherein R4 is as defined in claim 1 and X is halogen;

Step 3: deprotection of the resultant compound of formula (VI)

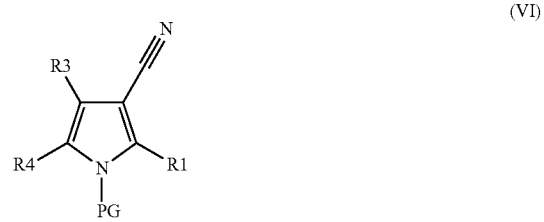

(VI)

wherein R1, R3 and R4 are as defined in claim 1 and PG is a protecting group being 2-(trimethylsilyl)ethoxymethyl, tert-butyloxycarbonyl, or benzenesulfonyl to give a compound of formula (Ia)

(Ia)

wherein R1, R3 and R4 are as defined in claim 1, R2 is CN and R5 is hydrogen;

alternatively
Step 4: reaction of a compound of formula (VII)

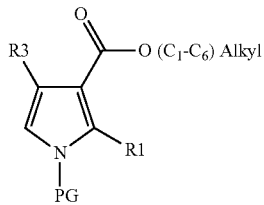
(VII)

wherein R1 and R3 are as defined in claim 1 and PG is a protecting group being benzenesulfonyl with 2-isopropoxy-4,4,5,5-tetramethyl-1,3,2-dioxyborolane;
Step 5: metal-catalyzed coupling reaction of the resultant compound of formula (VIII)

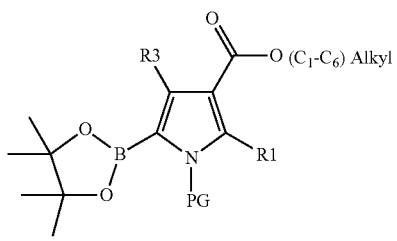
(VIII)

wherein R1 and R3 are as defined in claim 1 and PG is a protecting group being benzenesulfonyl with a halo compound of formula (V), as defined above;
Step 6: hydrolysis under basic conditions of the resultant carboxylic ester of formula (IX)

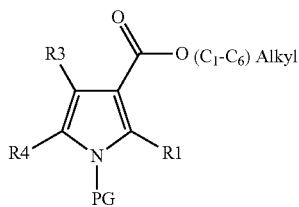
(IX)

wherein R1, R3, and R4 are as defined in claim 1 and PG is as defined above;
Step 7: amidation of the resultant carboxylic acid of formula (X)

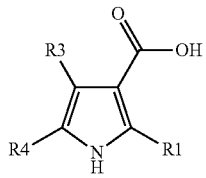
(X)

wherein R1, R3 and R4 are as defined in claim 1, through reaction with an amine of formula (XI)

NHR6R7 (XI)

wherein R6 and R7 are as defined in claim 1, to give a compound of formula (Ia)

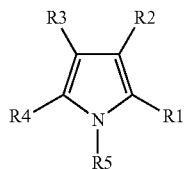
(Ia)

wherein R2 is CONR6R7, R5 is hydrogen, R1, R3, R4, R6 and R7 are as defined in claim 1;
alternatively
Step 8: reaction of a halo compound of formula (XII)

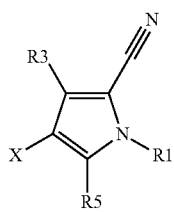
(XII)

wherein R1, R3 and R5 are as defined in claim 1 and X is halogen with 2-isopropoxy-4,4,5,5-tetramethyl-1,3,2-dioxyborolane;
Step 9: metal-catalyzed coupling reaction of the resultant compound of formula (XIII)

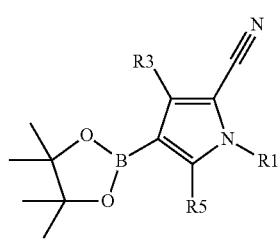
(XIII)

wherein R1, R3 and R5 are as defined in claim 1, with a halo compound of formula (V), as defined above, to give a compound of formula (Ib)

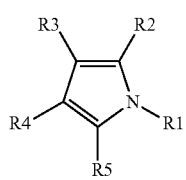
(Ib)

wherein R1, R3, R4 and R5 are as defined in claim 1 and R2 is CN;

alternatively
Step 10: reaction of a compound of formula (XIV)

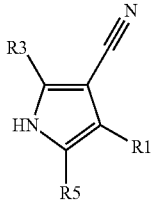
(XIV)

wherein R1, R3 and R5 are as defined in claim 1, with a halo compound of formula (V), as defined above, in the presence of a base or metal-catalyzed to give a compound of formula (Ic)

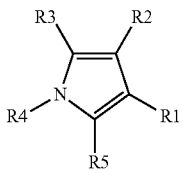
(Ic)

wherein R1, R3, R4 and R5 are as defined in claim 1 and R2 is CN;
alternatively
Step 11: reaction of a compound of formula (XV)

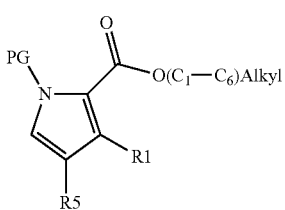
(XV)

wherein R1 and R5 are as defined in claim 1 and PG is a protecting group being benzenesulfonyl with 2-isopropoxy-4,4,5,5-tetramethyl-1,3,2-dioxyborolane;
Step 12: metal-catalyzed coupling reaction of the resultant compound of formula (XVI)

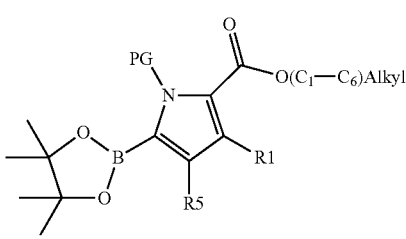
(XVI)

wherein R1 and R5 are as defined in claim 1 and PG is a protecting group being benzenesulfonyl with a halo compound of formula (V), as defined above;
Step 13: hydrolysis under basic conditions of the resultant carboxylic ester of formula (XVII)

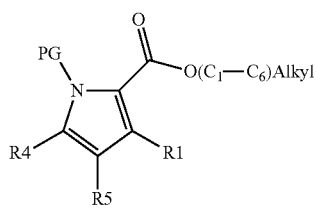
(XVII)

wherein R1, R4 and R5 are as defined in claim 1 and PG is a protecting group as defined above;
Step 14: amidation of the resultant carboxylic acid of formula (XVIII)

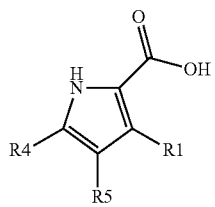
(XVIII)

wherein R1, R4 and R5 are as defined in claim 1, through reaction with an amine of formula (XI), as defined above, to give a compound of formula (Id)

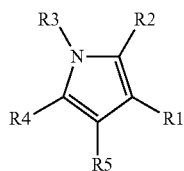
(Id)

wherein R1, R2, R4 and R5 are as defined in claim 1 and R3 is hydrogen;
alternatively
Step 15: reaction of a halo compound of formula (XIX)

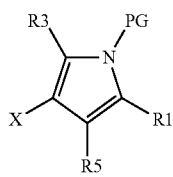
(XIX)

wherein R1, R3 and R5 are as defined in claim 1, PG is a protecting group being tert-butyloxycarbonyl and X is halogen with 2-isopropoxy-4,4,5,5-tetramethyl-1,3,2-dioxyborolane;
Step 16: metal-catalyzed coupling reaction of the resultant compound of formula (XX)

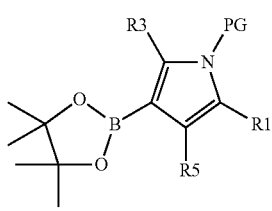

(XX)

wherein R1, R3 and R5 are as defined in claim 1 and PG is a protecting group being tert-butyloxycarbonyl, with a halo compound of formula (V), as defined above;

Step 17: deprotection of the resultant compound of formula (XXI)

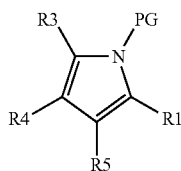

(XXI)

wherein R1, R3, R4 and R5 are as defined in claim 1 and PG is a protecting group being tert-butyloxycarbonyl;

Step 18: reaction of the resultant compound of formula (XXII)

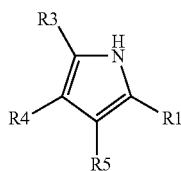

(XXII)

wherein R1, R3, R4 and R5 are as defined in claim 1, with an amine of formula (XI), as defined above, in the presence of triphosgene, to give a compound of formula (Ie)

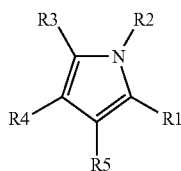

(Ie)

wherein R2 is CONR6R7 and R1, R3, R4, R5, R6 and R7 are as defined above;

optionally converting a compound of the formula (I) into another different compound of the formula (I), and, if desired, converting a compound of the formula (I) into a pharmaceutically acceptable salt thereof or converting a salt into the free compound (I).

6. A process for preparing a compound of formula (I) according to claim 5, wherein the optional conversion of a compound of formula (I) into another compound of formula (I) is carried out by one or more of the following reactions:

conv.1) converting a compound of the formula (I), wherein R2 is CN, into the corresponding compound of formula (I), wherein R2 is $CONH_2$, by hydrolyzing in acidic conditions,

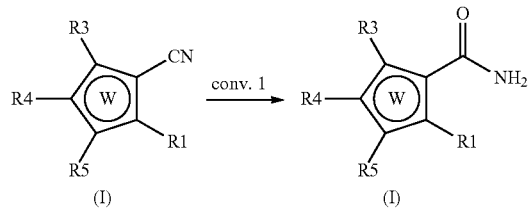

conv.2) converting a compound of the formula (I), wherein R2 is $CONH_2$, into the corresponding compound of formula (I), wherein R2 is CONR6R7 wherein R6 and R7 are independently hydrogen or an optionally substituted group selected from straight or branched $C_1$-$C_6$ alkyl, straight or branched $C_3$-$C_6$ alkenyl, straight or branched $C_2$-$C_6$ alkynyl, $C_3$-$C_7$ cycloalkyl, cycloalkyl-alkyl, aryl, aryl-alkyl, heteroaryl, heteroaryl-alkyl, heterocyclyl and heterocyclyl-alkyl, or R6 and R7, taken together with the nitrogen atom to which they are bonded, may form an optionally substituted 5 to 7 membered heterocyclyl group optionally containing one additional heteroatom selected from N, O and S, but not both hydrogen

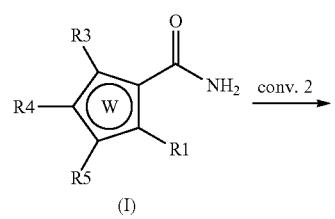

(I)

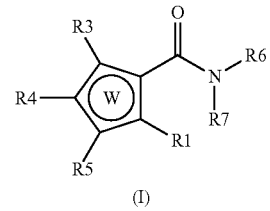

(I)

by exhaustive tert-butoxycarbonylation of a compound of the formula (I), treatment with an amine derivative of formula (XXIII)

NHR6R7                                    (XXIII)

wherein R6 and R7 are as defined above but not both hydrogen and deprotection of tert-butoxycarbonyl protecting groups;

conv.3) converting a compound of the formula (Ia), wherein R5 is hydrogen or (Id) wherein R3 is hydrogen, into the corresponding compound of formula (Ia) or (Id), wherein R5 or R3 respectively is an optionally substituted group selected from straight or branched $C_1$-$C_6$ alkyl, $C_3$-$C_7$ cycloalkyl, cycloalkyl-alkyl, heterocyclyl and heterocyclyl-alkyl,

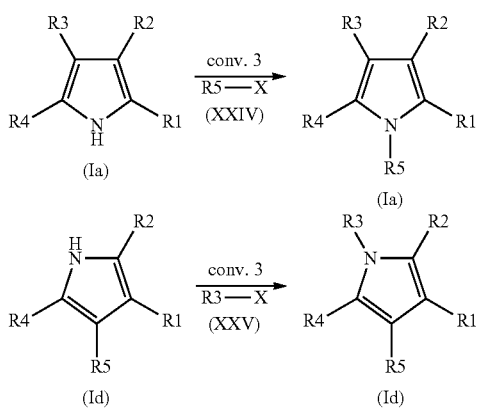

by treatment with optionally substituted alkyl halide of the formula R5X (XXIV) or R3X (XXV), wherein R5 or R3 respectively is an optionally substituted group selected from straight or branched $C_1$-$C_6$ alkyl, $C_3$-$C_7$ cycloalkyl, heterocyclyl and heterocyclyl-alkyl, and X is halogen.

7. A method for treating a disease, the disease selected from the group consisting of transplant rejection, rheumatoid arthritis, psoriasis, Crohn's disease, ulcerative colitis, atopic dermatitis, solid tumors, myelofibrosis, myeloproliferative disorders, polycythemia vera (PV), essential thrombocythemia (ET), acute myeloid leukemia (AML), chronic myelogenous leukemias (CML), and acute lymphoblastic leukemia (ALL), which comprises administering to a mammal in need thereof an effective amount of a compound of formula (I) as defined in claim 1.

8. The method according to claim 7 wherein the mammal in need thereof is a human.

9. The method according to claim 7 wherein said disease is selected from a carcinoma; hematopoietic tumors of lymphoid lineage; hematopoietic tumors of myeloid lineage; tumors of mesenchymal origin; and tumors of the central and peripheral nervous system.

10. The method according to claim 7 further comprising subjecting the mammal in need thereof to a radiation therapy or chemotherapy regimen in combination with at least one cytostatic or cytotoxic agent.

11. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

12. A pharmaceutical composition, according to claim 11, further comprising one or more chemotherapeutic agents.

13. An in vitro method for inhibiting the JAK family kinase protein activity which comprises contacting the said protein with an effective amount of a compound of formula (I) as defined in claim 1.

14. A product comprising a compound of formula (I) or a pharmaceutically acceptable salt thereof, as defined in claim 1, and one or more chemotherapeutic agents, as a combined preparation for simultaneous, separate or sequential use in anticancer therapy.

15. The method according to claim 7, wherein said solid tumors are selected from melanoma, seminoma, teratocarcinoma, osteosarcoma, xeroderma pigmentosum, keratoxanthoma, thyroid follicular cancer, Kaposi's sarcoma, and mesothelioma.

16. The method according to claim 9, wherein: said carcinoma is selected from bladder, breast, brain, colon, kidney, liver, lung, small cell lung cancer, head and neck, esophagus, gall-bladder, ovary, uterine, pancreas, stomach, cervix, thyroid, prostate, skin, and squamous cell carcinoma; said hematopoietic tumors of lymphoid lineage are selected from leukaemia, T and B acute lymphoblastic leukemia (ALL), DS-ALL, B-cell lymphoma, T-cell-lymphoma, Hodgkin's lymphoma, non-Hodgkin's lymphoma, Multiple Myeloma, hairy cell lymphoma, Burkett's lymphoma and mantle cell lymphoma; said hematopoietic tumors of myeloid lineage are selected from acute and chronic myelogenous leukemias, acute megakaryoblastic leukemia, myelodysplastic syndrome, promyelocytic leukemia, Primary myelofibrosis and myelofibrosis secondary to PV, and ET; said tumors of mesenchymal origin are selected from sarcoma, fibrosarcoma and rhabdomyosarcoma; and said tumors of the central and peripheral nervous system are selected from astrocytoma neuroblastoma, glioma and schwannomas.

* * * * *

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial
<220> FEATURE:
<223> OTHER INFORMATION: peptidic substrate

<400> SEQUENCE: 1

Leu Pro Leu Asp Lys Asp Tyr Tyr Val Val Arg Glu Pro Gly Gln
1               5                   10                  15

<210> SEQ ID NO 2
<211> LENGTH: 16
<212> TYPE: PRT
<213> ORGANISM: Artificial
<220> FEATURE:
```

<223> OTHER INFORMATION: Peptidic substrate

<400> SEQUENCE: 2

Lys Lys His Thr Asp Asp Gly Tyr Met Pro Met Ser Pro Gly Val Ala
1               5                   10                  15